US012779061B2

(12) United States Patent
Sigalov

(10) Patent No.: US 12,779,061 B2
(45) Date of Patent: Nov. 3, 2026

(54) METHODS FOR TARGETED IMAGING WITH SPHERICAL rHDLs

(71) Applicant: Signablok, Inc., Shrewsbury, MA (US)

(72) Inventor: Alexander B. Sigalov, Worcester, MA (US)

(73) Assignee: SIGNABLOK, INC., Shrewsbury, MA (US)

( * ) Notice: Subject to any disclaimer, the term of this patent is extended or adjusted under 35 U.S.C. 154(b) by 322 days.

(21) Appl. No.: 18/736,873

(22) Filed: Jun. 7, 2024

(65) Prior Publication Data

US 2024/0307565 A1 Sep. 19, 2024

Related U.S. Application Data

(60) Continuation of application No. 17/111,371, filed on Dec. 3, 2020, now Pat. No. 12,036,294, which is a division of application No. 16/712,215, filed on Dec. 12, 2019, now Pat. No. 10,894,098, which is a continuation of application No. 13/501,085, filed as application No. PCT/US2010/052117 on Oct. 10, 2010, now Pat. No. 10,525,152.

(60) Provisional application No. 61/250,465, filed on Oct. 9, 2009.

(51) Int. Cl.
*A61K 51/12* (2006.01)
*A61K 47/69* (2017.01)

(52) U.S. Cl.
CPC ...... *A61K 51/1224* (2013.01); *A61K 47/6917* (2017.08)

(58) Field of Classification Search
CPC ............ A61K 51/1224; A61K 47/6917; A61K 49/0466; A61K 49/1812
See application file for complete search history.

(56) References Cited

U.S. PATENT DOCUMENTS 5,059,528 A 10/1991 Bollen et al.
5,128,318 A 7/1992 Levine et al.
5,582,981 A 12/1996 Toole et al.
5,652,339 A 7/1997 Lerch et al.
5,676,928 A 10/1997 Klaveness et al.
5,840,688 A 11/1998 Tso
5,840,867 A 11/1998 Toole et al.
5,965,542 A 10/1999 Wasan et al.
6,004,925 A 12/1999 Dasseux et al.
6,008,202 A 12/1999 Huang et al.
6,037,323 A 3/2000 Dasseux et al.
6,046,166 A 4/2000 Dasseux et al.
6,139,819 A 10/2000 Unger et al.
6,248,353 B1 6/2001 Singh
6,287,590 B1 9/2001 Dasseux
6,306,433 B1 10/2001 Andersson et al.
6,498,946 B1 12/2002 Foo et al.
6,541,973 B1 4/2003 Danby et al.
6,559,284 B1 5/2003 Ageland et al.
6,580,936 B2 6/2003 Muraki et al.
6,586,933 B1 7/2003 Hardy et al.
6,590,391 B1 7/2003 Shudo et al.
6,591,128 B1 7/2003 Wu et al.
6,600,401 B2 7/2003 Zuk et al.
6,611,143 B2 8/2003 Kuhara
6,617,134 B1 9/2003 Sirtori et al.
6,953,840 B2 10/2005 Zhu et al.
7,179,484 B2 2/2007 Singh
7,288,266 B2 10/2007 Smyth-Templeton et al.
7,435,717 B2 10/2008 Bisgaier et al.
7,491,693 B2 2/2009 Hubsch et al.
7,588,751 B2 9/2009 Ueda et al.
(Continued)

FOREIGN PATENT DOCUMENTS

EP 0469017 2/1992
WO WO/1987/002062 4/1987
(Continued)

OTHER PUBLICATIONS

Ahrens, E. T. et al. (1998) "A model for MRI contrast enhancement using T(1) agents," *Proceedings of the National Academy of Sciences of the United States of America* 95(15), 8443-8448.
Aikawa, M. et al. (1999) "Dietary Lipid Lowering Reduces Tissue Factor Expression in Rabbit Atheroma," *Circulation* 100(11), 1215-1222.
Aime, S. et al. (2002) "Insights into the use of paramagnetic Gd(III) complexes in MR-molecular imaging investigations," *Journal of Magnetic Resonance Imaging* 16(4), 394-406.
(Continued)

*Primary Examiner* — Robert S Cabral
(74) *Attorney, Agent, or Firm* — Medlen & Carroll, LLP

(57) ABSTRACT

A new approach to targeting imaging agents to macrophage-rich sites of interest is disclosed. Compositions of the invention are rHDL and HDL-like liposomal compositions, protein constituents of which, apolipoproteins A-I and/or A-II or fragments thereof are used not only as structural but also as targeting agents. This is achieved by certain controlled chemical or enzymatic modification of apolipoproteins A-I or A-II or fragments thereof. Such modification converts these apolipoproteins to substrates for macrophage scavenger receptors and results in the improvement of contrast agent-(HDL/modified apolipoprotein)-particle association with macrophages and/or absorption (uptake) by macrophages when compared to that of the contrast agent-(HDL/apolipoprotein)-particle constructed with non-modified naturally occurring apo A-I. The compositions can be used for noninvasive specific in vivo molecular detection and localization of macrophage-rich sites of interest using imaging techniques such as computed tomography (CT), gamma-scintigraphy, positron emission tomography (PET), single photon emission computed tomography (SPECT), magnetic resonance imaging (MRI).

27 Claims, 37 Drawing Sheets

Specification includes a Sequence Listing.

(56) References Cited

U.S. PATENT DOCUMENTS

| | | | |
|---|---|---|---|
| 7,740,854 | B2 | 6/2010 | Low et al. |
| 2001/0002251 | A1 | 5/2001 | Woodburn et al. |
| 2002/0110604 | A1 | 8/2002 | Babish et al. |
| 2002/0156007 | A1 | 10/2002 | Graversen et al. |
| 2002/0177558 | A1 | 11/2002 | Meyerhoff et al. |
| 2003/0045460 | A1 | 3/2003 | Fogelman et al. |
| 2003/0087819 | A1 | 5/2003 | Bielicki |
| 2003/0171277 | A1 | 9/2003 | Fogelman et al. |
| 2003/0181372 | A1 | 9/2003 | Oda et al. |
| 2004/0067873 | A1 | 4/2004 | Dasseux et al. |
| 2004/0077541 | A1 | 4/2004 | Zhu et al. |
| 2004/0176473 | A1 | 9/2004 | Unger et al. |
| 2004/0229794 | A1 | 11/2004 | Ryan et al. |
| 2004/0254120 | A1 | 12/2004 | Fogelman et al. |
| 2004/0266660 | A1 | 12/2004 | Hubsch et al. |
| 2004/0266671 | A1 | 12/2004 | Fogelman et al. |
| 2005/0239136 | A1 | 10/2005 | Hazen et al. |
| 2005/0281740 | A1 | 12/2005 | Gong et al. |
| 2006/0099148 | A1 | 5/2006 | Fisher et al. |
| 2006/0204566 | A1 | 9/2006 | Smyth-Templeton et al. |
| 2006/0205643 | A1 | 9/2006 | Cuzzocrea et al. |
| 2006/0217312 | A1 | 9/2006 | Dasseux |
| 2007/0243136 | A1 | 10/2007 | Fisher et al. |
| 2008/0020400 | A1 | 1/2008 | Caulfield |
| 2008/0286353 | A1 | 11/2008 | Gregoriadis |
| 2009/0004113 | A1 | 1/2009 | Wolf |
| 2009/0012025 | A1 | 1/2009 | Hotchkiss et al. |
| 2009/0068264 | A1 | 3/2009 | Richardson et al. |
| 2009/0311191 | A1 | 12/2009 | Annapragada et al. |
| 2009/0312402 | A1 | 12/2009 | Contag et al. |
| 2010/0202974 | A1 | 8/2010 | Annapragada et al. |
| 2011/0312899 | A1 | 12/2011 | Sood et al. |

FOREIGN PATENT DOCUMENTS

| | | |
|---|---|---|
| WO | WO/1988/009165 | 12/1988 |
| WO | WO/1990/012879 | 5/1991 |
| WO | WO/2001/038395 | 5/2001 |

OTHER PUBLICATIONS

Amirbekian, V. et al. (2007) “Detecting and assessing macrophages in vivo to evaluate atherosclerosis noninvasively using molecular MRI,” *Proceedings of the National Academy of Sciences of the United States of America* 104(3), 961-966 published Jan. 10, 2007.

Anantharamaiah, G. M. et al. (1988) “Effect of oxidation on the properties of apolipoproteins A-I and A-II,” *Journal of Lipid Research* 29(3), 309-318 published Mar. 1, 1988.

Andreadis, A. A. et al. (2003) “Oxidative and nitrosative events in asthma,” *Free Radical Biology & Medicine* 35(3), 213-225 published Aug. 1, 2003.

Asselbergs, F. W. et al. (2004) “Myeloperoxidase polymorphism related to cardiovascular events in coronary artery disease,” *American Journal of Medicine* 116(6), 429-430.

Assinger, A. et al. (2008) “Oxidation by hypochlorite converts protective HDL into a potent platelet agonist,” *FEBS Letters* 582(5), 778-784.

Babaev, V. R. et al. (2000) “Macrophage Lipoprotein Lipase Promotes Foam Cell Formation and Atherosclerosis in Low Density Lipoprotein Receptor-deficient Mice,” *Journal of Biological Chemistry* 275(34), 26293-26299 published Aug. 25, 2000.

Badea, C. et al. (2004) “Micro-CT with respiratory and cardiac gating,” *Medical Physics* 31(12), 3324-3329.

Badimon, J. J. et al. (1999) “Local Inhibition of Tissue Factor Reduces the Thrombogenicity of Disrupted Human Atherosclerotic Plaques,” *Circulation* 99(14), 1780-1787.

Bared, S. M. et al. (2004) “Association of ABCA1 with Syntaxin 13 and Flotillin-1 and Enhanced Phagocytosis in Tangier Cells,” *Molecular Biology of the Cell* 15(12), 5399-5407 published Dec. 1, 2004.

Bartlett, G. R. (1959) “Phosphorus Assay in col. Chromatography,” *Journal of Biological Chemistry* 234(3), 466-468 published Mar. 1, 1959.

Bayburt, T. H. et al. (1998) “Reconstitution and Imaging of a Membrane Protein in a Nanometer-Size Phospholipid Bilayer,” *Journal of Structural Biology* 123(1), 37-44 published Sep. 1, 1998.

Bayburt, T. H. et al. (2002) “Self-Assembly of Discoidal Phospholipid Bilayer Nanoparticles with Membrane Scaffold Proteins,” *Nano Letters* 2(8), 853-856 published Aug. 1, 2002.

Beckmann, N. et al. (2009) “In vivo visualization of macrophage infiltration and activity in inflammation using magnetic resonance imaging,” *Wiley Interdisciplinary Reviews: Nanomedicine and Nanobiotechnology* 1(3), 272-298.

Bellin, M.-F. (2006) “MR contrast agents, the old and the new,” *European Journal of Radiology* 60(3), 314-323.

Bellin, M.-F. et al. (2008) “Extracellular gadolinium-based contrast media: An overview,” *European Journal of Radiology* 66(2), 160-167.

Bergt, C. et al. (2001) “Human neutrophils employ the myeloperoxidase/hydrogen peroxide/chloride system to oxidatively damage apolipoprotein A-I,” *European Journal of Biochemistry* 268(12), 3523-3531.

Bergt, C. et al. (2000) “Reagent or myeloperoxidase-generated hypochlorite affects discrete regions in lipid-free and lipid-associated human apolipoprotein A-I,” *Biochemical Journal* 346(Pt 2), 345-354.

Bergt, C. et al. (2003) “Oxidized HDL: The Paradox-idation of Lipoproteins,” *Arteriosclerosis, Thrombosis, and Vascular Biology* 23(9), 1488-1490 published Sep. 1, 2003.

Bergt, C. et al. (2004) “The myeloperoxidase product hypochlorous acid oxidizes HDL in the human artery wall and impairs ABCA1-dependent cholesterol transport,” *Proceedings of the National Academy of Sciences of the United States of America* 101(35), 13032-13037 published Aug. 23, 2004.

Bergt, C. et al. (1999) “Hypochlorite modification of high density lipoprotein: effects on cholesterol efflux from J774 macrophages,” *FEBS Letters* 452(3), 295-300.

Bharali, D. J. et al. (2010) “Emerging nanomedicines for early cancer detection and improved treatment: Current perspective and future promise,” *Pharmacology & Therapeutics* 128(2), 324-335 published Nov. 2010.

Biewenga, G. P. et al. (1997) “The pharmacology of the antioxidant lipoic acid,” *General Pharmacology: The Vascular System* 29(3), 315-331 published Sep. 1, 1997.

Biewenga, G. P. et al. (1998) “Effects of dihydrolipoic acid on peptide methionine sulfoxide reductase. Implications for antioxidant drugs,” *Arzneimittel-Forschung* 48(2), 144-148 published Feb.

Bitler, B. G. et al. (2010) “Anti-cancer therapies that utilize cell penetrating peptides,” *Recent Patents on Anti-Cancer Drug Discovery* 5(2), 99-108.

Blondel, C. et al. (2004) “3D tomographic reconstruction of coronary arteries using a precomputed 4D motion field,” *Physics in Medicine and Biology* 49(11), 2197.

Botnar, R. M. et al. (2000) “Noninvasive Coronary Vessel Wall and Plaque Imaging With Magnetic Resonance Imaging,” *Circulation* 102(21), 2582-2587.

Braschi, S. et al. (1999) “Apolipoprotein A-I charge and conformation regulate the clearance of reconstituted high density lipoprotein in vivo,” *Journal of Lipid Research* 40(3), 522-532 published Mar. 1, 1999.

Brewer, H. B. et al. (1978) “The amino acid sequence of human Apoa-I, an apolipoprotein isolated from high density lipoproteins,” *Biochemical and Biophysical Research Communications* 80(3), 623-630.

Brewer, H. B. et al. (2004) “Regulation of Plasma High-Density Lipoprotein Levels by the ABCA1 Transporter and the Emerging Role of High-Density Lipoprotein in the Treatment of Cardiovascular Disease,” *Arteriosclerosis, Thrombosis, and Vascular Biology* 24(10), 1755-1760 published Oct. 1, 2004.

Briley-Saebo, K. C. et al. (2009) “High relaxivity gadolinium modified high density lipoproteins as MRI contrast agents,” *Journal of Physical Chemistry B* 113(18), 6283-6289.

Briley-Saebo, K. C. et al. (2007) “Magnetic resonance imaging of vulnerable atherosclerotic plaques: Current imaging strategies and molecular imaging probes,” *Journal of Magnetic Resonance Imaging* 26(3), 460-479.

(56) References Cited

OTHER PUBLICATIONS

Briley-Saebo, K. C. et al. (2008) "Targeted Molecular Probes for Imaging Atherosclerotic Lesions With Magnetic Resonance Using Antibodies That Recognize Oxidation-Specific Epitopes," *Circulation* 117(25), 3206-3215.
Broome, D. R. et al. (2007) "Gadodiamide-associated nephrogenic systemic fibrosis: why radiologists should be concerned," *American Journal of Roentgenology* 188(2), 586-592 published Feb.
Brot, N. et al. (1981) "Enzymatic reduction of protein-bound methionine sulfoxide," *Proceedings of the National Academy of Sciences of the United States of America* 78(4), 2155-2158.
Brouillette, C. G. et al. (1995) "Structural models of human apolipoprotein A-I," *Biochim Biophys Acta* 1256(2), 103-129 published May 17.
Cai, J.-M. et al. (2002) "Classification of Human Carotid Atherosclerotic Lesions With In Vivo Multicontrast Magnetic Resonance Imaging," *Circulation* 106(11), 1368-1373.
Castro, G. R. et al. (1988) "Early incorporation of cell-derived cholesterol into pre-beta-migrating high-density lipoprotein," *Biochemistry* 27(1), 25-29 published Jan. 12.
Chambenoit, O. et al. (2001) "Specific Docking of Apolipoprotein A-I at the Cell Surface Requires a Functional ABCA1 Transporter," *Journal of Biological Chemistry* 276(13), 9955-9960 published Mar. 30, 2001.
Chen, W. et al. (2008) "Incorporation of an apoE-derived lipopeptide in high-density lipoprotein MRI contrast agents for enhanced imaging of macrophages in atherosclerosis," *Contrast Media & Molecular Imaging* 3(6), 233-242.
Chen, Y. H. et al. (1972) "Determination of the secondary structures of proteins by circular dichroism and optical rotatory dispersion," *Biochemistry* 11(22), 4120-4131 published Oct. 24.
Cheung, M. C. et al. (1987) "Characterization of high density lipoprotein subspecies: structural studies by single vertical spin ultracentrifugation and immunoaffinity chromatography," *Journal of Lipid Research* 28(8), 913-929 published Aug. 1, 1987.
Chin, J. H. et al. (1992) "Inactivation of endothelial derived relaxing factor by oxidized lipoproteins," *Journal of Clinical Investigation* 89(1), 10-18.
Choudhury, R. P. et al. (2002) "Atherosclerotic lesions in genetically modified mice quantified in vivo by non-invasive high-resolution magnetic resonance microscopy," *Atherosclerosis* 162(2), 315-321.
Choudhury, R. P. et al. (2003) "Serial, noninvasive, in vivo magnetic resonance microscopy detects the development of atherosclerosis in apolipoprotein E-deficient mice and its progression by arterial wall remodeling," *Journal of Magnetic Resonance Imaging* 17(2), 184-189.
Choudhury, R. P. et al. (2009) "Molecular Imaging in Atherosclerosis, Thrombosis, and Vascular Inflammation," *Arteriosclerosis, Thrombosis, and Vascular Biology* 29(7), 983-991 published Jul. 1, 2009.
Choudhury, R. P. et al. (2004) "High-Density Lipoproteins Retard the Progression of Atherosclerosis and Favorably Remodel Lesions Without Suppressing Indices of Inflammation or Oxidation," *Arteriosclerosis, Thrombosis, and Vascular Biology* 24(10), 1904-1909 published Oct. 1, 2004.
Choy, G. et al. (2003) "Current advances in molecular imaging: noninvasive in vivo bioluminescent and fluorescent optical imaging in cancer research," *Molecular Imaging* 2(4), 303-312 published Oct.
Chung, B. H. et al. (1980) "Preparative and quantitative isolation of plasma lipoproteins: rapid, single discontinuous density gradient ultracentrifugation in a vertical rotor," *Journal of Lipid Research* 21(3), 284-291 published Mar. 1, 1980.
Clarke, H. G. et al. (1968) "Quantitative immunoelectrophoresis of human serum proteins," *Clinical Science* 35(2), 403-413 published Oct.
Clay, M. A. et al. (2001) "Time sequence of the inhibition of endothelial adhesion molecule expression by reconstituted high density lipoproteins," *Atherosclerosis* 157(1), 23-29.
Collins, D. J. et al. (2004) "Dynamic magnetic resonance imaging of tumor perfusion. Approaches and biomedical challenges," *IEEE Engineering in Medicine and Biology Magazine* 23(5), 65-83 published Sep.-Oct.
Cormode, D. P. et al. (2008) "An ApoA-I Mimetic Peptide High-Density-Lipoprotein-Based MRI Contrast Agent for Atherosclerotic Plaque Composition Detection," *Small* 4(9), 1437-1444.
Cormode, D. P. et al. (2010) "Atherosclerotic Plaque Composition: Analysis with Multicolor CT and Targeted Gold Nanoparticles," *Radiology* 256(3), 774-782 published Sep. 2010.
Cormode, D. P. et al. (2008) "Nanocrystal Core High-Density Lipoproteins: A Multimodality Contrast Agent Platform," *Nano Letters* 8(11), 3715-3723 published Nov. 12, 2008.
Corti, R. et al. (2002) "Lipid Lowering by Simvastatin Induces Regression of Human Atherosclerotic Lesions," *Circulation* 106(23), 2884-2887.
Corti, R. et al. (2002) "In vivo noninvasive detection and age definition of arterial thrombus by MRI," *Journal of the American College of Cardiology* 39(8), 1366-1373.
Coulden, R. et al. (2000) "High resolution magnetic resonance imaging of atherosclerosis and the response to balloon angioplasty," *Heart* 83(2), 188-191.
Cuzick, J. et al. (2009) "Aspirin and non-steroidal anti-inflammatory drugs for cancer prevention: an international consensus statement," *Lancet Oncology* 10(5), 501-507.
Daugherty, A. et al. (1994) "Myeloperoxidase, a catalyst for lipoprotein oxidation, is expressed in human atherosclerotic lesions," *Journal of Clinical Investigation* 94(1), 437-444.
Daum, U. et al. (1999) "Apolipoprotein A-I (R151C)Paris is defective in activation of lecithin: cholesterol acyltransferase but not in initial lipid binding, formation of reconstituted lipoproteins, or promotion of cholesterol efflux," *Journal of Molecular Medicine (Berlin)* 77(8), 614-622 published Aug.
Davidson, W. S. et al. (1995) "The Effect of High Density Lipoprotein Phospholipid Acyl Chain Composition on the Efflux of Cellular Free Cholesterol," *Journal of Biological Chemistry* 270(11), 5882-5890 published Mar. 17, 1995.
Davies, M. J. et al. (1985) "Plaque fissuring—the cause of acute myocardial infarction, sudden ischaemic death, and crescendo angina," *British Heart Journal* 53(4), 363-373.
De Vrueh, R. L. A. et al. (2000) "Carrier-Mediated Delivery of 9-(2-Phosphonylmethoxyethyl) Adenine to Parenchymal Liver Cells: a Novel Therapeutic Approach for Hepatitis B," *Antimicrobial Agents and Chemotherapy* 44(3), 477-483.
De Winther, M. P. J. et al. (2000) "Macrophage Scavenger Receptor Class A: A Multifunctional Receptor in Atherosclerosis," *Arteriosclerosis, Thrombosis, and Vascular Biology* 20(2), 290-297 published Feb. 1, 2000.
Decossin, C. et al. (1997) "Subclasses of LpA-I in coronary artery disease: distribution and cholesterol efflux ability," *European Journal of Clinical Investigation* 27(4), 299-307.
Delikatny, E. J. et al. (2005) "MR techniques for in vivo molecular and cellular imaging," *Radiologic Clinics of North America* 43(1), 205-220 published Jan.
Department of Health and Human Service. (1997) *Federal Register* 62(247), 67376-67377.
Desai, M. Y. et al. (2005) "Atherosclerosis Imaging Using MR Imaging: Current and Emerging Applications," *Magnetic Resonance Imaging Clinics of North America* 13(1), 171-180.
Dhikav, V. et al. (2002) "Newer non-steroidal anti-inflammatory drugs—a review of their therapeutic potential and adverse drug reactions," *Journal of the Academy of Indian Clinical Medicine* 3(4), 332-338.
Dinarello, C. A. (2010) "Anti-inflammatory Agents: Present and Future," *Cell* 140(6), 935-950.
Durbin, D. M. et al. (1997) "The Effect of Apolipoprotein A-II on the Structure and Function of Apolipoprotein A-I in a Homogeneous Reconstituted High Density Lipoprotein Particle," *Journal of Biological Chemistry* 272(50), 31333-31339 published Dec. 12, 1997.
Duverger, N. et al. (1996) "Transgenic Rabbits Expressing Human Apolipoprotein A-I in the Liver," *Arteriosclerosis, Thrombosis, and Vascular Biology* 16(12), 1424-1429 published Dec. 1, 1996.

(56) References Cited

OTHER PUBLICATIONS

Edelstein, C. et al. (1972) "On the Subunit Structure of the Protein of Human Serum High Density Lipoprotein: I. a Study of Its Major Polypeptide Component (Sephadex, Fraction III)," *Journal of Biological Chemistry* 247(18), 5842-5849 published Sep. 25, 1972.
Elrod, D. B. et al. (2009) "An iodinated liposomal computed tomographic contrast agent prepared from a diiodophosphatidylcholine lipid," *Nanomedicine: Nanotechnology, Biology and Medicine* 5(1), 42-45.
Falk, E. (1992) "Why do plaques rupture?," *Circulation* 86(6 Suppl), III30-42 published Dec.
Fatterpekar, G. M. et al. (2002) "Cytoarchitecture of the Human Cerebral Cortex: MR Microscopy of Excised Specimens at 9.4 Tesla," *American Journal of Neuroradiology* 23(8), 1313-1321 published Sep. 1, 2002.
Fayad, Z. et al. (2000) "Characterization of Atherosclerotic Plaques by Magnetic Resonance Imaging," *Annals of the New York Academy of Sciences* 902(1), 173-186.
Fayad, Z. A. et al. (1998) "Noninvasive In Vivo High-Resolution Magnetic Resonance Imaging of Atherosclerotic Lesions in Genetically Engineered Mice," *Circulation* 98(15), 1541-1547.
Fayad, Z. A. et al. (2002) "Computed Tomography and Magnetic Resonance Imaging for Noninvasive Coronary Angiography and Plaque Imaging," *Circulation* 106(15), 2026-2034.
Fayad, Z. A. et al. (2000) "In Vivo Magnetic Resonance Evaluation of Atherosclerotic Plaques in the Human Thoracic Aorta," *Circulation* 101(21), 2503-2509.
Febbraio, M. et al. (2000) "Targeted disruption of the class B scavenger receptor CD36 protects against atherosclerotic lesion development in mice," *Journal of Clinical Investigation* 105(8), 1049-1056.
Fitzgerald, P. J. et al. (1992) "Intravascular ultrasound imaging of coronary arteries. Is three layers the norm?," *Circulation* 86(1), 154-158.
Forrester, J. S. et al. (2006) "Emerging Strategies for Increasing High-Density Lipoprotein," *American Journal of Cardiology* 98(11), 1542-1549.
Fossheim, S. L. et al. (1999) "Paramagnetic liposomes as MRI contrast agents: influence of liposomal physicochemical properties on the in vitro relaxivity," *Magnetic Resonance Imaging* 17(1), 83-89.
France, D. S. et al. (1989) "Nonimmunochemical quantitation of mammalian apolipoprotein A-I in whole serum or plasma by nonreducing gel electrophoresis," *Journal of Lipid Research* 30(12), 1997-2004 published Dec. 1, 1989.
Franceschini, G. et al. (1985) "Apolipoprotein AIMilano. Accelerated binding and dissociation from lipids of a human apolipoprotein variant," *Journal of Biological Chemistry* 260(30), 16321-16325 published Dec. 25, 1985.
Frank, P. G. et al. (1998) "Importance of Central α-Helices of Human Apolipoprotein A-I in the Maturation of High-Density Lipoproteins," *Biochemistry* 37(39), 13902-13909 published 1998/09/01.
Frias, J. C. et al. (2007) "Modified lipoproteins as contrast agents for imaging of atherosclerosis," *Contrast Media & Molecular Imaging* 2(1), 16-23.
Frias, J. C. et al. (2006) "Properties of a Versatile Nanoparticle Platform Contrast Agent To Image and Characterize Atherosclerotic Plaques by Magnetic Resonance Imaging," *Nano Letters* 6(10), 2220-2224 published Oct. 1, 2006.
Frias, J. C. et al. (2004) "Recombinant HDL-Like Nanoparticles: A Specific Contrast Agent for MRI of Atherosclerotic Plaques," *Journal of the American Chemical Society* 126(50), 16316-16317 published Dec. 1, 2004.
Fu, P. et al. (2009) "Oxidized phospholipids in control of inflammation and endothelial barrier," *Translational Research* 153(4), 166-176 published Jan. 21, 2009.
Fuki, I. V. et al. (1997) "The syndecan family of proteoglycans. Novel receptors mediating internalization of atherogenic lipoproteins in vitro," *Journal of Clinical Investigation* 100(6), 1611-1622.
Fuster, V. et al. (2005) "Frontiers in Cardiovascular Magnetic Resonance," *Circulation* 112(1), 135-144.
Garner, B. et al. (1998) "Oxidation of High Density Lipoproteins: II. Evidence for Direct Reduction of Lipid Hydroperoxides by Methionine Residues of Apolipoproteins AI and AII," *Journal of Biological Chemistry* 273(11), 6088-6095 published Mar. 13, 1998.
Garner, B. et al. (1998) "Oxidation of High Density Lipoproteins: I. Formation of Methionine Sulfoxide in Apolipoproteins AI and AII is an Early Event That Accompanies Lipid Peroxidation and Can Be Enhanced by α-Tocopherol," *Journal of Biological Chemistry* 273(11), 6080-6087 published Mar. 13, 1998.
Gaut, J. P. et al. (2002) "Myeloperoxidase produces nitrating oxidants in vivo," *Journal of Clinical Investigation* 109(10), 1311-1319.
Ghibu, S. et al. (2009) "Antioxidant properties of an endogenous thiol: Alpha-lipoic acid, useful in the prevention of cardiovascular diseases," *Journal of Cardiovascular Pharmacology* 54(5), 391-398 published Nov.
Gjetting, T. et al. (2010) "In vitro and in vivo effects of polyethylene glycol (PEG)-modified lipid in DOTAP/cholesterol-mediated gene transfection," *International Journal of Nanomedicine* 5, 371-383 published Aug. 2009.
Gløgård, C. et al. (2002) "Liposomes as carriers of amphiphilic gadolinium chelates: the effect of membrane composition on incorporation efficacy and in vitro relaxivity," *International Journal of Pharmaceutics* 233(1-2), 131-140 published Feb. 21, 2002.
Goldstein, J. L. et al. (1979) "Binding site on macrophages that mediates uptake and degradation of acetylated low density lipoprotein, producing massive cholesterol deposition," *Proceedings of the National Academy of Sciences of the United States of America* 76(1), 333-337.
Gough, P. J. et al. (1999) "Analysis of Macrophage Scavenger Receptor (SR-A) Expression in Human Aortic Atherosclerotic Lesions," *Arteriosclerosis, Thrombosis, and Vascular Biology* 19(3), 461-471 published Mar. 1, 1999.
Grant, C. W. et al. (1989) "A liposomal MRI contrast agent: phosphatidylethanolamine-DTPA," *Magnetic Resonance in Medicine* 11(2), 236-243 published Aug.
Gustafsson, B. et al. (2006) "Development of contrast agents targeted to macrophage scavenger receptors for MRI of vascular inflammation," *Bioconjugate chemistry* 17(2), 538-547.
Haacke et al. (1998) *In vivo NMR spectroscopy, Principles and Techniques,* John Wiley & Sons, Chichester, N.Y.
Hansson, G. K. (2005) "Inflammation, Atherosclerosis, and Coronary Artery Disease," *New England Journal of Medicine* 352(16), 1685-1695.
Hatsukami, T. S. et al. (2000) "Visualization of Fibrous Cap Thickness and Rupture in Human Atherosclerotic Carotid Plaque In Vivo With High-Resolution Magnetic Resonance Imaging," *Circulation* 102(9), 959-964.
Havel, R. J. et al. (2001) "Structure and metabolism of plasma lipoproteins," in *The Metabolic and Molecular Bases of Inherited Disease* (Scriver, C. R., et al., Eds.) 8th ed., pp. 2705-2716, McGraw-Hill, New York.
Hazell, L. J. et al. (1996) "Presence of hypochlorite-modified proteins in human atherosclerotic lesions," *Journal of Clinical Investigation* 97(6), 1535-1544.
Hazell, L. J. et al. (2001) "Correlation between intima-to-media ratio, apolipoprotein B-100, myeloperoxidase, and hypochlorite-oxidized proteins in human atherosclerosis," *Free Radical Biology & Medicine* 31(10), 1254-1262 published Nov. 15, 2001.
Hazell, L. J. et al. (1993) "Oxidation of low-density lipoprotein with hypochlorite causes transformation of the lipoprotein into a high-uptake form for macrophages," *Biochemical Journal* 290(Pt 1), 165-172.
Hazen, S. L. et al. (1997) "3-Chlorotyrosine, a specific marker of myeloperoxidase-catalyzed oxidation, is markedly elevated in low density lipoprotein isolated from human atherosclerotic intima," *Journal of Clinical Investigation* 99(9), 2075-2081.
Hazen, S. L. et al. (1999) "Formation of Nitric Oxide-Derived Oxidants by Myeloperoxidase in Monocytes: Pathways for Monocyte-Mediated Protein Nitration and Lipid Peroxidation In Vivo," *Circulation Research* 85(10), 950-958 published Nov. 12, 1999.

(56) References Cited

OTHER PUBLICATIONS

Heinecke, J. W. (1999) "Mechanisms of oxidative damage by myeloperoxidase in atherosclerosis and other inflammatory disorders," *Journal of Laboratory and Clinical Medicine* 133(4), 321-325.
Heinecke, J. W. (2003) "Oxidative stress: new approaches to diagnosis and prognosis in atherosclerosis," *American Journal of Cardiology* 91(3A), 12A-16A published Feb 6.
Helft, G. et al. (2002) "Progression and Regression of Atherosclerotic Lesions," *Circulation* 105(8), 993-998.
Helft, G. et al. (2001) "Atherosclerotic aortic component quantification by noninvasive magnetic resonance imaging: an in vivo study in rabbits," *Journal of the American College of Cardiology* 37(4), 1149-1154 published Mar. 15, 2001.
Herfst, M. J. et al. (1978) "Suction blister fluid as a model for interstitial fluid in rats," *Archives of Dermatological Research* 263(3), 325-334.
Hörkkö, S. et al. (1999) "Monoclonal autoantibodies specific for oxidized phospholipids or oxidized phospholipid-protein adducts inhibit macrophage uptake of oxidized low-density lipoproteins," *Journal of Clinical Investigation* 103(1), 117-128.
Hurtado, I. et al. (1996) "In vitro oxidised HDL exerts a cytotoxic effect on macrophages," *Atherosclerosis* 125(1), 39-46.
Hyafil, F. et al. (2006) "Ferumoxtran-10-Enhanced MRI of the Hypercholesterolemic Rabbit Aorta: Relationship Between Signal Loss and Macrophage Infiltration," *Arteriosclerosis, Thrombosis, and Vascular Biology* 26(1), 176-181 published Jan. 1, 2006.
Itskovich, V. V. et al. (2003) "Characterization of aortic root atherosclerosis in ApoE knockout mice: High-resolution in vivo and ex vivo MRM with histological correlation," *Magnetic Resonance in Medicine* 49(2), 381-385.
Jaffer, F. A. et al. (2009) "Optical and Multimodality Molecular Imaging: Insights Into Atherosclerosis," *Arteriosclerosis, Thrombosis, and Vascular Biology* 29(7), 1017-1024 published Jul. 1, 2009.
Johnstone, M. T. et al. (2001) "In Vivo Magnetic Resonance Imaging of Experimental Thrombosis in a Rabbit Model," *Arteriosclerosis, Thrombosis, and Vascular Biology* 21(9), 1556-1560 published Sep. 1, 2001.
Jonas, A. (1986) "Reconstitution of high-density lipoproteins," *Methods in Enzymology* 128, 553-582.
Jonas, A. et al. (1993) "Structural and functional properties of natural and chemical variants of apolipoprotein A-I," *Biochimica et Biophysica Acta* 1166(2-3), 202-210 published Feb. 24.
Jonasson, L. et al. (1987) "Lipoprotein lipase in atherosclerosis: its presence in smooth muscle cells and absence from macrophages," *Journal of Lipid Research* 28(4), 437-445 published Apr. 1, 1987.
Kabalka, G. W. et al. (1988) "Gadolinium-labeled liposomes containing paramagnetic amphipathic agents: targeted MRI contrast agents for the liver," *Magnetic Resonance in Medicine* 8(1), 89-95 published Sep.
Kaim, A. H. et al. (2002) "MR Imaging with Ultrasmall Superparamagnetic Iron Oxide Particles in Experimental Soft-Tissue Infections in Rats," *Radiology* 225(3), 808-814.
Kao, C. Y. et al. (2003) "Long-residence-time nano-scale liposomal iohexol for X-ray-based blood pool imaging," *Academic Radiology* 10(5), 475-483 published May.
Keller, S. et al. (2005) "Membrane-Mimetic Nanocarriers Formed by a Dipalmitoylated Cell-Penetrating Peptide," *Angewandte Chemie International Edition* 44(33), 5252-5255.
Kerwin, W. et al. (2007) "Magnetic resonance imaging of carotid atherosclerosis: plaque analysis," *Topics in Magnetic Resonance Imaging* 18(5), 371-378 published Oct.
Khurana, A. et al. (2007) "Nephrogenic systemic fibrosis: a review of 6 cases temporally related to gadodiamide injection (omniscan)," *Investigative Radiology* 42(2), 139-145 published Feb.
Kielley, W. W. et al. (1960) "A model for the myosin molecule," *Biochimica et Biophysica Acta* 41, 401-421.
Kim, S. I. et al. (2009) "Targeted delivery of siRNA against hepatitis C virus by apolipoprotein A-I-bound cationic liposomes," *Journal of Hepatology* 50(3), 479-488.
Klebanoff, S. J. (1980) "Oxygen Metabolism and the Toxic Properties of Phagocytes," *Annals of Internal Medicine* 93(3), 480-489.
Kolodgie , F. D. et al. (2003) "Intraplaque Hemorrhage and Progression of Coronary Atheroma," *New England Journal of Medicine* 349(24), 2316-2325.
Kooi, M. E. et al. (2003) "Accumulation of Ultrasmall Superparamagnetic Particles of Iron Oxide in Human Atherosclerotic Plaques Can Be Detected by In Vivo Magnetic Resonance Imaging," *Circulation* 107(19), 2453-2458.
Krieger, M. (1994) "Structures and Functions of Multiligand Lipoprotein Receptors: Macrophage Scavenger Receptors and LDL Receptor-Related Protein (LRP)," *Annual Review of Biochemistry* 63(1), 601-637.
Kunjathoor, V. V. et al. (2002) "Accumulation of Biglycan and Perlecan, but Not Versican, in Lesions of Murine Models of Atherosclerosis," *Arteriosclerosis, Thrombosis, and Vascular Biology* 22(3), 462-468 published Mar. 1, 2002.
Kuo, P. H. (2008) "Gadolinium-Containing MRI Contrast Agents: Important Variations on a Theme for NSF," *Journal of the American College of Radiology* 5(1), 29-35.
Lanza, G. M. et al. (2002) "Targeted Antiproliferative Drug Delivery to Vascular Smooth Muscle Cells With a Magnetic Resonance Imaging Nanoparticle Contrast Agent," *Circulation* 106(22), 2842-2847.
Lauffer, R. B. (1990) "Magnetic resonance contrast media: principles and progress," *Magnetic Resonance Quarterly* 6(2), 65-84 published Apr.
Leander, P. et al. (2001) "A new liposomal liver-specific contrast agent for CT: first human phase-I clinical trial assessing efficacy and safety," *European Radiology* 11(4), 698-704.
Leber, A. W. et al. (2004) "Accuracy of multidetector spiral computed tomography in identifying and differentiating the composition of coronary atherosclerotic plaques: A comparative study with intracoronary ultrasound," *Journal of the American College of Cardiology* 43(7), 1241-1247 published Apr. 7, 2004.
Lerch, P. G. et al. (1996) "Production and Characterization ofa Reconstituted High Density Lipoprotein for Therapeutic Applications," *Vox Sanguinis* 71(3), 155-164.
Li, D. et al. (2001) "Contrast-enhanced MR Imaging of Coronary Arteries: Comparison of Intra- and Extravascular Contrast Agents in Swine," *Radiology* 218(3), 670-678.
Lin, W. et al. (1997) "Contrast-enhanced magnetic resonance angiography of carotid arterial wall in pigs," *Journal of Magnetic Resonance Imaging* 7(1), 183-190.
Lipinski, M. J. et al. (2006) "MRI to detect atherosclerosis with gadolinium-containing immunomicelles targeting the macrophage scavenger receptor," *Magnetic Resonance in Medicine* 56(3), 601-610.
Louie, A. Y. et al. (2000) "In vivo visualization of gene expression using magnetic resonance imaging," *Nature Biotechnology* 18(3), 321-325.
Lowry, O. H. et al. (1951) "Protein Measurement with the Folin Phenol Reagent," *Journal of Biological Chemistry* 193(1), 265-275 published Nov. 1, 1951.
Lund-Katz, S. et al. (1986) "Packing of cholesterol molecules in human low-density lipoprotein," *Biochemistry* 25(7), 1562-1568 published Apr. 8.
Lusis, A. J. (2000) "Atherosclerosis," *Nature* 407(6801), 233-241.
Lutz, A. M. et al. (2004) "Detection of Synovial Macrophages in an Experimental Rabbit Model of Antigen-induced Arthritis: Ultrasmall Superparamagnetic Iron Oxide-enhanced MR Imaging," *Radiology* 233(1), 149-157.
Maczurek, A. et al. (2008) "Lipoic acid as an anti-inflammatory and neuroprotective treatment for Alzheimer's disease," *Advanced Drug Delivery Reviews* 60(13-14), 1463-1470.
Malle, E. et al. (2001) "Hypochlorite-Modified (Lipo)Proteins Are Present in Rabbit Lesions in Response to Dietary Cholesterol," *Biochemical and Biophysical Research Communications* 289(4), 894-900 published Dec. 14, 2001.
Manda, G. et al. (2009) "Reactive oxygen species, cancer and anti-cancer therapies," *Current Chemical Biology* 3, 342-366.
Marathe, S. et al. (1999) "Sphingomyelinase, an Enzyme Implicated in Atherogenesis, Is Present in Atherosclerotic Lesions and Binds to

(56) References Cited

OTHER PUBLICATIONS

Specific Components of the Subendothelial Extracellular Matrix," *Arteriosclerosis, Thrombosis, and Vascular Biology* 19(11), 2648-2658 published Nov. 1, 1999.
Markwell, M. A. K. et al. (1978) "A modification of the Lowry procedure to simplify protein determination in membrane and lipoprotein samples," *Analytical Biochemistry* 87(1), 206-210.
Marsche, G. et al. (2002) "Hypochlorite-modified High Density Lipoprotein, a High Affinity Ligand to Scavenger Receptor Class B, Type I, Impairs High Density Lipoprotein-dependent Selective Lipid Uptake and Reverse Cholesterol Transport," *Journal of Biological Chemistry* 277(35), 32172-32179 published Aug. 30, 2002.
Marten, K. et al. (2005) "Imaging of macrophage-related lung diseases," *European Radiology* 15(4), 727-741.
Mashima, R. et al. (1998) "Reduction of phosphatidylcholine hydroperoxide by apolipoprotein A-I: purification of the hydroperoxide-reducing proteins from human blood plasma," *Journal of Lipid Research* 39(6), 1133-1140 published Jun. 1, 1998.
Massamiri, T. et al. (1997) "Structural determinants for the interaction of lipopolysaccharide binding protein with purified high density lipoproteins: role of apolipoprotein A-I," *Journal of Lipid Research* 38(3), 516-525 published Mar. 1, 1997.
Matz, C. E. et al. (1982) "Micellar complexes of human apolipoprotein A-I with phosphatidylcholines and cholesterol prepared from cholate-lipid dispersions," *Journal of Biological Chemistry* 257(8), 4535-4540 published Apr. 25, 1982.
Mcconnell, M. V. et al. (1999) "MRI of Rabbit Atherosclerosis in Response to Dietary Cholesterol Lowering," *Arteriosclerosis, Thrombosis, and Vascular Biology* 19(8), 1956-1959 published Aug. 1, 1999.
Medarova, Z. et al. (2009) "MRI as a tool to monitor islet transplantation," *Nature Reviews. Endocrinology* 5(8), 444-452.
Merrifield, R. B. (1964) "Solid-Phase Peptide Synthesis. 3. An Improved Synthesis of Bradykinin," *Biochemistry* 3, 1385-1390 published Sep.
Michaud, C. M. et al. (2001) "Burden of disease-implications for future research," *JAMA* 285(5), 535-539.
Miida, T. et al. (1992) "Regulation of the concentration of pre beta high-density lipoprotein in normal plasma by cell membranes and lecithin-cholesterol acyltransferase activity," *Biochemistry* 31(45), 11112-11117 published Nov. 17.
Miller, P. W. et al. (2008) "Synthesis of 11C, 18F, 15O, and 13N Radiolabels for Positron Emission Tomography," *Angewandte Chemie International Edition* 47(47), 8998-9033.
Mowri, H. O. et al. (1992) "Different reactivities of high density lipoprotein2 subfractions with hepatic lipase," *Journal of Lipid Research* 33(9), 1269-1279 published Sep. 1, 1992.
Mukundan, S. et al. (2006) "A Liposomal Nanoscale Contrast Agent for Preclinical CT in Mice," *American Journal of Roentgenology* 186(2), 300-307 published Feb. 1, 2006.
Mulder, W. J. M. et al. (2007) "Molecular imaging of macrophages in atherosclerotic plaques using bimodal PEG-micelles," *Magnetic Resonance in Medicine* 58(6), 1164-1170.
Musanti, R. et al. (1993) "Interaction of oxidized HDLs with J774-A1 macrophages causes intracellular accumulation of unesterified cholesterol," *Arteriosclerosis, Thrombosis, and Vascular Biology* 13(9), 1334-1345 published Sep. 1, 1993.
Nagano, Y. et al. (1991) "High density lipoprotein loses its effect to stimulate efflux of cholesterol from foam cells after oxidative modification," *Proceedings of the National Academy of Sciences of the United States of America* 88(15), 6457-6461.
Nahrendorf, M. et al. (2008) "Activatable Magnetic Resonance Imaging Agent Reports Myeloperoxidase Activity in Healing Infarcts and Noninvasively Detects the Antiinflammatory Effects of Atorvastatin on Ischemia-Reperfusion Injury," *Circulation* 117(9), 1153-1160.
Nakajima, T. et al. (2004) "Characterization of the epitopes specific for the monoclonal antibody 9F5-3a and quantification of oxidized HDL in human plasma," *Annals of Clinical Biochemistry* 41(4), 309-315 published Jul. 1, 2004.
Nakano, T. et al. (2003) "Immunochemical detection of circulating oxidized high-density lipoprotein with antioxidized apolipoprotein A-I monoclonal antibody," *Journal of Laboratory and Clinical Medicine* 141(6), 378-384.
Nath, A. et al. (2007) "Applications of Phospholipid Bilayer Nanodiscs in the Study of Membranes and Membrane Proteins," *Biochemistry* 46(8), 2059-2069 published Feb. 1, 2007.
Newton, R. S. et al. (2002) "HDL therapy for the acute treatment of atherosclerosis," *Atherosclerosis Supplements* 3(4), 31-38.
Nicholls, S. J. et al. (2005) "Myeloperoxidase and Cardiovascular Disease," *Arteriosclerosis, Thrombosis, and Vascular Biology* 25(6), 1102-1111 published Jun. 1, 2005.
Nighoghossian, N. et al. (2005) "The Vulnerable Carotid Artery Plaque: Current Imaging Methods and New Perspectives," *Stroke* 36(12), 2764-2772 published Dec. 1, 2005.
Nissen, S. E. et al. (2003) "Effect of recombinant apoa-i milano on coronary atherosclerosis in patients with acute coronary syndromes: A randomized controlled trial," *JAMA* 290(17), 2292-2300.
Nissen, S. E. et al. (2001) "Intravascular Ultrasound: Novel Pathophysiological Insights and Current Clinical Applications," *Circulation* 103(4), 604-616 published Jan. 30, 2001.
Nunn, A. D. et al. (1997) "Can receptors be imaged with MRI agents?," *Quarterly Journal of Nuclear Medicine* 41(2), 155-162 published Jun.
O'Brien, K. D. et al. (1998) "Comparison of Apolipoprotein and Proteoglycan Deposits in Human Coronary Atherosclerotic Plaques," *Circulation* 98(6), 519-527.
O'Brien, K. D. et al. (1999) "Glycosylphosphatidylinositol-Specific Phospholipase D Is Expressed by Macrophages in Human Atherosclerosis and Colocalizes With Oxidation Epitopes," *Circulation* 99(22), 2876-2882.
O'Leary, D. H. et al. (2002) "Intima-media thickness," *American Journal of Cardiology* 90(10), L18-L21.
Olin-Lewis, K. et al. (2002) "Apolipoprotein E Mediates the Retention of High-Density Lipoproteins by Mouse Carotid Arteries and Cultured Arterial Smooth Muscle Cell Extracellular Matrices," *Circulation Research* 90(12), 1333-1339 published Jun. 28, 2002.
Oliver, M. et al. (2006) "MAGfect: a novel liposome formulation for MRI labelling and visualization of cells," *Organic & Biomolecular Chemistry* 4(18), 3489-3497.
Ouhlous, M. et al. (2002) "Evaluation of a dedicated dual phased-array surface coil using a black-blood FSE sequence for high resolution MRI of the carotid vessel wall," *Journal of Magnetic Resonance Imaging* 15(3), 344-351.
Pace, C. N. et al. (1979) "Determining globular protein stability: guanidine hydrochloride denaturation of myoglobin," *Biochemistry* 18(2), 288-292.
Packer, L. et al. (1995) "Alpha-lipoic acid as a biological antioxidant," *Free Radical Biology & Medicine* 19(2), 227-250 published Aug. 1, 1995.
Pankhurst, G. et al. (2003) "Characterization of specifically oxidized apolipoproteins in mildly oxidized high density lipoprotein," *Journal of Lipid Research* 44(2), 349-355 published Feb. 1, 2003.
Panzenböck, U. et al. (2000) "Oxidation of Methionine Residues to Methionine Sulfoxides Does Not Decrease Potential Antiatherogenic Properties of Apolipoprotein A-I," *Journal of Biological Chemistry* 275(26), 19536-19544 published Jun. 30, 2000.
Panzenboeck, U. et al. (1997) "Effects of Reagent and Enzymatically Generated Hypochlorite on Physicochemical and Metabolic Properties of High Density Lipoproteins," *Journal of Biological Chemistry* 272(47), 29711-29720 published Nov. 21, 1997.
Parra, H. J. et al. (1992) "A case-control study of lipoprotein particles in two populations at contrasting risk for coronary heart disease. The ECTIM Study," *Arteriosclerosis, Thrombosis, and Vascular Biology* 12(6), 701-707 published Jun. 1, 1992.
Paulson, E. K. (2007) "Pioneers in Surgical Gastroenterology," *American Journal of Roentgenology* 188(6), W586-W586 published Jun. 1, 2007.
Peiser, L. et al. (2002) "Scavenger receptors in innate immunity," *Current Opinion in Immunology* 14(1), 123-128 published Feb. 1, 2002.
Pennathur, S. et al. (2004) "Human Atherosclerotic Intima and Blood of Patients with Established Coronary Artery Disease Con-

(56) References Cited

OTHER PUBLICATIONS tain High Density Lipoprotein Damaged by Reactive Nitrogen Species," *Journal of Biological Chemistry* 279(41), 42977-42983 published Oct. 8, 2004.

Perez, J. M. et al. (2004) "Use of Magnetic Nanoparticles as Nanosensors to Probe for Molecular Interactions," *ChemBioChem* 5(3), 261-264.

Phillips, W. T. (1999) "Delivery of gamma-imaging agents by liposomes," *Advanced Drug Delivery Reviews* 37(1-3), 13-32 published Apr. 5, 1999.

Pietzsch, J. et al. (2004) "Fluorine-18 radiolabeling of low-density lipoproteins: A potential approach for characterization and differentiation of metabolism of native and oxidized low-density lipoproteins in vivo," *Nuclear Medicine and Biology* 31, 1043-1050 published Dec. 1, 2004.

Pitt, Andrew R. et al. (2008) "Mass spectrometric analysis of HOCI- and free-radical-induced damage to lipids and proteins," *Biochemical Society Transactions* 36(5), 1077-1082.

Platt, N. et al. (2001) "Is the class A macrophage scavenger receptor (SR-A) multifunctional?—The mouse's tale," *Journal of Clinical Investigation* 108(5), 649-654.

Podrez, E. A. et al. (2000) "Myeloperoxidase-generated oxidants and atherosclerosis," *Free Radical Biology & Medicine* 28(12), 1717-1725 published Jun. 15, 2000.

Podrez, E. A. et al. (2000) "Macrophage scavenger receptor CD36 is the major receptor for LDL modified by monocyte-generated reactive nitrogen species," *Journal of Clinical Investigation* 105(8), 1095-1108.

Podrez, E. A. et al. (1999) "Myeloperoxidase-generated reactive nitrogen species convert LDL into an atherogenic form in vitro," *Journal of Clinical Investigation* 103(11), 1547-1560.

Querol, M. et al. (2005) "DTPA-bisamide-Based MR Sensor Agents for Peroxidase Imaging," *Organic Letters* 7(9), 1719-1722 published Apr. 1, 2005.

Ramsamy, T. A. et al. (2000) "Apolipoprotein A-I Regulates Lipid Hydrolysis by Hepatic Lipase," *Journal of Biological Chemistry* 275(43), 33480-33486 published Oct. 27, 2000.

Rauch, U. et al. (2001) "Thrombus Formation on Atherosclerotic Plaques: Pathogenesis and Clinical Consequences," *Annals of Internal Medicine* 134(3), 224-238.

Raynal, I. et al. (2004) "Macrophage endocytosis of superparamagnetic iron oxide nanoparticles: mechanisms and comparison of ferumoxides and ferumoxtran-10," *Investigative Radiology* 39(1), 56-63 published Jan.

Reis, E. D. et al. (2001) "Dramatic remodeling of advanced atherosclerotic plaques of the apolipoprotein E-deficient mouse in a novel transplantation model," *Journal of Vascular Surgery* 34(3), 2A-547.

Rensen, P. C. N. et al. (2001) "Recombinant lipoproteins: lipoprotein-like lipid particles for drug targeting," *Advanced Drug Delivery Reviews* 47(2-3), 251-276 published Apr. 25, 2001.

Rifici, V. A. et al. (1996) "Oxidation of high density lipoproteins: characterization and effects on cholesterol efflux from J774 macrophages," *Biochimica et Biophysica Acta* 1299(1), 87-94 published Jan. 5.

Rong, J. X. et al. (2001) "Elevating High-Density Lipoprotein Cholesterol in Apolipoprotein E-Deficient Mice Remodels Advanced Atherosclerotic Lesions by Decreasing Macrophage and Increasing Smooth Muscle Cell Content," *Circulation* 104(20), 2447-2452.

Ross, R. (1999) "Atherosclerosis—An Inflammatory Disease," *New England Journal of Medicine* 340(2), 115-126.

Rothblat, G. H. et al. (1992) "Apolipoproteins, membrane cholesterol domains, and the regulation of cholesterol efflux," *Journal of Lipid Research* 33(8), 1091-1097 published Aug. 1, 1992.

Rothschild, S. I. et al. (2010) "Src Inhibitors in Lung Cancer: Current Status and Future Directions," *Clinical Lung Cancer* 11(4), 238-242.

Ruangkanchanasetr, P. et al. (2009) "Use of High-Dose Gadolinium as Contrast Media to Avoid Radiocontrast Media-Induced Nephropathy," *Journal of Renal Care* 35(1), 11-15.

Rudd, J. H. F. et al. (2009) "Inflammation Imaging in Atherosclerosis," *Arteriosclerosis, Thrombosis, and Vascular Biology* 29(7), 1009-1016 published Jul. 1, 2009.

Rumsey, S. C. et al. (1992) "Cryopreservation with sucrose maintains normal physical and biological properties of human plasma low density lipoproteins," *Journal of Lipid Research* 33(10), 1551-1561 published Oct. 1, 1992.

Salinthone, S. et al. (2008) "Lipoic acid: a novel therapeutic approach for multiple sclerosis and other chronic inflammatory diseases of the CNS," *Endocrine, Metabolic & Immune Disorders—Drug Targets* 8(2), 132-142 published Jun.

Sanz, J. et al. (2008) "Imaging of atherosclerotic cardiovascular disease," *Nature* 451(7181), 953-957 published Feb. 21, 2008.

Sauer, I. et al. (2005) "An Apolipoprotein E-Derived Peptide Mediates Uptake of Sterically Stabilized Liposomes into Brain Capillary Endothelial Cells," *Biochemistry* 44(6), 2021-2029 published Feb. 1, 2005.

Sauer, I. et al. (2006) "Dipalmitoylation of a cellular uptake-mediating apolipoprotein E-derived peptide as a promising modification for stable anchorage in liposomal drug carriers," *Biochimica et Biophysica Acta (BBA)—Biomembranes* 1758(4), 552-561 published 4//.

Schissel, S. L. et al. (1998) "Secretory Sphingomyelinase, a Product of the Acid Sphingomyelinase Gene, Can Hydrolyze Atherogenic Lipoproteins at Neutral pH: Implications for Atherosclerotic Lesion Development," *Journal of Biological Chemistry* 273(5), 2738-2746 published Jan. 30, 1998.

Schissel, S. L. et al. (1996) "Rabbit aorta and human atherosclerotic lesions hydrolyze the sphingomyelin of retained low-density lipoprotein. Proposed role for arterial-wall sphingomyelinase in subendothelial retention and aggregation of atherogenic lipoproteins," *Journal of Clinical Investigation* 98(6), 1455-1464.

Schmitz, S. A. et al. (2001) "Magnetic resonance imaging of atherosclerotic plaques using superparamagnetic iron oxide particles," *Journal of Magnetic Resonance Imaging* 14(4), 355-361.

Segrest, J. P. et al. (1974) "A molecular theory of lipid-protein interactions in the plasma lipoproteins," *FEBS Letters* 38(3), 247-253.

Shah, P. K. (2002) "Pathophysiology of coronary thrombosis: role of plaque rupture and plaque erosion," *Progress in Cardiovascular Diseases* 44(5), 357-368 published Mar.-Apr.

Shah, P. K. et al. (2001) "High-Dose Recombinant Apolipoprotein A-IMilano Mobilizes Tissue Cholesterol and Rapidly Reduces Plaque Lipid and Macrophage Content in Apolipoprotein E-Deficient Mice," *Circulation* 103(25), 3047-3050.

Shamir, R. et al. (1996) "Pancreatic carboxyl ester lipase: a circulating enzyme that modifies normal and oxidized lipoproteins in vitro," *Journal of Clinical Investigation* 97(7), 1696-1704.

Shao, B. et al. (2005) "Tyrosine 192 in Apolipoprotein A-I Is the Major Site of Nitration and Chlorination by Myeloperoxidase, but Only Chlorination Markedly Impairs ABCA1-dependent Cholesterol Transport," *Journal of Biological Chemistry* 280(7), 5983-5993 published Feb. 18, 2005.

Shao, B. et al. (2008) "Methionine oxidation impairs reverse cholesterol transport by apolipoprotein A-I," *Proceedings of the National Academy of Sciences of the United States of America* 105(34), 12224-12229 published Aug. 21, 2008.

Shao, B. et al. (2009) "HDL, lipid peroxidation, and atherosclerosis," *Journal of Lipid Research* 50(4), 599-601 published Apr. 1, 2009.

Shao, B. et al. (2006) "Myeloperoxidase Impairs ABCA1-dependent Cholesterol Efflux through Methionine Oxidation and Site-specific Tyrosine Chlorination of Apolipoprotein A-I," *Journal of Biological Chemistry* 281(14), 9001-9004 published Apr. 7, 2006.

Shao, B. et al. (2006) "Myeloperoxidase: an inflammatory enzyme for generating dysfunctional high density lipoprotein," *Current Opinion in Cardiology* 21(4), 322-328 published Jul.

Shao, B. et al. (2006) "Pathways for oxidation of high-density lipoprotein in human cardiovascular disease," *Current Opinion in Molecular Therapeutics* 8(3), 198-205 published Jun.

(56) References Cited

OTHER PUBLICATIONS

Shelness, G. S. et al. (1984) "Apolipoprotein II messenger RNA. Transcriptional and splicing heterogeneity yields six 5'-untranslated leader sequences," *Journal of Biological Chemistry* 259(15), 9929-9935 published Aug. 10, 1984.
Shelness, G. S. et al. (1985) "Secondary structure analysis of apolipoprotein II mRNA using enzymatic probes and reverse transcriptase. Evaluation of primer extension for high resolution structure mapping of mRNA," *Journal of Biological Chemistry* 260(14), 8637-8646 published Jul. 15, 1985.
Sigalov, A. et al. (1991) "Large-scale isolation and purification of human apolipoproteins A-I and A-II," *Journal of Chromatography* 537(1-2), 464-468 published Jan. 11.
Sigalov, A. B. (1993) "Comparison of apolipoprotein A-I values assayed in lyophilized and frozen pooled human sera by a non-immunochemical electrophoretic method and by immunoassay," *European Journal of Clinical Chemistry and Clinical Biochemistry* 31(9), 579-583 published Sep.
Sigalov, A. B. (1995) "Cryopreservation and long-term storage of human low density lipoproteins," *European Journal of Clinical Chemistry and Clinical Biochemistry* 33(2), 73-81 published Feb.
Sigalov, A. B. et al. (1997) "The ratio of non-oxidized/oxidized forms of apolipoprotein A-I can affect cholesterol efflux from human skin fibroblasts mediated by high density lipoprotein," European *Journal of Clinical Chemistry and Clinical Biochemistry* 35(5), 395-396 published May.
Sigalov, A. B. et al. (1998) "Enzymatic repair of oxidative damage to human apolipoprotein A-I," *FEBS Letters* 433(3), 196-200.
Sigalov, A. B. et al. (2001) "Oxidation of methionine residues affects the structure and stability of apolipoprotein A-I in reconstituted high density lipoprotein particles," *Chemistry and Physics of Lipids* 113(1-2), 133-146 published Nov. 2001.
Sigalov, A. B. et al. (2002) "Dihydrolipoic acid as an effective cofactor for peptide methionine sulfoxide reductase in enzymatic repair of oxidative damage to both lipid-free and lipid-bound apolipoprotein a-l," *Antioxidants & Redox Signaling* 4(3), 553-557 published Jun.
Singh, J. et al. (2008) "Iodinated Contrast Media and Their Adverse Reactions," *Journal of Nuclear Medicine Technology* 36(2), 69-74 published Jun. 1, 2008.
Sinusas, A. J. et al. (2008) "Multimodality Cardiovascular Molecular Imaging, Part I," *Circulation: Cardiovascular Imaging* 1(3), 244-256 published Nov. 1, 2008.
Skinner, M. P. et al. (1995) "Serial magnetic resonance imaging of experimental atherosclerosis detects lesion fine structure, progression and complications in vivo," *Nature Medicine* 1(1), 69-73 published Jan.
Slinkin, M. A. et al. (1991) "Terminal-modified polylysine-based chelating polymers: highly efficient coupling to antibody with minimal loss in immunoreactivity," *Bioconjugate Chemistry* 2(5), 342-348 published Sep.-Oct.
Sloop, C. H. et al. (1987) "Interstitial fluid lipoproteins," Journal of Lipid Research 28(3), 225-237 published Mar. 1, 1987.
Sohal, R. S. (2002) "Role of oxidative stress and protein oxidation in the aging process1,2," *Free Radical Biology & Medicine* 33(1), 37-44 published Jul. 1, 2002.
Solomon, R. (1998) "Radiocontrast-induced nephropathy," *Seminars in Nephrology* 18(5), 551-557 published Sep.
Sorci-Thomas, M. G. et al. (1998) "The Hydrophobic Face Orientation of Apolipoprotein A-I Amphipathic Helix Domain 143-164 Regulates Lecithin:Cholesterol Acyltransferase Activation," *Journal of Biological Chemistry* 273(19), 11776-11782 published May 8, 1998.
Sosnovik, D. E. (2009) "Will Molecular MR Imaging Play a Role in Identification and Treatment of Patients with Vulnerable Atherosclerotic Plaques?," *Radiology* 251(2), 309-310.
Sosnovik, D. E. et al. (2007) "Emerging concepts in molecular MRI," *Current Opinion in Biotechnology* 18(1), 4-10 published Feb. 2007.
Souto, E. B. et al. (2010) "Feasibility of Lipid Nanoparticles for Ocular Delivery of Anti-Inflammatory Drugs," *Current Eye Research* 35(7), 537-552 published Jul. 1, 2010.
Sparks, D. L. et al. (1992) "The charge and structural stability of apolipoprotein A-I in discoidal and spherical recombinant high density lipoprotein particles," *Journal of Biological Chemistry* 267(36), 25839-25847 published Dec. 25, 1992.
Sparks, D. L. et al. (1992) "Quantitative measurement of lipoprotein surface charge by agarose gel electrophoresis," *Journal of Lipid Research* 33(1), 123-130 published Jan. 1, 1992.
Spence, J. D. (2002) "Ultrasound measurement of carotid plaque as a surrogate outcome for coronary artery disease," *American Journal of Cardiology* 89(4), 10-15.
Stacul, F. (2001) "Current iodinated contrast media," *European Radiology* 11(4), 690-697.
Stary, H. C. et al. (1995) "A Definition of Advanced Types of Atherosclerotic Lesions and a Histological Classification of Atherosclerosis," *Circulation* 92(5), 1355-1374.
Strieth, S. et al. (2008) "Paclitaxel Encapsulated in Cationic Liposomes Increases Tumor Microvessel Leakiness and Improves Therapeutic Efficacy in Combination with Cisplatin," *American Association for Cancer Research* 14(14), 4603-4611.
Strijkers, G. J. et al. (2007) "MRI contrast agents: current status and future perspectives," *Anti-Cancer Agents in Medicinal Chemistry* 7(3), 291-305 published May.
Suc, I. et al. (2002) "Oxidative tyrosylation of high density lipoproteins impairs cholesterol efflux from mouse J774 macrophages: role of scavenger receptors, classes A and B," *Journal of Cell Science* 116(1), 89-99.
Suc, I. et al. (1997) "HDL and ApoA Prevent Cell Death of Endothelial Cells Induced by Oxidized LDL," *Arteriosclerosis, Thrombosis, and Vascular Biology* 17(10), 2158-2166 published Oct. 1, 1997.
Suzuki, H. et al. (1997) "A role for macrophage scavenger receptors in atherosclerosis and susceptibility to infection," *Nature* 386(6622), 292-296 published Mar. 20, 1997.
Swaney, J. B. (1986) "Use of cross-linking reagents to study lipoprotein structure," *Methods in Enzymology* 128, 613-626.
Tabas, I. et al. (1993) "Lipoprotein lipase and sphingomyelinase synergistically enhance the association of atherogenic lipoproteins with smooth muscle cells and extracellular matrix. A possible mechanism for low density lipoprotein and lipoprotein(a) retention and macrophage foam cell formation," *Journal of Biological Chemistry* 268(27), 20419-20432 published Sep. 25, 1993.
Tall, A. R. et al. (1981) "Incorporation of phosphatidylcholine into spherical and discoidal lipoproteins during incubation of egg phosphatidylcholine vesicles with isolated high density lipoproteins or with plasma," *Journal of Biological Chemistry* 256(4), 2035-2044 published Feb. 25, 1981.
Tall, A. R. et al. (1977) "Structure and thermodynamic properties of high density lipoprotein recombinants," *Journal of Biological Chemistry* 252(13), 4701-4711 published Jul. 10, 1977.
Tamat, S. R. et al. (1989) "Determination of the Concentration of Complex Boronated Compounds in Biological Tissues by Inductively Coupled Plasma Atomic Emission Spectrometry," *Pigment Cell Research* 2(4), 281-285.
Tang, M. F. et al. (2010) "Recent progress in nanotechnology for cancer therapy," *Chinese Journal of Cancer* 29(9), 775-780 published Sep.
Tape, C. et al. (1990) "Apolipoprotein A-I and apolipoprotein SAA half-lives during acute inflammation and amyloidogenesis," *Biochimica et Biophysica Acta* 1043(3), 295-300 published Apr. 17.
Tardif, J. et al. (2007) "Effects of reconstituted high-density lipoprotein infusions on coronary atherosclerosis: A randomized controlled trial," *JAMA* 297(15), 1675-1682.
Teicher, B. A. et al., (Eds.) (2004) *Anticancer drug development guide,* Second ed., Humana Press, Totowa, N.J.
Templeton, N. S. (2009) "Nonviral delivery for genomic therapy of cancer," *World Journal of Surgery* 33(4), 685-697 published Apr.
Thorne, R. F. et al. (2007) "CD36 is a receptor for oxidized high density lipoprotein: Implications for the development of atherosclerosis," *FEBS Letters* 581(6), 1227-1232.

(56) References Cited

OTHER PUBLICATIONS

Thukkani, A. K. et al. (2003) "Identification of α-Chloro Fatty Aldehydes and Unsaturated Lysophosphatidylcholine Molecular Species in Human Atherosclerotic Lesions," *Circulation* 108(25), 3128-3133.
Toledo, J. D. et al. (2000) "Cholesterol Flux between Lipid Vesicles and Apolipoprotein AI Discs of Variable Size and Composition," *Archives of Biochemistry and Biophysics* 380(1), 63-70 published Aug. 1, 2000.
Torchilin, V. P. (1996) "Liposomes as delivery agents for medical imaging," *Molecular Medicine Today* 2(6), 242-249 published Jun.
Torchilin, V. P. (2002) "PEG-based micelles as carriers of contrast agents for different imaging modalities," *Advanced Drug Delivery Reviews* 54(2), 235-252 published Feb. 21, 2002.
Torzewski, J. et al. (1998) "C-Reactive Protein Frequently Colocalizes With the Terminal Complement Complex in the Intima of Early Atherosclerotic Lesions of Human Coronary Arteries," *Arteriosclerosis, Thrombosis, and Vascular Biology* 18(9), 1386-1392 published Sep. 1, 1998.
Torzewski, M. et al. (2004) "Reduced In Vivo Aortic Uptake of Radiolabeled Oxidation-Specific Antibodies Reflects Changes in Plaque Composition Consistent With Plaque Stabilization," *Arteriosclerosis, Thrombosis, and Vascular Biology* 24(12), 2307-2312 published Dec. 1, 2004.
Toussaint, J.-F. o. et al. (1996) "Magnetic Resonance Images Lipid, Fibrous, Calcified, Hemorrhagic, and Thrombotic Components of Human Atherosclerosis In Vivo," *Circulation* 94(5), 932-938.
Tricerri, A. et al. (1998) "Conformation of apolipoprotein AI in reconstituted lipoprotein particles and particle-membrane interaction: Effect of cholesterol," *Biochimica et Biophysica Acta (BBA)—Lipids and Lipid Metabolism* 1391(1), 67-78 published Mar. 6, 1998.
UniProt. UniProtKB—P09813 (APOA2_Mouse).
UniProt. UniProtKB—Q00623 (APOA1_Mouse).
UniProt. UniProtKB—P02647 (APOA1_Human).
UniProt. UniProtKB—P02652 (APOA2_Human).
Van Veldhoven, P. P. et al. (1987) "Inorganic and organic phosphate measurements in the nanomolar range," *Analytical Biochemistry* 161(1), 45-48 published Feb. 15, 1987.
Veldhuis, W. B. et al. (2003) "Interferon-Beta Prevents Cytokine-Induced Neutrophil Infiltration and Attenuates Blood-Brain Barrier Disruption," *Journal of Cerebral Blood Flow & Metabolism* 23(9), 1060-1069 published Sep. 1, 2003.
Vessby, B. et al. (1987) "Lipoprotein composition of human suction-blister interstitial fluid," *Journal of Lipid Research* 28(6), 629-641 published Jun. 1, 1987.
Virmani, R. et al. (2000) "Lessons From Sudden Coronary Death: A Comprehensive Morphological Classification Scheme for Atherosclerotic Lesions," *Arteriosclerosis, Thrombosis, and Vascular Biology* 20(5), 1262-1275 published May 1, 2000.
Vogt, W. (1995) "Oxidation of methionyl residues in proteins: Tools, targets, and reversal," *Free Radical Biology & Medicine* 18(1), 93-105 published Jan. 1, 1995.
Von Eckardstein, A. et al. (1994) "Physiological role and clinical relevance of high-density lipoprotein subclasses," *Current Opinion in Lipidology* 5(6), 404-416 published Dec.
Von Eckardstein, A. et al. (1991) "Site-specific methionine sulfoxide formation is the structural basis of chromatographic heterogeneity of apolipoproteins A-I, C-II, and C-III," *Journal of Lipid Research* 32(9), 1465-1476 published Sep. 1, 1991.
Wakhloo, A. K. et al. (2004) "Hemodynamics of carotid artery atherosclerotic occlusive disease," *Journal of Vascular and Interventional Radiology* 15(1 Pt 2), S111-121 published Jan.
Wang, X.-S. et al. (1997) "Rapid elevation of neuronal cytoplasmic calcium by apolipoprotein E peptide," *Journal of Cellular Physiology* 173(1), 73-83.
Wang, X. et al. (2008) "Application of Nanotechnology in Cancer Therapy and Imaging," *CA: A Cancer Journal for Clinicians* 58(2), 97-110.
Weiss, S. J. et al. (1986) "Brominating oxidants generated by human eosinophils," *Science* 234(4773), 200-203.
Weissig, V. et al. (2000) "Long-circulating gadolinium-loaded liposomes: potential use for magnetic resonance imaging of the blood pool," *Colloids and Surfaces B: Biointerfaces* 18(3-4), 293-299 published Oct. 2000.
Weissleder, R. (2002) "Scaling down imaging: molecular mapping of cancer in mice," *Nature Reviews Cancer* 2(1), 11-18.
Williams, K. J. et al. (2007) "Cellular and molecular mechanisms for rapid regression of atherosclerosis: from bench top to potentially achievable clinical goal," *Current Opinion in Lipidology* 18(4), 443-450 published Aug.
Williams, K. J. et al. (2000) "Rapid Restoration of Normal Endothelial Functions in Genetically Hyperlipidemic Mice by a Synthetic Mediator of Reverse Lipid Transport," *Arteriosclerosis, Thrombosis, and Vascular Biology* 20(4), 1033-1039 published Apr. 1, 2000.
Williams, K. J. et al. (1986) "Uptake of endogenous cholesterol by a synthetic lipoprotein," *Biochimica et Biophysica Acta (BBA)—Lipids and Lipid Metabolism* 875(2), 183-194 published Feb. 12, 1986.
Williams, K. J. et al. (1995) "The Response-to-Retention Hypothesis of Early Atherogenesis," *Arteriosclerosis, Thrombosis, and Vascular Biology* 15(5), 551-561 published May 1, 1995.
Williams, K. J. et al. (1998) "The response-to-retention hypothesis of atherogenesis reinforced," *Current Opinion in Lipidology* 9(5), 471-474 published Oct.
Worthley, S. G. et al. (2000) "Noninvasive In Vivo Magnetic Resonance Imaging of Experimental Coronary Artery Lesions in a Porcine Model," *Circulation* 101(25), 2956-2961.
Worthley, S. G. et al. (2000) "Serial In Vivo MRI Documents Arterial Remodeling in Experimental Atherosclerosis," *Circulation* 101(6), 586-589.
Ylä-Herttuala, S. et al. (1991) "Macrophages and smooth muscle cells express lipoprotein lipase in human and rabbit atherosclerotic lesions," *Proceedings of the National Academy of Sciences of the United States of America* 88(22), 10143-10147.
Yonemura, A. et al. (2005) "Effect of lipid-lowering therapy with atorvastatin on atherosclerotic aortic plaques detected by noninvasive magnetic resonance imaging," *Journal of the American College of Cardiology* 45(5), 733-742 published Mar. 1, 2005.
Yuan, C. et al. (1998) "Measurement of Atherosclerotic Carotid Plaque Size In Vivo Using High Resolution Magnetic Resonance Imaging," *Circulation* 98(24), 2666-2671.
Zarutskie, J. A. et al. (1999) "A Conformational Change in the Human Major Histocompatibility Complex Protein HLA-DR1 Induced by Peptide Binding," *Biochemistry* 38(18), 5878-5887 published May 1, 1999.
Zhang, R. et al. (2002) "Myeloperoxidase Functions as a Major Enzymatic Catalyst for Initiation of Lipid Peroxidation at Sites of Inflammation," *Journal of Biological Chemistry* 277(48), 46116-46122 published Nov. 29, 2002.
Zhang, R. et al. (2001) "Association between myeloperoxidase levels and risk of coronary artery disease," *JAMA* 286(17), 2136-2142.
Zheng, G. et al. (2005) "Rerouting lipoprotein nanoparticles to selected alternate receptors for the targeted delivery of cancer diagnostic and therapeutic agents," *Proceedings of the National Academy of Sciences of the United States of America* 102(49), 17757-17762 published Nov. 25, 2005.
Zheng, J. et al. (2010) "Liposome contrast agent for CT-based detection and localization of neoplastic and inflammatory lesions in rabbits: validation with FDG-PET and histology," *Contrast Media & Molecular Imaging* 5(3), 147-154.
Zheng, J. et al. (2009) "Quantitative CT Imaging of the Spatial and Temporal Distribution of Liposomes in a Rabbit Tumor Model," *Molecular Pharmaceutics* 6(2), 571-580 published Apr. 6, 2009.
Zheng, L. et al. (2004) "Apolipoprotein A-I is a selective target for myeloperoxidase-catalyzed oxidation and functional impairment in subjects with cardiovascular disease," *Journal of Clinical Investigation* 114(4), 529-541.
Zheng, L. et al. (2005) "Localization of Nitration and Chlorination Sites on Apolipoprotein A-I Catalyzed by Myeloperoxidase in Human Atheroma and Associated Oxidative Impairment in ABCA1-

(56) References Cited

OTHER PUBLICATIONS dependent Cholesterol Efflux from Macrophages," *Journal of Biological Chemistry* 280(1), 38-47 published Jan. 7, 2005.
PCT International Search Report of International Application No. PCT/US2010/052117 dated Jul. 29, 2011.
Bellamy, A. J. et al. (2007) "The Use of Trifluoroacetyl as an N- and O-Protecting Group during the Synthesis of Energetic Compounds containing Nitramine and/or Nitrate Ester Groups," Propellants, Explosives, Pyrotechnics 32(1), 20-31.
Li, T. et al. (2009) "Feasibility and midterm outcomes of percutaneous transhepatic balloon angioplasty for symptomatic Budd-Chiari syndrome secondary to hepatic venous obstruction," Journal of Vascular Surgery 50(5), 1079-1084.
Llovet, J. M. et al. (1999) "Intention-to-treat analysis of surgical treatment for early hepatocellular carcinoma: Resection versus transplantation," Hepatology 30(6), 1434-1440.
Metzker, M. L. (2010) "Sequencing technologies—the next generation," Nature Reviews Genetics 11(1), 31-46 published 01//print.
Reddy, S. D. et al. (2015) "Midazolam as an anticonvulsant antidote for organophosphate intoxication—A pharmacotherapeutic appraisal," Epilepsia 56(6), 813-821.
Samarasinghe, N. et al. (2012) "Algal cell rupture using high pressure homogenization as a prelude to oil extraction," Renewable Energy 48, 300-308 published 12//.

1. Unoxidized apo A-I
2. Oxidized apo A-I
3. Reduced apo A-I

SEQUENCE LISTING

```
Sequence total quantity: 1
SEQ ID NO: 1            moltype = AA  length = 30
FEATURE                 Location/Qualifiers
REGION                  1..30
                        note = Synthetic
source                  1..30
                        mol_type = protein
                        organism = synthetic construct
SEQUENCE: 1
LQEKLSPLGE EMRDRARAHV DALRTHLAPY                                   30
```

METHODS FOR TARGETED IMAGING WITH SPHERICAL rHDLs

CROSS-REFERENCE TO A RELATED APPLICATION

The present application is a Continuation and claims priority to U.S. Non-Provisional application Ser. No. 17/111,371, filed on Dec. 3, 2020; which is a Divisional of U.S. Non-Provisional application Ser. No. 16/712,215, filed on Dec. 12, 2019, now U.S. Pat. No. 10,894,098, issued Jan. 19, 2021; which is a Continuation of U.S. Non-Provisional application Ser. No. 13/501,085, filed Apr. 9, 2012, now U.S. Pat. No. 10,525,152, issued on Jan. 7, 2020; which is a National Stage entry of International Application No. PCT/US2010/052117 filed on Oct. 10, 2010; which claims priority to and the benefit of U.S. Provisional application Ser. No. 61/250,465, filed Oct. 9, 2009. The entire content of the aforementioned provisional application is incorporated herein by reference.

REFERENCE TO A SEQUENCE LISTING SUBMITTED AS A XML ST26 FILE VIA PATENT CENTER

A Sequence Listing has been submitted in XML ST26 Format named "20587.xml" created on Jun. 4, 2024, consisting of 3 KB, the entire content of which is herein incorporated by reference

FIELD OF THE INVENTION

The present invention relates to a composition comprising a metallic or non-metallic contrast agent covalently or noncovalently conjugated to lipoprotein nanoparticles wherein said nanoparticles comprise at least one modified apolipoprotein and at least one lipid. The invention further relates to the use of these compositions in imaging techniques such as computed tomography (CT), gamma-scintigraphy, positron emission tomography (PET), single photon emission computed tomography (SPECT), magnetic resonance imaging (MRI), and combined imaging techniques.

BACKGROUND OF THE INVENTION

1. Cancer and Macrophage Imaging

Cancer is one of the major causes of mortality in the United States, and the worldwide incidence of cancer continues to increase. At present, noninvasive imaging approaches, including x-ray-based computer-assisted tomography (CT), positron emission tomography (PET), single-photon emission tomography, and magnetic resonance imaging (MRI), are used as important tools for detection of human cancer (Wang et al. C A Cancer J Clin 2008; 58:97-110). However, in vivo studies have shown that only 1 to 10 parts per 100,000 of intravenously administered mAbs, therapeutic, or imaging agents can reach their parenchymal targets. Thus, greater targeting selectivity and better delivery efficiency are the 2 major goals in the development of imaging contrast formulations. The development of tumor-targeted contrast agents based on a nanoparticle formulation may offer enhanced sensitivity and specificity for in vivo tumor imaging using currently available clinical imaging modalities.

Cancer cells secrete a variety of chemoattractants that attract macrophages and cause them to accumulate in the tumor tissue wherein the macrophage becomes a tumor-associated macrophage (TAM) (Beckmann et al. WIREs Nanomed Nanobiotech 2009; 1:272-98). TAMs have a range of functions with the capacity to affect diverse aspects of neoplastic tissues including angiogenesis and vascularisation, stroma formation and dissolution, and modulation of tumor cell growth (enhancement and inhibition). These macrophages of M2 phenotype promote tumor cell proliferation and metastasis by secreting a wide range of growth and proangiogenic factors as well as metalloproteinases and by their involvement in signaling circuits that regulate the function of fibroblasts in the tumor stroma. The prognosis associated with TAMs is dependent on tumor type, but in breast cancer and prostate cancer, TAM accumulation has been linked to decreased survival. This fact obviously brings an important perspective for macrophage tracking as a potential diagnostic tool in cancer.

One molecular imaging strategy to improve the specificity of cancer detection is target-specific imaging of TAMs. The macrophage image of regions of the subject's body at cancer risk can be used to assess macrophage density and displacement associated with any primary cancer or metastatic cancer in the subject, such density and displacement being indicative of neoplasia. This image also can be used to identify the site of biopsy in the subject, macrophage density being an indicator of tumor growth. For example, whole body MRI scanning and cancer staging using ultrasmall superparamagnetic iron oxide (USPIO) particles as macrophage-seeking MRI agents to perform macrophage-enhanced MRI has been suggested (US Pat Appl 20090004113).

In sum, the prior art teaches the use of contrast agents that are not specific to cancer at all, namely gadolinium chelates and manganese compounds, or contrast agents including perfluorocarbon compounds and biofunctionalized nanoparticles containing perfluorocarbons and gadolinium for imaging arterial plaques and atherosclerotic vessels. The clinical application of USPIO particles in cancer imaging (US Pat Appl 20090004113) is limited: (i) iron oxide particles induce signal loss, making differentiation between iron-laden macrophages and imaging artifacts challenging (Hyafil et al. Arterioscler Thromb Vase Biol 2006; 26:176-81); (ii) two MRI studies are required before and after infusion of contrast medium; and, finally, (iii) the uptake of iron oxide particles seems to be nonspecific, which may limit their use for cancer imaging.

2. Atherosclerotic Plaques and their Role in the Thromboembolic Events

Atherosclerosis remains the leading cause of death in industrialized societies, including the US. It accounts for half of the morbidity and mortality in Western countries, and incidence of atherosclerosis is projected to increase worldwide in the next 2 decades (Michaud et al. Jama 2001; 285:535-39). It represents a systemic disease affecting the vessel walls of all the major arteries, including the aorta, coronary, carotid, and peripheral arteries, and leads to a myriad of diseases, including stroke, myocardial infarction, peripheral vascular disease, aortic aneurysms, and sudden death (Ross, R. N Engl J Med 1999; 340:115-26). Accurate in vivo tracking of progressive lesions would be extremely useful clinically to determine the status of patients' atherosclerotic disease. In addition, accurate identification of atherosclerotic wall mass, rather than the degree of lumen narrowing, is needed to better understand the factors that result in plaque progression and regression, and to precisely determine the effectiveness of potential interventions such as aggressive lipid-lowering therapy.

A vast majority of the thromboembolic events result from rupture or erosion of atherosclerotic plaques prone to rupture in the coronary arteries, so-called "high-risk" or "vulnerable" plaques (Shah, P. K. Prog Cardiovasc Dis 2002; 44:357-68; Virmani et al. Arterioscler Thromb Vase Biol 2000; 20:1262-75), which is characterized by further thinning and rupture of the thin fibrous cap (about 65-150 micron) overlying the thrombogenic large lipid core (Falk, E. Circulation 1992; 86:III30-42; Davies, M. J. & Thomas, A. C. Br Heart J 1985; 53:363-73). The characteristics of high-risk or vulnerable plaques vary depending on the arterial region (i.e., coronaries, carotids, or aorta) in which they are found. By using molecular probes that contain contrast-producing elements and specifically and sensitively bind or target different molecular and functional components of atherosclerotic plaque, molecular imaging enables imaging and identification high-risk and vulnerable plaques. By targeting appropriate components in the cascade of atherosclerosis pathogenesis, this approach makes possible to precisely discern plaque constitution as well as stage/classify plaques. Thus, these molecularly targeted contrast agents/probes will be and are able to detect features indicative of instability or vulnerability of atheromatous plaques.

3. Non-MRI Techniques Used to Identify the Atherosclerotic Plaques

Different techniques have been used to target specific components or molecules of atheromatous plaque (Choudhury, R. P. & Fisher, E. A. Arterioscler Thromb Vase Biol 2009; 29:983-91; Jaffer et al. Arterioscler Thromb Vase Biol 2009; 29:1017-24; Rudd et al. Arterioscler Thromb Vase Biol 2009; 29:1009-16; Sosnovik, D. E. & Weissleder, R. Curr Opin Biotechnol 2007; 18:4-10; Desai, Ni Y. & Bluemke, D. A. Magn Reson Imaging Clin N Am 2005; 13:171-80,vii). Perfusion imaging, Doppler flow imaging studies, and angiography help detect luminal narrowing but not the presence of inflamed and vulnerable atherosclerotic plaques in nonstenotic vessels (Sosnovik, D. E. Radiology 2009; 251:309-10). X-ray angiography is a frequently used imaging modality to diagnose coronary artery diseases and assess their severity. Traditionally, this assessment is performed directly from the angiograms, and thus, can suffer from viewpoint orientation dependence and from lack of precision of quantitative measures due to magnification factor uncertainty. Using of three dimensional (3D) reconstruction of the coronary arteries from the angiograms can lead to higher accuracy and reproducibility in the diagnosis and to better precision in the quantification of the severity of the diseases (Blondel et al. Phys Med Biol 2004; 49:2197-208). Still, because a major limitation of X-ray angiography is being a "luminogram," alternative imaging modalities to detect atherosclerotic plaque are needed and have been developed. Intravascular ultrasound is a catheter-based technique which produces tomographic two-dimensional cross-sectional images of vessel wall architecture and plaque (Fitzgerald et al. Circulation 1992; 86:154-8) and allows to discern plaque components accurately (Nissen, S. E. and Yock, P. Circulation 2001; 103:604-16), but it is an invasive procedure and is associated with procedure-related complications. In addition, the ability of intravascular ultrasound to image the vessel wall downstream from a stenosis is limited. Furthermore, because of its high cost, intravascular ultrasound is not suitable for screening purposes in an asymptomatic population. Accuracy of B-mode ultrasonography that can also be used to measure plaque volume in the carotid arteries is limited by the plane of acquisition and the fact that atherosclerosis is a focal process (O'Leary, D. H. & Polak, J. F. Am J Cardiol 2002; 90:18L-21L; Spence, J. D. Am J Cardiol 2002; 89:10B-15B; discussion 15B-16B). Computer tomography (CT), including its powerful modification, the electron beam tomography and multidetector computed tomography (Leber et al J Am Coll Cardiol 2004; 43:1241-7), is one of the major imaging modalities that allows to evaluate patients with heart disease and detect and quantify coronary calcification, but its ability to detect soft, noncalcified plaques is not yet fully determined (Fayad et al. Circulation 2002; 106:2026-34).

4. Identification of the Atherosclerotic Plaques Using the MRI Technique

MRI is a non-invasive diagnostic technique that has the potential to image some events at the cellular or subcellular level (Sosnovik, D. E. & Weissleder, R. Curr Opin Biotechnol 2007; 18:4-10). This technology is based on the interaction of protons with each other and with surrounding molecules in a tissue of interest. MRI produces images by measuring the resonance frequency (RF) signals arising from the magnetic moments of lipid and mainly water protons in living tissues (Strijkers et al. Anticancer Agents Med Chem 2007; 7:291-305; Haacke et al., De Graaf, R. A. In vivo NMR spectroscopy, Principles and Techniques. John Wiley & Sons: Chichester, New York, 1998).

The normal contrast in the MR images depends mainly on the proton spin density and the longitudinal (T1) and transverse (T2 and T2*) relaxation times. There are many pathological conditions that do not lead to significant morphological changes and do not display specific enough changes in the relaxation times. Under those circumstances the pathology may be detected using an MRI contrast agent that locally changes the relaxation times of the diseased tissue. The advantages of the use of contrast agents are considerable, although the use of contrast agents violates the non-invasive character of MRI to some extent. The combination of MRI and contrast agents greatly enhances the possibilities to depict inflamed tissues like in arthritis (Lutz et al. Radiology 2004; 233:149-57), tumor angiogenesis (Collins, D. J. & Padhani, A. R. IEEE Eng Med Biol Mag 2004; 23:65-83), atherosclerotic plaques (Rudd et al. Arterioscler Thromb Vase Biol 2009; 29:1009-16; Sanz, J. & Fayad, Z. A. Nature 2008; 451:953-7), and the break down of the blood brain barrier related to pathologies such as multiple sclerosis (Veldhuis et al. J Cereb Blood Flow Metab 2003; 23:1060-9).

MRI offers several advantages over other imaging modalities: 1) it is non-ionizing as it detects the magnetic signals generated by protons and other molecules; 2) the technique is tomographic, enabling any tomographic plane through a three-dimensional volume to be imaged; 3) high-resolution images with excellent soft tissue contrast between different tissues can be obtained; 4) multiple contrast mechanisms are possible using MRI, and 5) the technique can be used to provide anatomical as well as physiological read-outs. Because of its high resolution, 3D capabilities, noninvasive nature, and capacity for soft tissue characterization, is emerging as a powerful modality to assess the atherosclerotic plaque burden in the arterial wall and has been used to monitor atherosclerosis in vivo (Yuan et al. Circulation 1998; 98:2666-71; Amirbekian et al. Proc Natl Acad Sci USA 2007; 104:961-6; US Pat Appl 20070243136). MRI allows high-resolution imaging of the arterial wall without ionizing radiation (Rudd et al. Arterioscler Thromb Vase Biol 2009; 29:1009-16). Spatial resolutions of 250 micron are possible for aorta (Yonemura et al. J Am Coll Cardiol 2005; 45:733-42) and carotid plaque (Yuan et al. Circulation 1998; 98:2666-71). MRI can image the extent of atherosclerosis and monitor the efficacy of antiatherosclerotic treatments (Fayad et al. Circulation 2000; 101:2503-9; Corti et al. Circulation 2002; 106:2884-7). In addition, elements of the mature atherosclerotic plaque (fibrous cap, lipid core, hemorrhage) can be identified using MRI (Kerwin et al. Top Magn Reson Imaging 2007; 18:371-8). However, imaging inflammation within atherosclerotic plaque using MRI requires the injection of a contrast agent.

5. MRI Contrast Agents

The developments in recent years in the field of cellular and molecular imaging have boosted the search for new and better MRI contrast agents. Cellular and molecular imaging aim to visualize molecular and cellular processes non-invasively in vivo (Choy et al. Mol Imaging 2003; 2:303-12; Delikatny, E. J. & Poptani, H. Radiol Clin North Am 2005; 43:205-20; Frias et al. Contrast Media Mol Imaging 2007; 2:16-23). This is achieved by directing a detectable reporter, e.g. a nuclear tracer or an MRI contrast agent, towards the target molecules or processes of interest.

Today, magnetic resonance (MR) contrast media (or contrast agents) are used in 40-50% of all MR examinations worldwide and the degree of contrast utilization is expected to increase in the future (Bellin, M. F. Eur J Radiol 2006; 60:314-23; Bellin, M. F. & Van Der Molen, A. J. Eur J Radiol 2008; 66:160-7). MR contrast media are administered to enhance tissue contrast, to characterize lesions and to evaluate perfusion and flow-related abnormalities. They include non-specific extracellular contrast agents and organ-specific contrast agents, mostly liver specific contrast agents. In 2007, of the 27.5 million MRI procedures performed in the U.S., 43% used a contrast agent as part of the imaging procedure.

MR contrast agents are diagnostic pharmaceutical compounds containing superparamagnetic or paramagnetic metal ions that affect the MR-signal properties of surrounding tissues. Superparamagnetic contrast agents shorten the transverse magnetization (T2*) and induce MR signal loss on T2*-weighted sequences ("negative" contrast). These agents are based on iron oxide particles and can be classified according to particle size. Microparticles of iron oxide (MPIO) are largest, followed by superparamagnetic iron oxides (SPIO), and finally USPIO. Iron-laden macrophages can be detected in the aortic subendothelium, and the effect of cytokine injection upon cell infiltration can be studied. Following a retrospective clinical study (Schmitz et al. J Magn Reson Imaging 2001; 14:355-61), this work has recently translated into a prospective patient trial (Kooi et al. Circulation 2003; 107:2453-8), where it was found that uptake occurred mainly in ruptured and rupture-prone plaques and not in stable lesions, suggesting that the two can be differentiated in order to assess the relative risk for stroke and embolic complications. However, iron oxide-based T2 contrast agents have several disadvantages which limit their use in MRI imaging: a) the ambiguity of the signal void which is a general disadvantage of negative contrast imaging; b) the contrast generated by the labeled cells is limited if background signal is low; c) negative contrast on T2-weighted scans, which can be nonspecific and difficult to distinguish from other causes of signal hypointensity (such as calcification, susceptibility artifacts, flow-related signal loss, or air) and thus make image interpretation subjective; d) the correlation between iron oxide concentration and T2 contrast is not always linear; and finally, e) heavy loading can increase transverse relaxivity (R2), disproportionate to the amount of iron present per image voxel (compartmentalized iron oxide can cause a more substantial reduction in local relaxation time than non-compartmentalized iron oxide), which complicates quantitative interpretation of the results (Medarova, Z. & Moore, A. Nat Rev Endocrinol 2009; 5:444-52). In addition, because of the disadvantageous large T2*/T1 ratio, USPIO compounds are less suitable for arterial bolus contrast enhanced MR angiography than paramagnetic gadolinium complexes. Paramagnetic Gd3+ (gadolinium; a member of the lanthanide group of elements) ion represents the stable ion with seven unpaired electrons, the largest number of unpaired electrons that are paramagnetic. Gd-based contrast agents (GBCAs) enhance the longitudinal magnetization (T1) of nearby water protons resulting, in contrast to superparamagnetic contrast agents, in a positive signal on the MR image.

6. Use of Iron Oxide Particles for Imaging of Atherosclerosis

Iron oxide particles have been used for imaging of atherosclerosis (Amirbekian et al. Proc Natl Acad Sci USA 2007; 104:961-6). Macrophage uptake of iron oxide nanoparticles involves macrophage scavenger receptor (MSR)-mediated endocytosis and depends mainly on the size of contrast agents (Raynal et al. Invest Radiol 2004; 39:56-63). However, there are factors that limit the clinical application of this approach: (i) iron oxide particles induce signal loss, making differentiation between iron-laden macrophages and imaging artifacts challenging (ii) due to limited plaque permeation, high doses (several times the clinical dose) and long delay times (up to 5 days post-injection) are required; and finally, (iii) the uptake of iron oxide particles seems to be nonspecific, which may limit their use for plaque imaging.

7. Gadolinium-Containing MRI Contrast Agents

All available GBCAs are chelates that contain the gadolinium ion Gd3+ (Bellin, M. F. & Van Der Molen, A. J. Eur J Radiol 2008; 66:160-7). Free gadolinium is highly toxic. Chelation of gadolinium by appropriate ligands dramatically reduces its acute toxicity. Gadolinium chelates are the most widely used extracellular, non-specific contrast agents. Approximately 30% of 20 million MR imaging scans that are performed only in the US annually, use GBCAs, and therefore approximately 6 million doses of GBCAs are administered annually (Kuo, P. H. J Am Coll Radiol 2008; 5:29-35).

Nine intravenous GBCAs have been approved for clinical use in the US and/or international market: Magnevist® (gadopentetate dimeglumine; Bayer Shering Pharma), Dotarem® (gadoterate meglumine; Guerbet, Aulnay-sous-bois, France), Omniscan® (gadodiamide; Nycomed, Oslo, Norway), ProHance® (gadoteridol; Bracco SpA, Milan, Italy), Gadovist® (gadobutrol; Bayer Shering Pharma), MultiHance® (gadobenate dimeglumine; Bracco SpA), OptiMARK® (gadoversetamide; Mallinkrodt, St. Louis, USA), Primovist® (gadoxetic acid; Bayer Shering Pharma) in Europe, or Eovist® in USA, and Vasovist® (gadofosveset trisodium; Epix Pharmaceuticals, Cambridge, USA). To these figures one must add the administration of agents approved outside the US: Dotarem, Gadovist, Vasovist and Primovist. As of 2007, Magnevist was the leading MRI contrast agent in the US and worldwide. Since its introduction, Magnevist has been used in over 80 million procedures worldwide and continues to be the most studied MRI contrast agent on the market.

8. Gadolinium-Induced Nephrogenic Systemic Fibrosis

Nephrogenic systemic fibrosis (NSF) is a severe delayed fibrotic reaction of the body tissues to GBCAs. NSF is a rare systemic disorder first described in 1997 which affects patients with chronic kidney disease. Within weeks, it may lead to disability by formation of contractures. It may also lead to death. Since its recognition, there have been more than 200 cases reported worldwide. The disease is exclusively seen in patients with various degree of renal failure and most of whom have been exposed to GBCAs. The ratio of Gd to calcium in tissue deposits correlates positively with the gadodiamide (Omniscan) dose and with serum ionized calcium at the time of Gd exposure. To date, the disease mechanism is still unclear and there is no proven treatment for NSF.

In 2007, NSF emerged as a major adverse consequence of gadolinium chelate injection, although primarily involving weaker chelates of gadolinium that were later approved (Khurana et al. Invest Radiol 2007; 42:139-45). The first case was filed in 2007 by the mother of a patient who died three years earlier after receiving a Magnevist injection as part of an MRI procedure. As of February 2009, 241 U.S. lawsuits involving Magnevist, which is the member of GBCA family, were pending and it was anticipated that more would be lodged.

Currently, there is no cure for NSF and there are no alternatives for Gd-based MRI contrast agents. Moreover, in angiographic studies, for example, GBCAs have been suggested as a safer alternative to radiocontrast media (Ruangkanchanasetr et al. J Ren Care 2009; 35:11-5) that are known to cause acute renal failure (Solomon, R. Semin Nephrol 1998; 18:551-7). Furthermore, the lowest possible dose of gadolinium should be used because development of NSF might be dose-related (Broome et al. Am J Roentgenol 2007; 188:586-92).

All currently approved agents use the same basic principle for clinical utility in MR scanning. Gd3+ ion is chelated for safety while maintaining its ability to provide enhancement on T1-weighted imaging (Kuo, P. H. J Am Coll Radiol 2008; 5:29-35). The chemical differences in the chelates, which were previously of little clinical relevance, now have become very important in light of their potential differences in propensity to cause NSF because free gadolinium is hypothesized to induce NSF.

9. Targeted Delivery of Gadolinium-Containing MRI Contrast Agents

It is important to note that gadolinium chelates, currently the only clinically approved imaging agents in cardiovascular MRI, distribute passively to the extracellular space and do not reflect the degree of active inflammation, as acute and chronic infarction enhance alike (Fuster V. & Kim R. J. Circulation 2005; 112:135-44). In order to achieve good resolution of the MR image, a certain quantity of the imaging agent must accumulate at the site of interest being examined (US Pat Appl 20070243136). Preferably, the imaging agent should specifically accumulate at the site being examined. For example, the required tissue concentration of an MR contrast agent is about $10^{-4}$-$10^{-6}$ M (Aime et al. J Magn Reson Imaging 2002; 16:394-406). For radionuclide imaging it is only about $10^{-10}$ M. This is a great challenge since the molecular epitopes expressed at $10^{-9}$ or $10^{-12}$ molar concentrations must be detected. Another challenge is to get the imaging agent to and into the site of interest. The lower efficacy of the GBCAs, relative to iron oxides, necessitates the need for high paramagnetic payloads at the site of interest. One way to reach the required local concentration of an MR contrast agent is to increase the intravenously injected dose. However, for GBCAs this leads to higher risk of NSF and other adverse outcomes. Alternative and very promising approach is molecular MRI that entails delivering MRI contrast agents to locations of interest using molecular targeting techniques and relies on the use of contrast agents that target specific cells or molecular pathways of relevance to disease. In molecular MRI, targeted carriers with the high affinity toward specific molecular epitopes are used to deliver the imaging agents to the site of interest. Importantly, as the specificity of the delivery vehicle toward the target increases, the portion of the injected GBCAs that is delivered directly to the site of interest increases as well. This allows for a significant reduction of the overall systemic dose of the contrast agent and, in case of GBCAs, diminishes the risk of NSF without compromising the MRI quality.

Currently, contrast agents for tracking potentially important components of atherosclerotic disease are at various stages of development (Sanz, J. & Fayad, Z. A. Nature 2008; 451:953-7). Most of the available probes are in experimental testing, although some have already advanced to clinical evaluation. By producing GBCA-containing carriers specific to components of atherosclerotic plaque, targeted imaging of atherosclerosis helps to detect vulnerable (unstable) lesions prone to atherothrombotic effects (Frias et al. Contrast Media Mol Imaging 2007; 2:16-23).

10. Atherosclerotic Plague Instability Correlates with its Macrophage Content

Inflammation has a crucial role at all stages of atherosclerosis. For this reason, macrophages are key in the progression of atherosclerosis, entering the intima as monocytes and being activated to macrophages via interaction with and uptake of modified low density lipoprotein until they become foam cells and eventually forming the necrotic lipid core associated with unstable plaques (Lusis, A. J. Nature 2000; 407:233-41). There is a known link between a high and active macrophage content of atherosclerotic plague and plaque instability (Hansson, G. K. N Engl J Med 2005; 352:1685-95). Furthermore, in humans, high macrophage content in plaques is characteristic of vulnerability to rupture, which is the proximal cause of acute coronary syndromes (Amirbekian et al. Proc Natl Acad Sci USA 2007; 104:961-6). Unstable (symptomatic) carotid artery plaques have been demonstrated to contain significantly higher number of lipid-laden macrophages than the stable (asymptomatic) ones (385+/−622 vs. 1,114+/−1,104, P value <0.009) (Wakhloo et al. J Vasc Interv Radiol 2004; 15:S111-21). Thus, the macrophage count that correlates with the progression and prognosis of human atherosclerosis in general, and the atherosclerotic plaques in particular, can be used as a distinctive feature of unstable plaques for molecular imaging purposes. It should be noted that because activated macrophages are the reliable indicators of not only atherosclerotic plaques but also any infected tissues, their presence may therefore allow more accurate imaging evaluation of other pathologies such as, for example, infected bone marrow (Kaim et al. Radiology 2002; 225:808-14), cancer (US Pat Appl 20090004113) and other diseases mediated by activated macrophages such as rheumatoid arthritis, ulcerative colitis, Crohn's disease, psoriasis, osteomyelitis, multiple sclerosis, atherosclerosis, pulmonary fibrosis, sarcoidosis, systemic sclerosis, organ transplant rejection (graft-versus-host disease, GVHD) and chronic inflammations (U.S. Pat. No. 7,740,854). Therefore, the macrophages are the most appealing targets for the MRI contrast agents.

Recently, investigators used BSA to deliver Gd to macrophages ex vivo and in vitro (Gustafsson et al. Bioconjug Chem 2006; 17:538-47). However, in vivo data are currently unavailable, and the specificity of targeting with albumin remains to be seen, because it is a ubiquitous substance that is taken up by many tissues and diffuses into interstitial spaces nonspecifically.

11. Myeloperoxidase as a Target for the MRI Contrast Agents

A possible way to quantify the level of macrophages is to determine the concentration of myeloperoxidase (MPO), a CD11b-positive cell (neutrophils, macrophages) secreted enzyme, and related components of the MPO pathway (Nicholls S. J. & Hazen S. L. Arterioscler Thromb Vasc Biol 2005; 25:1102-11). Myeloperoxidase (MPO) which emerged as a potential participant in the promotion and/or propagation of atherosclerosis, is a member of the heme peroxidase superfamily. MPO generates numerous reactive oxidants and diffusible radical species (Klebanoff SJ. Ann Intern Med 1980; 93:480-9) that are capable of both initiating lipid peroxidation (Zhang et al. J Biol Chem 2002; 277:46116-22) and promoting an array of post-translational modifications to target proteins, including halogenation, nitration, and oxidative cross-linking (Heinecke J W. Am J Cardiol 2003; 91:12A-6A). MPO, the most abundant component of azurophilic granules of leukocytes, is secreted on leukocyte activation, contributing to innate host defenses. Found predominantly in neutrophils, monocytes, and some subtypes of tissue macrophages, MPO amplifies the oxidative potential of its cosubstrate hydrogen peroxide, forming potent oxidants capable of chlorinating and nitrating phenolic compounds (Heinecke J W. Am J Cardiol 2003; 91:12A-6A; Podrez et al. Free Radic Biol Med 2000; 28:1717-25; Gaut et al. J Clin Invest 2002; 109, 1311-9). The hydrogen peroxide substrate may be derived from a number of sources in vivo, including leukocyte NADPH oxidases, xanthine oxidase, uncoupled nitric oxide synthase (NOS), and various Nox isoenzymes. MPO is unique in its ability to generate reactive chlorinating and brominating species such as hypochlorous acid (HOCl) and hypobromous acids (HOBr), which react with electron-rich moieties of a large range of biomolecules (Podrez et al. Free Radic Biol Med 2000; 28:1717-25).

Spurred initially by the recognition that MPO is enriched within human atheroma (Daugherty et al. 1994; 94:437-44), both MPO and its reactive oxidants have been implicated as participants in tissue injury during a large number of inflammatory conditions (Heinecke J W. Am J Cardiol 2003; 91:12A-6A; Podrez et al. Free Radic Biol Med 2000; 28:1717-25; Gaut et al. J Clin Invest 2002; 109, 1311-9; Andreadis et al. Free Radic Biol Med 2003; 35:213-25; Heinecke J W. Mechanisms of oxidative damage by myeloperoxidase in atherosclerosis and other inflammatory disorders. J Lab Clin Med 1999; 133:321-5). Multiple lines of evidence suggest that MPO may play a role in atherogenesis in humans and that proatherogenic biological consequences may be triggered by oxidative modification of targets in the artery wall by MPO-generated reactive species. Immunohistochemical and biochemical analyses localize the enzyme and its oxidation products within human atherosclerotic lesions (Hazell et al. Free Radic Biol Med 2001; 31:1254-62; Hazen S. L. & Heinecke J. W. J Clin Invest 1997; 99:2075-81). Lipid oxidation products of plasmalogens generated by the MPO-derived oxidant HOCl are both enriched within human atheroma and possess potent leukocyte chemotactic activity (Thukkani et al. Circulation 2003; 108:3128-33). Incubation of HOCl and low-density lipoproteins (LDL) results in oxidation of lysine residues in apolipoprotein B-100, the predominant protein of LDL (Hazell L. J. & Stocker R. Biochem J 1993; 290 (Pt 1):165-72). Increased anionic surface charge as well as HOCl-induced lipoprotein aggregation, both convert LDL into a high-uptake form for macrophages, and appear to occur within human atheroma (Hazell et al. J Clin Invest 1996; 97:1535-44).

Under physiological conditions, activated human monocytes also use MPO-generated reactive nitrogen species to render LDL atherogenic, converting it into a high-uptake form for macrophages (Podrez et al. J Clin Invest 1999; 103:1547-60) while simultaneously promoting both apolipoprotein B-100 protein nitration and initiation of LDL lipid peroxidation. The oxidized form of LDL has been demonstrated to be selectively recognized by the scavenger receptor CD36 (Podrez et al. J Clin Invest 2000; 105:1095-108), a major participant in fatty streak and atherosclerotic lesion development (Febbraio et al. J Clin Invest 2000; 105:1049-56). High density lipoproteins (HDL) isolated from atherosclerotic lesions contain numerous MPO-derived peptides of apolipoprotein A-I (apo A-I), the major constituent protein of HDL, including site-specific oxidative modifications by reactive chlorinating and nitrating species (Zheng et al. J Clin Invest 2004; 114:529-41; Zheng et al. J Biol Chem 2005; 280:38-47). It has been shown that MPO-catalyzed oxidation of apo A-I preferentially occurs in the arterial wall. Consistent with this finding, immunohistochemical analysis of human atheroma specimens reveals MPO- and HOCl-modified proteins co-localize with apo A-I in the region of macrophages (Hazell et al. J Clin Invest 1996; 97:1535-44).

The correlation between MPO levels and angiographic evidence of atherosclerotic plaque (Zhang et al. JAMA 2001; 286:2136-42), as well as the apparent atheroprotective effects of genetic deficiencies of MPO (Asselbergs et al. Am J Med 2004; 116:429-30), are consistent with the hypothesis that MPO participates in the initiation and/or propagation of coronary vascular disease (CVD). The ability of systemic MPO levels to predict the likelihood of clinical events suggests that MPO plays a role in the transition of a mature atherosclerotic plaque to the vulnerable state.

Activatable paramagnetic MRI contrast agents can be used to directly image MPO activity in humans (Nighoghossian et al. Stroke 2005; 36:2764-72; Sinusas et al. Circulation: Cardiovascular Imaging 2008; 1:244-56). These agents include Gd complexes that, when cleaved by MPO, expose the shielded Gd to water resulting in alterations of T1 relaxivity (Louie et al. Nat Biotechnol 2000; 18:321-5). A different approach involves the derivatization of Gd chelators such as diethylenetriaminepentaacetic acid-Gd (DTPA-Gd) with 5-hydroxytryptamide [bis-5HT-DTPA(Gd)]. Myeloperoxidase activates the small-molecule substrate, which then polymerizes and exhibits increased T1 relaxivity, protein binding, and "trapping" in areas of high myeloperoxidase (MPO) activity, all leading to increased enhancement on T1-weighted MRI (Nahrendorf et al. Circulation 2008; 117:1153-60; Querol et al. Org Lett 2005; 7:1719-22). Others have engineered magnetic nanoparticles that assemble and disassemble, which can be used for detection of enzymatic activity (Perez et al. Chembiochem 2004; 5:261-4).

12. Macrophage Scavenger Receptor as a Target for Imaging Agents

Another, clinically more promising approach to evaluate plaque macrophage burden in vivo, is to target MSR, a macrophage-specific cell-surface protein, which is significantly overexpressed on atherosclerotic macrophages and foam cells (Gough et al. Arterioscler Thromb Vase Biol 1999; 19:461-71; Amirbekian et al. Proc Natl Acad Sci USA 2007; 104:961-6). The MSR is not expressed on normal vessel wall cells (de Winther et al. Arterioscler Thromb Vase Biol 2000; 20:290-7). The MSR plays an important role in LDL uptake as well as in clearance of debris, including necrotic and apoptotic cell fragments (Peiser et al. Curr Opin Immunol 2002; 14:123-8). Such an integral position in the pathogenesis of atherosclerosis makes the scavenger receptor an excellent target for molecular imaging. There are several reasons for selecting MSR as a target for assessing atherosclerosis. First, MSR plays a key role in the pathogenesis of atherosclerosis and knocking out either of the MSR receptors results in marked decreases in atherosclerotic plaque size (Suzuki et al. Nature 1997; 386:292-6). In addition, MSR is a primary route of lipoprotein uptake, including uptake of modified lipoproteins such as oxidized LDL (Goldstein et al. Proc Natl Acad Sci USA 1979; 76:333-7). Second, MSR is widely expressed on atheroma-associated macrophages (Gough et al. Arterioscler Thromb Vasc Biol 1999; 19:461-71), cells that are present through all stages of atherosclerosis development, from the initiation of plaques through the formation of complex plaques containing foam cells, lipid accumulations, necrotic debris, and thrombus (Hansson GK. N Engl J Med 2005; 352:1685-95). A third key reason (for selecting macrophages and MSR) is that high macrophage content has been specifically associated with plaque vulnerability to rupture and sequelae, including complete vessel obstruction, myocardial infarction, sudden cardiac death, and stroke (Kolodgie et al. N Engl J Med 2003; 349:2316-25). Finally, MSR is a high-affinity receptor, in the picomolar to nanomolar range (depending on the ligand) and is present in great numbers on atherosclerosis-associated macrophages (Gough et al. Arterioscler Thromb Vasc Biol 1999; 19:461-71; Krieger M. & Herz J. Annu Rev Biochem 1994; 63:601-37).

MSR targeting can be accomplished either by using receptor-specific antibodies that bind to the receptor on the macrophage surface or by employing MSR-specific ligands that are uptaken by the macrophages via the MSR-mediated route. Gd-based micelles have been previously developed and used to target macrophages in plaques (Chen et al. Contrast Media Mol Imaging 2008; 3:233-42). Micelles and liposomes have the advantages of high lipid capacity and high pay-load of GBCAs (Briley-Saebo et al. J Magn Reson Imaging 2007; 26:460-79; Briley-Saebo et al. Circulation 2008; 117:3206-15; Mulder et al. Magn Reson Med 2007; 58:1164-70; Lipinski et al. Magn Reson Med 2006; 56:601-10). Antibodies to mouse MSRs, CD204, have been conjugated to this platform as targeting moeities to form immunomicelles (Mulder et al. Magn Reson Med 2007; 58:1164-70) that provided excellent in vivo enhancement of atherosclerotic plaques, which was thoroughly validated by histology. However, these immunomicelles targeting MSRs are rapidly removed from the circulation by the liver because Kupffer cells also express scavenger receptors and play a prominent role in the uptake of a wide variety of ligands. Therefore targeting the macrophage with relatively inexpensive MSR-specific ligands appears to be much more attractive than using monoclonal antibodies, which are expensive to produce and purify.

13. Delivery Vehicles that can Carry Imaging Agents

In addition to micelles, other nanoparticulate carriers, such as emulsions or liposomes can be potentially used to carry the imaging agent to the site of interest (U.S. Pat. Nos. 7,179,484; 5,676,928; Sanz, J. & Fayad, Z. A. Nature 2008; 451:953-7; US Pat Appl 20070243136). However, the size of these liposomes and emulsions is such that it exceeds the size required to readily permeate into the extracellular space and hence into a plaque (Sloop et al. J Lipid Res 1987; 28:225-37). For example, liposomes typically have a diameter of about 100-400 nm and cannot enter a plaque unless the endothelium is damaged (e.g., Lanza et al. Circulation 2002; 106:2842-7; Li et al. Radiology 2001; 218:670-8). Therefore, delivery of imaging agents through the use of such nanoparticles is practically restricted to either targets on the endothelium or in lesions in which endothelial integrity has been breached, for example, after balloon angioplasty (Lanza et al. Circulation 2002; 106, 2842-7).

Reconstituted lipoproteins have previously been used as delivery vehicles for lipophilic drugs (U.S. Pat. No. 6,306,433). Lipoproteins are produced mainly by the intestine and liver (or by processing of intestine or liver-derived lipoproteins) and are the native transporters in the circulation of a variety of lipophilic and hydrophilic compounds and are classified into four main categories depending on size and composition (i.e., in order of decreasing diameter: chylomicrons, very low density lipoproteins (VLDL), LDL and HDL (Havel et al., The Metabolic and Molecular Bases of Inherited Disease. New York: McGraw-Hill; 2001:2705-16). With the exception of HDLs, the lipoproteins also suffer the same drawbacks as micelles, conventional emulsions and liposomes, in that the entities are too large to serve as good vehicles for the delivery of imaging agents.

LDLs are particularly unsuitable for such delivery because, in addition to being larger than the optimal size (on average LDLs are larger than 20 nm), the major protein constituent of LDLs is apoB, a very large and hydrophobic protein, which makes it difficult to reconstitute LDL (rLDL) particles. Furthermore, LDL moieties are spontaneously retained in atherosclerotic lesions (Williams K. J. & Tabas I. Arterioscler Thromb Vasc Biol 1995; 15:551-61), thereby making it difficult to selectively detect specific molecular targets of interest within the plaque. Yet another factor that makes LDLs unattractive as delivery vehicles is that LDL is an atherogenic particle, and so it is difficult to justify the possible risks from administration of rLDL to patients already at high risk for cardiovascular disease.

Micelles, much like LDLs, also do not serve well as delivery vehicles to enter atherosclerotic plaques, because they are spontaneously retained for prolonged periods of time, rendering them unsuitable for the selective detection of specific molecules of interest.

14. Macrophage Targeting Using HDL

Reconstituted HDL (rHDL) and recombinant HDL have been recently used for the treatment and prevention of acute coronary symptoms, stroke and other disorders (Tardif et al. JAMA 2007; 297:1675-82; Newton R. S. & Krause B. R. Atheroscler Suppl 2002; 3:31-8; Nissen et al. JAMA 2003; 290:2292-300; Choudhury et al. Arterioscler Thromb Vasc Biol 2004; 24:1904-9; U.S. Pat. Nos. 7,435,717; 6,953,840; 7,491,693).

Recently, HDL have been suggested as a specific contrast agent for MRI of atherosclerotic plaques (US Pat Appl 20070243136; Frias et al. Contrast Media Mol Imaging 2007; 2:16-23; Frias et al. J Am Chem Soc 2004; 126:16316-7; Cormode et al. Small 2008; 4:1437-44; Chen et al. Contrast Media Mol Imaging 2008; 3:233-42; Frias et al. Nano Lett 2006; 6:2220-4). It should be noted that the term "modified lipoproteins" used by Frias et al. (Frias et al. Contrast Media Mol Imaging 2007; 2:16-23) accurately speaking refers to the lipoproteins labeled (rather than modified) with radioisotopes for nuclear imaging, chelates for MRI or other possible contrast agents for computed tomography imaging techniques. It should be further noted that based on the description provided in the aforementioned article, protein (apolipoprotein) part of the lipoprotein is not labeled or modified. Importantly, the term "modified lipoproteins" is also used in the art to describe lipoproteins modified by any means, for example by peroxidation of lipids or HOCl-mediated oxidative modification of proteins by reactive chlorinating and nitrating species. These chemically modified lipoproteins represent a high affinity substrate for MSR-mediated uptake by macrophages whereas “modified lipoproteins” as defined by Frias et al. may not demonstrate this quality (Frias et al. Contrast Media Mol Imaging 2007; 2:16-23).

In comparison to other Gd-based macrophage targeting platforms (e.g., LDL and immunomicelles), HDL have several advantages that make them attractive as a specific contrast agent for imaging: they can be readily reconstituted from their components; they contain an endogenous protein component (apolipoprotein A-I) that does not trigger immunoreactions, and they play a key role in reverse cholesterol transport by removing excess cellular cholesterol from the macrophages thus demonstrating a therapeutic potential in addition to their imaging function (Forrester, J. S. & Shah, P. K. Am J Cardiol 2006; 98:1542-9; Williams et al. Curr Opin Lipidol 2007; 18:443-50). In plaque imaging, the small size of the HDL particle allows it to enter and accumulate in the plaque. The HDL-based contrast agent can be obtained as spherical or discoidal forms with similar relaxivity values. Both forms target atherosclerotic plaques and enhance the MRI signal in a manner dependent on plaque macrophage content. While not specifically studied, intracellular uptake would be expected to occur through the MSR for both spherical and discoidal forms with no differences in the diffusion of either particle into the atherosclerotic plaque.

Despite multiple advantages of the HDL nanoparticles as delivery platform, the currently suggested HDL compositions for use as imaging agents in MRI, CT, Gamma-scintigraphy, or optical imaging techniques (US Pat Appl 20070243136) have low specificity of targeted delivery of contrast molecules such as GdBCAs to the plaque and, importantly, low subsequent retention within the arterial wall. This results in the low amount of contrast agent delivered and, therefore, low MRI contrast enhancement which does not significantly reduce the dosage of Gd required. In order to increase the delivery and retention of rHDL within the arterial wall, antibodies for different plaque components can be incorporated in rHDL as targeting moieties (US Pat Appl 20070243136). However, the suggested imaging agents would share all the disadvantages of antibodies (unstable, expensive to produce, potentially immunogenic, etc.).

Alternatively, an apo E-derived lipopeptide has been shown to increase efficacy of the rHDL platform for molecular MR imaging of atherosclerotic plaques in vivo (Chen et al. Contrast Media Mol Imaging 2008; 3:233-42). This synthetic lipopeptide represents a dipalmitoylated version of apo E-derived highly positive peptide, which has the amino acid sequence $(LRKLRKRLLR)_2$, and is a tandem dimer $(141\text{-}150)_2$ derived from the LDL receptor binding domain of apo E. Despite resulting in an improved in vivo MR imaging signal enhancement in atherosclerotic mice (90% vs. 53% enhancement within the arterial vessel 24 h after administration of a 50 micromol Gd/kg dose), incorporation of this detergent-like highly positive molecule in the rHDL platform can also bring the apo E-derived tandem peptide-associated disadvantages to the platform. For example, this tandem peptide and its dipalmitoylated version are known to mediate uptake of liposomes or micelles into endothelial cells of brain microvessels (Keller et al. Angew Chem Int Ed Engl 2005; 44:5252-5; Sauer et al. Biochemistry 2005; 44:2021-9; Sauer et al. Biochim Biophys Acta 2006; 1758: 552-61). In addition, this tandem peptide can exert neurotoxic effects (Wang X. S. & Gruenstein E. J Cell Physiol 1997; 173:73-83).

Recently, Gd-containing HDL obtained by incubation of native human HDL (commercially available HDL preparations purified from human plasma; Calbiochem, San Diego, CA) with Gd-DTPA-1,2-dimyristoyl-sn-glycero-3-phosphoethanolamine (Gd-DTPA-DMPE) and Gd/6-amino-6-methylperhydro-1,4-diazepinetetraacetic acid with a 17-carbon long aliphatic chain (Gd-AAZTA-C17) have been suggested as high-relaxivity MRI contrast agents (Briley-Saebo et al. J Phys Chem B 2009; 113:6283-9). However, incubation of native HDL with Gd-DTPA-DMPE resulted in the uncontrolled particle fusion due to detergent perturbations whereas the composition and integrity of HDL-Gd-AAZTA-C17 adducts was not characterized. In contrast to rHDL platform, both native HDL-based agents lack the control and reproducibility between batches because native HDL is a heterogeneous lipoprotein class with different subspecies that vary in apolipoprotein and lipid composition, in size and charge, and in physiological functions (Castro G. R. & Fielding C. J. Biochemistry 1988; 27:25-9; Miida et al. Biochemistry 1992; 31:11112-7; Mowri et al. J Lipid Res 1992; 33:1269-79; von Eckardstein et al. Curr Opin Lipidol 1994; 5:404-16). For this reason, the size, shape, protein and lipid composition, structure, properties and physiological function of native HDL purified from human plasma using ultracentrifugation vary significantly depending on donors, isolation procedure variations and storage conditions and therefore cannot be well controlled.

15. An Unmet Need

Hence, there is a need for a targeted delivery vehicle that can freely enter an atherosclerotic plaque or other sites of interest such as tumor sites and that provides sufficient quantities of an imaging agent to meet the needs of MRI or MR spectroscopy or other imaging techniques such as CT, gamma-scintigraphy, and optical, positron emission tomography (PET), and combined imaging techniques. This agent should possess a high affinity for macrophages and their components in order to significantly reduce the contrast agent dosage required and thus limit concerns related to systemic toxicity, which is especially important for Gd-based contrast agents.

SUMMARY OF THE INVENTION

The present invention provides various nanoparticles that contain chemically and/or enzymatically modified apolipoproteins and are used for the delivery of an imaging contrast agent. The compositions of the present invention include, but are not limited to, a synthetic nanoparticle, the synthetic nanoparticle comprising at least one chemically and/or enzymatically modified apolipoprotein (apo) A-I and/or A-II, at least one amphipathic lipid, and at least one metallic or non-metallic contrast agent linked through a chelator to a component of the nanoparticle or encapsulated into the nanoparticle, the one metallic or non-metallic contrast agent being present in an amount of between 5% to about 50% (w/w) of the nanoparticle, and the synthetic nanoparticle having a diameter of from about 5 nm to about 50 nm. It is contemplated that greater amounts of contrast agent e.g., up to 100% (w/w) of the component of the nanoparticle to which the contrast agent is bonded may be present. Furthermore, while the size of the nanoparticles is preferably between 5 nm and 25 nm, the diameter may be up to 150 nm. The nanoparticles may be spherical, discoidal or a distorted disc shape, e.g., ellipsoidal.

BRIEF DESCRIPTION OF THE FIGURES

The following figures form part of the present specification and are included to further illustrate aspects of the present invention. The invention may be better understood by reference to the figures in combination with the detailed description of the specific embodiments presented herein.

DETAILED DESCRIPTION OF THE INVENTION

Definitions

Figure 1:
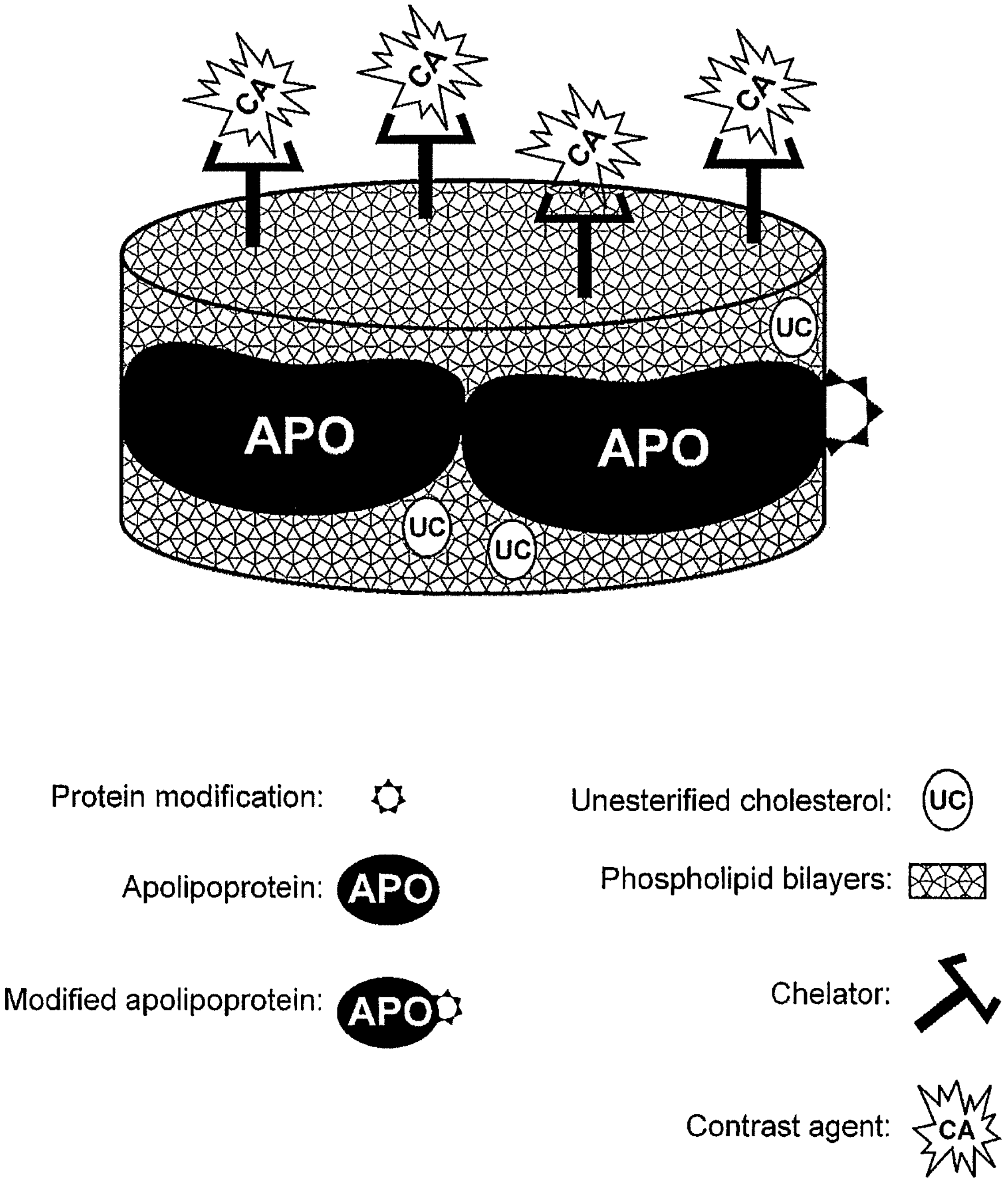
FIG. 1 presents a schematic representation of one embodiment of a discoidal imaging agent of the present invention. Chelated contrast agent is shown for illustrative purposes. The contrast agent may or may not be the chelated one.

It is understood by a person of ordinary skill in the art that the terms "APOA1_HUMAN", "Apolipoprotein A-I", "Apolipoprotein A-1", "APOA1", "ApoA-I", "Apo-AI", "ApoA-1", "apo-A1", "apoA-1" and "Apo-A1" refer to the naturally occurring human protein listed in the UniProt Knowledgebase (UniProtKB, www.uniprot.org) under the name "APOA1_HUMAN". The protein amino acid sequence can be found under the entry UniProt KB/Swiss-Prot P02647 (www.uniprot.org/uniprot/P02647, last modified on Jul. 28, 2009, version 137). It is further understood by the person of ordinary skill in the art that the terms "APOA2_HUMAN", "Apolipoprotein A-II", Apolipoprotein A-2", "APOA2", "ApoA-II", "Apo-AII", "ApoA-2", "apo-A2", "apoA-2" and "Apo-A2" refer to the naturally occurring human protein listed in the UniProt Knowledgebase (UniProtKB, www.uniprot.org) under the name "APOA2_HUMAN". The protein amino acid sequence can be found under the entry UniProt KB/Swiss-Prot P02652 (http//www.uniprot.org/uniprot/P02652, last modified on Jul. 28, 2009, version 121).

As understood by those of ordinary skill in the art, the amino acid composition of the human apo A-I can be determined by reviewing the UniProtKB entry which describes the naturally occurring unmodified protein that consists of 267 amino acids and has a molecular weight of 30,778 Dalton. As further understood by those of ordinary skill in the art, the amino acid composition of the human apo A-II can be determined by reviewing the UniProtKB entry which describes the naturally occurring unmodified protein that consists of 100 amino acids and has a molecular weight of 11,175 Dalton. As employed herein, the term "apo A-II" describes apo A-II either in homodimeric or monomeric form.

It is understood by the ordinary skill in the art that when apo A-I is modified such that its molecular weight changes, the resultant modified protein is referred to as either apoA-1 (+X) wherein "X" is the increase in protein's molecular weight in Daltons or as apoA-I (−Y) wherein "Y" is the decrease in protein's molecular weight in Daltons (Garner et al. J Biol Chem 1998; 273:6080-7; Pankhurst et al. J Lipid Res 2003; 44:349-55). It is further understood by the ordinary skill in the art that when apo A-II is modified such that its molecular weight changes, the resultant modified protein is referred to as either apoA-II (+X) wherein "X" is the increase in protein's molecular weight in Daltons or as apoA-II (−Y) wherein "Y" is the decrease in protein's molecular weight in Daltons (Garner et al. J Biol Chem 1998; 273:6080-7; Pankhurst et al. J Lipid Res 2003; 44:349-55).

As employed herein and understood by the ordinary skill in the art the term "recombinant protein" describes the protein obtained from bacterial or other sources using the recombinant DNA technology (Nissen et al. JAMA 2003; 290:2292-300). Furthermore, a suffix or a prefix indicating the species from which the protein is derived is added to the protein's name when a non-human protein such as non-human apo A-I or apo A-II is described (U.S. Pat. No. 6,953,840; http://www.uniprot.org/uniprot/Q00623; http://www.uniprot.org/uniprot/P09813). In special cases a suffix or a prefix may also indicate a well-known apoA-1 variant, e.g. apo A-I Milano (U.S. Pat. No. 7,435,717; Nissen et al. JAMA 2003; 290:2292-300). As used herein, the term "aptamer" or "specifically binding oligonucleotide" refers to an oligonucleotide that is capable of forming a complex with an intended target substance. The complexation is target-specific in the sense that other materials which may accompany the target do not complex to the aptamer. It is recognized that complexation and affinity are a matter of degree; however, in this context, "target-specific" means that the aptamer binds to target with a much higher degree of affinity than it binds to contaminating materials. The term "peptidomimetic" as used herein refers to a peptide-like molecule containing non-hydrolyzable chemical moieties in place of one or more hydrolyzable moieties existing in naturally occurring peptides. Thus, regions of a peptide which are hydrolyzable, such as carboxyl moieties, are replaced by non-hydrolyzable moieties, such as methylene moieties, in a peptidomimetic.

In the present invention, the term "modified protein" is used to describe chemically or enzymatically or chemically and enzymatically modified oligopeptides, oligopseudopeptides, polypeptides, pseudopolypeptides, and native proteins (synthetic or otherwise derived), regardless of the nature of the chemical and/or enzymatic modification. The term "pseudopeptide" refers to a peptide where one or more peptide bonds are replaced by non-amido bonds such as ester or one or more amino acids are replaced by amino acid analogs. The term "peptides" refers not only to those comprised of all natural amino acids, but also to those which contain unnatural amino acids or other non-coded structural units. The terms "peptides", when used alone, include pseudopeptides. It is worth mentioning that "modified proteins" have utility in many biomedical applications because of their increased stability against in vivo degradation, superior pharmacokinetics, and altered immunogenicity compared to their native counterparts.

The term "modified protein," as employed herein, also includes oxidized proteins. The term "oxidized protein" refers to a protein in which at least one amino acid residue is oxidized. The term "oxidized protein fragment" refers to a protein fragment in which at least one amino acid residue is oxidized. The term "oxidation status" refers to a metric of the extent to which specific amino acid residues are replaced by corresponding oxidized amino acid residues in a protein or a protein fragment. The term "extent of oxidation" refers to the degree to which potentially oxidizable amino acids in a protein or fragment have undergone oxidation. For example, if the protein fragment contains a single tyrosine residue which is potentially oxidized to 3-chlorotyrosine, then an increase in mass of about 34 Dalton (i.e., the approximate difference in mass between chlorine and hydrogen) indicates oxidation of tyrosine to 3-chlorotyrosine (Pitt, A. R. and Spickett, C. M. 2008; 36:1077-82; Shao et al. J Biol Chem 2006; 281:9001-4; Shao et al. J Biol Chem 2005; 280:5983-93). Similarly, if the protein fragment contains a single methionine residue which is potentially oxidized to methionine sulfoxide, then an increase in mass of 16 Dalton (i.e., the difference in mass between methionine and methionine containing one extra oxygen) indicates oxidation of methionine to methionine sulfoxides (Garner et al. J Biol Chem 1998; 273:6080-7).

The oxidation status can be measured by metrics known to the arts of protein and peptide chemistry (US Pat Appl 20080020400; US Pat Appl 20050239136) including, without limitation, assay of the number of oxidized residues, mass spectral peak intensity, mass spectral integrated area, and the like. In some embodiments of any of the aspects provided herein, oxidation status is reported as a percentage, wherein 0% refers to no oxidation and 100% refers to complete oxidation of potentially oxidizable amino acid residues within apo A-I or apo A-II or fragments thereof. The term "potentially subject to oxidation," "potentially oxidizable amino acid residues", and the like refer to an amino acid which can undergo oxidation, for example by nitration or chlorination.

In the context of the present invention, the term "oxidation fraction" refers to the term "oxidation status" as defined herein expressed as a fraction in the range 0-1, e.g., 0.0, 0.1, 0.2, 0.3, and the like up to 1.0. It is understood that the number of significant digits in an oxidation status, oxidation fraction, or other experimental result herein is a function of the sensitivity of the instruments and experimental protocols and can assume values of 1, 2, 3, 4, or even more significant digits. Methods for the calculation of significant digits are well known in the art. The phrase "determining the oxidation fraction" refers to determining the oxidation status, as defined herein, and expressing the result as a fraction of amino acids of the protein or protein fragment which can be replaced by corresponding oxidized amino acid residues. The term "total amount of protein in a sample" and like terms refer to the total amount of protein irrespective of the oxidation state of the constituent amino acids thereof. In some embodiments of this aspect, the total amount of apoA-I or A-II is determined by assay, for example without limitation, a standard immunoassay well known in the art. Examples of reagents readily available for immunometric determination of apo A-I and A-II include antiserum to apo A-I and A-II, respectively (Dade Behring, Deerfield, Ill.). In some embodiments of this aspect, the total amount of apoA-I or A-II is multiplied by the oxidation fraction to provide a quantitation of the amount of oxidized apoA-I or A-II in a biological sample. For example without limitation, if the oxidation fraction were 0.5 and the total concentration of apo A-I or A-II in the biological sample were 1.0 mg/mL, the amount of oxidized apoA-I or A-II in the biological sample would be reported as 0.5 mg/mL (i.e., 0.5.times.1.0 mg/mL).

The term "encapsulation" as used herein refers to the enclosure of a molecule, such as a contrast agent or therapeutics, inside the nanoparticle. Such encapsulation may be generated, according to an embodiment, by synthesis of nanoparticles in the presence of a liquid solution containing a contrast agent or therapeutics. The term "incorporation" as used herein refers to imbibing or adsorbing the contrast agent or therapeutics onto the nanoparticle. A "site of interest" on a target as used herein is a site to which modified proteins and protein fragments of the present invention bind. The term "target site", as used herein, refers to sites/tissue areas of interest. As used in this invention, the terms "target cells" or "target tissues" refer to those cells or tissues, respectively that are intended to be visualized in imaging techniques such as computed tomography (CT), gamma-scintigraphy, positron emission tomography (PET), single photon emission computed tomography (SPECT), magnetic resonance imaging (MRI), and combined imaging techniques, using the compositions of the present invention delivered in accord with the invention. Target cells or target tissues take up or link with the modified proteins or protein fragments of the invention. Target cells are cells in target tissue, and the target tissue includes, but is not limited to, atherosclerotic plaques, vascular endothelial tissue, abnormal vascular walls of tumors, solid tumors, and other tissues or cells related to cardiovascular, inflammatory, and autoimmune disease. Further, target cells include virus-containing cells, and parasite-containing cells. Also included among target cells are cells undergoing substantially more rapid division as compared to non-target cells. The term "target cells" also includes, but is not limited to, microorganisms such as bacteria, viruses, fungi, parasites, and infectious agents. Thus, the term "target cell" is not limited to living cells but also includes infectious organic particles such as viruses. "Target compositions" or "target biological components" include, but are not be limited to: toxins, peptides, polymers, and other compounds that may be selectively and specifically identified as an organic target that is intended to be visualized in imaging techniques using the compositions of the present invention. The term "macrophage-related diseases" include diseases associated with macrophages such as atherosclerosis and other disease associated with abnormal cholesterol metabolism. Examples of macrophage-related diseases, include, but are not limited to, heart disease, peripheral artery disease, and stroke (e.g., ischemic stroke, hemorrhagic stroke). Other examples include the cancers: sarcoma, lymphoma, leukemia, carcinoma and melanoma, and other activated macrophage-related disorders including autoimmune diseases (e.g., rheumatoid arthritis, Sjogrens, scleroderma, systemic lupus erythematosus, non-specific vasculitis, Kawasaki's disease, psoriasis, Type I diabetes, pemphigus vulgaris), granulomatous diseases (e.g., tuberculosis, sarcoidosis, lymphomatoid granulomatosis, Wegener's granulomatosus), inflammatory diseases (e.g., inflammatory lung diseases such as interstitial pneumonitis and asthma, inflammatory bowel disease such as Crohn's disease, and inflammatory arthritis), and transplant (e.g., heart/lung transplants) rejection reactions. The term "plaque" includes, for example, an atherosclerotic plaque.

DETAILED DESCRIPTION

Because of the leading position of cardiovascular disease as a cause of mortality in industrialized societies, applications in this area are thus highlighted. However, it should be noted that the techniques and compositions listed and described below are applicable to a broad range of disease states such, for example, as cancer and multiple sclerosis. Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

Magnetic resonance imaging (MRI) has been effectively used as a non-invasive method for cancer imaging and for the quantification of atherosclerosis to document its progression and regression of atherosclerosis in vivo (Skinner et al. Nat Med 1995; 1, 69-73; Corti et al. J Am Coll Cardiol 2002; 39:1366-73; Helft et al. Circulation 2002; 105:993-8; Toussaint et al. Circulation 1996; 94:932-8; Cai et al. Circulation 2002; 106:1368-73; Weissleder, R. Nat Rev Cancer 2002; 2:11-8). However, significant progress is still needed in spatial and temporal resolution of plaque characteristics and in the molecular imaging of plaque components. Such progress will be greatly facilitated by the availability of novel imaging compositions that are small enough to freely enter an atherosclerotic plaque in sufficient quantities to provide an enhanced MR image. These particles should preferably possess the following properties be a) small enough to readily penetrate into the interstitial fluid, b) able to carry large amounts of a contrast agent, c) non-toxic including non-atherogenic, d) poorly retained in diseased tissue without the addition of a targeting agent, e) able to carry large amounts of a targeting agent, and f) easy to manufacture and store.

Chemical or enzymatic modification of fully assembled HDL particles (without Gd) has been shown to enhance their absorption by the macrophages (Bergt et al. Biochem J 2000; 346 Pt 2:345-54; Pankhurst et al. J Lipid Res 2003; 44:349-55; Panzenboeck et al. J Biol Chem 1997; 272: 29711-20; Suc et al. J Cell Sci 2003; 116:89-99). However, published data demonstrate that in the modified HDL particle described in (Panzenboeck et al. J Biol Chem 1997; 272:29711-20) both, the protein and the lipid portion of the particle have undergone the chemical modification. The prior art (US Pat Appl 20070243136) neither suggests nor teaches one of ordinary skill in the art to investigate the performance of HDL particles in which only the apolipoprotein portion has been chemically altered.

Surprisingly advantageous compositions are demonstrated by the present invention which meet the requirements mentioned above. Compositions of the invention are rHDL, protein constituents of which, apolipoproteins A-I and/or A-II or fragments thereof are modified. Certain controlled chemical or enzymatic modification of apolipoproteins (apo) A-I or A-II or fragments thereof converts these apolipoproteins to substrates for macrophage scavenger receptors and results in the improvement of association of the Gd-(HDL/modified apolipoprotein)-particle with macrophages and/or absorption (uptake) of the Gd-(HDL/modified apolipoprotein)-particle by macrophages when compared to that of the Gd-(HDL/apolipoprotein)-particle constructed with non-modified naturally occurring apo A-I, apo A-II or fragments thereof. These advantageous compositions are demonstrated by the present invention to solve numerous problems which otherwise are associated with high dosages of Gd and other contrast agents required and the lack of control and reproducibility of formulations, especially in large-scale production.

In preferred embodiments, the modified apolipoprotein is selected from a modified apo A-I or a fragment thereof and a modified apo A-II or a fragment thereof. In proffered embodiments, the modified apolipoprotein is any combination of a modified apo A-I and a modified A-II and fragments thereof. In preferred embodiments, a modified apo A-I is an oxidized apoA-I or an oxidized apoA-I fragment that comprises one or more of the following amino acid residues: 3-chlorotyrosine, 3-nitrotyrosine, 3,5-dibromotyrosine, dityrosine, trihydroxyphenylalanine, dihydroxyphenylalanine, methionine sulphoxide, and tyrosine peroxide. In still other preferred embodiments, a modified apo A-II is an oxidized apoA-II or an oxidized apoA-II fragment that comprises one or more of the following amino acid residues: 3-chlorotyrosine, 3-nitrotyrosine, 3,5-dibromotyrosine, dityrosine, trihydroxyphenylalanine, dihydroxyphenylalanine, methionine sulphoxide, and tyrosine peroxide. In particularly preferred embodiments, a modified apo A-I is an oxidized apo A-I or an oxidized apoA-I fragment that comprises methionine sulfoxide at any one of positions 86, 112, 148, or any combination of said positions. In still particularly preferred embodiments, a modified apo A-II is an oxidized apo A-II or an oxidized apoA-II fragment that comprises methionine sulfoxide at position 26. In still preferred embodiments apo A-$I_{unox}$ is unoxidized apo A-I contained in initial serum apo A-I. In other preferred embodiments apo A-$II_{unox}$ is unoxidized apo A-II contained in initial serum apo A-II. In other preferred embodiments, apo A-$I_{ox}$ is oxidized apo A-I (with sulfoxidized methionines at positions 112 and 148) contained in serum apo A-I or obtained from unoxidized apo A-I using hydrogen peroxide. In still other preferred embodiments; apo A-$I_{red}$ is reduced apo A-I obtained by reduction of oxidized apo A-I (with sulfoxidized methionines at positions 112 and 148) using peptide methionine sulfoxide reductase (PMSR). In preferred embodiments, rHDL-1 are reconstituted HDL particles containing only apo A-$I_{unox}$. In preferred embodiments, rHDL-2 are reconstituted HDL particles containing only apo A-$I_{unox}$. In preferred embodiments, rHDL-3 are reconstituted HDL particles containing apo A-$I_{unox}$ and apo A-$I_{ox}$ with a molar ratio of 1:1. In preferred embodiments, rHDL-4 are reconstituted HDL particles containing apo A-$I_{unox}$, apo A-$I_{ox}$ and apo A-$II_{unox}$ with a molar ratio of 3:3:1.

In preferred embodiments, apo A-I, apo A-II or fragments thereof are first chemically or enzymatically modified and then the synthetic nanoparticle of the invention is assembled using this modified apolipoprotein. It might be possible, however, to selectively modify only apolipoprotein portion of the fully assembled synthetic nanoparticle of the invention.

The metallic contrast agent may preferably be selected from the group consisting of Gd(III), Mn(II), Mn(III), Cr(II), Cr(III), Cu(II), Fe(III), Pr(III), Nd(II) Sm(III), Tb(III), Yb(III) Dy(III), Ho(III), Eu(II), Eu(III), and Er(III), $Tl^{201}$, $K^{42}$, $In^{111}$, $Fe.^{59}$, $Tc^{99m}$, $Cr^{51}$, $Ga^{67}$, $Ga^{68}$, $Cu^{64}$, $Rb^{82}$, $Mo^{99}$, $Dy^{165}$. In addition, the metallic contrast agents could include crystals and other particulate materials (oxides, quantum dots, etc.) The non-metallic contrast agent may preferably be selected from the group consisting of Fluorescein, Carboxyfluorescein, Calcein, $F^{18}$, $Xe^{133}$, $I^{125}$, $I^{131}$, $I^{123}$, $P^{32}$, $C^{11}$, $N^{13}$, $O^{15}$, $Br^{76}$, $Kr^{81}$. In specific embodiments, the metallic contrast agent is gadolinium. The non-metallic contrast agent may still preferably be selected from the group of iodinated contrast media consisting of ionic monomers and dimers, and nonionic monomers and dimers, including, but not limiting to, Diatrizoate, Metrizoate, Isopaque, Ioxaglate, Iopamidol, Iohexol, and Iodixanol (Singh J. & Daftary A. J Nucl Med Technol 2008; 36:69-74; Stacul F. Eur Radiol 2001; 11:690-7). In particularly preferred embodiments, the metallic or non-metallic contrast agent is conjugated to a lipid component of the synthetic nanoparticle. Such a lipid component of the synthetic nanoparticle may selected from the group consisting of a sterol, a phospholipid, a sterol ester, a diacylglycerol and a triacylglycerol. In preferred embodiments the non-metallic contrast agent is 1-palmitoyl-2-((E)-10,11-diiodo-undec-10-enoyl)-sn-glycero-3-phosphocholine. In certain embodiments, the sterol of the imaging agent is cholesterol. In other embodiments, the sterol ester is cholesteryl ester. In still preferred embodiments, the metallic or non-metallic contrast agent is encapsulated into the synthetic nanoparticle.

In preferred embodiments, the metallic or non-metallic contrast agent is associated with a phospholipid and preferably, selected from the group consisting of phosphatidylcholine (PC), phosphatidylethanolamine (PE), phosphatidylserine (PS), phosphatidylinositol (PI), phosphatidylglycerol (PG), cardiolipin (CL), a sphinolipid, sphingomyelin (SM), and phosphatidic acid (PA). In particularly preferred embodiments, the phospholipid is PC. The PC (or indeed any other phospholipids) may comprise any fatty acid of e.g., between 4 and 24 carbon chains in length. The two fatty acids of the phospholipids may be the same or they may be different. In preferred embodiments, the PC is POPC. In yet other preferred embodiments, the phospholipid is PE. In specific embodiments, the phospholipid is dimyristoyl-PE (DMPE). In still other preferred embodiments, the phospholipid is a modified PE. Preferably, the modified PE is poly-lysine PE. In still other embodiments, the poly-lysine PE is poly-lysine dimyristoyl-PE.

It is contemplated that the metallic or non-metallic contrast agent may alternatively be conjugated to a modified protein component of the synthetic nanoparticle. Such a modified protein may be selected from the group consisting of a modified apo A-I or fragments thereof, a modified A-II or fragments thereof, and any combination of a modified apo A-I and a modified A-II and fragments thereof.

According to the present invention, a high density lipoprotein (HDL), e.g. nascent HDL, reconstituted HDL (rHDL), recombinant HDL or an HDL-like particle is particularly preferred which has a molar ratio of a modified apolipoprotein (selected the group consisting of a modified apo A-I or fragments thereof, a modified A-II or fragments thereof, and any combination of a modified apo A-I and a modified A-II and fragments thereof) and phospholipid in the range of 1:50 to 1:250, particularly about 1:150. Further, rHDL may optionally contain additional lipids such as cholesterol, cholesterol esters, triglycerides and/or sphingolipids, preferably in a molar ratio of up to 1:20, e.g. 1:5 to 1:20 based on the apolipoprotein. Preferred rHDL is described in Eur Pat EP-A-0663 407. Further, HDL-like particle may optionally contain 1,2-dioleoyl-3-trimethylammonium-propane (DOTAP) and cholesterol.

Production of reconstituted lipoprotein nanoparticles such as reconstituted high-density lipoproteins (rHDL) and other HDL-like nanoparticles is described, by way of example, in (US Pat Appl 20060217312; US Pat Appl 20060205643; U.S. Pat. No. 5,652,339; Lerch et al. Vox Sang 1996; 71:155-64; Matz C. E. & Jonas A. J Biol Chem 1982; 257:4535-40; Toledo et al. Arch Biochem Biophys 2000; 380:63-70; Sigalov A. B. & Stern L. J. Chem Phys Lipids 2001; 113:133-46; Kim et al. Journal of Hepatology 2009; 50:479-88; US Pat Appl 2009/0312402; U.S. Pat. No. 6,008, 202; Mukundan et al. AJR Am J Roentgenol 2006; 186:300-7; U.S. Pat. No. 7,588,751). Production of recombinant HDL is described, by way of example, in Eur Pat EP 469017 (in yeast), U.S. Pat. No. 6,559,284 (in *E. coli*), and WO 87/02062 (in *E. coli*, yeast and Cho cells) and WO 88/03166 (in *E. coli*). The contents of each of these documents are incorporated herein by reference. Preferably, the HDL is reconstituted HDL. In some aspects of the present invention, rHDL may be prepared from a modified apolipoprotein (selected the group consisting of a modified apo A-I or fragments thereof, a modified A-II or fragments thereof, and any combination of a modified apo A-I and a modified A-II and fragments thereof), and soybean-derived PC, mixed in molar ratios of approximately 1:150 apolipoprotein:PC.

In preferred embodiments, the synthetic nanoparticle in the imaging agent comprises a phospholipid:sterol:apolipoprotein ratio of 180:5:3 (mol:mol:mol). In other preferred embodiments, the synthetic nanoparticle in the imaging agent comprises a phospholipid:apolipoprotein ratio of 100:3 (mol:mol). In still preferred embodiments, the synthetic nanoparticle in the imaging agent comprises a phospholipid:steryl estersterol:triglycerides (TG):apo A-I ratio (w/w) of 100:62:25:11:2. In other preferred embodiments, the synthetic nanoparticle comprises a DOTAP:cholesterol ratio of 1:1 (mol:mol) and a lipid/apo A-I protein ratio of 10:1 (w/w).

In the imaging agents of the invention, at least one apolipoprotein molecule (or fragment thereof) per synthetic nanoparticle is modified. In specific embodiments, the imaging agent comprises between 1 and 50 metallic or non-metallic contrast agent molecules per synthetic nanoparticle. In various aspects of the invention, the metallic or non-metallic contrast agent molecule is conjugated to a phospholipid moiety and the phospholipid moiety accommodates more than one metallic or non-metallic agent molecule. In more specific aspects, the imaging agent comprises 10 metallic or non-metallic contrast agent molecules per synthetic nanoparticle. The imaging agent of the invention may comprise between about 80 and about 180 phospholipids per synthetic nanoparticle. Other embodiments define the imaging agent as comprising 2, 3 or 4 apolipoprotein molecules per synthetic nanoparticle. In still further embodiments, the synthetic nanoparticle comprises 1 apolipoprotein molecule to between about 30 and about 60 phospholipid molecules.

The imaging agents of the invention may further comprise an additional targeting moiety to further facilitate targeting of the agent to a specific site in vivo. The additional targeting moiety may be any moiety that is conventionally used to target an agent to a given in vivo site and may include but is not limited to, an antibody, a receptor, a ligand, a peptidomimetic agent, an aptamer, a polysaccharide, a drug and a product of phage display. In particular embodiments, the targeting moiety may be conjugated to a detectable label. For example, apo E-derived lipopeptide (Chen et al. Contrast Media Mol Imaging 2008; 3:233-42), an apo A-I mimetic peptide (Cormode et al. Small 2008; 4:1437-44), murine (MDA2 and E06) or human (IK17) antibodies that bind unique oxidation-specific epitopes (Briley-Saebo et al. Circulation 2008; 117:3206-15), USPIO particles (US Pat Appl 2009/0004113), and gold particles (Cormoe et al.

Radiology 2010; 256:774-82) may be used in the present invention to further improve specific targeting macrophages, decrease the required dosage of administered contrast agents including, but not limiting to, Gd-based contrast agents, and increase an image quality of vulnerable plaques.

Preferably, the diameter or the longest dimension of the nanoparticle is between about 5 nm to about 18 nm. The diameter may be between about 5 to about 12 mu. In particularly preferred embodiments, the diameter is less than 10 nm. In some embodiments the diameter is more than 100 nm.

The imaging agent may be one which comprises two or more different contrast agents. These two or more different contrast agents may all be metallic, all be non-metallic or the imaging agent may comprise some metallic contrast agents and some non-metallic contrast agents. In additional embodiments, the agent may further comprise a drug to be delivered at an in vivo site targeted by the targeting moiety.

Other aspects of the present application describe a pharmaceutical composition comprising an imaging agent as described herein and a pharmaceutically acceptable carrier or diluent.

Also contemplated are methods of in vivo imaging of a site within a subject comprising administering to the subject an imaging agent comprising a metallic or non-metallic contrast agent conjugated to component of a synthetic nanoparticle. The imaging agent of the invention used in such a method comprises a targeting moiety that specifically targets the imaging agent to the in vivo site. In specific embodiments, the in vivo site being imaged is the site of an atherosclerotic plaque. In specific embodiments, an additional targeting moiety is selected from the group consisting of antibodies against lipoprotein lipase, oxidized epitopes on atherosclerotic plaques oxLDL MDA, antibodies against matrix metalloproteinases and anti-tissue factor antibodies.

In other embodiments, the in vivo site is the site of a tumor and the additional targeting moiety comprises a moiety that recognizes a tumor-specific binding partner present on the tumor. More particularly, the binding partner is selected from the group consisting of an antibody against a tumor-specific antigen, a receptor for a ligand expressed by the tumor, a ligand for a receptor expressed on the tumor.

Further aspects of the invention are directed to methods of making an imaging composition, the method comprising: obtaining a composition comprising a phospholipid optionally covalently linked to a chelating moiety and reacting the composition with a composition comprising a first metallic or non-metallic contrast agent to produce a phospholipid-chelating (optionally) agent-metallic/non-metallic agent conjugate; co-sonicating the conjugate of step (a) with: a predetermined amount of HDL apolipoprotein; a predetermined amount of a mixture of phospholipids mixed in a ratio found in circulating HDL; a predetermined amount of sterol; and a predetermined amount of HDL core lipids comprising triglycerides (TAG) and cholesteryl ester in a ratio found in circulating HDL; for a time period sufficient to allow the conjugate and the individual components of nanoparticle to coalesce into nanoparticulate structures; and isolating structures that have a size of between about 5 to about 12 nm diameter. In preferred embodiments, the first metallic contrast agent is selected from the group consisting of Gd(III), Mn(II), Mn(III), Cr(II), Cr(III), Cu(III), Fe(III), Pr(III), Nd(III) Sm(III), Tb(III), Yb(III) Dy(III), Ho(III), Eu(II), Eu(III), and Er(III), $Tl^{201}$, $K^{42}$, $In^{111}$, $Fe.^{59}$, $Tc^{99m}$, $Cr^{51}$, $Ga^{67}$, $Ga^{68}$, $Cu^{64}$, $Rb^{82}$, $Mo^{99}$, $Dy^{165}$. The first non-metallic contrast agent is selected from the group consisting of Fluorescein, Carboxyfluorescein, Calcein, $F^{18}$, $Xe^{133}$, $I^{125}$, $I^{131}$, $I^{123}$, $P^{32}$, $C^{11}$, $N^{13}$, $O^{15}$, $Br^{76}$, $Kr^{81}$. The non-metallic contrast agent may still preferably be selected from the group of iodinated contrast media consisting of ionic monomers and dimers, and nonionic monomers and dimers, including, but not limiting to, Diatrizoate, Metrizoate, Isopaque, Ioxaglate, Iopamidol, Iohexol, and Iodixanol (Singh J. & Daftary A. J Nucl Med Technol 2008; 36:69-74; Stacul F. Eur Radiol 2001; 11:690-7).

The methods of the making the compositions may further comprise providing a second phospholipid-chelating agent-metallic or non-metallic contrast agent, wherein the second contrast agent is different from the first contrast agent. In exemplary embodiments, one of the contrast agents may be a metallic agent whereas the second contrast agent is a non-metallic agent. In those embodiments that employ a chelating agent, the chelating agent preferably is selected from the group consisting of DTPA, EDTA, BOPTA, DOTA, DO3A and aDO3A. In preferred embodiments, the sterol component is selected from the group consisting of cholesterol, stigmasterol, ergosterol, lanosterol, and sitosterol. In other preferred embodiments, the phospholipid in the phospholipid-chelating agent-metallic (or non-metallic) contrast agent conjugate is selected from the group consisting of consisting of PC, PE, PS, PI, PG, CL, SM and PA. Preferably, the phospholipid mixture is a mixture of two or more phospholipids selected from the group consisting of consisting of PC, PE, PS, PI, PG, CL, SM and PA.

In preferred embodiments, the phospholipids, sterol, and apolipoprotein are mixed in a phospholipid:sterol:apolipoprotein ratio of 180:5:3 (mol:mol:mol). In other preferred embodiments, the phospholipids and apolipoprotein are mixed in a phospholipid:apolipoprotein ratio of 100:3 (mol:mol). In other preferred embodiments, the phospholipids, core lipids, sterol, and apolipoprotein are mixed in a phospholipids:steryl ester:sterol:TG:apo A-I (w/w) of 100:62:25:11:2. In preferred embodiments, the method produces reconstituted synthetic nanoparticle particles that comprise between about 80 and about 180 phospholipids per synthetic nanoparticle. Preferably, the method produces a lipoprotein nanoparticle that comprise 2, 3 or 4 apolipoprotein molecules at least one of which is modified per synthetic particle. Still preferably, the method produces nanoparticle that comprises 1 apolipoprotein molecule to between about 30 and about 60 phospholipid molecules. The methods are used to produce synthetic nanoparticle that comprise between 1 and 30 metallic contrast ions per synthetic nanoparticle. In specific embodiments, the phospholipid covalently linked to a chelating moiety is a modified phospholipid that can accommodate more than one metallic or non-metallic contrast agent. Preferably, the modified phospholipid is a poly-L-lysine-PE. Still more preferably, the poly-L-lysine-PE is dimyristoyl-poly-L-lysine. In preferred aspects the method further comprises obtaining a composition comprising a biotinylated phospholipid reacting the composition with a composition comprising an additional targeting agent to produce a phospholipid-targeting agent conjugate, and providing the phospholipid-targeting agent conjugate in the co-sonicating mixture.

In still preferred embodiments, a typical liposomal HDL-like composition comprises a lipid or phospholipid, a stabilizing excipient such as cholesterol, a polymer-derivatized phospholipid, and apolipoprotein. Suitable examples of lipids or phospholipids, stabilizing excipients, and polymer-derivatized phospholipids are set forth in, for example, US Pat Appls 20090311191 and 20100202974, all of which are incorporated by reference in their entireties herein. The liposomal HDL-like compositions typically encapsulate or associate a contrast agent. It should be noted that for purposes of the present application, the identity of the contrast agent is not of substantial importance. Rather, the modified apolipoprotein, the liposome composition (e.g., cholesterol; at least one phospholipid; and at least one phospholipid which is derivatized with a polymer chain) and the small size (e.g., less than 150 nm, as described below) provide the desired localization. In some aspects of the present invention, the liposomal HDL-like compositions may be prepared from a modified apolipoprotein selected the group consisting of a modified apo A-I or fragments thereof, a modified A-II or fragments thereof and any combination of a modified apo A-I and a modified A-II and fragments thereof. Nonetheless, suitable contrast agents include, for example, fluorescent dyes, such as, for example, fluorescein iso-thiocynate (FITC) and rhodamine; CT contrast agents including iodinated compounds such as iohexol, iodixanol, and iotrolan, and as otherwise described in US Pat Appl 20100202974, US Pat Appl 20090311191, U.S. Pat. No. 7,588,751, and U.S. patent application Ser. Nos. 10/830,190, 11/595,808, and 11/568,936; and MRI contrast agents including lanthanide aminocarboxylate complexes such as Gadolinium (III) DTPA, Gd-DOTA, Gd-DOTAP, and Gd-DOTMA.

Also contemplated herein are diagnostic kits comprising a metallic or non-metallic contrast agent conjugated to component of the composition of the invention in a pharmaceutically acceptable carrier or diluent; and a device for delivering the composition to a subject prior to diagnostic imaging of the subject. Other kits contemplated herein are kits for producing an imaging agent the kit comprising a first composition comprising a metallic or non-metallic contrast agent; a second composition comprising a phospholipid covalently linked to a chelating moiety; a third composition comprising apolipoproteins A-I and A-II; and a fourth composition comprising free phospholipid. In addition, the kits may comprise instructions for reconstituting HDL. Preferred metallic agents for the first composition include but are not limited to, Gd(III), Mn(II), Mn(III), Cr(II), Cr(III), Cu(II), Fe(III), Pr(III), Nd(III) Sm(III), Tb(III), Yb(III) Dy(III), Ho(III), Eu(II), Eu(III), and Er(III), $Tl^{201}$, $K^{42}$, $In^{111}$, $Fe.^{59}$, $Tc^{99m}$, $Cr^{51}$, $Ga^{67}$, $Ga^{68}$, $Cu^{64}$, $Rb^{82}$, $Mo^{99}$, $Dy^{165}$. In addition, the metallic contrast agents include crystals and other particulate materials (oxides, quantum dots, etc.). Preferred non-metallic agents for the first composition include but are not limited to Fluorescein, Carboxyfluorescein, Calcein, $F^{18}$, $Xe^{133}$, $I^{125}$, $I^{131}$, $I^{123}$, $P^{32}$, $C^{11}$, $N^{13}$, $O^{15}$, $Br^{76}$, $Kr^{81}$. The non-metallic contrast agent for the first composition may still preferably be selected from the group of iodinated contrast media consisting of ionic monomers and dimers, and nonionic monomers and dimers, including, but not limiting to, Diatrizoate, Metrizoate, Isopaque, Ioxaglate, Iopamidol, Iohexol, and Iodixanol (Singh J. & Daftary A. J Nucl Med Technol 2008; 36:69-74; Stacul F. Eur Radiol 2001; 11:690-7).

Any contrast agent that is employed in MRI, CT, Gamma-scintigraphy, or optical imaging techniques may be used in the present invention. The kits may further comprise a fifth composition comprising sterol, such as e.g., cholesterol, stigmasterol, ergosterol, lanosterol, and sitosterol. The kits may further comprise a sixth composition comprising a HDL core lipids. In particular aspects, the fourth composition comprising the phospholipid comprises either individually or as a mixture one or more phospholipids selected from the group consisting of consisting of PC, PE, PS, PI, PG, CL, SM and PA. In certain embodiments, the phospholipids is covalently linked to a chelating moiety such as e.g., DTPA, EDTA, BOPTA, DOTA, DO3A and aDO3A.

Preferably, the second phospholipid composition is a poly-L-lysine-PE. More particularly, poly-L-lysine-PE is poly-L-lysine-DMPE. As used herein the "core lipids" are those lipids that form the core of the nanoparticle. Preferably, the core lipids comprise cholesteryl ester and/or TG.

Figure 2A:
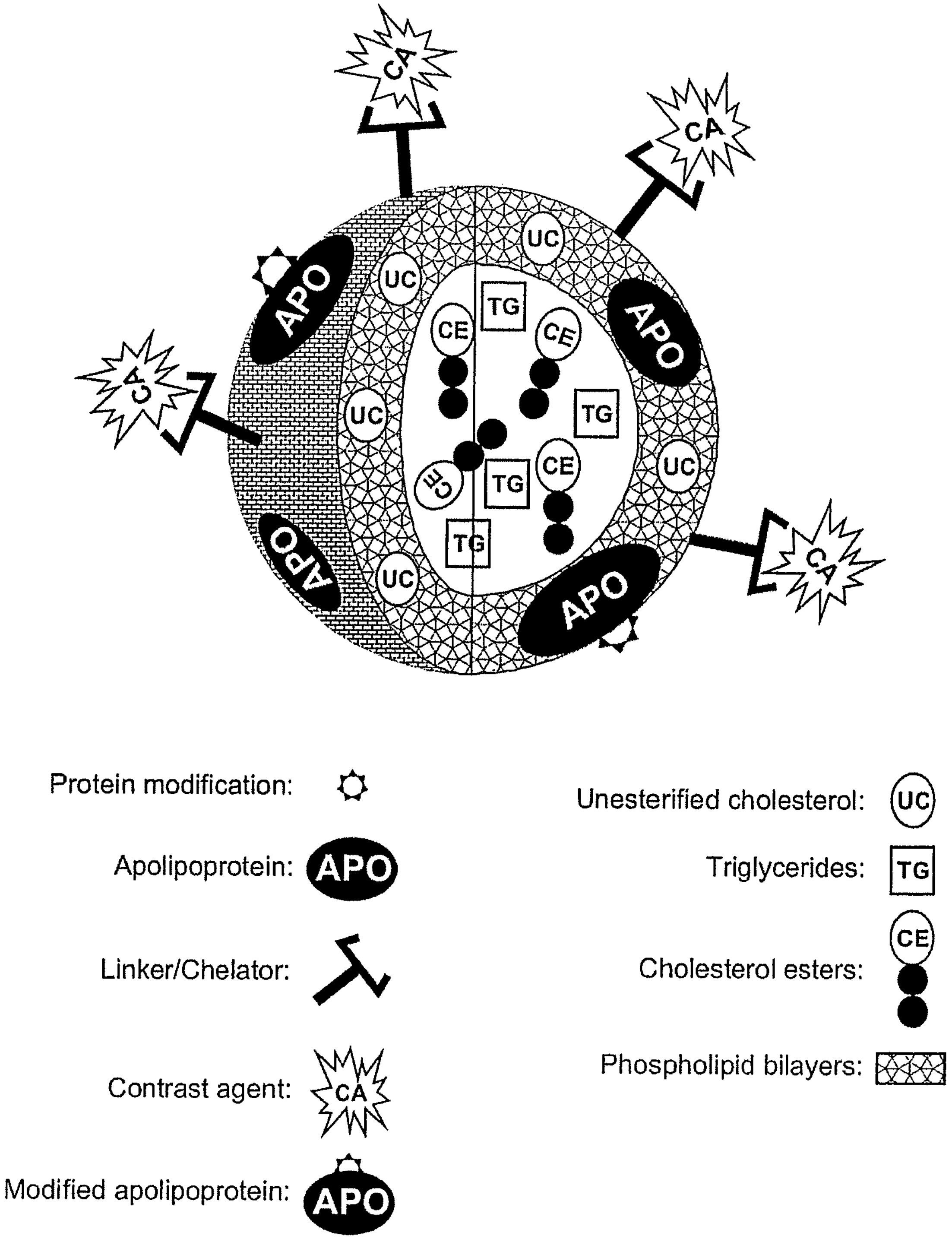
FIG. 2A presents a schematic representation of one embodiment of a spherical imaging agent of the present invention with surface-bound contrast agents. Chelated contrast agent is shown for illustrative purposes. The contrast agent may or may not be the chelated one.
Figure 2B:
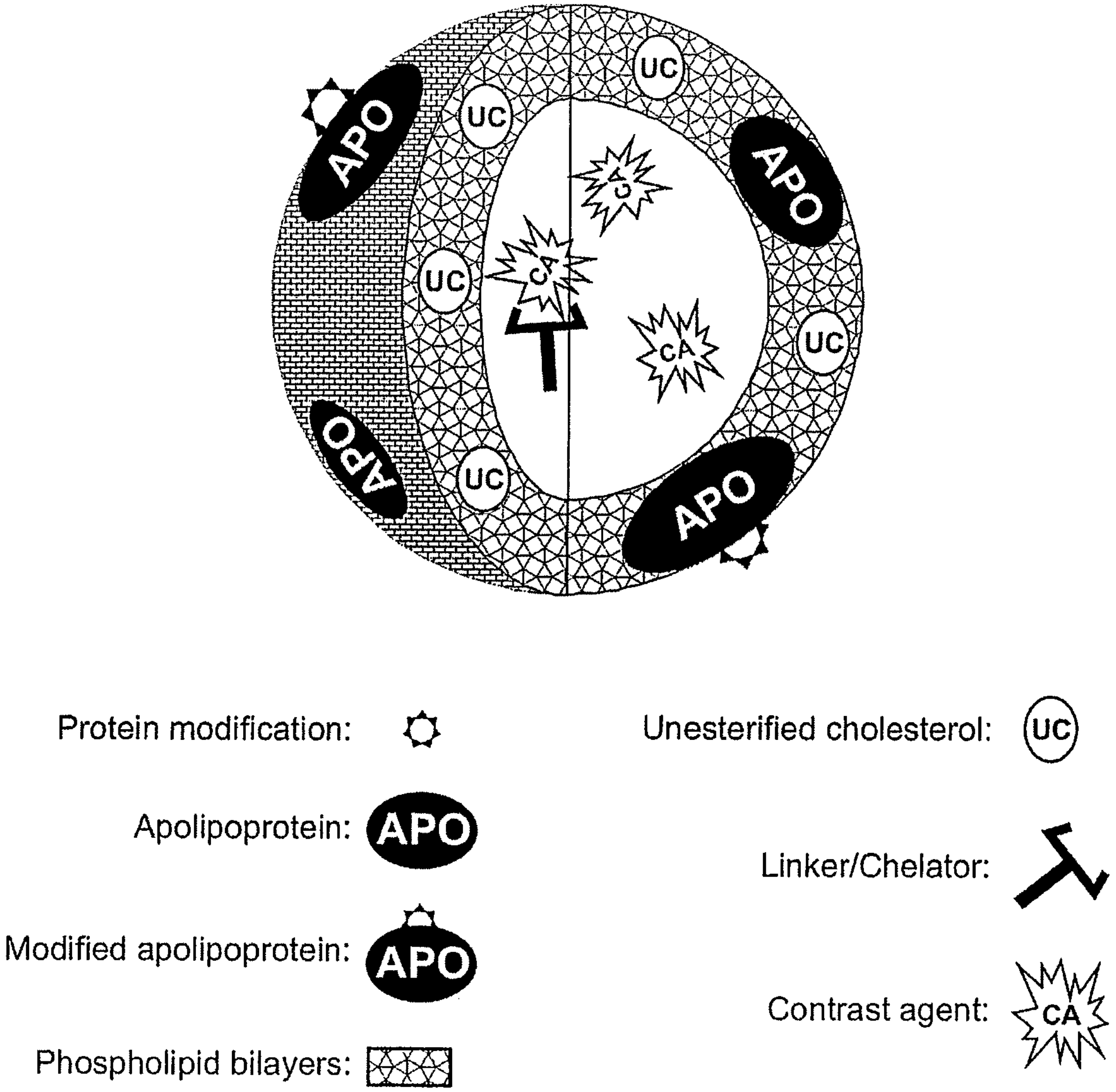
FIG. 2B presents a schematic representation of one embodiment of a spherical imaging agent of the present invention with encapsulated contrast agents. Chelated contrast agent is shown for illustrative purposes. The contrast agent may or may not be the chelated one.
Figure 3A:
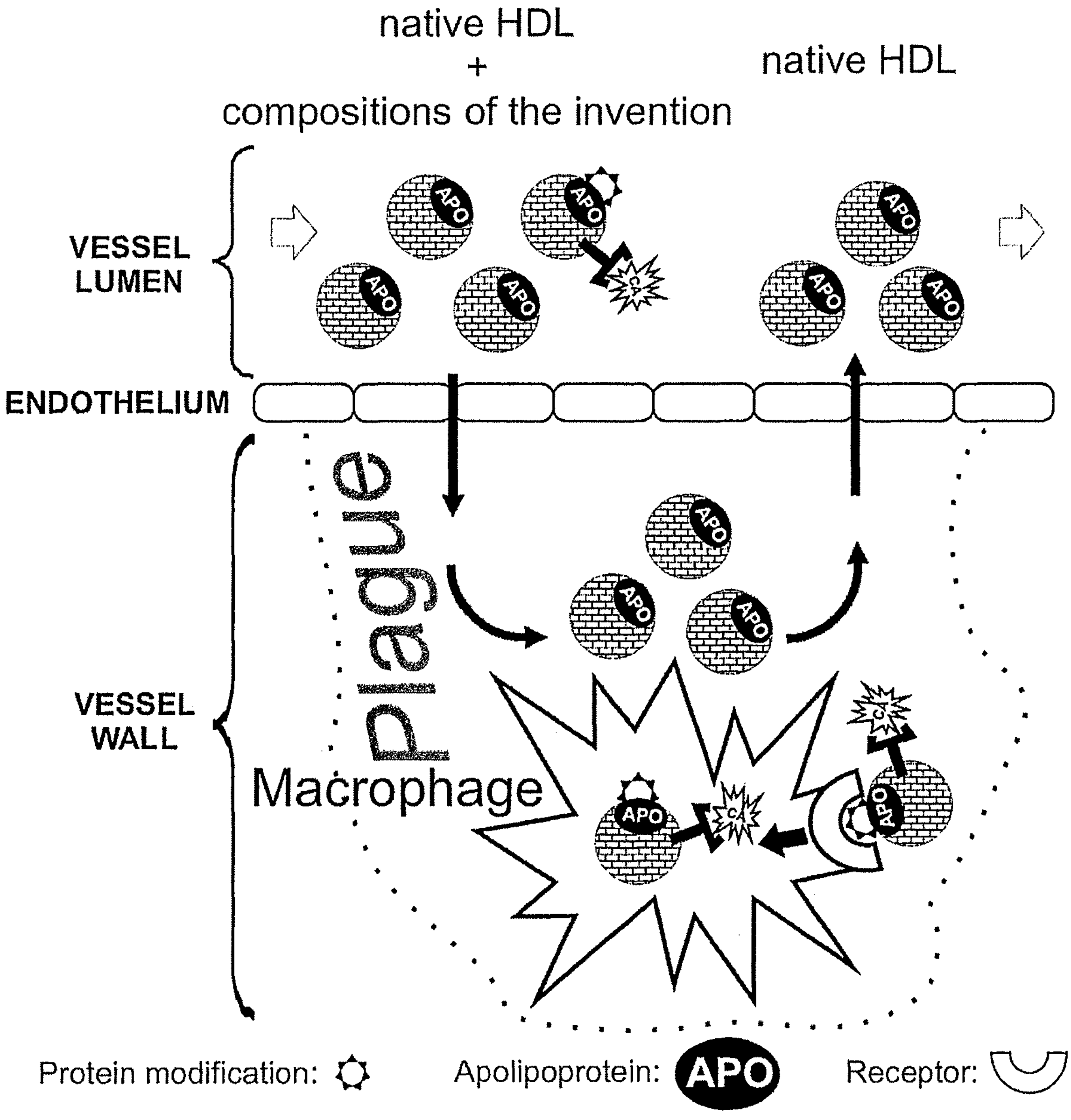
FIG. 3A illustrates a hypothesized molecular mechanism of action of an imaging agent of the present invention as applied to cardiovascular imaging. While not being bound to any particular theory, it is believed that chemical and/or enzymatic modification of protein constituents of high density lipoprotein (HDL) particles of the present invention leads to the recognition of these particles by the macrophage scavenger receptors and results in an irreversible binding to and consequent uptake by macrophages of such HDL particles. It is further believed that accumulation of these particles in the macrophages is accompanied by accumulation of contrast agents (CAs) covalently or non-covalently bound to the particles. In contrast, HDL particles that contain only unmodified apolipoprotein molecules are not recognized by macrophages and return to the circulation. Chelated contrast agent is shown for illustrative purposes. The contrast agent may or may not be the chelated one.
Figure 3B:
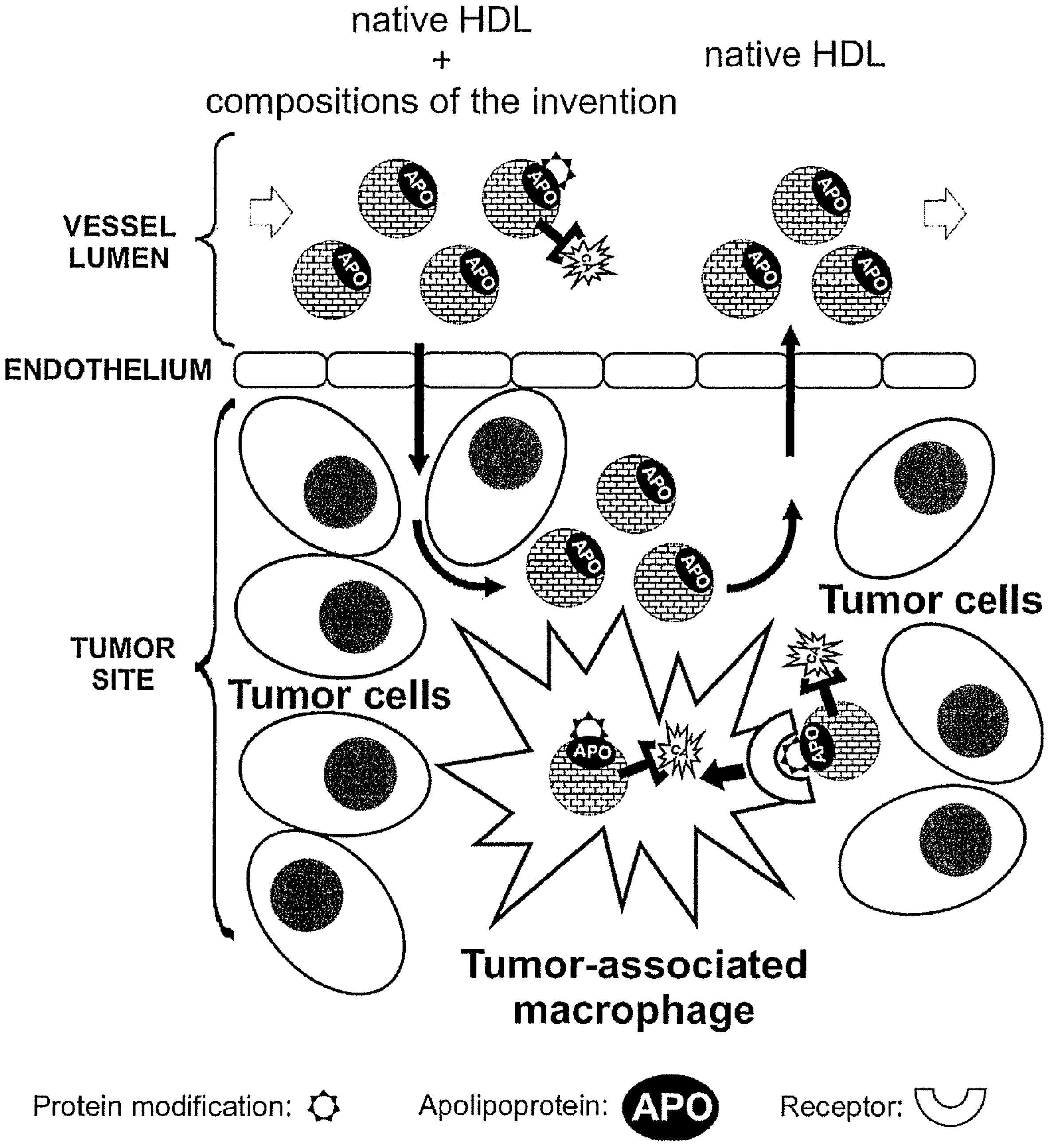
FIG. 3B illustrates a hypothesized molecular mechanism of action of an imaging agent of the present invention as applied to cancer imaging. While not being bound to any particular theory, it is believed that chemical and/or enzymatic modification of protein constituents of high density lipoprotein (HDL) particles of the present invention leads to the recognition of these particles by the macrophage scavenger receptors and results in an irreversible binding to and consequent uptake by tumor-associated macrophages of such HDL particles. It is further believed that accumulation of these particles in the macrophages is accompanied by accumulation of contrast agents (CAs) covalently or non-covalently bound to the particles. In contrast, HDL particles that contain only unmodified apolipoprotein molecules are not recognized by macrophages and return to the circulation. Chelated contrast agent is shown for illustrative purposes. The contrast agent may or may not be the chelated one.

The present invention addresses this need by providing reconstituted high density lipoprotein (rHDL) particles and liposomal HDL-like compositions that contain modified apolipoproteins or fragments thereof (FIGS. 1, 2A, and 2B). The particles of the invention are used for targeted delivery of imaging contrast agents conjugated to a component (or components) of rHDL to sites of interest. By "rHDL" it should be understood that the present invention contemplates a synthetic molecule that exhibits some of the characteristics and features of plasma-derived HDL moieties (e.g., small diameter, non-atherogenic, ability to promote cholesterol efflux, stability, etc.) but is a synthetic molecule and is not formed from plasma HDL. Commercial sources of HDL include: Biodesign International; Athens Research and Technology; Intracel Corp; Scripps Laboratories; Academy Biomedical Co; CSL Behring AG, Pfizer, Inc. Thus, the compositions of the present invention comprise a contrast agent-containing synthetic rHDL moiety, major protein constituents of which, apolipoproteins, or fragments thereof are modified in a means for converting them into targeting moieties (for example, into substrates for macrophages) for targeted delivery of rHDL-associated contrast agents to sites of interest (for example, an atherosclerotic plaque). The use of synthetic rHDL containing modified apolipoproteins or fragments thereof for imaging in vivo sites is advantageous because after administration, most of these particles get bound and/or uptaken by cells at sites of interest (FIGS. 3A and 3B). This allows a significant reduction in the contrast agent dosage required and thereby limits concerns related to systemic toxicity reduce the contrast agent dosage required and thus limit concerns related to systemic toxicity, which is especially important for Gd-based contrast agents.

Native HDL that contain unmodified lipids and apolipoproteins are not recognized by macrophage scavenger receptors (Platt N. and Gordon S. J Clin Invest 2001; 108:649-54). As a result, native HDL do not irreversibly bind to macrophages and are not uptaken by macrophages. In contrast, modified (for example, oxidized) HDL are readily absorbed by macrophages resulting to accumulation of the modified HDL and their components such in macrophage-enriched atherosclerotic plaques (Bergt et al. Eur J Biochem 2001; 268:3523-31; Bergt et al. Biochem J 200; 346 Pt 2:345-54; Bergt et al. Arterioscler Thromb Vase Biol 2003; 23:1488-90; Bergt et al. Proc Natl Acad Sci USA 2004; 101:13032-7; Bergt et al. FEBS Lett 1999; 452:295-300; Pankhurst et al. J Lipid Res 2003; 44:349-55; Panzenboeck et al. J Biol Chem 1997; 272:29711-20). Further, oxidation of native HDL by a natively occurring oxidative system, the myeloperoxidase/hydrogen peroxide/chloride system, results in oxidative modification of both lipid and protein constituents of HDL (Panzenboeck et al. J Biol Chem 1997; 272:29711-20; Bergt et al. Eur J Biochem 2001; 268:3523-31). In line with this, both oxidized lipids and oxidatively damaged apolipoprotein A-I molecules such as apolipoprotein $A\text{-}I_{+32}$ (containing two sulfoxidized methionine residues) and apolipoprotein moieties containing 3-Chloro- or 3-Nitrotyrosine residue at position 192 have been found in atherosclerotic plaques (Pankhurst et al. J Lipid Res 2003; 44:349-55; Bergt et al. Proc Natl Acad Sci USA 2004; 101:13032-7; Hazen S. L. & Heinecke J. W. J Clin Invest 1997; 99:2075-81; Hazen et al. Circ Res 1999; 85:950-8; Malle et al. Biochem Biophys Res Commun 2001; 289:894-900). As described herein, it is unexpectedly found that oxidative modification of only protein constituents or peptide fragments thereof of rHDL is sufficient to convert these particles to substrates for macrophage scavenger receptors and to result therefore in the improvement of association of Gd-(HDL/modified apolipoprotein)-particle with macrophages and/or absorption (uptake) of Gd-(HDL/modified apolipoprotein)-particle by macrophages when compared to that of the Gd-(HDL/apolipoprotein)-particle constructed with non-modified naturally occurring apo A-I, apo A-II or fragments thereof. Compositions of the invention, rHDL, contain certain chemical or enzymatic modification of apolipoproteins (apo) A-I or A-II or fragments thereof and can be easily and reproducibly produced. These advantageous compositions are demonstrated by the present invention to solve numerous problems which otherwise are associated with high dosages of Gd required and the lack of control and reproducibility of formulations, especially in large-scale production.

In addition, the particles of the present invention have all other known advantages of synthetic rHDL conjugated to contrast agents (US Pat Appl 20070243136): first, of all of the lipoprotein compositions, rHDL are the easiest to reproducibly reconstitute, and they are sufficiently small (about 10 nm diameter) (Rensen et al. Adv Drug Deliv Rev 2001; 47:251-76) to penetrate readily into the extracellular space and freely enter and exit sites such as the sites of atherosclerotic plaques (Sloop et al. J Lipid Res 1987; 28:225-37; O'Brien et al. Circulation 1998; 98, 519-27; Kunjathoor et al. Arterioscler Thromb Vase Biol 2002; 22:462-8). Second, rHDL has the advantage of not being atherogenic and, therefore, will not pose the same cardiovascular risks that might be associated with the use of LDL moieties. Moreover, unlike LDL moieties and micelles, the HDL moieties are not retained at the in vivo site for prolonged periods of time.

The preferred particles of the invention comprise at least one modified apolipoprotein A-I and/or A-II or peptide fragments thereof and at least one amphipathic lipid, to form a structure that can be spherical or discoidal. To readily penetrate into the interstitial fluid, the particles must be 25 nm or less in diameter, if spherical, or 25 nm or less in their longest dimension, if discoidal. For structural stability, ease of manufacture, and ability to carry significant amounts of contrast and/or targeting agents, the particles should be at least 5 nm in their largest dimension. Furthermore, to carry large amounts of a contrast agent, said agent is incorporated through the inclusion of an amphipathic chelator, that is, a molecule that has a hydrophobic portion that incorporates into the particle, and a chelating portion that binds an MRI contrast agent.

The inclusion of an amphipathic protein or peptide aids the structural stability of the particle, particularly when the particle has a discoidal shape. Exemplary proteins or peptides are selected from the major protein constituents of HDL, an apolipoprotein A-I, an apolipoprotein A-II, and peptide fragments thereof. Apolipoproteins that may be used herein are commercially available from e.g., Biodesign International; Athens Research and Technology; Intracel Corp; Scripps Laboratories; Academy Biomedical Co). Alternatively, standard procedures that are well known in the art can be used to isolate and purify apolipoproteins A-I and A-II from human serum (Sigalov et al. J Chromatogr 1991; 537, 464-8). One skilled in the art, using the known primary sequences of apolipoproteins A-I and A-II, can easily synthesize the peptide fragments of this invention. Standard procedures for preparing synthetic peptides are well known in the art. The fragments can be synthesized using the solid phase peptide synthesis method of Merrifield (Merrifield, R. B. Biochemistry 1964; 3:1385-90), which is incorporated herein by reference) or modifications of this method. The inclusion of an amphipathic lipid creates a hydrophobic zone within the particle that allows the incorporation of an amphipathic chelator or other attaching agent. Lipids that may be used herein are commercially available from e.g., Avanti Polar Lipids.

The hydrophobic zone also allows the incorporation of an amphipathic complex that comprises an additional targeting agent. Said complexes include, but are not limited to, an amphipathic lipid covalently linked to an antibody; and an amphipathic lipid covalently linked to an avidin, which is then non-covalently linked to a biotinylated antibody. Other complexes include polylysine phospholipids-Gd complexes in which the additional targeting moiety is provided. Other complexes include 1-palmitoyl-2-((E)-10,11-diiodo-undec-10-enoyl)-sn-glycero-3-phosphocholine as described in (Elrod et al. Nanomedicine: Nanotech, Biol and Med 2009; 5:42-5).

Apolipoproteins and fragments thereof of the present invention must be modified first and then used (alone or in combination with unmodified apolipoprotein molecules and fragments thereof) for reconstitution of rHDL particles rather than modified in the context of assembled HDL particles. The use of preliminary modified apolipoproteins and fragments thereof of the invention is advantageous for several reason. Firstly, it is well known in the art that modification, for example, of lipid-free and lipid-bound apolipoprotein A-I affects discrete regions of the proteins and cannot be controlled for lipid-bound protein (Bergt et al. Biochem J 200; 346 Pt 2:345-54). Secondly, modified lipid-free protein can be easily purified and well characterized using standard procedures well known in the art. Thirdly, having only one molecule of modified apolipoprotein A-I, modified apolipoprotein A-II, or modified fragments thereof of the present invention per rHDL particle is sufficient to target this particle to sites of interests, for example, to macrophages of atherosclerotic plaques. Thus, the structural stability of the particle can be provided by other, unmodified apolipoprotein molecules, minimizing any potential side effects of modified proteins of the invention. Exemplary methods of modifying and purifying the apolipoproteins and fragments thereof of the invention are described in further detail in the examples herein below.

Finally, for several reasons, the rHDL particles must be synthetic rather than isolated from human plasma. In particular, the use of naturally occurring lipoproteins isolated from human plasma is not contemplated, rather the rHDL particles described herein are synthetic. The use of synthetic molecules have a number of potential advantages. Firstly, the use of such molecules avoids transmission of blood-borne infectious agents, which are frequently present in conventionally isolated human plasma lipoproteins. Secondly, isolation of large quantities of human plasma lipoproteins is impractical and expensive, because it requires large amounts of human plasma as starting material and then tedious isolation procedures. Thirdly, human plasma lipoproteins vary substantially from batch to batch, depending on the individual donor(s), recent dietary intake, and other factors. Fourthly, synthetic particles allows the skilled artisan to circumvent the problems of oxidized or readily oxidizable lipids, such as highly unsaturated lipids. Oxidized or readily oxidizable lipids can be toxic and can impair stability during storage. As noted elsewhere, the preferred amphipathic lipid is POPC, which is relatively resistant to oxidation and is readily available commercially in pure form. Fifthly, incorporation of large amounts of contrast agents and/or targeting agents into a pre-existing lipoprotein is difficult, if not impossible, without significant disruption of said pre-existing lipoprotein. Exemplary methods of forming the synthetic rHDL compositions of the invention using modified apolipoproteins and fragments thereof of the invention are described in further detail in the examples herein below.

In particularly preferred aspects of the invention the synthetic rHDL are reconstituted with the contrast agent, modified apolipoproteins and fragments thereof, and a second agent that allows the additional targeting of the imaging composition to a specific site. While some of the discussion herein focuses on atherosclerotic plaques, it should be understood that other sites in the body also may be targeted with the compositions of the invention. These compositions of the invention are able to locate to a specific target site and produce a desirable result of a large increase in signal intensity from plaque retention of the synthetic rHDL because of the presence of a specific targeting molecule of interest. This is of particular interest because it has previously been noted that, for example, in atherosclerotic plaques HDL is very inefficiently retained in the plaque site. Although it may be possible to increase the retention of HDL moiety by increasing the relative amount of apo E or C-reactive protein present in the HDL, it is contemplated that the presence of the targeting moieties comprised of chemically or enzymatically modified apolipoproteins or fragments thereof is advantageous because it facilitates the controlled retention of the imaging agent at the site of interest, thereby promoting an increase in the signal at that site. The presence of an additional targeting moiety can further facilitate the controlled retention of the imaging agent at the site of interest, thereby further promoting an increase in the signal at that site as compared to use of the modified apolipoproteins and fragments thereof alone.

As described herein it is unexpectedly found that the targeted MRI contrast compositions can be formulated as conjugates of a component of a synthetic rHDL composition comprised of chemically or enzymatically modified apolipoproteins or fragments thereof of the present invention. These metal imaging agents are useful in all areas of diagnostics that can employ MRI imaging of a given tissue or in vivo site. In exemplary embodiments, the compositions of the present invention are generated by incorporating a paramagnetic metal ion complexed with a chelating agent having a lipophilic moiety, into synthetic rHDL moieties of the invention. Preferably, the chelating agent is a polyaminopolycarboxylate chelating agent. Further, it is preferred that there are multiple metal ions complexed per synthetic rHDL entity. The lipophilic paramagnetic chelate that serves as the metallic contrast agent will preferably be conjugated to a phospholipid moiety. As phospholipids are an integral are relatively easily incorporated into synthetic rHDL moieties, and so the metal contrast agent is thus easily incorporated into the synthetic rHDL compositions of the present invention. The entire complex which contains the HDL reconstituted using modified apolipoproteins and fragments thereof as targeting moieties and the metal contrast agent, and optionally also contains an additional targeting moiety, is referred to herein as an "imaging agent."

Advantageously, complexing the metallic contrast agent in the manner described herein eliminates or reduces the toxicity and other undesirable side effects of the metallic agent whilst at the same time retaining the paramagnetic properties of the metal ion that confer the imaging action of the paramagnetic ion, i.e., change in relaxivity of the hydrogen atoms of water. As discussed herein below, numerous chelating agents may be used to produce a paramagnetic ion composition that would be suitable for reconstitution in synthetic rHDL compositions herein. However, it is envisioned that polyaminopolycarboxylic acids will be particularly useful for complexing the paramagnetic ions intended for MRI imaging of human or animal body.

Methods and compositions for making and using the imaging agents of the present invention are described in further detail herein below. As described herein it was unexpectedly found that the MRI contrast compositions formulated as conjugates of a component of a synthetic rHDL composition (US Pat Appl 20070243136) can be specifically targeted to sites of interest by chemical or enzymatic modification of the major protein constituents of HDL, apolipoproteins A-I and A-II, or fragments thereof, solving therefore numerous problems which otherwise are associated with high dosages of Gd required and the lack of control and reproducibility of formulations, especially in large-scale production. These metal imaging agents are useful in all areas of diagnostics that can employ MRI imaging of a given tissue or in vivo site.

A. Apolipoproteins and Apolipoprotein Peptides

In the methods of the present invention, the lipoproteins of interest are HDLs and their synthetic reconstituted analogues. The functional characteristics of HDL particles are mainly determined by their major apolipoprotein (apo) components such as apo A-I and A-II. Each HDL particle usually comprises at least 1 molecule, and usually two to 4 molecules, of apo A-I. Apo A-I is synthesized by the liver and small intestine as preproapolipoprotein A-I, which is secreted as proapolipoprotein A-I (proApoA-I) and rapidly cleaved to generate the plasma form of ApoA-I, a single polypeptide chain of 243 amino acids (Brewer et al. Biochem Biophys Res Commun 1978; 80:623-30). Apo A-I comprises 6 to 8 different 22-amino acid alpha-helices or functional repeats spaced by a linker moiety that is frequently proline. The repeat units exist in amphipathic helical conformation (Segrest et al. FEBS Lett 1974; 38:247-58) and confer the main biological activities of apo A-I, i.e., lipid binding and lecithin cholesterol acyl transferase (LCAT) activation. Apo A-I plays an important role in lipid transport and metabolism. It promotes cholesterol efflux (Chambenoit et al. J Biol Chem 2001; 276:9955-60; Rothblat et al. J Lipid Res 1992; 33:1091-7), acts as a cofactor for the LCAT enzyme (Jonas et al. Biochim Biophys Acta 1993; 1166: 202-10; Frank et al. Biochemistry 1998; 37:13902-9) and as a ligand that binds to the class B scavenger receptor SR-BI (Acton et al. Science 1996; 271:518-20). Apo A-I shows endotoxin neutralization (Massamiri et al. J Lipid Res 1997; 38:516-25) and also protects against the cytotoxic effects of oxidized LDL (Suc et al. Arterioscler Thromb Vasc Biol 1997; 17:2158-66).

The nature of the apolipoproteins comprising the apolipoprotein fraction of the compositions of the present invention is not critical for success. Examples of suitable apolipoproteins include, but are not limited to, preproapolipoprotein forms of apoA-I and apoA-II; pro- and mature forms of human apoA-I and apoA-II; and active polymorphic forms, isoforms, variants and mutants as well as truncated forms, the most common of which are apoA-$I_{Milano}$ and apoA-$I_P$, as disclosed in US Pat Appl 20060217312, the disclosure of which is incorporated herein by reference. Apolipoproteins mutants containing cysteine residues are also known, and can also be used (see, e.g., US Pat Appl 20030181372). The apolipoproteins may be in the form of monomers or dimers, which may be homodimers or heterodimers. For example, homo- and heterodimers (where feasible) of pro- and mature apoA-I (Duverger et al. Arterioscler Thromb Vasc Biol 1996; 16:1424-9), apoA-$I_{Milano}$ (Franceschini et al. J Biol Chem 1985; 260:16321-5), apoA-$I_P$ (Daum et al. J Mol Med 1999; 77:614-22), and apoA-II (Shelness G. S. & Williams D. L. J Biol Chem 1984; 259:9929-35; Shelness G. S. & Williams D. L. J Biol Chem 1985; 260:8637-46) may be used. The apolipoproteins may include residues corresponding to elements that facilitate their isolation, such as His tags, or other elements designed for other purposes, so long as the apolipoprotein retains some biological activity when included in a complex.

Such apolipoproteins can be purified from animal sources (and in particular from human sources) or produced recombinantly as is well-known in the art (see, e.g., Sigalov et al. J Chromatogr 1991; 537:464-8; Chung et al. J Lipid Res 1980; 21:284-91; Cheung et al. J Lipid Res 1987; 28:913-29; see also U.S. Pat. Nos. 5,059,528, 5,128,318, 6,617,134, and U.S. Pat Appls 20020156007, 20040067873, 20040077541, and 20040266660).

Non-limiting examples of peptides and peptide analogs that correspond to apoA-I, apoA-$I_{Milano}$, and apoA-II, and are suitable for enzymatic and/or chemical modifications and subsequent use as peptide fragments of modified apolipoproteins in the complexes and compositions described herein are disclosed in U.S. Pat. Nos. 6,004,925, 6,037,323 and 6,046,166, 5,840,688, US Appls 20040266671, 20040254120, 20030171277, 20030045460, 20030087819, and 20060217312, the disclosures of which are incorporated herein by reference in their entities. These peptides and peptide analogues can be composed of L-amino acid or D-amino acids or mixture of L- and D-amino acids. They may also include one or more non-peptide or amide linkages, such as one or more well-known peptide/amide isosteres. Such "peptide and/or peptide mimetic" apolipoproteins can be synthesized or manufactured using any technique for peptide synthesis known in the art, including, e.g., the techniques described in U.S. Pat. Nos. 6,004,925, 6,037,323 and 6,046,166.

The complexes and compositions of the present invention may include a single type of apolipoprotein and/or peptide fragments thereof, or mixtures of two different apolipoproteins and peptide fragments thereof, which may be derived from the same or different species. Although not required, the charged lipoprotein complexes will preferably comprise apolipoproteins that are derived from, or correspond in amino acid sequence to, the animal species being treated, in order to avoid inducing an immune response to the therapy. The use of peptide mimetic apolipoproteins may also reduce or avoid an immune response.

B. Modified Apolipoproteins and Apolipoprotein Peptides

Figure 4:
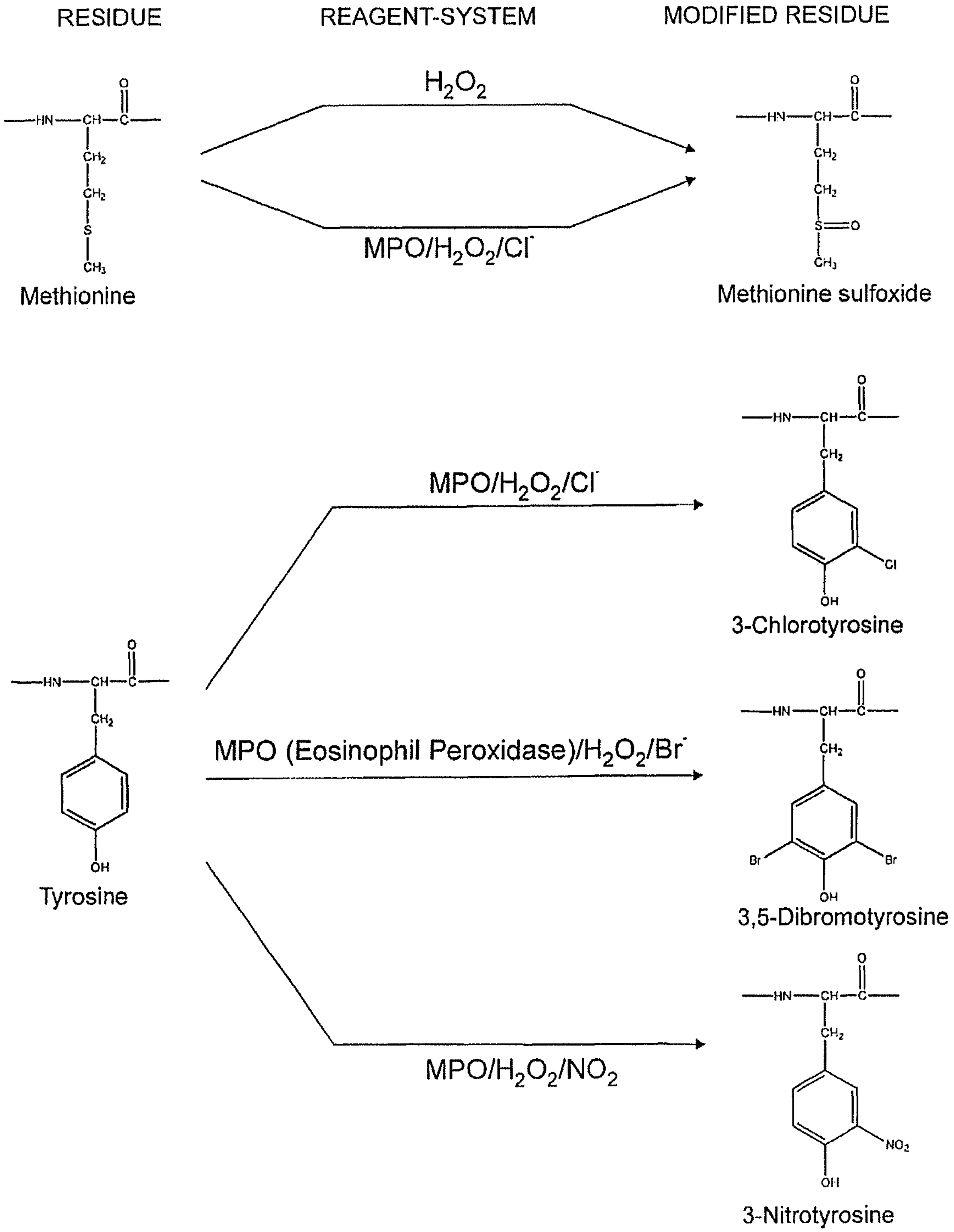
FIG. 4 contains examples of naturally occurring chemical and enzymatic modifications of amino acid residues of proteins including, but not limited to, apolipoproteins of the present invention and fragments thereof. Abbreviation used: MPO—myeloperoxidase.

Free radicals, oxidative stress, and antioxidants have become commonly used terms in modern discussions of disease mechanisms. Oxidative modifications of proteins plays a crucial role in aging and other physiological processes because oxidized proteins lose catalytic function (Sohal R. S. Free Radic Biol Med 2002; 33:37-44). Most commonly occurred oxidative modifications of amino acids include methionine sulfoxidation and tyrosine chlorination, bromination and nitrosylation that are mediated by such oxidants as $H_2O_2$, $MPO/H_2O_2/Cl^-$, $MPO/H_2O_2/Br^-$, and $MPO/H_2O_2/NO_2^-$, are illustrated in FIG. 4. Oxidative damage to specific proteins is considered to constitute one of the major mechanisms linking oxidative stress/damage and losses in physiological functions.

Methionine (Met) is one of the most readily oxidized amino acid constituents of proteins. It is attacked by $H_2O_2$, hydroxyl radicals, hypochlorite, chloramines, and peroxynitrite, all these oxidants being produced in biological systems. The oxidation product, Met sulfoxide, can be reduced back to Met by peptide methionine sulfoxide reductase (PMSR). Functional changes by Met oxidation in a given protein appear to have pathophysiological significance in some cases. Formation of methionine sulfoxides during oxidative stress has been shown to lead to complete inactivation of such physiologically important peptides and proteins as Alzheimer's amyloid beta-peptide 1-42, alpha1-protease inhibitor, ribosomal protein L12 and Met-enkephalin (Sohal R. S. Free Radic Biol Med 2002; 33:37-44; Vogt, W. Free Radic Biol Med 1995; 18:93-105). Methionine side chains can be oxidized in vitro using hydrogen peroxide, which is considered to be a physiological oxidizer since it mimics the methionine oxidation pattern found in vivo.

Figure 5A:
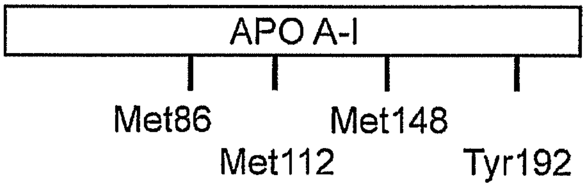
FIG. 5A presents a schematic representation of one possible apolipoprotein (apo) of the present invention—apo A-I. Three methionine (Met) residues at positions 86, 112, and 148 and one tyrosine (Tyr) residue at position 192 that most often undergo chemical and/or enzymatic modifications are shown.
Figure 5B:
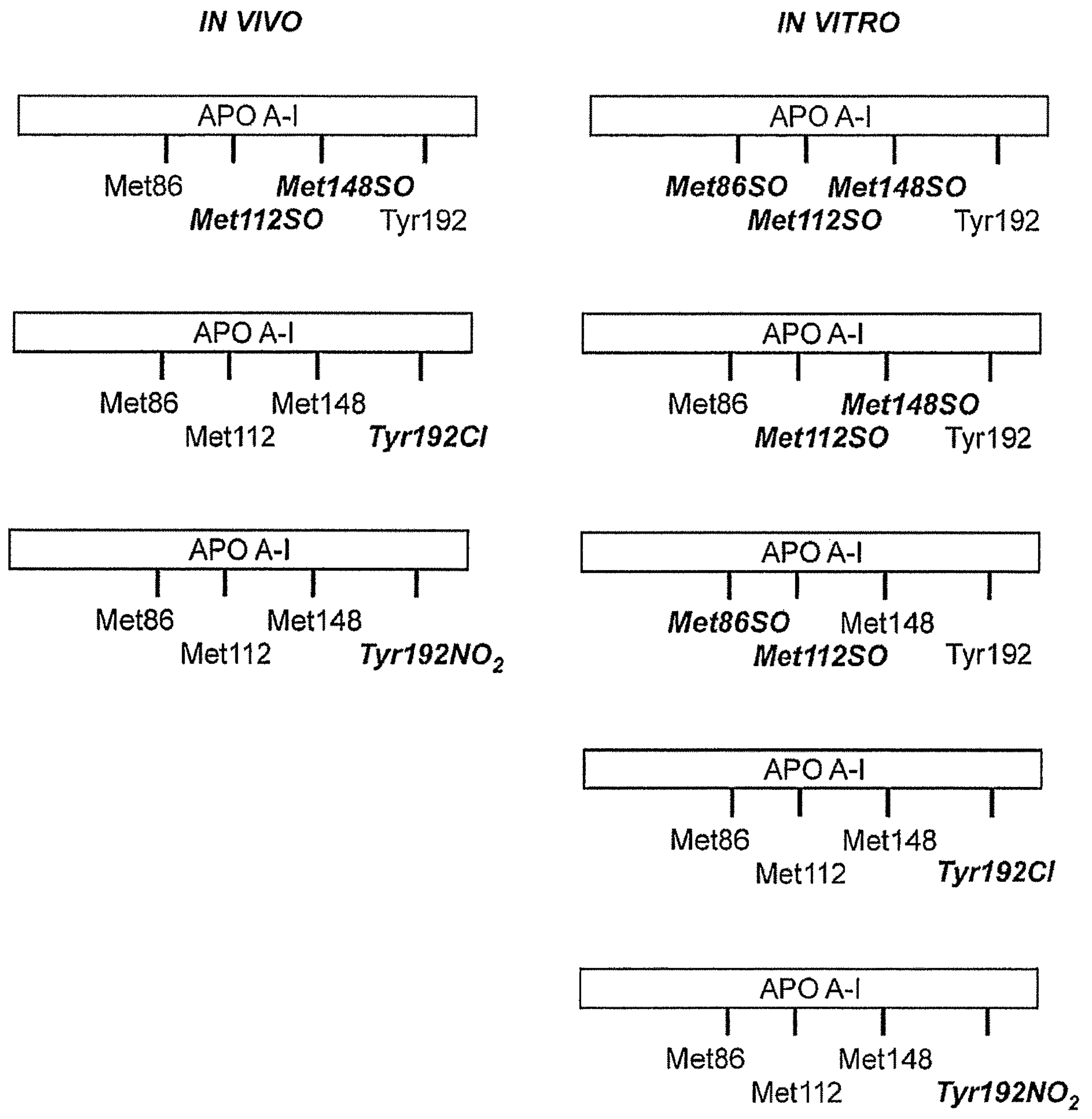
FIG. 5B presents a schematic representation of several modifications of apolipoprotein (apo) A-I naturally occurring in vivo and artificially produced in vitro. While not being bound to any particular theory, it is believed that Met residues at positions 112 and 148 are the major sites of sulfoxidation by hydrogen peroxide alone or in combination with myeloperoxidase in vivo, whereas sulfoxides of all three Met residues of apo A-I can be produced in different combinations in vitro, depending on the oxidant used. It is also believed that Tyr residue at the position 192 is the major of nitration and chlorination by myeloperoxidase in vivo and in vitro.

Those of skill in the art are aware that apolipoprotein (apo) A-I contains three methionines that can potentially undergo sulfoxidation, Met-86, Met-112, and Met-148 (FIG. 5A). Sulfoxidation of apo A-I methionines 112 and 148 occurs in vivo (FIG. 5B) and affects many HDL functions including uptake by macrophages (von Eckardstein et al. J Lipid Res 1991; 32:1465-76; Sigalov et al. Eur J Clin Chem Clin Biochem 1997; 35:395-6; Shao et al. Proc Natl Acad Sci USA 2008; 105:12224-9; Shao, B. & Heinecke, J. W. J Lipid Res 2009; 50:599-601; Shao et al. Curr Opin Cardiol 2006; 21:322-8; Shao et al. Curr Opin Mol Ther 2006; 8:198-205; Assinger et al. FEBS Lett 2008; 582:778-84; Bergt et al. Eur J Biochem 2001; 268:3523-31; Bergt et al. Arterioscler Thromb Vase Biol 2003; 23:1488-90; Bergt et al. Proc Natl Acad Sci USA 2004; 101:13032-7; Bergt et al. FEBS Lett 1999,452:295-300). In addition, the content of oxidized apo A-I between individuals displays the significant variability (Sigalov A. B. & Stern L. J. FEBS Lett 1998; 433:196-200; von Eckardstein et al. J Lipid Res 1991; 32:1465-76). Apo A-I containing two methionine sulfoxides was also observed in human aortic lesions (Pankhurst et al. J Lipid Res 2003; 44:349-55). In summary, this naturally occurring apo A-I modification can be suggested to play an important role in atherogenesis including conversion of native HDL into a macrophage substrate. In addition, tyrosine chlorination, bromination and nitrosylation (FIGS. 5A-B) have been also reported as a naturally occurring oxidative modification of apo A-I (Zheng et al. J Clin Invest 2004; 114:529-41; Zheng et al. J Biol Chem 2005; 280:38-47; Panzenboeck et al. J Biol Chem 1997; 272:29711-20; Suc et al. J Cell Sci 2003; 116:89-99; Pennathur et al. J Biol Chem 2004; 279:42977-83) and tyrosine 192 in apo A-I is believed to be the major site of nitration and chlorination by myeloperoxidase in vivo (Shao et al. J Biol Chem 2005; 280:5983-93).

In most studies, oxidized HDL generally were either obtained in vitro using a variety of chemical oxidizing agents under the conditions for which oxidation of both lipid and protein HDL constituents can occur or isolated from athrosclerotic tissues but not analyzed for lipid peroxidation products (Bergt et al. FEBS Lett 1999; 452:295-300; Marsche et al. J Biol Chem 2002; 277:32172-9; Panzenboeck et al. J Biol Chem 1997; 272:29711-20; Nakano T. & Nagata A. J Lab Clin Med 2003; 141:378-84; Hurtado et al. Atherosclerosis 1996; 125:39-46; Nagano et al. Proc Natl Acad Sci USA 1991; 88:6457-61; Nakajima et al. Ann Clin Biochem 2004; 41:309-15; Rifici V. A. & Khachadurian, A. K. Biochim Biophys Acta 1996; 1299:87-94; Pennathur et al. J Biol Chan 2004; 279:42977-83; Zheng et al. J Clin Invest 2004; 114:529-41; Zheng et al. J Biol Chan 2005; 280:38-47), thus making impossible to evaluate a contribution of oxidatively damaged protein HDL constituents, in general, and certain oxidative protein modifications, in particular, to the change of the HDL functional outcome. In addition, the different oxidants that are widely used to oxidize lipid-free apolipoproteins or apolipoproteins in the context of HDL particles, such as $Cu^{2+}$ ions (Chin et al. J Clin Invest 1992; 89:10-8; Hurtado et al. Atherosclerosis 1996; 125:39-46; Nagano et al. Proc Natl Acad Sci USA 1991; 88:6457-61; Nakajima et al. Ann Clin Biochem 2004; 41:309-15), $H_2O_2$ (Anantharamaiah et al. J Lipid Res 1988; 29:309-18; Sigalov A. B. & Stern L. J. FEBS Lett 1998; 433:196-200; Sigalov A. B. & Stem L. J. Chem Phys Lipids 2001; 113:133-46; Sigalov A. B. & Stem L. J. Antioxid Redox Signal 2002; 4:553-7; von Eckardstein et al. J Lipid Res 1991; 32:1465-76), chloramine T (von Eckardstein et al. J Lipid Res 1991; 32:1465-76), myeloperoxidase-$H_2O_2$-halide system (Bergt et al. FEBS Lett 1999; 452:295-300; Marsche et al. J Biol Chem 2002; 277:32172-9; Panzenboeck et al. J Biol Chem 1997; 272:29711-20), cholesteryl ester (Garner et al. J Biol Chem 1998; 273:6088-95; Garner et al. J Biol Chem 1998; 273:6080-7) and phosphatidylcholine (Mashima et al. J Lipid Res 1998; 39:1133-40) hydroperoxides, and 2,2-azo-bis(2-amidinopropane) dihydrochloride (AAPH) (Garner et al. J Biol Chem 1998; 273:6080-7; Mashima et al. J Lipid Res 1998; 39:1133-40; Pankhurst et al. J Lipid Res 2003; 44:349-55; Panzenbock et al. J Biol Chem 2000; 275:19536-44) modify apo A-I in different ways and to varying extent (see, e.g. FIG. 5B). Also, for both myeloperoxidase-$H_2O_2$-halide system (Bergt et al. Biochem J 2000; 346 Pt 2:345-54) and AAPH (Horkko et al. J Clin Invest 1999; 103:117-28), it has been reported that lipid-free and lipid-bound apo A-I is also oxidized in different ways. This variety of the oxidizing reagents used and, therefore, the variety of oxidized HDL studied has lead to contradictory conclusions about the effect of oxidative damage to apo A-I on HDL function (Marsche et al. J Biol Chem 2002; 277:32172-9; Panzenbock et al. J Biol Chem 2000; 275:19536-44).

Thus, the prior art neither suggests nor teaches one of ordinary skill in the art to investigate the performance of HDL particles in which only the apolipoprotein portion has been chemically altered. As described herein, it is surprisingly found that oxidative modification of only protein constituents or peptide fragments thereof of HDL is sufficient to convert these particles to substrates for macrophage scavenger receptors.

It is well known to those of ordinary skill in the art that the modified apo A-I molecules containing methionine sulfoxides at any one of positions 86, 112, 148, or any combination of said positions can be prepared and purified using the standard procedures well known in the art (see e.g. Anantharamaiah et al. J Lipid Res 1988; 29:309-18; Sigalov A. B. & Stern L. J. FEBS Lett 1998; 433:196-200; Sigalov A. B. & Stern L. J. Chem Phys Lipids 2001; 113:133-46; Sigalov A. B. & Stern L. J. Antioxid Redox Signal 2002; 4:553-7; von Eckardstein et al. J Lipid Res 1991; 32:1465-76; Panzenbock et al. J Biol Chem 2000; 275:19536-44). It should be also understood by those of ordinary skill in the art that apo A-I peptide fragments containing methionine residues at positions 86, 112, 148 can be easily synthesized or manufactured by any technique for peptide synthesis known in the art, including, e.g., the techniques described in U.S. Pat. Nos. 6,004,925, 6,037,323 and 6,046,166 and using the well known primary sequence of human apo A-I that can be found under the entry UniProt KB/Swiss-Prot P02647 (www.uniprot.org/uniprot/P02647, last modified on Jul. 28, 2009, version 137). It is further understood by those of ordinary skill in the art that methionine residues in these peptide fragments can be oxidized to methionine sulfoxides using, for example, the procedures described in (Sigalov A. B. & Stern L. J. FEBS Lett 1998; 433:196-200; Sigalov A. B. & Stern L. J. Chem Phys Lipids 2001; 113:133-46; Sigalov A. B. & Stein L. J. Antioxid Redox Signal 2002; 4:553-7; von Eckardstein et al. J Lipid Res 1991; 32:1465-76; Panzenbock et al. J Biol Chem 2000; 275:19536-44; Garner et al. J Biol Chem 1998; 273:6088-95; Garner et al. J Biol Chem 1998; 273:6080-7) and the modified peptides can be purified by any method known in the art, including high performance liquid chromatography (HPLC).

It is well known to those of ordinary skill in the art that the modified apo A-I molecules containing 3-chloro-, 3-nitro- or 3,5-dibromotyrosine at position 192 (FIGS. 4 and 5) can be prepared and purified using the standard procedures well known in the art (Shao et al. J Biol Chan 2005; 280:5983-93; Weiss et al. Science 1986; 234:200-3). It should be also understood by those of ordinary skill in the art that apo A-I peptide fragments containing tyrosine residue at position 192 can be easily synthesized or manufactured by any technique for peptide synthesis known in the art, including, e.g., the techniques described in U.S. Pat. Nos. 6,004,925, 6,037,323 and 6,046,166 and using the well known primary sequence of human apo A-I that can be found under the entry UniProt KB/Swiss-Prot P02647 (www.uniprot.org/uniprot/P02647, last modified on Jul. 28, 2009, version 137). It is further understood by those of ordinary skill in the art that tyrosine residue of these peptide fragments can be oxidized to 3-chloro-, 3-nitro- or 3,5-dibromotyrosine, using, for example, the procedures described in (Shao et al. J Biol Chem 2005; 280:5983-93; Weiss et al. Science 1986; 234:200-3) and the modified peptides can be purified by any method known in the art, including high performance liquid chromatography HPLC.

It will be clear to those of ordinary skill in the art that the modified apo A-II molecules containing methionine sulfoxide at position 26 can be prepared and purified using the standard procedures well known in the art (see e.g. Anantharamaiah et al. J Lipid Res 1988; 29:309-18; Gamer et al. J Biol Chem 1998; 273:6080-7; Sigalov A. B. & Stern L. J. FEBS Lett 1998; 433:196-200; Sigalov A. B. & Stem L. J. Chem Phys Lipids 2001; 113:133-46; Sigalov A. B. & Stern L. J. Antioxid Redox Signal 2002; 4:553-7; von Eckardstein et al. J Lipid Res 1991; 32:1465-76; Panzenbock et al. J Biol Chem 2000; 275:19536-44). It should be also understood by those of ordinary skill in the art that apo A-II peptide fragments containing methionine residue at position 26 can be easily synthesized or manufactured by any technique for peptide synthesis known in the art, including, e.g., the techniques described in U.S. Pat. Nos. 6,004,925, 6,037,323 and 6,046,166 and using the well known primary sequence of human apo A-II that can be found under the entry UniProt KB/Swiss-Prot P02652 (http://www.uniprot.org/uniprot/P02652, last modified on Jul. 28, 2009, version 121). It is further understood by those of ordinary skill in the art that methionine residue in these peptide fragments can be oxidized to methionine sulfoxide using, for example, the procedures described in (Sigalov A. B. & Stern L. J. FEBS Lett 1998; 433:196-200; Sigalov A. B. & Stern L. J. Chem Phys Lipids 2001; 113:133-46; Sigalov A. B. & Stern L. J. Antioxid Redox Signal 2002; 4:553-7; von Eckardstein et al. J Lipid Res 1991; 32:1465-76; Panzenbock et al. J Biol Chem 2000; 275:19536-44; Anantharamaiah et al. J Lipid Res 1988; 29:309-18) and the modified peptides can be purified by any method known in the art, including HPLC.

In preferred embodiments, the chemically or enzymatically modified apolipoprotein is selected from a modified apo A-I or a fragment thereof and a modified apo A-II or a fragment thereof. In preferred embodiments, the modified apolipoprotein is any combination of a modified apo A-I and a modified A-II and fragments thereof. In preferred embodiments, a modified apo A-I is an oxidized apoA-I or an oxidized apoA-I fragment that comprises one or more of the following amino acid residues: 3-chlorotyrosine, 3-nitrotyrosine, 3,5-dibromotyrosine, dityrosine, trihydroxyphenylalanine, dihydroxyphenylalanine, methionine sulphoxide, and tyrosine peroxide. In still other preferred embodiments, a modified apo A-II is an oxidized apoA-II or an oxidized apoA-II fragment that comprises one or more of the following amino acid residues: chlorotyrosine, nitrotyrosine, dityrosine, trihydroxyphenylalanine, dihydroxyphenylalanine, methionine sulphoxide, and tyrosine peroxide. In particularly preferred embodiments, a modified apo A-I is an oxidized apo A-I or an oxidized apoA-I fragment that comprises methionine sulfoxide at any one of positions 86, 112, 148, or any combination of said positions. In still particularly preferred embodiments, a modified apo A-II is an oxidized apo A-II or an oxidized apoA-II fragment that comprises methionine sulfoxide at position 26. In still particularly preferred embodiments, a modified apo A-I is an oxidized apo A-I or an oxidized apoA-I fragment that comprises methionine sulfoxide at positions 112 and 148.

In certain embodiments, methionine sulfoxidation and the functional changes associated with the oxidation can be reversed by PMSR in the presence of physiologically important universal antioxidant dihydrolipoic acid (DHLA) as a cofactor (Sigalov A. B. & Stern L. J. Antioxid Redox Signal 2002; 4:553-7; Biewenga et al. Arzneimittelforschung 1998; 48:144-8). DHLA is a metabolic product formed in vivo from lipoic acid (Biewenga et al. Gen Pharmacol 1997:29: 315-31), which is widely used as a therapeutic agent in a variety of diseases. Several lines of evidence suggest that the antioxidant properties of lipoic acid and more importantly, its reduced form, DHLA, are at least in part responsible for the therapeutic effect. Currently, DHLA alone or in equimolar mixture with lipoic acid is widely used as a supplement. DHLA is also suggested for the amelioration of diabetes mellitus types 1 and 2 (including impaired glucose tolerance, pre-diabetes, insulin resistance, metabolic syndrome X and as an adjunct to oral antidiabetic agents and/or insulin), diabetic and non-diabetic microvascular diseases (including nephropathy, neuropathy and retinopathy), diabetic and non-diabetic macrovascular diseases (including heart attack, stroke, peripheral vascular disease and ischemia-reperfusion injury), hypertension, vasoconstriction, obesity, dyslipedemia, and neurodegenerative disorders (including Parkinson's disease, mild cognitive impairment, senile dementia, Alzheimer's disease, hearing loss and chronic glaucomas (see e.g., US Pat Appls 20090068264, 20020110604, and 20020177558), the disclosures of which are incorporated herein by reference in their entities.

To the extent that the present application is directed to methods and compositions which employ modified apolipoproteins A-I and A-II and fragments thereof that include protein and peptide molecules containing sulfoxidized methionines, it is important to discuss potential use of DHLA in combination with one embodiment of the compositions described herein. This discussion is provided in the section on methods of using the rHDL of the present invention.

C. Reconstituted HDL

To the extent that the present application is directed to methods and compositions which employ HDL, the present section is provided as a discussion of HDL and major protein constituents of HDL, apolipoproteins (apo) A-I and A-II, that are to be used in the present invention.

Those of skill in the art are aware of methods and compositions for producing reconstituted lipoproteins (US Pat Appl 20070243136; 20060217312; and 20060205643; U.S. Pat. No. 5,652,339; Lerch et al. Vox Sang 1996; 71:155-164; Matz C. E. & Jonas, A. J Biol Chem 1982; 257:4535-40; Toledo et al. Arch Biochem Biophys 2000; 380:63-70; Sigalov A. B. & Stern L. J. Chem Phys Lipids 2001; 113:133-46; Jonas, A. Methods Enzymol 1986; 128: 553-82), in general, and as vehicles for drug delivery, in particular (Rensen et al. Adv Drug Deliv Rev 2001; 47:251-76). As is detailed in Rensen et al., lipoproteins are spherical macromolecular particles made up of a hydrophobic core of triglycerides (TG) and cholesteryl esters, which are emulsified by a shell of amphipathic phospholipids, unesterified cholesterol, and one or more apolipoproteins. The unesterified sterol and the apolipoproteins in the outer layer of the lipoproteins stabilize the overall structure. These naturally occurring structures circulate in vivo and are intrinsically involved in lipid transport. These structures are ideal candidates for drug delivery because being endogenous, these agents are less likely to promote an immune response, and they readily evade detection and elimination through the reticuloendothelial system.

There are four major classes of lipoproteins circulating in human blood, and they differ from each other with respect to size, lipid composition and apolipoprotein composition. These lipoprotein classes are distinguishable from each other based on their density in ultracentrifugation. All four major classes of circulating lipoprotein particles are involved in the fat-transport system: chylomicrons, very low density lipoprotein (VLDL), low density lipoprotein (LDL) and high density lipoprotein (HDL). Chylomicrons constitute a short-lived product of intestinal fat absorption. VLDL and particularly, LDL, are responsible for the delivery of cholesterol from the liver (where it is synthesized or obtained from dietary sources) to extrahepatic tissues, including the arterial walls. HDL, by contrast, mediates reverse cholesterol transport (RCT), the removal of cholesterol lipids, in particular from extrahepatic tissues to the liver, where it is stored, catabolized, eliminated or recycled. HDL also plays a role in inflammation, transporting oxidized lipids and interleukin. Apo A-I, the major protein constituent of HDL, forms three types of stable complexes with lipids: small, lipid-poor complexes referred to as pre-beta-1 HDL; flattened discoidal particles comprising polar lipids (phospholipid and cholesterol) referred to as pre-beta-2 HDL; and spherical particles, comprising both polar and nonpolar lipids, referred to as spherical or mature HDL ($HDL_3$ and $HDL_2$). Most HDL in the circulating population comprise both apo A-I and apo A-II, another protein constituent of HDL, (the "AI/AII-HDL fraction"). However, the fraction of HDL comprising only apo A-I (the "AI-HDL fraction") appears to be more effective in RCT. Certain epidemiologic studies support the hypothesis that the apo A-I/HDL fraction is anti-atherogenic (Parra et al. Arterioscler Thromb 1992; 12:701-7; Decossin et al. Eur J Clin Invest 1997; 27:299-307).

In the methods of the present invention, the lipoproteins of interest are synthetic reconstituted HDLs. These lipoproteins are characterized by a density of about 1.063 g/ml to about 1.21 g/ml, and as such, are the densest of the four classes of lipoproteins. However, the diameter of these lipoproteins is the smallest of the lipoprotein classes and varies between 5 to 12 nm. In preferred embodiments of the present invention the synthetic rHDL compositions have an average diameter of between about 5 nm and about 15 nm. A particularly preferred range is a range of between 5-10 nm. It is envisioned that in any imaging composition of the present invention may contain a range of sizes of synthetic rHDL, but the average size of the particles will be in the above range. Thus, the compositions may have particles that range have diameters of between 5-15 nm, other exemplary ranges of diameters in a given composition are between 5-10 nm, 5-8 nm, 5-6 nm. In preferred embodiments the average diameter size of the synthetic rHDLs is about 10 nm, alternatively, the average diameter is about 6 nm, 7 nm, 8 nm, 9 nm, 10 nm, 11 nm, 12 nm, 13 nm, 14 nm or 15 nm. The average size of the synthetic rHDLs may be as large as 18 nm. Preferably, the above recited average sizes are those sizes that are achieved when the synthetic rHDL has been reconstituted with at the least the metallic contrast agent.

In those embodiments, in which the imaging composition comprises both a metallic (or non-metallic) agent and an additional targeting agent, it is preferred that the average diameter of the synthetic rHDL moiety comprised of the synthetic rHDL, metallic agent (or non-metallic) and targeting moiety does not exceed 18 nm.

Schematically, the rHDLs of the present invention that contain modified apolipoproteins or fragments thereof as targeting moieties are depicted in FIGS. 1 and 2. In those figures, the metallic contrast agent is linked through a polyaminopolycarboxylate chelating agent that comprises a hydrophobic group to the phosphate-linked headgroup of a phospholipid moiety in the rHDL. Of course, it should be understood that this is a preferred embodiment, and those of skill in the art may produce synthetic rHDLs in which the metallic or non-metallic contrast agent is covalently linked to, or otherwise associated with, another component of the synthetic rHDL, such as for example, the apolipoprotein component, or the sterol component. In particular embodiments, it may be desirable to have the metallic or non-metallic contrast agent sequestered in the core of the synthetic rHDL. For such embodiments, the metallic contrast agent may be linked through a polyaminopolycarboxylate chelating agent to a fatty acyl residue of the TG or even the fatty acyl residue of the cholesteryl ester, or another hydrophobic molecule.

The synthetic rHDL compositions of the present invention in which the paramagnetic metal ion is bonded to a chelator that is attached to the phosphate-linked headgroup of a phospholipid has shown strikingly high contrast efficiency in MRI imaging, particularly of atherosclerotic plaques. This is due to the fact that HDL that contain targeting moieties, the modified apolipoproteins and fragments thereof, are able to effectively and efficiently locate to such plaques. Such location to the plaques is further enhanced by the presence of additional targeting moieties such as e.g., an antibody, or other specific binding partner of a moiety that is present at the site being imaged.

It is contemplated that the compositions of the present invention produce a contrast effect at least 20% better than the contrast seen when the metallic ion is presented alone or in phospholipid, micellar, LDL or rHDL (with no apolipoproteins or with unmodified apolipoproteins) forms of delivery. More preferably, the compositions produce a 30%, 35%, 40%, 45%, 50%, 55%, 60%, 70% 75% or higher percentage better contrast, than that of comparative compositions of the prior art in which these other forms of delivery vehicles are used. Without being bound by particular theory or mechanism, the compositions of the present invention are more effective contrast agents than those available in the art because they have the advantage of having a particle sizes between 5 and 25 nm, thus being small enough to integrate into the site being imaged. Further, the agents of the present invention also optionally may comprise targeting agents that facilitate a increased affinity for the imaged site such that the imaging agent is retained and accumulated at the site. The preferred agent of the invention preferably has a diameter (if spherical), or longest dimension (if discoidal), of less than 20 nm and greater than 5 nm, more preferably the rHDLs have a diameter or longest dimension of between about 5 nm and about 15 nm.

As discussed above, the metallic agent preferably comprises a chelating moiety that facilitates the conjugation of the metallic agent to for example, the phospholipid moiety. In certain embodiments, it is desirable to have the metallic agent chelating moiety present near the outer surface of the synthetic rHDL hydrophobic portion of a sphingolipid, and/or the two fatty acyl groups of a phosphatidylcholine, phosphatidylethanolamine, or other glycerophospholipid in the inner side of the HDL moeity. The fatty acids of the phospholipids may include, but are not limited to, e.g., saturated and unsaturated $C_1$ to $C_{24}$ fatty acids. The chelating moiety may be selected from EDTA, DTPA, DTPAGlu, DTPALys, DTPASer, BOPTA, DOTA, DO3A and/or their derivatives, all containing a free function unit for covalent linkage to the other monomer units. The chelating molecule may also be provided with the hydrophobic group in form of a carboxylate amide with hydrophobic aliphatic or aromatic amines. Such amines may be saturated and unsaturated $C_1$ to $C_{24}$ amines like methylamine, ethylamine, propylamine, butylamine (n-, iso-, tert-), pentylamine, hexylamine (and isomers), octylamine (and isomers), nonylamine, decylamine, aminoadamantan and fatty amines; as aromatic amines, one may cite substituted and unsubstituted benzyl- and higher phenylalkyl-amines. Alternatively, the polycarboxylic chelating agent can be provided with lipophilic hydrophobic groups linked to the alkylene segments of the molecular back-bone, or to the alpha-carbon of the carboxylate functions or to a hydroxyl group when present in the chelating agent.

In preferred embodiments, the present invention employs Gd-DTPA as the metallic contrast agent comprising the polyaminopolycarboxylate agent chelating agent. In preferred embodiments the chelating agent is DTPA, however, those of skill in the art are aware that other chelating agents could readily be used in place of DTPA, such other agents include, but are not limited to EDTA, BOPTA, DOTA, DO3A and/or their derivatives. In the imaging agents of the invention, the paramagnetic metal may be any paramagnetic metal traditionally used in MRI techniques and may for example be selected from e.g., Gd(III), Mn(II), Mn(III), Cr(II), Cr(III), Cu(II), Fe(III), Pr(III), Nd(III) Sm(III), Tb(III), Yb(III) Dy(III), Ho(III), Eu(II), Eu(III), and Er(III), $Tl^{201}$, $K^{42}$, $In^{111}$, Fe.$^{59}$, $Tc^{99m}$, $Cr^{51}$, $Ga^{67}$, $Ga^{68}$, $Cu^{64}$, $Rb^{82}$, $Mo^{99}$, $Dy^{165}$. In other aspects of the invention, non-metallic agents are used as contrast agents. Exemplary, but non-limiting non-metallic contrast agents include Fluorescein, Carboxyfluorescein, Calcein, $F^{18}$, $Xe^{133}$, $I^{125}$, $I^{131}$, $I^{123}$, $P^{32}$, $C^{11}$, $N^{13}$, $O^{15}$, $Br^{76}$, $Kr^{81}$. The non-metallic contrast agent may still preferably be selected from the group of iodinated contrast media consisting of ionic monomers and dimers, and nonionic monomers and dimers, including, but not limiting to, Diatrizoate, Metrizoate, Isopaque, Ioxaglate, Iopamidol, Iohexol, and Iodixanol (Singh J. & Daftary A. J Nucl Med Technol 2008; 36:69-74; Stacul F. Eur Radiol 2001; 11:690-7).

A preferred composition for use in the preparation of the rHDL compositions of the present invention is Gd-DTPA-phosphatidylethanolamine (PE). Those of skill in the art are aware of how to produce and use DTPA-PE as a liposomal MRI contrast agent (Grant et al. A liposomal MRI contrast agent: phosphatidylethanolamine-DTPA. Magn Reson Med 1989; 11:236-43). While in preferred embodiments, it is envisioned that the phospholipid is PE, it should be understood that the metallic contrast agent may be conjugated to any phospholipid using techniques such as those that have previously been used to generate DTPA-PE. Such phospholipids include but are not limited to phosphatidic acid (PA), phosphatidyleholine (PC), phosphatidylethanolamine (PE, particularly dimyristoyl-sn-glycero-phosphatidylethanolamine (DMPE)), phosphatidylserine (PS), phosphatidylglycerol (PG), phosphatidylinositol (PI), cardiolipin (CL), sphingomyelin (SM), and other sphingolipids. In addition to being conjugated to a phospholipid, it may be possible to conjugate the metallic agent to e.g., a monophosphate ester of a substituted or partially substituted glycerol, at least one functional group of said glycerol being esterified by saturated or unsaturated aliphatic fatty acid, or etherified by saturated or unsaturated alcohol, the other two acidic functions of the phosphoric acid being either free or salified with alkali or earth-alkali metals. Preferably the phosphate esters will include monophosphates of fatty acid glycerides selected from dimyristoylphosphatidic acid, dipalmitoylphosphatidic acid, or distearoylphosphatidic acid. Also, it should be understood that the fatty acyl moieties of the phospholipids may vary in length. For example, it is envisioned that the phospholipids, TG, cholesteryl esters, and monophosphate esters of the glycerol may comprise fatty acids of between $C_4$ to $C_{24}$ carbons in length. Thus, it should be noted that that the fatty acyl moieties of the phospholipids may be any fatty acyl moiety commonly found in phospholipids. For example, the fatty acyl moieties may comprise between 4 and 24 carbons and may be saturated, or alternatively may comprise one, two, three or more double bonds. Further, the two fatty acid chains of the phospholipids may be the same fatty acid or alternatively, the phospholipid may comprise two different fatty acyl moieties. In particularly, preferred embodiments, the phospholipids contain two myristoyl moieties as in DMPE. However, while DMPE is a preferred phospholipid it is contemplated that DMPC, DMPA, DMPI and the like also may be used.

In preferred embodiments, the phospholipids may also include diacyl and dialkyl glycerophospholipids in which the aliphatic chains have at least twelve carbon atoms.

As can be seen from FIGS. 1 and 2, in addition to having phospholipid conjugated to the metallic contrast agent, the rHDLs also comprise phospholipids as part of the overall HDL structure. It is contemplated that the rHDL may be made up only of one type of phospholipid or more preferably, the rHDL will be made up of a mixture of phospholipids. Preferably, in the mixture of phospholipids, the ratio of the individual types of phospholipid may be comparable to the ratio of the same phospholipids seen in HDLs circulating in the blood.

In addition to the phospholipid and TG lipid components of the rHDL, the compositions also comprise sterol esters in the core of the rHDL and sterols interspersed between the phospholipid layer of the rHDL. While in preferred embodiments the sterol moiety of the steryl ester and the sterol in the phospholipid layer is cholesterol, it should be understood that other common sterols, such as ergosterol, stigmasterol, phytosterol, sitosterol, and lanosterol, also may serve as the sterol moiety. Other sterols, whether isolated from natural sources or synthetically generated, also may be used.

The ratios of the various HDL components to each other in the rHDL compositions of the present invention should be guided by the molar w/w ratios well known in the art for HDL moieties (Rensen et al. Adv Drug Deliv Rev 2001; 47:251-76; US Pat Appls 20060217312 and 20060205643; U.S. Pat. No. 5,652,339; Lerch et al. Vox Sang 1996; 71:155-64; Matz C. E. & Jonas A. J Biol Chem 1982; 257:4535-40; Toledo et al. Arch Biochem Biophys 2000; 380:63-70; Sigalov A. B. & Stem L. J. Chem Phys Lipids 2001; 113:133-46). In the compositions containing phospholipids, the weight proportion of the phospholipids:steryl ester:sterol:TG may vary in a wide range e.g. from 100±50%:62±50%:25±50%:11±50% with 1-4 apolipoprotein molecules per particle. Composition will affect particle size (because of the surface-to-core ratio), and can even affect particle shape (discoidal if there is insufficient core lipid). However, those of skill in the art are aware of variations in the ratios of phospholipids (e.g., DMPC and DPPC) mixed with different ratios of apo A-I (Tall et al. J Biol Chem 1977; 252:4701-11) Compositions such as those described by Tall et al. may be varied by addition of differing quantities of core lipids as was described, for example, in a later study on phospholipid-enrichment of HDL (Tall A. R. & Green P. H. J Biol Chem 1981; 256:2035-44).

In preferred embodiments, the synthetic nanoparticle in the imaging agent comprises a phospholipid:sterol:apolipoprotein ratio of 180:5:3 (mol:mol:mol). In other preferred embodiments, the synthetic nanoparticle in the imaging agent comprises a phospholipid:apolipoprotein ratio of 100:3 (mol:mol). In still preferred embodiments, the synthetic nanoparticle in the imaging agent comprises a phospholipid:steryl ester:sterol:triglycerides (TG):apo A-I ratio (w/w) of 100:62:25:11:2. The use of a large excess of chelate may result in unnecessary waste of the chelating/imaging agent while an excess of phospholipid beyond certain concentration does not provide extra benefit. Within these ratios, it is contemplated that the ratio of phospholipid:metallic agent can vary from 75:25 to 0:100, and the ratio of phospholipid:sterol can vary from 5:10 to 20:1. In other embodiments, the rHDL may contain no sterol (i.e., be composed of phospholipids only with no sterol).

In preferred embodiments apo A-$I_{unox}$ is unoxidized apo A-I contained in initial serum apo A-I. In other preferred embodiments apo A-$II_{unox}$ is unoxidized apo A-II contained in initial serum apo A-II. In other preferred embodiments, apo A-$I_{ox}$ is oxidized apo A-I (with sulfoxidized methionines at positions 112 and 148) contained in serum apo A-I or obtained from unoxidized apo A-I using hydrogen peroxide. In still other preferred embodiments; apo A-$I_{red}$ is reduced apo A-I obtained by reduction of oxidized apo A-I (with sulfoxidized methionines at positions 112 and 148) using peptide methionine sulfoxide reductase (PMSR). In preferred embodiments, rHDL-1 are reconstituted HDL particles containing only apo A-$I_{unox}$. In preferred embodiments, rHDL-2 are reconstituted HDL particles containing only apo A-$I_{ox}$. In preferred embodiments, rHDL-3 are reconstituted HDL particles containing apo A-$I_{unox}$ and apo A-$I_{ox}$ with a molar ratio of 1:1. In preferred embodiments, rHDL-4 are reconstituted HDL particles containing apo A-$I_{unox}$, apo A-$I_{ox}$ and apo A-$II_{unox}$ with a molar ratio of 3:3:1.

It is contemplated that the compositions of the present invention may be produced by lyophilisation of the composition whereby a dry, pulverulent formulation is obtained. This form of the paramagnetic composition is particularly convenient for long term storage. The storage in the powder form is simplified by the fact that reconstitution of the composition be achieved by dispersion of the lyophilised powder in a physiologically acceptable liquid carrier, will form a suspension useful as a blood pool NMR imaging contrast agent. The lyophilisation is a straight forward freeze-drying process requiring no particular precautions or measures. In certain embodiments, it may be desirable to produce HDLs in a lyophilized form and then re-constituted such HDLs using a sonicator or an extruder. Alternatively, the compositions of the present invention can by cryopreserved for long storage purposes using standard procedures of cryopreservation of lipoproteins well known in the art (Rumsey et al. J Lipid Res 1992; 33:1551-61; Sigalov A. B. Eur J Clin Chem Clin Biochem 1995; 33:73-81).

The methods for making compositions according to the invention generally comprise selecting as components a paramagnetic contrast agent with an appropriate polycarboxylic acid chelating agent provided with a suitable lipophilic group in admixture with one or more phospholipids, TGs, sterols and steryl, particularly cholesteryl, esters and apolipoproteins dispersing the components together so they coalesce into rHDL form. Preferably, the components are dispersed in a physiologically acceptable aqueous liquid carrier such as water or saline, neat or buffered, according to usual practice. Depending upon the choice of components, the dispersion can be achieved by gentle mixing, by detergent dialysis (e.g., cholate dialysis) or by more energetic means such as homogenization, microfluidization, other shear methods, or sonication.

In specific embodiments, the rHDLs of the present invention that contain targeting moieties of which represent apolipoproteins or fragments thereof with sulfoxidized methionine residues may contain dihydrolipoic acid (DHLA) to reverse this oxidative modification at sites of interest. Although it is not necessary to understand the mechanism of an invention, it is believed that at sites of interest, DHLA serves as a cofactor for peptide methionine sulfoxide reductase (PMSR) enzyme to reduce methionine sulfoxides back to their native form.

Those of skill in the art are aware of methods for reconstituting HDL moieties (Jonas A. Methods Enzymol 1986; 128:553-82). Such methods include detergent mediated synthesis, cosonication of HDL components, or through the spontaneous interaction of apolipoproteins with the lipid vesicles and are described below in more detail.

D. Additional Targeting Moieties

As disclosed in US Pat Appl 20070243136, the disclosure of which is incorporated herein by reference, a major advantage of using rHDL is that while it can freely enter and exit lesions, its steady-state levels in plaques should be relatively low, unless deliberate steps are made to promote its retention. Ideally, this retention should be dependent on specific molecules of interest, resulting in an obvious increase in signal intensity (relative to the low background). In the methods and compositions of the present invention, modified apolipoproteins and fragments thereof serve not only as structural proteins that keep stability, integrity and functionality of rHDL but importantly, as specific targeting molecules that target rHDL to sites of interest. In specific embodiments, modified apolipoproteins and fragments thereof are substrates for macrophage scavenger receptors. This causes contrast agent-rHDL particles (i.e., for example, Gd-rHDL particles) to be delivered and retained in atherosclerotic plaques. Similarly, this causes contrast agent-rHDL particles (i.e., for example, Gd-rHDL particles) to be delivered to tumor-associated macrophages.

It is understood by those of ordinary skill in the art, that all described in the literature methods that enhance binding to and or absorption by macrophages of lipoprotein nanoparticles can be used in the present invention. Thus, the imaging agents of the invention may further comprise an additional targeting moiety to further facilitate targeting of the agent to a specific site in vivo. The additional targeting moiety may be any moiety that is conventionally used to target an agent to a given in vivo site and may include but is not limited to, an antibody, a receptor, a ligand, a peptidomimetic agent, an aptamer, a polysaccharide, a drug and a product of phage display as disclosed in US Pat Appl 20070243136 and incorporated herein by reference. In particular embodiments, the targeting moiety may be conjugated to a detectable label. For example, apo E-derived lipopeptide (Chen et al. Contrast Media Mol Imaging 2008; 3:233-42), an apo A-I mimetic peptide (Cormode et al. Small 2008; 4:1437-44), and murine (MDA2 and E06) or human (IK17) antibodies that bind unique oxidation-specific epitopes (Briley-Saebo et al. Circulation 2008; 117:3206-15) may be used in the present invention to further improve specific targeting macrophages, decrease the dosage of administered Gd required and increase an image quality of vulnerable plaques.

In preferred embodiments, the targeting moiety is an antibody. By "antibody" the present invention intends to encompass antibody fragments and derivatives, thus the term includes, but is not limited to, polyclonal, monoclonal, chimeric, single chain, Fab fragments and fragments produced by a Fab expression library. Such fragments include fragments of whole antibodies which retain their binding activity for an antigen or other marker expressed at the site that is to be targeted by the rHDL compositions of the invention. Such fragments include Fv, F(ab') and F(ab')2 fragments, as well as single chain antibodies (scFv), fusion proteins and other synthetic proteins which comprise the antigen-binding site of the antibody. While the antibodies are principally being used herein as targeting agents, such antibodies and fragments thereof may also be neutralizing antibodies, i.e., those which inhibit biological activity of the polypeptides which they recognize, and therefore may serve the additional purpose of rendering the rHDL compositions as being useful as diagnostics and therapeutics. In exemplary embodiments, in the rHDL compositions of the invention Fab or other antibody fragments discussed above can be conjugated to avidin then complexed to biotinylated PE as described in e.g., Example 2 of US Pat Appl 20070243136.

In preferred embodiments, the choice of antibody will be directed by knowledge of plaque biology, which provides a reasonable set of candidates for plaques in general and at different stages of development as disclosed in US Pat Appl 20070243136 and incorporated herein by reference. For general plaque markers, antibodies against lipoprotein lipase (Williams K. J. & Tabas I. Arterioscler Thromb Vasc Biol 1995; 15:551-61; Jonasson et al. J Lipid Res 1987; 28:437-45; Yla-Herttuala et al. Proc Natl Acad Sci USA 1991; 88:10143-7; Babaev et al. J Biol Chem 2000; 275:26293-9), oxidized epitopes (O'Brien et al. Circulation 1999; 99:2876-82), including oxLDL MDA (Herfst M. J. & van Rees H. Arch Dermatol Res 1978; 263:325-334) are suitable. For markers of unstable plaques, antibodies against matrix metalloproteinases (Aikawa et al. Circulation 1998; 97:2433-44) and tissue factor may be used (Rong et al. Circulation 2001; 104:2447-52; Aikawa et al. Circulation 1999; 100: 1215-22; Badimon et al. Circulation 1999; 99:1780-7; Rauch et al. Ann Intern Med 2001; 134:224-38). The antibodies for these plaque components are either commercially available and known to those of skill in the art and have previously used a number of them in studies of mouse atherosclerosis (e.g., Rong et al. Circulation 2001; 104: 2447-52). Also, contemplated for use herein are antibodies or other agents that bind matrix components. Such agents include apo E and C-reactive protein, as well as antibodies against biglycan, chondroitin sulfate, and versican (see, for example, Olin-Lewis et al. Circ Res 2002; 90:1333-9). In certain embodiments, oxidation specific antibodies are used. Those of skill in the art are referred to Torzewski et al. which provides a teaching in the art of oxidized antibodies to malondialdehyde and uses thereof in imaging plaques and plaque stabilization (Torzewski et al. Arterioscler Thromb Vasc Biol 2004; 24, 2307-12).

For each incorporated antibody, the final rHDL particles should be tested as above (size, surface charge, penetration of interstitial fluid, biodistribution and relaxivity) and the results compared to native and rHDL-Gd-DPTA-PE particles before testing as a plaque imaging agent by undergoing the series of in vivo and ex vivo studies described below.

As disclosed in US Pat Appl 20070243136 and incorporated herein by reference, other markers that can be used as additional targeting agents include arterial-wall sphingomyelinase, a key factor that promotes lipoprotein retention and aggregation (Williams et al. Arterioscler Thromb Vase Biol 1995; 15:551-61; Tabas et al. J Biol Chem 1993; 268:20419-32; Marathe et al. Arterioscler Thromb Vase Biol 1999; 19:2648-58; Schissel et al. J Biol Chem 1998; 273:2738-46; Schissel et al. J Clin Invest 1996; 98:1455-64; Williams et al. Curr Opin Lipidol 1998; 9:471-4). Sphingomyelinase is abundant in atherosclerotic plaques, and its role in atherogenesis is to digest sphingomyelin in lipoproteins, thereby generating ceramide. Ceramide is a fusogen that causes the lipoproteins to aggregate, forming large complexes that can no longer leave the plaque. There are two conditions required for sphingomyelinase to mediate this process: i) the lipoproteins must have a sufficiently high content of sphingomyelin, to allow efficient digestion by arterial-wall sphingomyelinase (Schissel et al. J Biol Chem 1998; 273:2738-46); and ii) the particles must initially remain in the lesion long enough to become digested. Thus, certain of the rHDL compositions of the invention comprise both an antibody to promote some initial retention, but also a high sphingomyelin content to promote digestion by sphingomyelinase to increase particle aggregation and trapping in the plaque. Thus, based on a well-characterized pathophysiologic process, sphingomyelin containing rHDL compositions of the invention will amplify the signal from antibody-mediated retention of Gd-rHDL in atherosclerotic plaques. In addition, it is contemplated that the agents of the invention may be targeted to the extracellular matrix components. Illustrative, but not restrictive, examples of extracellular matrix components include, but are not limited to, a proteoglycan, a chondroitin sulfate proteoglycan, a heparan sulfate proteoglycan, a mixed proteoglycan, versican, perlecan, biglycan, decorin, a small leucine-rich proteoglycan, a syndecan, a glypican, betaglycan, macrophage colony-stimulating factor, a collagen, a type I collagen, a type III collagen, an elastin, a fibronectin, a laminin, a non-proteoglycan, a macrophage-derived molecule, a smooth muscle cell-derived molecule, a mast cell-derived molecule, a molecule derived from an inflammatory cell, a molecule derived from a non-inflammatory cell, an endothelial-derived molecule, and a cell-derived matrix component.

Further it has been shown that the apoAI moiety of HDL interacts with ABCA1 and undergoes an intracellular travel route (called retroendocytosis; Bared et al. Mol Biol Cell 2004; 15:5399-407). It is contemplated that the proteins encountered during this route would be in close proximity to HDL. The rHDL compositions of the present invention contain at least one modified apolipoprotein molecule per particle whereas other apolipoprotein moieties can be unmodified. As such, the rHDL compositions of the present invention, with or without additional targeting agents, could be employed to transport materials to intracellular locations within the cell. It is contemplated that macrophage intracellular localization of the Gd can be achieved using the compositions of the present invention, consistent with the retroendocytosis pathway delivery HDL to the interior of the cells. Since HDL interacts with ABCAI, by extension, the HDL may further interact with proteins associated with ABCA1, the rHDL compositions of the invention can those be used to target such intracellular proteins. Other transporters in the ABC family, such as ABCG1 and ABCG4, and SR-BI, all known to interact with HDL, may also serve as "bridges" between the rHDL with imaging (with or without additional targeting agents) so that the presence of a variety of intracellular molecules may be sensed. Besides assessing the presence of such molecules, the rHDL-imaging agent approach may also be useful to explore cellular pathways—i.e., the subcellular localization and transfers of the rHDL would serve as a tracer and could provide direct physical evidence of any process used in the cellular itinerary of rHDL. Proteins that interact with ABCA1 or ABC-family proteins include CFTR, GTPases (Cdc42), apoptosis proteins (FADD, PDZ proteins (Beta2-syntrophin, alpha 1-syntrophin, Lin7), SNARE proteins (syntaxin-13, syntaxin 1A, SNAP-23), phagosome proteins (flotillin-1, syntaxin-13). The rHDL compositions could be used to target the plasma membrane or intracellular locations within endosomes and lysosomes.

As disclosed in US Pat Appl 20070243136 and incorporated herein by reference, cell surface proteins that may serve as an additional target for the rHDL compositions of the invention can be divided up into 3 groups-receptors, adhesion molecules, and miscellaneous proteins. The proteins should be on the cell surface of the major types of cells found in plaques; i.e., endothelial cells, macrophages, smooth muscle cells, and lymphocytes.

Receptors that can serve as main and additional targets in the present invention include, e.g., scavenger receptor, SR-BI, LDLR, LRP, apo E receptor, VLDL receptor, CD36, oxidized LDL receptor, sphingosine-1P receptor, CD44. Of course there are many other receptors, such as FGF, insulin, EGF, etc, that may also be targeted. Adhesion molecules that may be targeted include e.g., VCAM, ICAM, cadherins, integrins, selectins, and their binding partners (which are also cell surface molecules). In specific embodiments, it is contemplated that the skilled artisan could prepare rHDL compositions to additionally target T cells for imaging with reagents against CD2 (all T cells) CD3 (all T cells), CD4 (major subset of T cells), CD8 (major subset of T cells),and CD90 (all T cells). Markers for B cells include, e.g., B220 (a B cell-specific isoform of CD45), CD19 and CD20 (both useful pan-targets for both human and mouse B cells). Other useful markers may include NK1.1 that targets NKT cells as well as CD3 (for T cells).

Of course, in addition to antibodies other agents may be used as additional targeting moieties. Such agents include, but are not limited to, ligands for receptors (or vice versa) that are expressed on the surface of a given site to be targeted.

In certain embodiments, the additional targeting moiety is an aptamer. Aptamers are DNA or RNA molecules that have been selected from random pools based on their ability to bind other molecules. Aptamers have been selected which bind nucleic acid, proteins, small organic compounds, and even entire organisms. Methods and compositions for identifying and making aptamers are known to those of skill in the art and are described e.g., in U.S. Pat. Nos. 5,840,867 and 5,582,981 each incorporated herein by reference. In addition to aptamers, DNA, RNA, or modified DNA or RNA molecules also may be included as targeting moieties.

Receptors such as e.g., cytokine receptors may specifically be targeted by using a cytokine having a receptor binding domain capable of interacting with a cell receptor site. Such cytokines include but are not limited to IL-1, IL-2, IL-3, IL-4, IL-5, IL-6, IL-7, IL-8, IL-9, IL-10, IL-11, IL-12, IL-13, EPO, G-CSF, M-CSF, GM-CSF, IGF-1, and LIF. It should be understood that these are merely exemplary ligands of certain receptors and the compositions of the invention may readily be adapted to comprise any ligand to any receptor that is expressed on the cell surface, so long as that ligand can be modified to be attached to e.g., a phospholipid moiety of the rHDLs of the present invention and yet retain its receptor binding capability. In addition, C-reactive protein (CRP) and/or to activated complement could also be targeted. Those of skill in the art are referred to Torzewski et al., (Torzewski et al. Arterioscler Thromb Vasc Biol 1998; 18:1386-92) and which provide additional teachings of the role of CRP in the arterial intima and show that CRP frequently colocalizes with the terminal complement complex in the intima of early atherosclerotic lesions of human coronary arteries. As such, targeting CRP will likely be useful in imaging atherosclerotic lesions at an early stage of atherosclerosis. Drugs designed to treat atherosclerosis may be added to the gadolinium-based complexes to achieve an effective intervention of the disorder at an early stage. Example is DHLA (or its precursor, lipoic acid, LA) which is well known to serve as a cofactor for PMSR and reduce sulfoxidized methionines back to their native form (Biewenga et al. Arzneimittelforschung 1998; 48:144-8; Sigalov A. B. & Stern L. J. Antioxid Redox Signal 2002; 4:553-7)

E. Methods of Making Reconstituted Lipoprotein Complexes

As disclosed in US Pat Appl 20070243136 and incorporated herein by reference, the lipoprotein complexes described herein can be prepared in a variety of forms, including, but not limited to vesicles, liposomes, proteoliposomes, micelles, discoidal and spherical particles. A variety of methods well known to those skilled in the art can be used to prepare the charged lipoprotein complexes. A number of available techniques for preparing liposomes or proteoliposomes may be used. For example, apolipoprotein can be co-sonicated (using a bath or probe sonicator) with the appropriate phospholipids to form complexes. Alternatively, apolipoprotein can be combined with preformed lipid vesicles resulting in the spontaneous formation of charged lipoprotein complexes (U.S. Pat. No. 6,248,353). The charged lipoprotein complexes and liposomal HDL-like compositions can also be formed by a detergent dialysis method; e.g., a mixture of apolipoprotein, charged phospholipid(s) SM and/or lecithin and a detergent such as cholate is dialyzed to remove the detergent and reconstituted to form lipoprotein complexes, or by using an extruder device or by homogenization (see, e.g., Jonas A. Methods Enzymol 1986; 128:553-82; US Pat Appls 20090311191 and 20100202974).

In some embodiments, charged lipoprotein complexes can be prepared by the cholate dispersion method described in US Pat Appls 20040067873 and 20060217312, the disclosures of which is incorporated herein by reference. Cholate can be removed by methods well known in the art. For example cholate can be removed by dialysis, ultrafiltration or by removal of cholate molecules by adsorption absorption onto an affinity bead or resin. In one embodiment, the affinity beads, e.g., BIO-BEADS® (Bio-Rad Laboratories) are added to the preparation of charged lipoprotein complexes and cholate to adsorb the cholate. In another embodiment, the preparation, e.g., a micellar preparation of the charged lipoprotein complexes and cholate, is passed over a column packed with affinity beads.

In a specific embodiment, cholate is removed from a preparation of charged lipoprotein complexes by loading the preparation onto BIO-BEADS® within a syringe. The syringe is then sealed with barrier film and incubated with rocking at 4° C. overnight. Before use, the cholate is removed by injecting the solution through BIO-BEADS®, where it is adsorbed by the beads.

In preferred embodiments, the rHDL complexes are prepared by the sodium cholate dialysis method essentially as described (Sorci-Thomas et al. J Biol Chem 1998; 273: 11776-82) with an initial molar ratio of sodium cholate-POPC-cholesterol-apo A-I of 150:80:4:1. This method has been used previously to prepare rHDL with 2 or 3 apo A-I per particle and 9-11 nm diameter (Sorci-Thomas et al. J Biol Chem 1998; 273:11776-82; Durbin D. M. & Jonas A. J Biol Chan 1997; 272:31333-9; Toledo et al. Arch Biochem Biophys 2000; 380, 63-70; Davidson et al. J Biol Chem 1995; 270:5882-90; Sigalov A. B. & Stern, L. J. Chem Phys Lipids 2001; 113:133-46).

Stable preparations having a long shelf life may be made by lyophilization. For example, the co-lyophilization procedure described below provides a stable formulation and ease of formulation/particle preparation process. Co-lyophilization methods are also described in U.S. Pat. No. 6,287,590, which is incorporated herein by reference in its entirety. The lyophilized charged lipoprotein complexes can be used to prepare bulk supplies for pharmaceutical reformulation, or to prepare individual aliquots or dosage units that can be reconstituted by rehydration with sterile water or an appropriate buffered solution prior to administration to a subject.

U.S. Pat. Nos. 6,004,925, 6,008,202, 6,037,323, 6,046, 166, 6,287,590, 7,588,751, and US Pat Appl 20090312402 (incorporated herein by reference in their entireties) disclose a simple method for preparing charged lipoprotein and liposomal complexes that have characteristics similar to HDL. This method, which involves co-lyophilization of apolipoprotein and lipid solutions in organic solvent (or solvent mixtures) and formation of charged lipoprotein complexes during hydration of the lyophilized powder, has the following advantages: (1) the method requires very few steps; (2) the method uses inexpensive solvent(s); (3) most or all of the included ingredients are used to form the designed complexes, thus avoiding waste of starting material that is common to the other methods; (4) lyophilized complexes are formed that are very stable during storage such that the resulting complexes may be reconstituted immediately before use; (5) the resulting complexes usually need not be further purified after formation and before use; (6) toxic compounds, including detergents such as cholate, are avoided; and (7) the production method can be easily scaled up and is suitable for GMP manufacture (i.e., in an endotoxin-free environment).

In some embodiments, co-lyophilization methods commonly known in the art are used to prepare charged lipoprotein complexes. Briefly, the co-lyophilization steps include solubilizing the apolipoprotein and phospholipids together in an organic solvent or solvent mixture, or solubilizing the apolipoprotein and phospholipids separately and mixing them together. The desirable characteristics of solvent or solvent mixture are: (i) a medium relative polarity to be able to dissolve hydrophobic lipids and amphipatic protein, (ii) solvents should be class 2 or 3 solvent according to FDA solvent guidelines (Federal Register, volume 62, No. 247) to avoid potential toxicity associated with the residual organic solvent, (iii) low boiling point to assure ease of solvent removal during lyophilization, (iv) high melting point to provide for faster freezing, higher temperatures of condenser and, hence less ware of freeze-dryer. In a preferred embodiment, glacial acetic acid is used. Combinations of e.g., methanol, glacial acetic acid, xylene, or cyclohexane may also be used.

The apolipoprotein/lipid solution is then lyophilized to obtain homogeneous apolipoprotein/lipid powder. The lyophilization conditions can be optimized to obtain fast evaporation of solvent with minimal amount of residual solvent in the lyophilized apolipoprotein/lipid powder. The selection of freeze-drying conditions can be determined by the skilled artisan, and depends on the nature or solvent, type and dimensions of the receptacle, e.g., vial, holding solution, fill volume, and characteristics of freeze-dryer used. The concentration of lipid/apolipoprotein solution prior to the lyophilization, for organic solvent removal and successful formation of complexes, can range from 10 to 50 mg/ml concentration of apo A-I equivalent and from 20 to 100 mg/ml concentrations of lipid.

The apolipoprotein-lipid complexes form spontaneously after hydration of apolipoprotein-lipid lyophilized powder with an aqueous media of appropriate pH and osmolality. In some embodiments, the media may also contain stabilizers such as sucrose, trehalose, glycerin and others. In some embodiments, the solution must be heated several times above transition temperature for lipids for complexes to form. The molar ratio of lipid to protein for successful formation of charged lipoprotein complexes can be from 2:1 to 200:1 (expressed in apoA-I equivalents) and is preferably about 2:1 weight of lipid to weight of protein (wt/wt). Powder is hydrated to obtain final complex concentration of about 5-30 mg/ml expressed, in apoA-I protein equivalents.

In some embodiments, apolipoprotein powder is obtained by freeze-drying apolipoprotein solution in $NH_4CO_3$ aqueous solution. A homogeneous solution of apolipoprotein and lipids is formed by dissolving their powders and apolipoprotein in glacial acetic acid. The solution is then lyophilized, and HDL-like charged lipoprotein complexes are formed by hydration of lyophilized powder with aqueous media.

In some embodiments, homogenization is used to prepare apolipoprotein-lipid complexes. This method may be used to prepare apolipoprotein/soybean-PC complexes and is routinely used for formulation of apoA-$I_{Milano}$-POPC complexes. Homogenization can be easily adapted for formation of charged lipoprotein complexes. Briefly, this method comprises forming a suspension of lipids in aqueous solution of apolipoprotein by Ultraturex™, and homogenization of formed lipid-protein suspension using high-pressure homogenizer until suspension becomes clear-opalescent solution and complexes are formed. Elevated temperatures above lipid transition are used during homogenization. Solution is homogenized for extended period of time 1-14 hours and elevated pressure.

In some embodiments, lipoprotein complexes can be formed by co-lyophilization of phospholipid with peptide or protein solutions or suspensions. The homogeneous solution of peptide/protein, phospholipids, SM and/or lecithin (plus any other phospholipid of choice) in an organic solvent or organic solvent mixture can be lyophilized, and charged lipoprotein complexes can be formed spontaneously by hydration of the lyophilized powder with an aqueous buffer. Examples of organic solvents or their mixtures are include, but are not limited to, acetic acid, acetic acid and xylene, acetic acid and cyclohexane, and methanol and xylene.

A suitable proportion of protein (peptide) to lipid can be determined empirically so that the resulting complexes possess the appropriate physical and chemical properties; i.e., usually (but not necessarily) similar in size to HDL. The resulting mixture of apolipoprotein and lipid in solvent is frozen and lyophilized to dryness. Sometimes an additional solvent must be added to the mixture to facilitate lyophilization. It is expected that this lyophilized product will be able to be stored for long periods and will remain stable.

The lyophilized product can be reconstituted in order to obtain a solution or suspension of the charged lipoprotein complex. To this end, the lyophilized powder is rehydrated with an aqueous solution to a suitable volume (typically 5-20 mg charged lipoprotein complex/ml) which is convenient for e.g., intravenous injection. In a preferred embodiment the lyophilized powder is rehydrated with phosphate buffered saline, saline bicarbonate, or a physiological saline solution. The mixture may be agitated or vortexed to facilitate rehydration. In general, the reconstitution step should be conducted at a temperature equal to or greater than the phase transition temperature of the lipid component of the complexes. Within minutes of reconstitution, a clear preparation of reconstituted charged lipoprotein complexes should result.

Other methods include spray-drying, where solutions are sprayed and solvent evaporated (either at elevated temperatures or at reduced pressure). Lipids and apolipoproteins could be solubilized in the same solvent or in different solvents. Powder filling can then be used to fill vials.

Lyophilized powder from apolipoproteins and lipids could also be mixed mechanically. Homogeneous powder containing the apoplipoprotein and lipids could then be hydrated to form spontaneously complexes of the appropriate size and the appropriate lipid:apolipoprotein molar ratio.

An aliquot of the resulting reconstituted preparation can be characterized to confirm that the complexes in the preparation have the desired size distribution; e.g., the size distribution of HDL. Characterization of the reconstituted preparation can be performed using any method known in the art, including, but not limited to, size exclusion filtration, gel filtration, column filtration, gel permeation chromatography, and non-denaturating gel electrophoresis.

For example, after hydration of lyophilized charged lipoprotein powder or at the end of homogenization or cholate dialysis formed apolipoprotein/lipid HDL-like particles are characterized with respect to their size, concentration, final pH and osmolality of resulting solution, in some instances, integrity of lipid and/or apolipoprotein are characterized. The size of the resulting charged lipoprotein particles is determinative of their efficacy, therefore this measurement is typically included for characterization of the particles.

In some embodiments, gel permeation chromatography (GPC), e.g., a high pressure liquid chromatography system equipped with a 1×30 cm Superdex™ column (Pharmacia Biotech) and UV-detector may be used. Complexes are eluted with bicarbonate buffered saline comprised of 140 mM NaCl and 20 mM sodium bicarbonate delivered with 0.5 ml/min flow rate. A typical amount of complex injected is 0.1 to 1 mg based on protein weight. The complexes can be monitored by absorbance at 280 nm.

Protein and lipid concentration of charged lipoprotein particles solution can be measured by any method known in the art, including, but not limited to, protein and phospholipid assays as well as by chromatographic methods such as HPLC, gel filtration chromatography, GC coupled with various detectors including mass spectrometry, UV or diode-assay, fluorescent, elastic light scattering and others. The integrity of lipid and proteins can be also determined by the same chromatographic techniques as well as peptide mapping, SDS-PAGE, N- and C-terminal sequencing for proteins and standard assays to determine lipid oxidation for lipids.

The homogeneity and/or stability of the lipoprotein complexes or composition described herein can be measured by any method known in the art, including, but not limited to, chromatographic methods such as gel filtration chromatography. For example, in some embodiments a single peak or a limited number of peaks can be associated with a stable complex. The stability of the complexes can be determined by monitoring the appearance of new of peaks over time. The appearance of new peaks is a sign of reorganization among the complexes due to the instability of the particles.

The optimum ratio of phospholipids to apolipoprotein(s) in the charged complexes can be determined using any number of functional assays known in the art, including, but not limited to, gel electrophoresis mobility assay, size exclusion chromatography, interaction with HDL receptors, recognition by ATP-binding cassette transporter (ABCA1), uptake by the liver, binding to and uptake by macrophages, and pharmacokinetics/pharmacodynamics. For example, gel electrophoresis mobility assays can be used to determine the optimum ratio of phospholipids to apolipoproteins in the charged complexes. The charged complexes described herein should exhibit an electrophoretic mobility that is similar to natural pre-beta-HDL or alpha-HDL particles. Thus, in some embodiments, natural pre-beta-HDL or alpha-HDL particles can be used as standard for determining the mobility of the charged complexes.

As another example, size exclusion chromatography can be used to determine the size of the charged complexes described herein as compared to natural pre-beta-HDL particles. Natural pre-beta-HDL particles generally are not larger than 10-12 nm, and discoidal particles are usually around 7-10 nm.

As another example, HDL receptors can be used in a functional assay to identify which complex is closest to natural pre-beta-HDL particles, or to identify which complex is the most effective in removing and/or mobilizing cholesterol or lipids from a cell In one assay, the complexes can be tested for their ability to bind ABCA-1 receptors. Such an assay can differentiate ABCA-1 dependent on independent removal of cholesterol. Even though apoA-I is considered the best ligands for such an assay, complexes such as small micellar or small discoidal particles are also potent ABCA-I ligands. ABCA-1 binding assays that can be used are described (Brewer et al. Arterioscler Thromb Vasc Biol 2004; 24, 1755-60).

As another example, ABCA1 expressing cells are known to recognize free apoA-1 and to a lesser extent, natural pre-beta-HDL particles (Brewer et al. Arterioscler Thromb Vasc Biol 2004; 24, 1755-60). In these embodiments, recognition of ABCA1 cells of natural pre-beta-HDL particles can be compared to any one of the complexes described herein to identify the complex that most closely resembles natural pre-beta-HDL particles.

As another example, macrophage scavenger receptors can be used in a functional assay to identify which complex is the most effective in being absorbed and/or uptaken by macrophages. In one assay, the complexes can be tested for their ability to bind macrophage scavenger receptors. Such an assay can differentiate macrophage scavenger receptor-dependent on independent binding to and/or uptake by macrophages. Assays to assess binding, uptake and degradation of the compositions of the present invention by macrophages that can be used herein are well known in the art (e.g., Suc et al. J Cell Sci 2003; 116:89-99; Panzenboeck et al. J Biol Chem 1997; 272:29711-20; Musanti R. & Ghiselli G. Arterioscler Thromb 1993; 13:1334-45; Thome et al. FEBS Lett 2007; 581:1227-32).

A relatively simple approach for identifying lipoprotein complexes that most closely resemble natural pre-beta-HDL particles is to perfuse livers with a solution containing the reconstituted charged complexes and measure the amount that is taken up by the liver.

In some embodiments, the pharmacokinetics/pharmacodynamics (PK/PD) of the compositions of the invention can be measured following a single injection in rabbits. In these embodiments, the concentration of apo A-1 or apo A-II (or fragments thereof) is used as a marker of the kinetics. The pharmacodynamics can be measured as the amount of cholesterol mobilized above baseline after a single injection, as well s the amount of cholesterol in the HDL fraction. PK and PD depend on the nature of the phospholipids, the composition of the phospholipids, the lipid:apolipoprotein molar ratio and the phospholipid concentration of the complex. For example, dipalmitoylphosphatidylcholine (DPPC)/apoA-1 complexes have a longer half-live than egg phosphatidylcholine (EPC)/apoA-I complexes. Sphingomyelin/apoA-1 complexes have a longer half-life than EPC/apoA-1 complexes. The half-life of human apoA-1 in humans is approximately 5 to 6 days.

F. rHDL Moieties as Drug Delivery Vehicles

As disclosed in US Pat Appl 20070243136 and incorporated herein by reference, in certain embodiments, it may be desirable to have rHDL moieties in which the metallic contrast agent is conjugated to a component of the core of the HDL, such as e.g., a cholesteryl ester. Methods and compositions for making DTPA mono- and di-stearyl esters corresponding to metal, e.g., gadolinium chelates, or non-metals, e.g., iodine, are known to those of skill in the art and have previously been described (Kabalka et al. Magn Reson Med 1988; 8:89-95; Torchilin V. P. Mol Med Today 1996; 2:242-9; Weissig et al. Colloids Surf B Biointerfaces 2000; 18:293-9) Such methods may be used to produce rHDLs in which the rHDLs of the present invention comprise a targeting apolipoprotein moiety at the surface and a metallic or non-metallic agent in the core. Such compositions may be useful, for example, to target the imaging agent to a specific site and to later apply an enzyme or other composition that would promote the metabolism or breakdown of the HDL particle, such as a lipoprotein lipase, cholesteryl ester transfer protein or a phospholipid transfer protein, to effect release the imaging agent in a control manner. Imaging agent can be released enzymatically. The characterization of the signal can change and be used to improve detection of any disease/disorder or any organ in the body. Such a composition would be useful is the imaging agent was being used to track the delivery of a drug or other therapeutic component to a specific in vivo site.

Therefore, it is contemplated that the compositions of the present invention, in addition to comprising a targeting moiety and a metallic or non-metallic contrast agent, also may comprise a third agent that is being delivered to effect a therapeutic outcome. Any agent can be delivered in this manner and methods of using lipoproteins to deliver drugs are well known to those of skill in the art (Rensen et al. Adv Drug Deliv Rev 2001; 47:251-276). The therapeutic agent that may be used in the compositions of the invention is limited only by the features that it should not destroy the structural integrity of the rHDL particle or render it larger than 18 nm. Further, the drug should be such that it does not quench or otherwise interfere with the signal generated by the metallic or non-metallic ion.

In specific embodiments, the compositions of the present invention may contain naturally occurring DHLA or its precursor, lipoic acid, LA, to deliver these therapeutic agents to sites of interest such, for example, as atherosclerotic plague. DHLA is a metabolic product formed in vivo from lipoic acid (Biewenga et al. Gen Pharmacol 1997; 29:315-31), which is widely used as a therapeutic agent in a variety of diseases. Several lines of evidence suggest that the antioxidant properties of lipoic acid and more importantly, its reduced form, DHLA, are at least in part responsible for the therapeutic effect. Currently, DHLA alone or in equimolar mixture with lipoic acid is widely used as a supplement. DHLA is also suggested for the amelioration of diabetes mellitus types 1 and 2 (including impaired glucose tolerance, pre-diabetes, insulin resistance, metabolic syndrome X and as an adjunct to oral antidiabetic agents and/or insulin), diabetic and non-diabetic microvascular diseases (including nephropathy, neuropathy and retinopathy), diabetic and non-diabetic macrovascular diseases (including heart attack, stroke, peripheral vascular disease and ischemia-reperfusion injury), hypertension, vasoconstriction, obesity, dyslipedemia, and neurodegenerative disorders (including Parkinson's disease, mild cognitive impairment, senile dementia, Alzheimer's disease, hearing loss and chronic glaucomas (see e.g., US Pat Appls 20090068264, 20020110604, and 20020177558), the disclosures of which are incorporated herein by reference in their entities. In addition, DHLA is well known in the art to serve as a cofactor for PMSR and reduce sulfoxidized methionines back to their native form (Biewenga et al. Arzneimittelforschung 1998; 48:144-8; Sigalov A. B. & Stern L. J. Antioxid Redox Signal 2002; 4:553-7). Therefore, it is contemplated, the compositions of the present invention, in addition to comprising a targeting moiety and a metallic or non-metallic contrast agent, also may comprise DHLA and/or LA that is being delivered to effect a therapeutic outcome (for example, to reduce methionine sulfoxides in human apolipoproteins A-I and A-II of atherosclerotic plagues back to their native form). In certain embodiments, the modified apolipoprotein targeting moieties of the rHDL compositions of the invention are methionine sulfoxide-containing apolipoproteins A-I, A-II and/or fragments thereof. Incorporation of DHLA and/or LA in these compositions may result in reducing apolipoprotein methionine sulfoxides of the rHDL compositions back to native methionines after delivery of contrast agents to sites of interest such, for example, as atherosclerotic plagues.

G. Methods of Using the rHDL

The rHDL and HDL-like liposomal compositions of the present invention will be useful in any imaging techniques such as computed tomography (CT), gamma-scintigraphy, positron emission tomography (PET), single photon emission computed tomography (SPECT), magnetic resonance imaging (MRI), and combined imaging techniques. These compositions will provide effective delivery of a contrast agent to macrophage-rich sites of interest in vivo. In particularly preferred embodiments, the compositions are used to image atherosclerotic plaques. As disclosed in US Pat Appl 20070243136 and incorporated herein by reference, such techniques have previously been used in pigs, primates and humans as well as mice and other animals to document, e.g., progression and regression of atherosclerosis in vivo (Skinner et al. Nat Med 1995; 1:69-73; McConnell et al. Arterioscler Thromb Vase Biol 1999; 19; 1956-9; Worthley et al. Circulation 2000; 101:2956-61; Worthley et al. Circulation 2000; 101:586-9; Johnstone et al. Arterioscler Thromb Vase Biol 2001; 21:1556-60; Helft et al. Circulation 2002; 105:993-8; Helft et al. J Am Coll Cardiol 2001; 37:1149-54; Li et al. Radiology 2001; 218:670-8; Lin et al. J Magn Reson Imaging 1997; 7:183-90; Corti et al. J Am Coll Cardiol 2002; 39:1366-1373; Toussaint et al. Circulation 1996; 94:932-8; Yuan et al. Circulation 1998; 98:2666-71; Coulden et al. Heart 2000; 83:188-91; Hatsukami et al. Circulation 2000; 102:959-64; Fayad et al. Ann N Y Acad Sci 2000; 902:173-86; Fayad et al. Circulation 2000; 101:2503-9; Botnar et al. Circulation 2000; 102:2582-7; Jaffer et al. Arterioscler Thromb Vase Biol 2009; 29:1017-24; Ouhlous et al. J Magn Reson Imaging 2002; 15:344-51; Cai et al. Circulation 2002; 106:1368-73; Weissleder R. Nat Rev Cancer 2002; 2, 11-8). Any such techniques may now be modified and conducted using the compositions of the present invention.

In addition, as disclosed in US Pat Appl 20070243136 and incorporated herein by reference, it is contemplated that, as HDLs are found circulating within the blood, the compositions of the invention may be used in imaging other tissues and sites within the body. As HDLs have the advantage of not being atherogenic, these compositions may be used in blood pool analyses to facilitate imaging of, e.g., myocardial and cerebral ischemia, pulmonary embolism, vascularization of tumors, tumor imaging, tumor perfusion, and the like. Given that the rHDL compositions of the invention comprise targeting agents, rHDLs may be designed to target any site within the body that contains a site-specific marker such, for example, as macrophages in atherosclerotic plagues. As HDL is able to enter into interstitial fluid in general (i.e., across the endothelial layer of all blood vessels), the rHDL of the invention may be used to deliver imaging agents and drugs to any site.

The compositions will generally be injected into the animal to be imaged. By way of example, and in order to test the efficacy of the rHDL compositions, the rHDL compositions may be injected into mice or other test animals and their targeting to a site of interest may thus be determined. Preferably, prior to injection into mice, the rHDL will be tested for pyrogens. The initial volume to be injected is not expected to exceed about 0.3 ml per mouse, based on the projected rHDL dose of about 8 mg of apo A-I or equivalent dose of apo A-II and/or fragments thereof per mouse and previous literature indicating that rHDL mixtures containing about 26 mg apoA-I/ml can be prepared and injected without difficulty (Shah et al. Circulation 2001; 103:3047-50). This volume can be routinely injected by jugular vein. This route has the added advantage of allowing an increase in the volume of injectate, in case it becomes necessary to increase the amount of Gd to increase the signal being generated.

Those of skill in the art also routinely monitor in vitro relaxivity measurement for contrast agents. It is contemplated that the contrast agents in the imaging compositions of the present invention have a greater relaxivity than the metallic contrast agents being administered through conventional methods because of the substantial load of Gd on rHDL. Any increase in relativity of the instant contrast agents as compared related compositions prepared in other non-HDL vehicles will be an advantageous property of the compositions of the present invention. Preferably, there is a 30-250% greater relaxivity of the present compositions as compared to those known to those of skill in the art. Thus, the higher relaxivities coupled to the specific targeting of the contrast agent using the rHDL compositions of the invention provide an important advance (advantage) in comparison to the known in the art NMR contrast agent compositions.

In specific embodiments, in vitro relaxivity measurements of rHDL-DTPA-PE-Gd will be prepared in saline with different concentrations from 0-3 mM in 1.0 ml centrifuge tubes. The samples will be placed in a 30 mm diameter birdcage coil and placed in the 9.4 T MR system. All experiments will be performed at 37° C. T1 relaxation data will be collected with a spin-echo sequence with a variable TR (300, 800, 1500, 2000, 3000 msec) and with a TE of 12.8 msec. T1 values of the samples will then be calculated from a 3 parameter exponential fit and plotted as 1/T1 vs. Gd concentration. The slope of this line will be molar relaxivity, R1. This would be used to perform quality control and dosage adjustments.

As disclosed in US Pat Appl 20070243136 and incorporated herein by reference, interstitial penetration of the particles of the invention reflects the traversal across endothelium (required for entry into plaques). In order to assess this parameter, groups of young adult apo E-KO (n=1 5) and WT (n=15) mice are administered one of the following: $^{125}$I-labeled native human HDL (positive control), $^{125}$I-labeled rHDL, $^{125}$I-labeled Gd-rHDL, or $^{125}$I-human VLDL (too large to significantly cross the endothelium; negative control) (Sloop et al J Lipid Res 1987; 28:225-37; Vessby et al. J Lipid Res 1987; 28:629-41). The lipoproteins may be labeled in either the apo A-I (HDL) or apoB (VLDL) moieties using a standard iodination protocols (Fuki et al. J Clin Invest 1997; 100:1611-22). To simulate the first series of imaging studies, each mouse will receive at least $10^{17}$ lipoprotein particles. The $t_{1/2}$ for HDL/apoA-I in the circulation of a mouse is roughly 10 h (Tape C. & Kisilevsky R. Biochim Biophys Acta 1990; 1043:295-300). Thus, during the 10th hour after injection (i.e., from 9 to 10 h after injection), a suction blister will be induced on the back of each mouse, following a standard procedure used extensively in rodents (and humans) to induce the extravasation of interstitial fluid (e.g., see Vessby et al. J Lipid Res 1987; 28:629-41; Herfst M. J. & van Rees H. Arch Dermatol Res 1978; 263:325-34). At 10 h (i.e., about 1 half-life of native HDL) after injection, interstitial fluid will be harvested from each suction blister, and then the mice will be sacrificed and plasma samples taken for gamma counting. Based on the predicted physical properties of the native and rHDL particles, both are expected to exhibit ratios of interstitial-to-plasma concentrations of approximately 1:3. In contrast, the labeled VLDL should be almost entirely excluded from the interstitial space (Sloop et al. J Lipid Res 1987; 28:225-37; Vessby et al. J Lipid Res 1987; 28:629-41). If the Gd-rHDL particles exhibit substantially less interstitial penetration than $^{125}$I-HDL, the size and/or surface charge of the reconstituted particles may require adjustment.

In certain embodiments it may be desirable to monitor the biodistribution, autoradiography, and metallic contrast ion content of the rHDL compositions of the present invention. In exemplary methods a group of apo E-KO (n=15) and WT (n=15) mice can be fed on the well-known "Western diet" for 16 weeks (to accelerate the formation of lesions in the aorta of apo E-KO mice). The imaging compositions of the present invention, e.g., rHDL-DTPA-PE can be labeled with $^{111}$In (rHDL-DTPA-PE-$^{111}$In) using standard methods (Phillips W. T. Adv Drug Deliv Rev 1999; 37:13-32) and injected via the tail vein. After 4 h, 12 hrs, and 24 his post injection, randomly selected mice (5 in each group) can be sacrificed and the following tissues harvested: blood, heart, lungs, liver, kidneys, spleen, stomach, bone, muscle, skin, urine and aorta.

The organs are weighed and the radioactivity counted. The organ biodistribution values is expressed as % injected dose/g tissue (% ID/g). The aorta should be subjected to further study. As lesions will be diffusely distributed, half of the aorta is reserved for sectioning of lesioned and non-lesioned areas and the other half opened longitudinally and stained with Sudan IV to visualize lesions. Autoradiographic images are obtained using routine techniques of exposure of the stained aorta to Kodak Biomax high-speed film for a desired period of time, e.g., 1 week. By comparing the location of the autoradiographic signals to the Sudan staining, it is possible to determine the presence of rHDL and if there is enrichment in lesioned vs. nonlesioned areas. In the absence of a targeting molecule (or other strategies to promote retention of the rHDL in lesions) detectable, but relatively low, signals are expected, including at lesion sites. An advantage of the compositions of the present invention as compared to the use of iron particles or small micelles, which also can enter lesions, but are retained "non-specifically," the molecules of the present invention are specifically targeted to a specific site. Thus, while iron particles and small micelles produce only non-specific signaling, the molecules of the present invention provide an excellent alternative for signal enhancement based on the presence of specific cells (e.g., macrophages) and/or molecules of interest within the plaque.

The portions of aorta reserved for sectioning may be processed using methods known to those of skill in the art, (e.g., Rong et al. Circulation 2001; 104:2447-52; Choudhury R. P. & Fisher E. A. Arterioscler Thromb Vasc Biol 2009; 29:983-91; Choudhury et al. Arterioscler Thromb Vasc Biol 2004; 24:1904-9; Fayad et al. Circulation 1998; 98:1541-7), but with the addition here of autoradiography and immunostaining for human apoA-I and or apo A-II. Human-specific monoclonal antibodies against apoA-I and apo A-II for this purpose are known to those of skill in the art. These data allow confirmation of the entry of the rHDL into the aortic wall and to determine its distribution within the tissue. These assays (on Sudan-stained intact aorta as well as on aortic sections) may be repeated for the rHDL engineered to promote its retention in plaques.

In a parallel mouse study as above (15 apoE-KO and 15 WT), the Gd content in the aorta after sacrifice is assessed by inductively coupled plasma (ICP) analyses (Gailbraith Labs, Inc.) (Glogard et al. Int J Pharm 2002; 233:131-40; Fossheim et al. Magn Reson Imaging 1999; 17:83-9; Tamat et al. Pigment Cell Res 1989; 2:281-5).

As disclosed in US Pat Appl 20070243136 and incorporated herein by reference, methods of performing in vivo MRM also may be used to test the efficacy of the present imaging compositions. Contrast agent injection of rHDL-DTPA-PE-Gd into animals (15 apoE-KO; and 15 WT) and in vivo MRM may be performed. Briefly, to assess the plaque the following MRM may be conducted: 1) in vivo multicontrast black-blood pre-contrast enhanced (CE) MRM; 2) in vivo postcontrast (rHDL-DTPA-PE-Gd complex) CE MRM black-blood T1W imaging; and 3) ex vivo post-CE MRM. Multiple different contrast agent concentrations should be tested based on the relaxivity and biodistribution results. As noted herein, initial injections should preferably contain ~$10^{18}$ Gd ions, delivered as rHDL-Gd-DPTA-PE in an injection volume of ~0.3 ml per mouse.

Following in vivo experiments, ex vivo MRM also may be performed. The animals are euthanized, and perfused fixed at physiological pressure. The heart is harvested and fixed in 4% paraformaldehyde for at least 24 hr. Ex vivo MRM experiments are performed using a 10-mm birdcage coil using methods previously described (Itskovich et al. Magn Reson Med 2003; 49:381-5; Fatterpekar et al. AJNR Am J Neuroradiol 2002; 23:1313-21). Briefly, each specimen will be washed and placed in an 8-mm polyethylene tube filled with Fomblin (perfluoropolyether, Ausimont USA Inc., Morristown, N.J.) and sealed to prevent air bubbles. The use of Fomblin limits tissue dehydration and MR artifacts on the surface of the specimen. Multicontrast MR images are acquired with same parameters as in the in vivo sequence but now with a 25-50 um/pixel resolution. The specimens may further be histologically analyzed.

The apparati for use in imaging tissues are not considered limiting to the invention and the compositions may be used in any MRI technique known to those of skill is the art. Simply by way of example, those of skill in the art referred to e.g., U.S. Pat. Nos. 6,590,391; 6,591,128; 6,586,933; 6,580,936; 6,600,401; 6,611,143; and 6,541,973, which describe MRI apparati in detail. These are merely exemplary descriptions and those of skill in the art will be aware that other imaging techniques may be used in other to perform the methods of the present invention using the compositions described herein.

The methods described in U.S. Pat. No. 6,498,946 may be particularly useful in magnetic resonance microscopy (MRM) and atherosclerotic plaque imaging as discussed infra. In particular embodiments, the compositions of the present invention may be used to assess the efficacy or dosing of a particular existing drug. For example, in the case of atherosclerosis, the atherosclerotic lesion size or composition may be monitored prior to and after the administration of a given drug treatment to assess whether the treatment is effective at reducing the size or composition of a lesion.

In particularly preferred embodiments, the compositions of the present invention can be used for targeting macrophages in imaging of macrophage-related diseases characterized by neoplastic tissue (US Pat Appl 20010002251) including, but not limiting to, the cancers sarcoma, lymphoma, leukemia, carcinoma and melanoma, cardiovascular diseases (e.g., arteriosclerosis, atherosclerosis, intimal hyperplasia and restenosis) and other activated macrophage-related disorders including autoimmune diseases (e.g., rheumatoid arthritis, Sjogrens, scleroderma, systemic lupus erythematosus, non-specific vasculitis, Kawasaki's disease, psoriasis, Type I diabetes, pemphigus vulgaris), granulomatous diseases (e.g., tuberculosis, sarcoidosis, lymphomatoid granulomatosis, Wegener's granulomatosus), inflammatory diseases (e.g., inflammatory lung diseases such as interstitial pneumonitis and asthma, inflammatory bowel disease such as Crohn's disease, and inflammatory arthritis), and in transplant rejection (e.g., in heart/lung transplants). Examples of macrophage-related diseases are also macrophage-related pulmonary diseases such as emphysema (Marten K. & Hansell D. M. Eur Radiol 2005; 15:727-41; US Pat Appl 20050281740).

H. Pharmaceutical Compositions and Kits Comprising rHDL

It is contemplated that that rHDL compositions of the invention will be used in MRI or other imaging method in any in which it is desired to obtain an image of an internal site. Thus, the compositions of the invention will be administered, in vivo. Therefore, it will be desirable to prepare the compositions of the invention as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

As disclosed in US Pat Appl 20070243136 and incorporated herein by reference, aqueous compositions of the present invention comprise an effective amount of the rHDL to deliver an appropriate amount of metallic or non-metallic contrast agent, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As HDL is normally found circulating in the system of an animal, it is contemplated that the rHDL imaging compositions of the invention should not produce such an adverse effect. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the rHDL of the invention (e.g., so long as the agent does not destroy the structural integrity of the molecule or quench the signal of the metallic ion), its use in the compositions of the invention is contemplated. Supplementary contrast enhancing ingredients also can be incorporated into the compositions.

The term "effective amount" as used herein refers to any amount of the rHDL compositions of the invention that produce a reproducible and evaluable image of a given in vivo site. Thus, it should be understood that the effective amount of the rHDL may vary depending on the size of the animal, the site at which the composition is to be administered and the route of such administration. The field of MRI technology is advanced and technicians are experienced in determining whether a given composition is producing the desired intensity of signal. In specific embodiments discussed in the examples, it was determined that 10 Gd-DPTA-PE molecules/rHDL particle may be an exemplary dose to image atherosclerotic plaques in mice. It should, however, be understood that more or less than 10 Gd-DPTA-phospholipid molecules/rHDL particle also are contemplated. For example, the imaging compositions may advantageously comprise 1, 2, 3, 4, 5, 6, 7, 8, 9, 10, 11, 12, 13, 14, 15, 16, 17, 18, 19, 20 or more Gd-DPTA-phospholipid particles/rHDL molecule. It should be understood that the number of Gd-DPTA-phospholipid/rHDL particle is limited only by how many such molecules can be incorporated into the rHDL particle without destroying the structural integrity of the HDL or making it larger than would be effective as an imaging compositions of the invention (i.e., larger than 18 nm.)

With respect to the administration of rHDL, and using the apoAI content of the rHDL as a measuring parameter, it is contemplated that the amounts of rHDL administered to mice may comprise 8 mg, 10 mg, 12 mg, 14 mg, 16 mg, 18 mg, 20 mg, 22 mg, 24 mg, 26 mg, 28 mg, or even 30 mg of apoAI. Such compositions can be extrapolated to humans. For example, infusion of rHDL compositions of the present invention that comprise 45 mg apoA-I protein (or equivalent amount of apo A-II and/or peptide fragments of apo A-I and A-II)/kg body weight of animal to be treated will be particularly useful. The compositions may thus comprise 40 mg apoA-I protein/kg, 45 mg apoA-I protein/kg, 50 mg apoA-I protein/kg, 55 mg apoA-I protein/kg, 60 mg apoA-I protein/kg or more. Given the characteristics of HDLs discussed herein above, those of skill in the art should readily be able to determine the amounts of other HDL components being administered in a given dose.

In certain embodiments, the amounts of phospholipid doses that can be used in the compositions described herein may be inferred from experience in administering Intralipid™ (Kabivitrum Inc., California and Stockholm, an aqueous suspension of lipid droplets that is sterile and suitable for intravenous feeding of patients. Other similar lipid solutions that may provide guidance as to amounts and proportions of lipids that may safely be provided to patients include Nutralipid™ (Pharmicia, Quebec), Liposyn™ (Abbot Labs, Montreal)). These compositions are used by the biomedical optics community as a scattering media in optical experiments. In other embodiments, the amount of rHDL that is administered in the imaging embodiments of the present invention is guided by the typical concentrations of HDL in human plasma, and the dose used in the imaging modalities described herein may use up to double the concentration of HDL normally found in human plasma. Those of skill in the art are aware of amounts of apo A-I and HDL that may typically be administered. See e.g., U.S. Pat. Nos. 6,953,840; 7,435,717; and 7, 491,693; Nissen et al. JAMA 2003; 290:2292-300, which are incorporated herein by reference as showing parameters for the selection of patients that receive HDL and amounts of HDL that may typically be administered. For example, the patients may receive between 15 mg/kg or 45 mg/kg of rHDL. Those of skill in the art will be able to vary the amount administered depending on the size and weight of the patient and the like.

The rHDL particles of the present invention are intended for use in any MRI regimen that is conventional in the art, including MRI of humans. Administration of the imaging compositions according to the present invention will be via any common route used in imaging so long as the target tissue is available via that route. This includes administration by orthotopic, intradermal subcutaneous, intramuscular, intraperitoneal, intrathecal, or intravenous injection. Alternatively, oral, nasal, buccal, rectal, vaginal or topical administration also are contemplated. For imaging atherosclerotic plaques intravenous injection is contemplated. Such injections compositions would normally be administered as pharmaceutically acceptable compositions that include physiologically acceptable carriers, buffers or other excipients. For imaging of tumors, direct intratumoral injection, injection of a resected tumor bed, regional (i.e., lymphatic) or general administration is contemplated. It also may be desired to perform continuous perfusion over hours or days via a catheter to a disease site, e.g., a tumor or tumor site.

The imaging compositions of the present invention are advantageously administered in the form of injectable compositions either as liquid solutions or suspensions; solid forms suitable for solution in, or suspension in, liquid prior to injection may also be prepared. The rHDL compositions of the invention can be sterilized by heat, radiation and/or filtration, and used as such, or the compositions can be further dehydrated for storage, for instance by lyophilization. The dehydrated material in form of a powder from which the MRI contrast agent may be produced by admixing the powder with a portion of carrier liquid and shaking. For practical application the compositions of the invention in the medical field, it is contemplated that the dried components and the carrier liquid can be marketed separately in a kit form whereby the contrast agent is reconstituted by mixing together the kit components prior to injection into the circulation of patients.

A typical composition for such purpose comprises a pharmaceutically acceptable carrier. For instance; pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, buffered solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the imaging composition may be adjusted according to well known parameters the amount and degree of signal intensity observed and required.

The individual components of the rHDL imaging compositions of the present invention may be provided in a kit, which kit may further include instructions for formulating and/or using the imaging agents of the invention. Such a kit will comprise a first composition comprising a metallic or non-metallic contrast agent, a second composition comprising a phospholipid covalently linked to a chelating moiety, a third composition comprising HDL modified apolipoproteins A-I and A-II and/or fragments thereof, a fourth composition comprising a free phospholipid, and a fifth composition comprising a sterol. The kit may further comprise a sixth composition comprising HDL core lipids (e.g., cholesteryl ester, and TG).

The kit also may comprise a device for delivering the composition to a mammal.

EXAMPLES

The invention now being generally described, it will be more readily understood by reference to the following examples, which are included merely for purposes of illustration of certain aspects and embodiments of the present invention, and are not intended to limit the invention.

The following non-limiting Examples are put forth so as to provide those of ordinary skill in the art with illustrative embodiments as to how the compounds, compositions, articles, devices, and/or methods claimed herein are made and evaluated. The Examples are intended to be purely exemplary of the invention and are not intended to limit the scope of what the inventor regard as his invention. Efforts have been made to ensure accuracy with respect to numbers (e.g., amounts, temperature, etc.) but some errors and deviations should be accounted for. Unless indicated otherwise, parts are parts by weight, temperature is in ° C., or is at ambient temperature, and pressure is at or near atmospheric.

Example 1: Synthesis and Modification of Peptides

This example demonstrates one embodiment of a synthesized apo A-I peptide containing methionine residues at position 148 as referred to the full-length apo A-I primary sequence. It also illustrates one embodiment of a modified synthetic apo A-I peptide containing methionine sulfoxide at positions 148 as referred to the full-length apo A-I primary sequence. Although it is not necessary to understand the mechanism of an invention, it is believed that being incorporated into the rHDL compositions of the present invention, this modified peptide targets the rHDL of the invention to sites of interest such, for example, as macrophages in atherosclerotic plague.

It is well known to those of ordinary skill in the art that other apo A-I peptide fragments such as those containing methionine residues at positions 86 or 112 can be easily synthesized using standard procedures described below or manufactured by any technique for peptide synthesis known in the art. It is further understood by those of ordinary skill in the art that methionine residues in these peptide fragments can be oxidized to methionine sulfoxides using the standard procedures described below (including those incorporated herein by reference) and the modified peptides can be purified by any method known in the art, including HPLC. It should be also understood by those of ordinary skill in the art that apo A-I peptide fragments containing tyrosine residue at position 192 can be easily synthesized or manufactured by any technique for peptide synthesis known in the art (including those incorporated herein by reference). It is further understood by those of ordinary skill in the art that tyrosine residue of these peptide fragments can be oxidized to 3-chloro-, 3-nitro- or 3,5-dibromotyrosine, using, for example, the standard procedures known in the art (Shao et al. J Biol Chem 2005; 280:5983-93; Weiss et al. Science 1986; 234:200-3). It is well known to those of ordinary skill in the art that apo A-II peptide fragments containing methionine residue at position 148 as referred to the full-length apo A-II primary sequence, can be easily synthesized using standard procedures described below or manufactured by any technique for peptide synthesis known in the art (including those incorporated herein by reference). It is further understood by those of ordinary skill in the art that methionine residues in these peptide fragments can be oxidized to methionine sulfoxides using the standard procedures described below (including those incorporated herein by reference) and the modified peptides can be purified by any method known in the art, including HPLC.

The first step is to synthesize the peptide corresponding to a portion of an apo A-I sequence. Although it is not necessary to understand the mechanism of an invention, it is believed that being incorporated into the rHDL compositions of the present invention, this peptide mimics structural and functional properties of full-length apo A-I.

The synthesis of peptides may involve the use of protecting groups. Peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the .alpha.-amino group of the component containing the activated carboxyl group can be blocked with a tertbutyloxycarbonyl group. This protecting group can be subsequently removed by exposing the peptide to dilute acid, which leaves peptide bonds intact.

In one embodiment, the amino acid sequence of a peptide comprises $NH_2$-LQEKLSPLGEEMRDR-ARAHVDALRTHLAPY-OH (SEQ ID NO:1), hereafter referred to as "apo A-I Met148 peptide".

An unprotected peptide can be synthesized or manufactured by any technique for peptide synthesis known in the art, including, e.g., the techniques described in U.S. Pat. Nos. 6,004,925, 6,037,323 and 6,046,166 with greater than 95% purity as assessed by HPLC. Alternatively, an unprotected peptide can be purchased from companies such as AnaSpec (Fremont, CA, USA). Peptide molecular mass can be checked by matrix-assisted laser desorption ionization mass spectrometry.

To convert methionine in apo A-I Met148 peptide to methionine sulfoxide, the standard procedure known in the art to prepare apo A-I containing methionine sulfoxides can be used (Anantharamaiah et al. J Lipid Res 1988; 29:309-18; Sigalov A. B. & Stern L. J. FEBS Lett 1998; 433:196-200; Sigalov A. B. & Stem L. J. Chem Phys Lipids 2001; 113:133-46; von Eckardstein et al. J Lipid Res 1991; 32:1465-76). Briefly, a purified (about 15 mg) can be dissolved in 1 ml of 3 M guanidine-HCl, pH 7.4, and then hydrogen peroxide was added to a final concentration of 300 mM. The mixture is incubated at 20° C. for 15 min, and an oxidized peptide is purified by preparative HPLC using a BioCAD/SPRINT System from PerSeptive Biosystems (Cambridge, MA, USA), a Vydac C-18 column (22 mm×250 mm) and a two-solvent system: A, trifluoroacetic acid/water (1:1000, v/v); B, trifluoroacetic acid/acetonitrile/water (1:900:100, v/v). The column is heated to 50° C. in a water bath and peptides (modified and unmodified) are eluted at a flow rate of 15 ml/min with 28-49%, 49-53% and 53-73% gradient steps of solvent B over 12, 9 and 12 min, respectively. Then the content of solvent B is increased to 100% over 3 min, and finally decreased to 28% over 2 min. Peaks are identified by analytical HPLC. Analytical HPLC is performed using a Waters Automated Gradient Controller, a Waters 745B Data Processor and a Thermo Separation Products Spectra 100 UV-visible detector, coupled to a Vydac C-18 column (4.6 mm×250 mm) heated to 50° C. and eluted with the same two-solvent system at a flow rate of 1.2 ml/min and 28-64% gradient of B over 33 min. Then the content of B was increased to 100% over 2 min, and finally decreased to 28% over 2 min. The HPLC column eluates are monitored by absorbance at 214 nm. Mass spectra of a purified modified peptide is measured using a Voyager Elite STR mass spectrometer from PerSeptive Biosystems (Cambridge, MA, USA). As expected, conversion of one methionine residue to methionine sulfoxide results in increasing the molecular weight of the peptide by 16 atomic mass units corresponding to an addition of one extra oxygen atom to the peptide molecule.

Example 2: Isolation and Purification of Apolipoproteins A-I and A-II

As discussed herein throughout, the present invention is related to imaging compositions that comprise rHDL as a backbone structure. The apolipoproteins for the production of the rHDL composition may be derived from an animal as a source of the apolipoproteins for the production of the rHDLs. In a preferred method for the producing rHDLs the apolipoproteins are from human HDL.

Figure 6A:
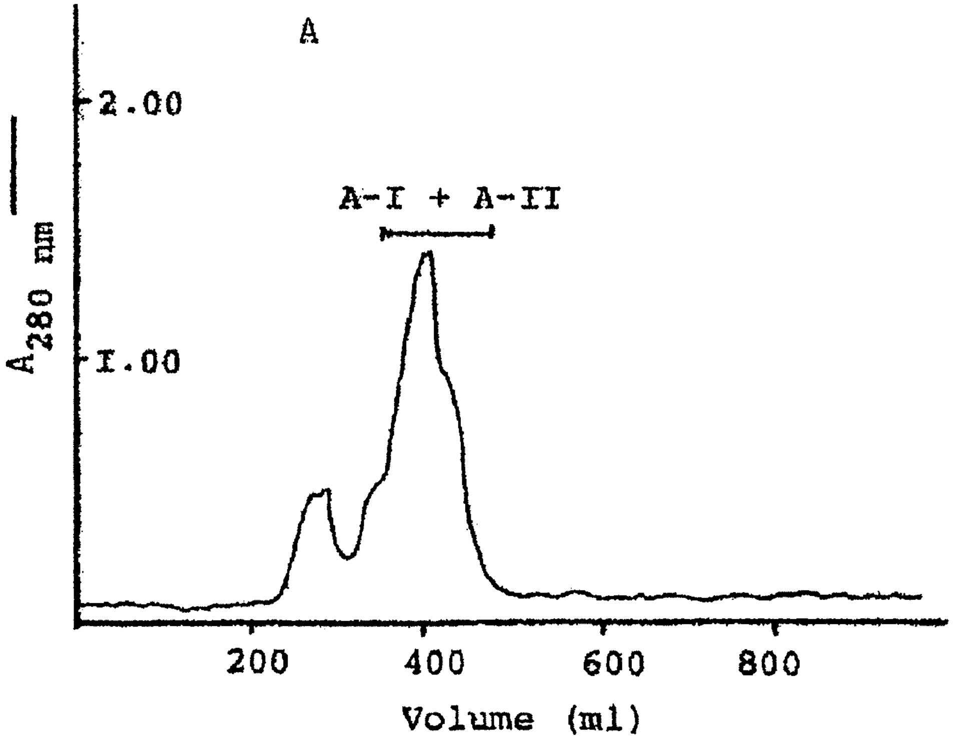
FIG. 6A presents the exemplary data showing isolation of pooled apolipoproteins A-I- and A-II-containing fractions from delipidated 1.063-1.210 g/ml human high density lipoproteins (HDL) using a Toyopearl HW-55F chromatography. Elution buffer: 10 mM Tris-HCl, 8 M urea, pH 8.6.
Figure 6B:
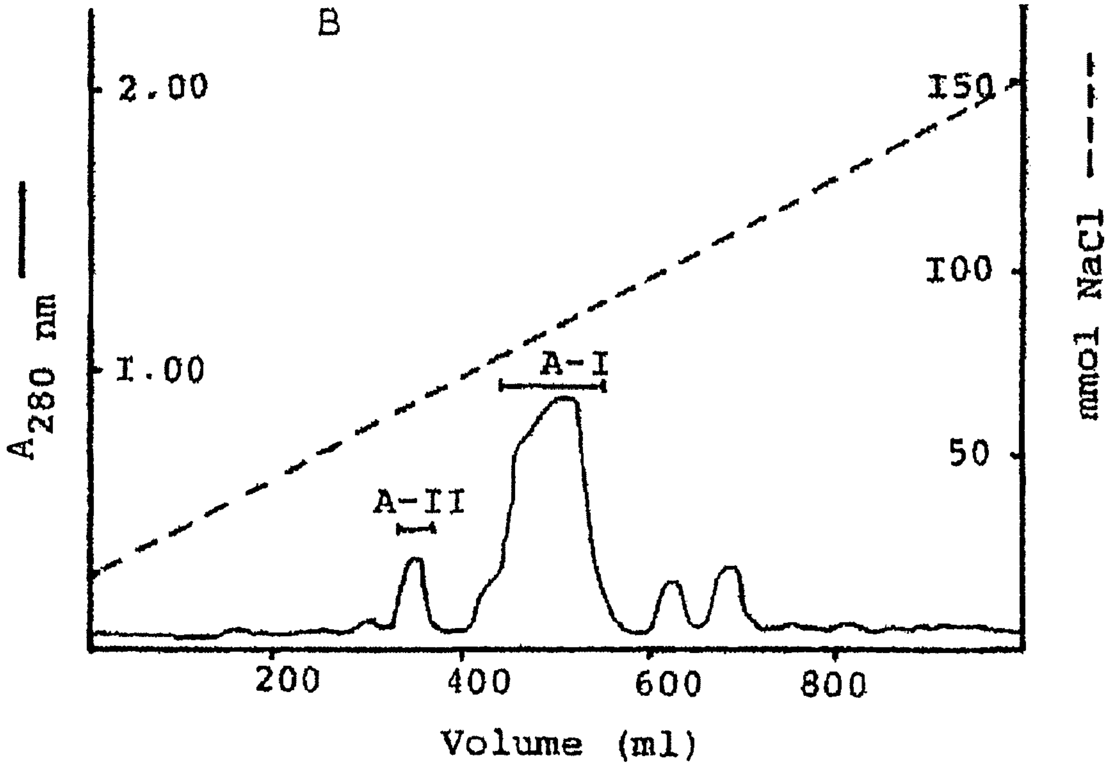
FIG. 6B presents the exemplary data showing purification of apolipoproteins A-I and A-II from pooled apolipoproteins A-I- and A-II-containing fractions using a DEAE-Toyopearl 650M chromatography. Starting buffer, 10 mM Tris-HCl, 0.02 M sodium chloride (NaCl), 8 M urea, pH 8; linear gradient of NaCl from 0.02 to 0.15 M in the same buffer, total gradient volume 1000 ml; flow-rate, 60 ml/h.

To isolate and purify human apolipoproteins A-I and A-II the standard procedure known in the art can be used (Sigalov et al. J Chromatogr 1991; 537:464-8). Briefly, HDL of density 1.063-1.210 g/ml were isolated from fasting serum of normo-lipidaemic donors by sequential ultracentrifugation in a Beckman (Berkeley, CA, U.S.A.) Model L8-7Q ultracentrifuge using a 45.Ti rotor. The isolated HDL fraction was extensively dialysed against 50 mM ammonium hydrogencarbonate buffer (pH 8.2), lyophilized and delipidated by an original procedure using a chloroform-methanol-diethyl ether solvent system as disclosed in (USSR/RUSSIA Pat 1752187), the disclosure of which is incorporated herein by reference. The proteins were solubilized in 10 mM Tris-HCl buffer (pH 8.6) containing 8 M urea (Tris-urea buffer) and applied to a Toyopearl HW-55F (Toyo Soda, Tokyo, Japan) column (90.0×3.5 cm I.D.). Elution was carried out with the same buffer at a flow-rate of 40 ml/h and 8-ml fractions were collected. A typical gel filtration profile is shown in FIG. 6A. Following analysis by polyacrylamide gel electrophoresis (PAGE), fractions containing apo A-I and apo A-II were pooled (FIG. 6A). The apolipoprotein pool was applied to a DEAE-Toyopearl 650M (Toyo Soda) column (40.0×3.2 cm I.D.), equilibrated with Tris-urea buffer. Elution was performed with a linear gradient of sodium chloride from 0.02 to 0.15 M in Tris-urea buffer (1000 ml total gradient volume) at a flow-rate of 60 ml/h. Fractions of 6 ml each were collected. A typical ion-exchange profile is shown in FIG. 6B. Those containing apo A-T and apo A-II were pooled separately (FIG. 6B) and extensively dialysed against 50 mM ammonium hydrogencarbonate buffer (pH 8.2). After dialysis, the samples were desalted by gel permeation chromatography using a Toyopearl HW-40F (Toyo Soda) column (70.0×2.2 cm I.D.) with the same buffer at a flow-rate of 80 ml/h and finally lyophilized.

Example 3: Characterization of Apolipoproteins A-I and A-II

Figure 7:
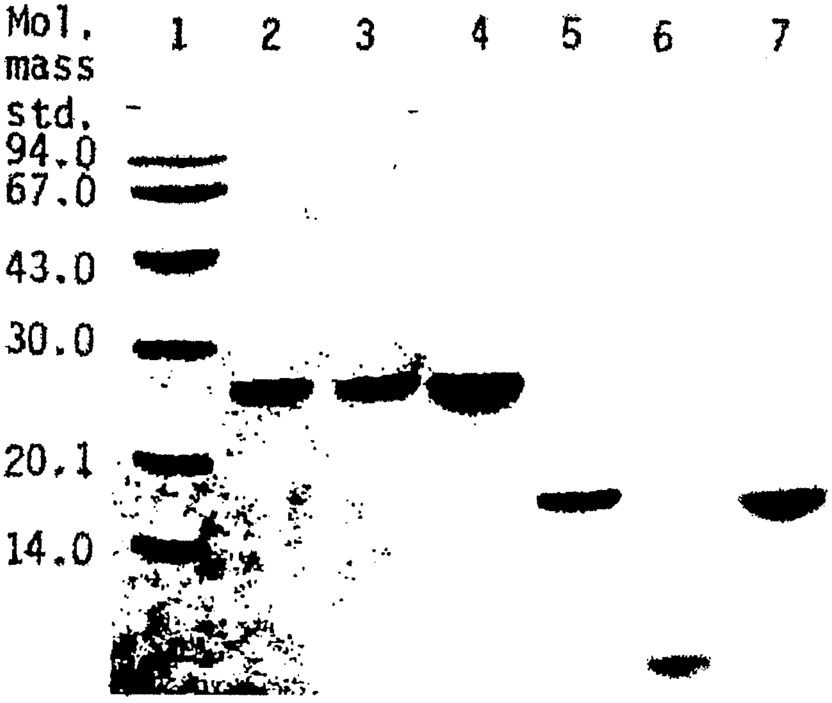
FIG. 7 presents the exemplary data demonstrating purity and homogeneity of apolipoproteins (apo) purified from human serum. SDS-PAGE in 15% polyacrylamide gel of purified apo A-1 and apo A-II. Lanes: 1—low-molecular-mass standards from Pharmacia (molecular masses of the standards are those provided by Pharmacia ($\times 10^{-3}$); 2, 3, 4-10 ug, 10 ug (with 2% of 2-mercaptoethanol) and 30 ug of purified apo A-I, respectively; 5, 6, 7-10 ug, 10 ug (with 2% of 2-mercapioethanol) and 30 ug of purified apo A-II, respectively. Apo A-I and apo A-II are identified by comparison with known standards.

Apolipoproteins A-I and A-II isolated and purified as described in Example 2 were quantified according to Lowry et al. (Lowry et al. J Biol Chem 1951; 193:265-75) and spectrophotometrically at 280 nm using extinction coefficients of 1.22 and 1.82 AU/mg protein/ml for apo A-I and apo A-II, respectively (Edelstein et al. J Biol Chem 1972; 247:5842-9). Lipid phosphorus analysis was performed utilizing the method of Bartlett (Bartlett G. R. J Biol Chem 1959; 234:466-8). No phospholipid was detected in either the isolated apo A-I or apo A-II. Homogeneity was confirmed using the standard procedures well known in the art such as SDS-PAGE on 15% polyacrylamide gels under both reducing (FIG. 7) and non-reducing conditions and by urea-PAGE. Identification of apo A-I and apo A-II was confirmed by electrophoretic mobility and immunoelectrophoresis with monospecific antibodies to human apo A-I and apo A-II (Clarke H. G. & Freeman T. Clin Sci 1968; 35:403-13). Amino acid analyses of purified apo A-I and apo A-II were made in a Beckman 6300 amino acid analyser after 72 h of acid hydrolysis and were shown to be compatible with the compositions derived from the primary sequences of human apo A-I and A-II well known in the art. The real yields of purified proteins were ~50% and ~40% for apo A-I and apo A-II, respectively, considering the volume of the initial human serum and the average concentrations of the proteins in the serum used (Sigalov et al. J Chromatogr 1991; 537:464-8).

Figure 8:
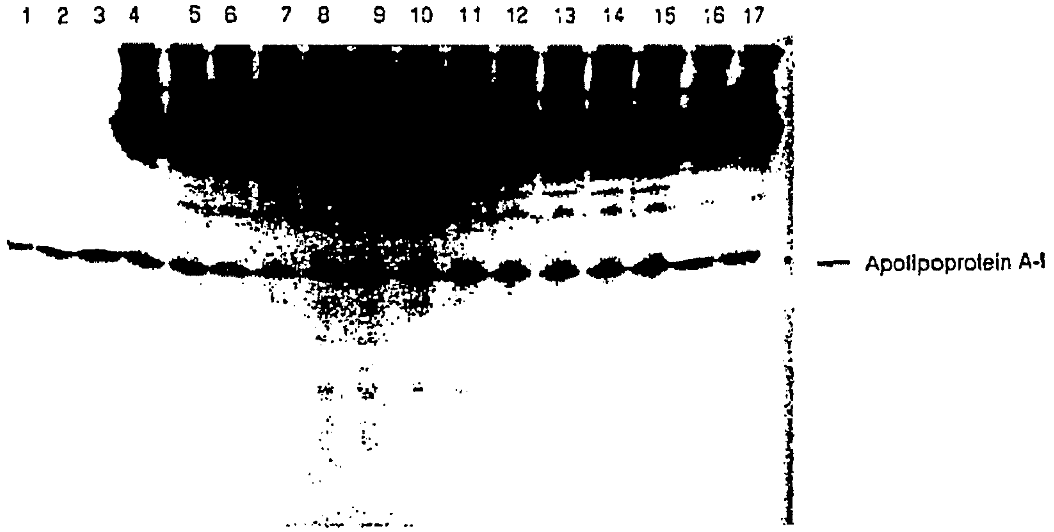
FIG. 8 presents the exemplary data showing the electrophoretic assay suitable for the quantitation of apolipoprotein (apo) A-I in fresh, frozen and lyophilized serum pools. Non-reducing SDS-PAGE of 0.5, 1.0 and 2.0 ug of apo A-I (lanes 1-3) along with fresh (lanes 4-7), frozen (lanes 8-13) and lyophilized (lanes 14-17) different serum samples.
Figure 9:
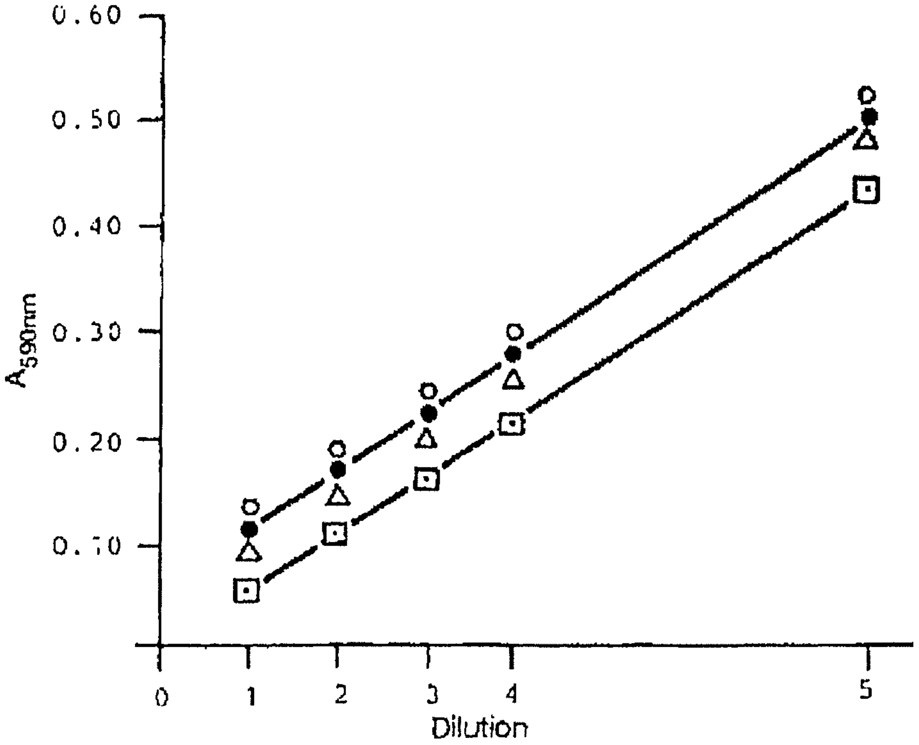
FIG. 9 presents the exemplary data showing calibration curves prepared with three samples of the pooled serum: fresh (open circles), frozen (filled circles), and lyophilized (triangles) samples. The data for purified apolipoprotein A-I is shown using open squares with dots. All samples were diluted as follows: 1:29 (1), 1:14 (2), 1:9 (3), 1:6.5 (4) and 1:2.75 (5).

To determine apo A-I concentration in human serum, the non-immunochemical electrophoretic apo A-1 assay using pure and well-characterized apo A-I as a primary standard can be used (Sigalov A. B. Eur J Clin Chem Clin Biochem 1993; 31:579-83). This is a precise, specific, and reproducible technique utilizing SDS-gradient(g)PAGE for direct apo A-I measurement in human serum that does not depend on any immunoreaction and therefore avoids the problems associated with antibody-antigen interaction (the heterogeneity of antigenic sites in apo A-I, heterogeneity in their expression, and heterogeneity of antibodies raised against apo A-I). The assay is inexpensive and requires no radioisotopes, and the method possesses intrinsically high recovery, due to minimal sample manipulation. No special sample pretreatment is required, and serum samples subjected to freezing or lyophilization can be used without any statistically significant change in results. Briefly, electrophoresis was performed in 18 cm×16 cm×1.5 mm gels with a linear gradient gel of 15-20% acrylamide, using homemade apparatus. The stacking gel consisted of 3.75% acrylamide, 0.125 mol/1 Tris-HCl, 1 g/l SDS, pH 6.8. A 1.5-mm-thick 17-well comb was used in all experiments. Resultant wells were 5.0 mm wide and 2.0 cm high, allowing up to 60 ul of sample to be applied per line. Sample preparation, electrophoresis, gel staining and destaining were performed as described (France et al. J Lipid Res 1989; 30:1997-2004). A typical non-reducing SDS-gPAGE of 0.5, 1.0 and 2.0 ug of apo A-I (lanes 1-3), and fresh (lanes 4-7), frozen (lanes 8-13) and lyophilized (lanes 14-17) different serum samples is shown in FIG. 8. After gel destaining the apo A-I bands were excised and placed into 3.0-ml glass screw-top vials containing 1.0 ml distilled water-dimethylformamide (1+1, by volume). Vials were heated at 90° C. in a heating block for 1 h with periodic mixing. The absorbance was measured at 590 nm in a disposable semi-micro cuvette (Bio-Rad Laboratories, Richmond, CA) with a Spectronic-2000 spectrophotometer (Bausch and Lomb, USA) blanked against distilled water-dimethylformamide (1+1, by volume). Typical calibration curves prepared with fresh, frozen and lyophilized samples of the pooled serum are shown in FIG. 9.

Example 4: Oxidative Modification of Apolipoprotein A-I and Reduction of Methionine Sulfoxides by PMSR This example demonstrates one embodiment of naturally occurring oxidized apo A-I (apo A-$I_{ox}$) containing methionine sulfoxides at positions 112 and 148 as referred to the apo A-I primary sequences. Although it is not necessary to understand the mechanism of an invention, it is believed that being incorporated into the rHDL compositions of the present invention, this modified protein targets the rHDL of the invention to sites of interest such, for example, as macrophages in atherosclerotic plague. The example also demonstrates that oxidative damage to apo A-I can be reversed by PMSR in the presence of a source of reducing equivalents.

As described herein, apo A-$I_{unox}$ refers to unoxidized apo A-I contained in initial serum apo A-I and apo A-$II_{unox}$ is unoxidized apo A-II contained in initial serum apo A-II. Further, apo A-$I_{ox}$ is oxidized apo A-I (with sulfoxidized methionines at positions 112 and 148) contained in serum apo A-I or obtained from unoxidized apo A-I using hydrogen peroxide. Apo A-$I_{red}$ is reduced apo A-I obtained by reduction of oxidized apo A-I (with sulfoxidized methionines at positions 112 and 148) using PMSR. In preferred embodiments, rHDL-1 are reconstituted HDL particles containing only apo A-$I_{unox}$. In preferred embodiments, rHDL-2 are reconstituted HDL particles containing only apo A-$I_{ox}$. In preferred embodiments, rHDL-3 are reconstituted HDL particles containing apo A-$I_{unox}$ and apo A-$I_{ox}$ with a molar ratio of 1:1. In preferred embodiments, rHDL-4 are reconstituted HDL particles containing apo A-Lm, apo A-$I_{unox}$ and apo A-$II_{unox}$ with a molar ratio of 3:3:1.

Figure 10A:
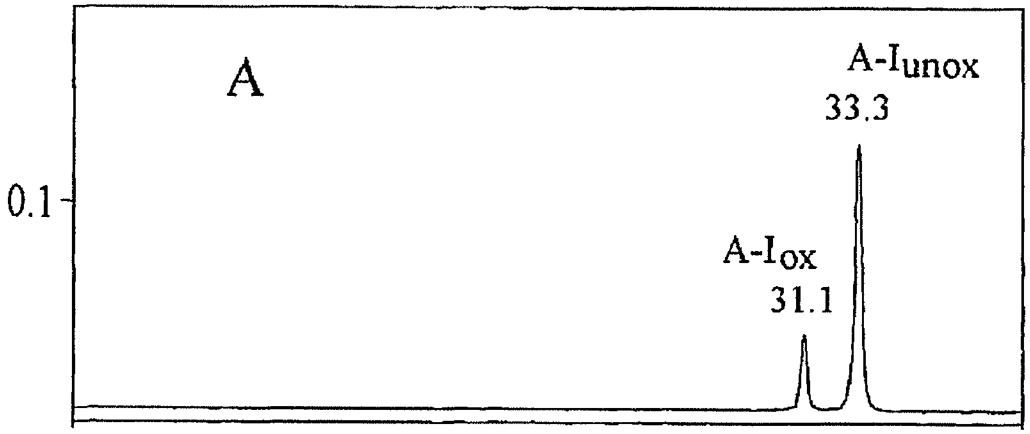
FIG. 10A presents the exemplary data showing an analytical reversed-phase HPLC profile of the initial apo A-I isolated and purified from human serum. The retention times (in minutes) are shown above each peak.
Figure 10B:
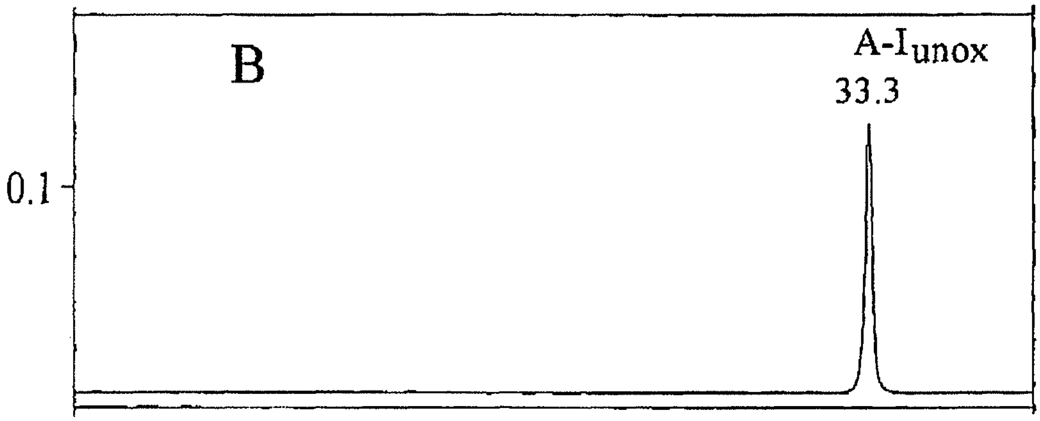
FIG. 10B presents the exemplary data showing an analytical reversed-phase HPLC profile of apo A-$I_{unox}$ isolated from the initial apo A-I by preparative reversed-phase HPLC. The retention times (in minutes) are shown above each peak.
Figure 11A:
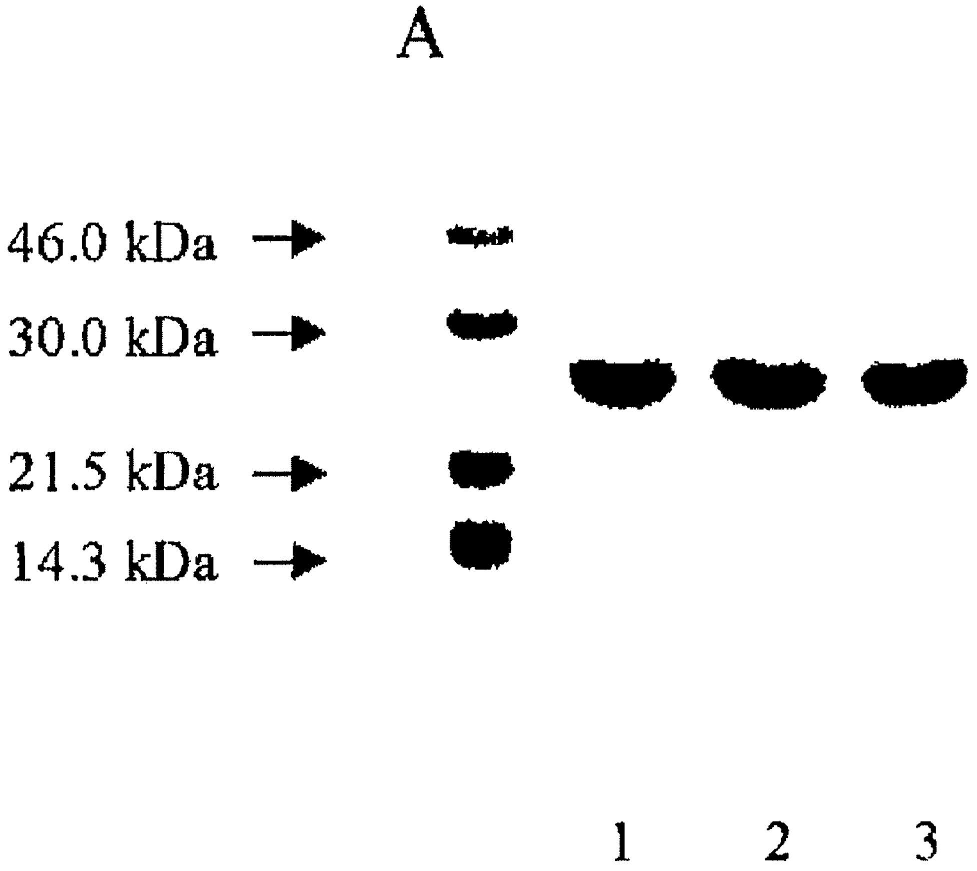
FIG. 11A presents the exemplary data showing 12.5% SDS-PAGE analysis of purified unoxidized, oxidized and reduced apo A-I (lanes 1, 2, and 3, respectively). The positions and molecular masses of protein standards are indicated on the left of the gels.

The initial apo A-I preparation isolated from pooled human serum and used in this example was a mixture of both apo A-$I_{ox}$ (~20%) and apo A-$I_{unox}$ (~80%) protein species, as shown by analytical reversed-phase HPLC (FIG. 10A). This protein mixture migrated as a single band on SDS-PAGE (data not shown) and its chromatographic profile and retention times of apo A-$I_{ox}$ and apo A-$I_{unox}$ were consistent with previously reported data (Anantharamaiah et al. J Lipid Res 1988; 29:309-18; von Eckardstein et al. J Lipid Res 1991; 32:1465-76). The percentage of apo A-$I_{ox}$ in eight other apo A-I preparations obtained from pooled human sera (about 200 individual specimens in each pool) using the same isolation technology had varied from 3% to 25%, providing further indirect evidence of considerable interindividual variability of the ratio oxidized/unoxidized apo A-I (von Eckardstein et al. J Lipid Res 1991; 32:1465-76). The two components (apo A-$I_{ox}$ and apo A-$I_{unox}$) in the initial serum apo A-I preparation were separated by preparative HPLC. The isolated apo A-$I_{unox}$ exhibited a single peak by analytical HPLC (FIG. 10B) and a single band on SDS-PAGE (FIG. 11A, lane 1).

It is well known to those of ordinary skill in the art that the modified apo A-I molecules containing methionine sulfoxides at any one of positions 86, 112, 148, or any combination of said positions can be prepared and purified using the standard procedures described in this invention (including those incorporated herein by reference) and well known in the art. It should be also understood by those of ordinary skill in the art that tyrosine residue at position 192 in apo A-I can be oxidized to 3-chloro-, 3-nitro- or 3,5-dibromotyrosine (and the modified protein can be purified) using the standard procedures known in the art (Shao et al. J Biol Chem 2005; 280:5983-93; Weiss et al. Science 1986; 234:200-3). It is well known to those of ordinary skill in the art that methionine residue at position 26 in apo A-II protein can be oxidized to methionine sulfoxide using the standard procedures described in this invention (including those incorporated herein by reference) and the modified protein can be purified by any method known in the art, including HPLC. It should be also understood by those of ordinary skill in the art that methionine sulfoxides in any protein including but not limiting to, apo A-I and apo A-II, can be reduced back to methionine native form using PMSR and a source of reducing equivalents by the standard procedures well known in the art and described in this invention (including those incorporated herein by reference) (see e.g. Biewenga et al. Arzneimittelforschung 1998; 48:144-8; Sigalov A. B. & Stem L. J. FEBS Lett 1998; 433:196-200; Sigalov A. B. & Stem L. J. Chem Phys Lipids 2001; 113:133-46; Sigalov A. B. & Stem L. J. Antioxid Redox Signal 2002; 4:553-7; Brot et al. Proc Natl Acad Sci USA 1981; 78:2155-8).

To prepare apo A-I containing methionine sulfoxides at positions 112 and 148, the standard procedure known in the art to can be used (Anantharamaiah et al. J Lipid Res 1988; 29:309-18; von Eckardstein et al. J Lipid Res 1991; 32:1465-76; Sigalov A. B. & Stem L. J. FEBS Lett 1998; 433:196-200; Sigalov A. B. & Stem L. J. Chem Phys Lipids 2001; 113:133-46; Sigalov A. B. & Stem L. J. Antioxid Redox Signal 2002; 4:553-7). Briefly, the unoxidized protein (approx. 25 mg) was dissolved in 1 ml of 3 M guanidine-HCl, pH 7.4, and then hydrogen peroxide was added to a final concentration of 300 mM. The mixture was incubated at room temperature for 15 min, and an oxidized protein was purified using preparative HPLC. As has been shown (von Eckardstein et al. J Lipid Res 1991; 32:1465-76), two methionine residues 112 and 148 (but not 86) in apo A-I are oxidized in parallel in a result of this procedure.

Figure 10C:
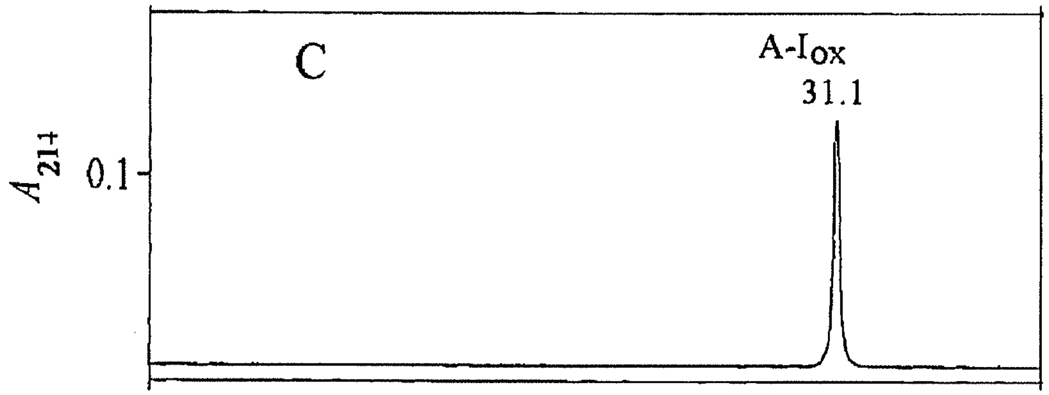
FIG. 10C presents the exemplary data showing an analytical reversed-phase HPLC profile of apo A-$I_{ox}$ obtained by treatment of apo A-$I_{unox}$ with hydrogen peroxide for 15 min and subsequent isolation by preparative reversed-phase HPLC. The retention times (in minutes) are shown above each peak.

Treatment of apo A-$I_{unox}$ with hydrogen peroxide resulted in the formation of apo A-$I_{ox}$ which exhibited the same retention time as the apo A-$I_{ox}$ component of the initial preparation (FIG. 10C). The electrophoretic pattern of purified apo A-$I_0$a on SDS-PAGE (FIG. 11A, lane 2) did not differ from that for the unoxidized form (FIG. 11A, lane 1) while on non-denaturing PAGE the oxidized form exhibited a band with about 1.8 times higher electrophoretic mobility in comparison with a relevant band of apo A-$I_{unox}$.

Figure 10D:
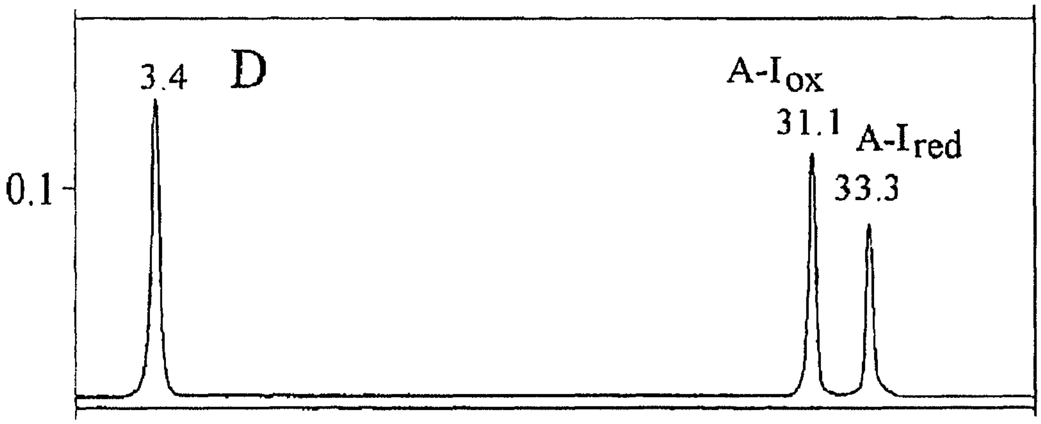
FIG. 10D presents the exemplary data showing an analytical reversed-phase HPLC profile of apo A-$I_{ox}$ after incubation with peptide methionine sulfoxide reductase for 60 min. The retention times (in minutes) are shown above each peak.
Figure 10E:
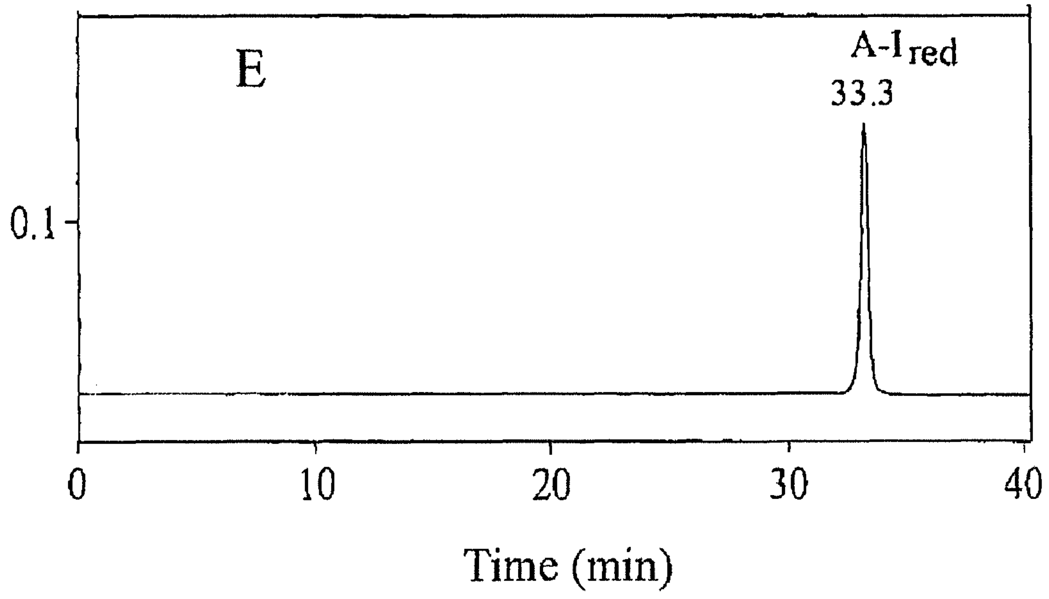
FIG. 10E presents the exemplary data showing an analytical reversed-phase HPLC profile of apo A-$I_{red}$ isolated by preparative reversed-phase HPLC. The retention times (in minutes) is shown above the peak.

Incubation of apo A-$I_{ox}$ with purified PMSR in the presence of DTT resulted in the appearance of a new peak on analytical HPLC chromatogram (apo A-$I_{red}$) with the same retention time as for apo A-$I_{unox}$ (FIG. 10D). Similar results were obtained when a spinach S-30 cell-free extract prepared as described (Brot et al. Proc Natl Acad Sci USA 1981; 78:2155-8) was added as the source of the enzyme. Apo A-$I_{red}$ protein formed as a result of enzymatic reduction was isolated as a homogeneous preparation (FIG. 10E), having the same electrophoretic mobility as apo A-$I_{unox}$ on SDS-PAGE (FIG. 11A, lane 3) and on nondenaturing PAGE.

Matrix-assisted laser desorption mass spectrometry revealed that apo A-$I_{ox}$ was 32 mass units greater than the initial apo A-$I_{ox}$ and apo A-$I_{unox}$. Peptide mapping data demonstrated that methionine residues at positions 112 and 148 are sulfoxidized under these conditions. Therefore, under the conditions used in this example, both of the labile methionine residues Met-112 and Met-148 are oxidized by $H_2O_2$, consistent with previously reported data (von Eckardstein et al. J Lipid Res 1991; 32:1465-76), and both are reduced by PMSR.

Importantly, naturally occurring apo A-$I_{ox}$ purified from human serum and apo A-$I_{ox}$ artificially obtained from unoxidized protein using $H_2O_2$ represent the same apo A-I molecule containing methionine sulfoxides at positions 112 and 148.

Figure 11B:
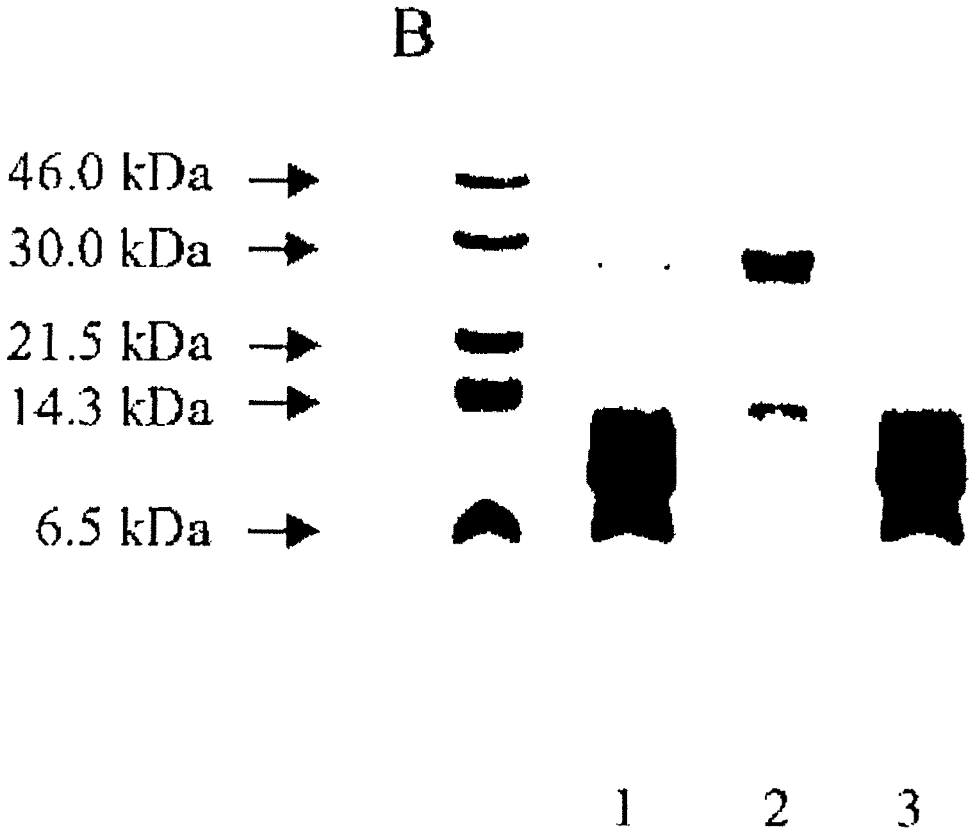
FIG. 11B presents the exemplary data showing 15% SDS-PAGE analysis of unoxidized, oxidized and reduced apo A-I digested with CNBr (lanes 1, 2, and 3, respectively). The positions and molecular masses of protein standards are indicated on the left of the gels.
Figure 11C:
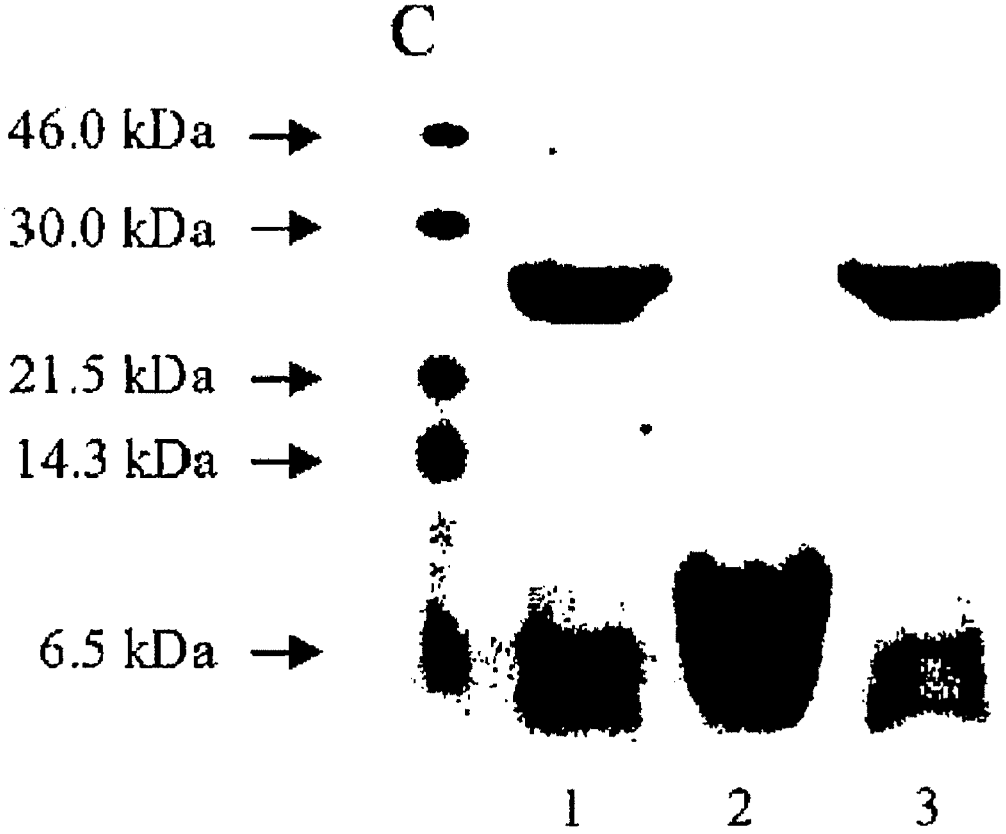
FIG. 11C presents the exemplary data showing 15% SDS-PAGE analysis of unoxidized, oxidized and reduced apo A-I digested with chymotrypsin (lanes 1, 2, and 3, respectively). The positions and molecular masses of protein standards are indicated on the left of the gels.

To further confirm the presence of methionines and methionine sulfoxides in apo A-I preparations, cleavage by CNBr can be used. CNBr cleaves proteins by conversion of methionine to homoserine lactone with concomitant peptide bond cleavage, but methionine sulfoxides are resistant to reaction. Unoxidized and reduced apo A-I had the same electrophoretic pattern and were almost completely cleaved by CNBr while apo A-$I_{ox}$ was much more resistant (FIG. 11B). Oxidation of the two methionine residues of apo A-$I_{ox}$ results in a dramatic increase in the protease susceptibility (FIG. 11C, lane 2) in comparison with the unoxidized and reduced forms (FIG. 11C, lanes 1 and 3).

Figure 12A:
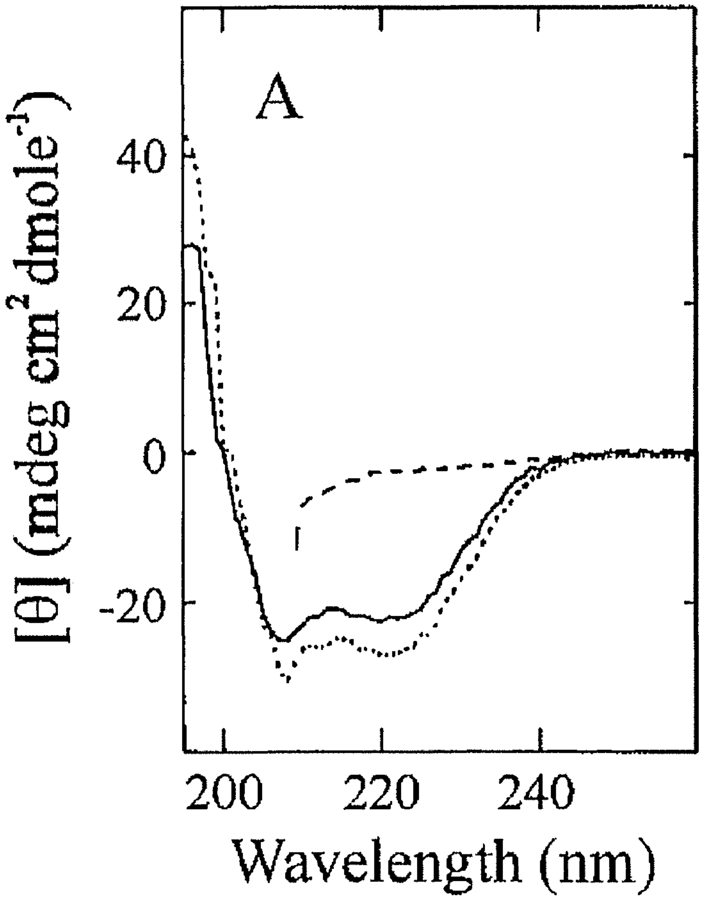
FIG. 12A presents the exemplary data showing far-UV circular dichroism spectra of 7.2 uM unoxidized apo A-I with (dotted line) and without (solid line) 2.3 mM 1,2-diheptanoyl-sn-glycero-3-phosphocholine (DHPC); and in the presence of 4 M urea (dashed line) in 10 mM ammonium bicarbonate, 0.005% sodium azide, pH 7.8; in a 1 mm path-length cell at 25° C., with 1 nm bandwidth and 1.0 s averaging per point.
Figure 12B:
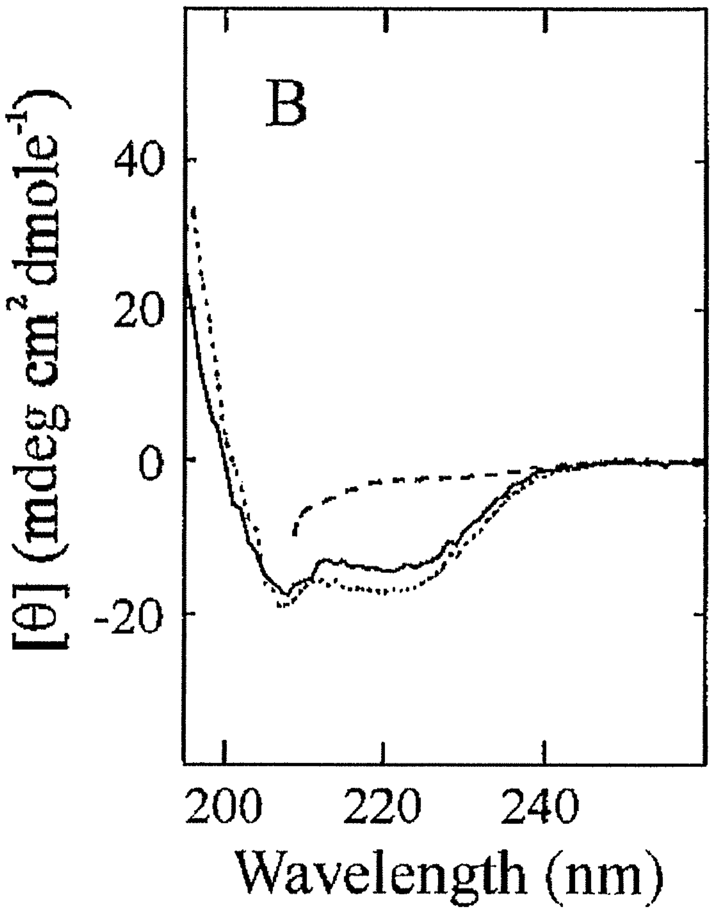
FIG. 12B presents the exemplary data showing far-UV circular dichroism spectra of 7.2 uM oxidized apo A-I with (dotted line) and without (solid line) 2.3 mM 1,2-diheptanoyl-sn-glycero-3-phosphocholine (DHPC); and in the presence of 4 M urea (dashed line) in 10 mM ammonium bicarbonate, 0.005% sodium azide, pH 7.8; in a 1 mm path-length cell at 25° C., with 1 nm bandwidth and 1.0 s averaging per point.
Figure 12C:
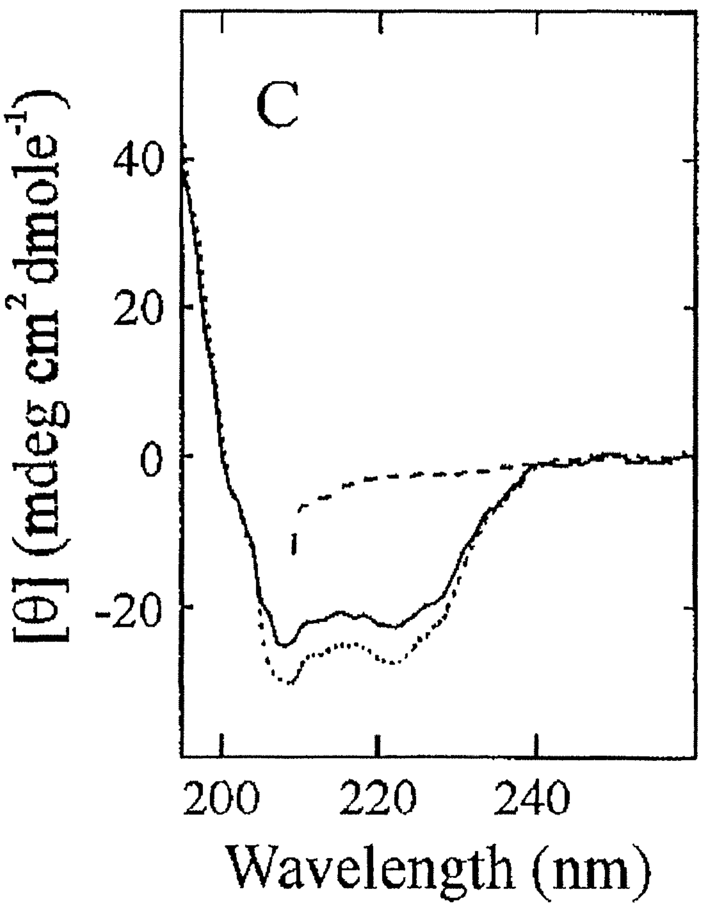
FIG. 12C presents the exemplary data showing far-UV circular dichroism spectra of 7.2 uM reduced apo A-I with (dotted line) and without (solid line) 2.3 mM 1,2-diheptanoyl-sn-glycero-3-phosphocholine (DHPC); and in the presence of 4 M urea (dashed line) in 10 mM ammonium bicarbonate, 0.005% sodium azide, pH 7.8; in a 1 mm path-length cell at 25° C., with 1 nm bandwidth and 1.0 s averaging per point.
Figure 12D:
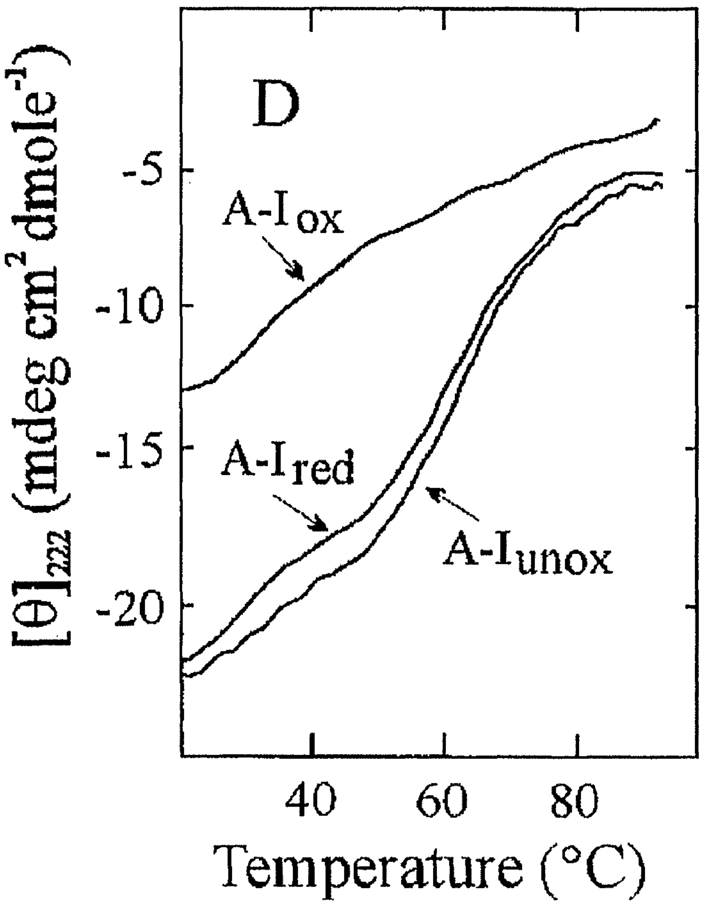
FIG. 12D presents the exemplary data showing temperature-induced unfolding spectra collected in a temperature range of 25-95° C. at 222 nm on a solution of 7.2 uM unoxidized, oxidized, and reduced apo A-I in 10 mM ammonium bicarbonate, 0.005% sodium azide, pH 7.8; in a 1 mm path-length cell; with 1 nm bandwidth, 1° C. temperature increment, and 5.0 s averaging per point.

Far-UV circular dichroism spectra and temperature-induced unfolding of unoxidized, oxidized, and reduced apo A-I can be used to characterize structural features of these proteins (FIGS. 12A-D). Briefly, circular dichroic spectra were measured for unoxidized (FIG. 12A), oxidized (FIG. 12B) and reduced (FIG. 12C) apo A-I (7.2 uM) with (dotted line) and without (solid line) 2.3 mM 1,2-diheptanoyl-sn-glycero-3-phosphocholine (DHPC) or in the presence of 4 M urea (dashed line) in 10 mM ammonium bicarbonate, 0.005% sodium azide, pH 7.8; in a 1 mm path-length cell at 25° C., with 1 nm bandwidth and 1.0 s averaging per point. Temperature-induced unfolding data (FIG. 12D) were collected in a temperature range of 25-95° C. at 222 nm on a solution of 7.2 uM apo A-I in 10 mM ammonium bicarbonate, 0.005% sodium azide, pH 7.8; in a 1 mm path-length cell; with 1 nm bandwidth, 1° C. temperature increment, and 5.0 s averaging per point. The spectrum of apo A-I. (FIG. 12B) was considerably less intense than that of the unoxidized form (FIG. 12A), indicating a reduction of apo A-I helical content upon oxidation. Thermodynamically, apo A-$I_{unox}$ was characterized by a weakly cooperative unfolding with midpoint temperature 65±2° C. indicative of a globular, folded structure, while apo A-$I_{ox}$ did not exhibit any cooperative unfolding transition, suggestive of a largely unfolded structure (FIG. 12D).

Thus, reduction of A-$I_{ox}$ with PMSR in the presence of DTT completely restored protein secondary structural features and the characteristic thermal denaturation of the native unoxidized protein (FIG. 12C-D).

Alternatively, clinically relevant DHLA can be used instead of DTT as a cofactor for PMSR-mediated reduction of methionine sulfoxides at positions 112 and 148 in apo A-$I_{ox}$ back to native methionine form (see e.g., Sigalov A. B. & Stern L. J. Antioxid Redox Signal 2002; 4:553-7), restoring protein secondary structural features and the thermodynamic stability of the native unoxidized protein (Table 1). Thermodynamic stability of the proteins can be measured by the standard procedures known in the art. Briefly, the effect of guanidine hydrochloride (GdnHCl) concentration on the structure of lipid-free apo A-I was monitored by fluorescence emission of Trp using a FluoroMax-2 spectrofluorimeter (SPEX Industries, Inc., Edison, NY, U.S.A.). Denaturation curves were analyzed as previously described in detail (Sigalov A. B. & Stern L. J. Chem Phys Lipids 2001; 113:133-46). Stability of lipid-free apo A-I was also determined by plotting the 353 nm/333 nm fluorescence emission ratio versus the molar GdnHCl concentration, and expressed as the concentration of the denaturant that reduced this ratio by 50% (Din).

TABLE 1

Secondary structure and thermodynamic stability of lipid-free apo A-I

| Protein | alpha-Helix[a] (%) | $D_{1/2}$[b] (M GdnHCl) | $\Delta G_D^{\circ c}$ (kcal/mol of apo) | $\Delta n^d$ (mol GdnHCl/mol of apol) | Tm[e] (° C.) |
|---|---|---|---|---|---|
| apo A-$I_{unox}$ | 62 ± 4 | 1.0 ± 0.1 | 4.7 ± 0.3 | 29 ± 4 | 64 ± 3 |
| apo A-$I_{ox}$ | 42 ± 4[f] | 0.4 ± 0.1[f] | 1.4 ± 0.1[f] | 15 ± 3[f] | — |
| apo A-$I_{red}$[g] | 64 ± 4 | 0.9 ± 0.1 | 4.4 ± 0.3 | 27 ± 4 | 62 ± 3 |

Results are given as means ± SD (n = 3).

[a]Determined from molar ellipticities at 222 nm.

[b]Midpoints of GdnHCl denaturation.

[c]Free energy of denaturation at zero GdnHCl concentration.

[d]The number of the GdnHCl moles bound during denaturation.

[e]Midpoints of thermal denaturation.

[f]$P < 0.05$, comparison versus apo A-$I_{unox}$.

[g]Reduced with DHLA as a cofactor of PMSR.

Example 5: Methods of Reconstitution and Characterization of rHDL

The purified unmodified and modified apo A-I and A-II as well as peptide fragments thereof described in Examples 1-4 can then be reconstituted in any combination of said agents with two different sets of lipids. As disclosed in US Pat Appl 20070243136 and incorporated herein by reference, as the major circulating form of HDL is spherical, and spherical rHDL has been successful in delivering drugs to tissues, it is preferable to reconstitute HDL as spherical particles. Thus, the first of lipids in which the apolipoproteins may be reconstituted in are lipids that will produce spherical HDL particles. This set includes surface lipids, chiefly phospholipids, plus core lipids, chiefly TG and cholesteryl ester. This composition preferably should mimic natural HDL and generate small spherical particles (about 10 nm diameter). Particular reference is made to Rensen et al. (Rensen et al. Adv Drug Deliv Rev 2001; 47:251-76), for characteristics of circulating HDL that could be mimicked.

Alternatively, it may be desirable to produce a discoidal rHDL particle. This is achieved with the second set of lipids for reconstitution, which is limited exclusively to surface lipids (i.e., preparing rHDL composition that lacks the core lipids). At high protein:lipid ratios, this composition generates small discoidal particles, which are essentially segments of lipid bilayers with the edges stabilized by the HDL apolipoproteins. These disks are about 10 nm in diameter and 5.5 nm thick and are thought to resemble nascent HDL as it is secreted from the liver. As discussed further below, discoidal reconstituted particles are an attractive alternative to spherical rHDLs in those circumstances in which the loading to the HDL particles with the imaging or targeting agent makes the spherical HDL particles too large (Shamir et al. J Clin Invest 1996; 97:1696-704). Discoidal particles can be made by a standard sonication method (Lund-Katz S. & Phillips M. C. Biochemistry 1986; 25:1562-8) that has also been used for the incorporation of drugs (de Vrueh et al. Antimicrob Agents Chemother 2000; 44:477-83).

Based on the weight % composition of the components of native HDL (Rensen et al. Adv Drug Deliv Rev 2001; 47:251-76) and the molecular weights of POPC (palmitoyl oleoyl PC), triolein (the triglyceride component), cholesterol, cholesteryl oleate (cholesteryl ester) and apoA-I, the molar composition of the rHDL, should be (PC:CE:C:TG:apoA-I):100:62:25:11:2 to simulate the native particles (assuming apoA-I represents approximately 50% of HDL protein). Alternatively, equivalent amounts of apo A-II or peptide fragments apo A-I and apo A-II can be used in these preparations. For the compositions of the present invention, it is critical that the rHDL prepared contain at least one modified molecule of apo A-I and/or apo A-II and/or fragments thereof described in Examples 1-4. For ease of manufacture and storage, these components, particularly POPC, were selected to be relatively resistant to lipid peroxidation, yet they remain fluid within the reconstituted particle at body temperature.

To produce reconstituted particles, the lipids (separately maintained in stock solutions of chloroform or hexane) are combined in the appropriate molar amounts in a glass tube and dried under nitrogen and then high vacuum to remove all traces of organic solvents. After suspension in Tris pH 8.0 buffer, the lipids are dispersed by sonication, followed by low speed centrifugation to remove any shards from the sonicator probe tip. ApoA-I (in Tris pH 8.0 buffer) is then added (to 2 mol %) and incubated at 37° C. for 30 min, after which the mixture is again sonicated and re-centrifuged at low speed. The resulting dispersion is filtered (0.22 um), and the rHDL isolated by size exclusion chromatography through a Superose 6 column. Typically, this procedure results in spherical HDL particles of 7-9 nm diameter with approximately 80-90 phospholipid molecules and 2 apoA-I molecules per particle (Braschi et al. J Lipid Res 1999; 40:522-32; Ramsamy et al. J Biol Chem 2000; 275:33480-6). Extrusion, cholate dialysis, and/or shear methods e.g., using microfluidizers also can be used for reconstitution.

As PE is readily incorporated into liposomes (at least 50% by weight of the phospholipid content) (Grant et al. Magn Reson Med 1989; 11:236-43) and HDL (at least 10 mole %) (Lund-Katz et al., Biochemistry. 1986; 25:1562-8), and owing to its close structural similarity to PC, Gd-DPTA-PE should readily be incorporated into the rHDL particles using co-sonication (Lund-Katz S. & Phillips M. C. Biochemistry 1986; 25:1562-8).

As disclosed in US Pat Appl 20070243136 and incorporated herein by reference, in preparing the rHDL compositions, it may be necessary to consider is how much chelate should be incorporated into each HDL particle. Administration of $10^{18}$ Gd ions per mouse is sufficient to obtain high-quality images of lesional aorta (Nunn et al. Q J Nucl Med 1997; 41:155-62; Aime et al. J Magn Reson Imaging 2002; 16:394-406; Lauffer R. B. Magn Reson Q 1990; 6:65-84; Ahrens et al. Proc Natl Acad Sci USA 1998; 95:8443-8). Using rHDL compositions of the present invention, this dose of Gd is easily accomplished by incorporating 10 Gd-DPTA-PE molecules per rHDL particle and administering approx. $10^{17}$ particles per mouse. To maintain particle structure, the Gd-DPTA-PE would replace POPC, molecule for molecule. Based on the stoichiometry given in the preceding paragraph, $10^{17}$ rHDL particles contain approximately 8 mg of apoA-I and 13 mg of phospholipid. Because rHDL and phospholipid liposomes have been used to deliver far higher doses to mice (up to 13 mg of apoA-I) (Shah et al. Circulation 2001; 103:3047-50) and 30 mg PC per mouse (Williams et al. Arterioscler Thromb Vasc Biol 2000; 20:1033-9), the dose of rHDL proposed for use here (i.e., 10 Gd-DPTA-PE molecules/rHDL particle) should be readily achievable without toxicity.

Producing Discoidal rHDL

This example demonstrates one embodiment of the homogeneous discoidal rHDL prepared with or without naturally occurring oxidized apo A-I containing methionine sulfoxides at positions 112 and 148 as referred to the apo A-I primary sequences. Although it is not necessary to understand the mechanism of an invention, it is believed that being incorporated into the rHDL compositions of the present invention, this modified protein targets the rHDL of the invention to sites of interest such, for example, as macrophages in atherosclerotic plague. The example also demonstrates that oxidative damage to apo A-I in the context of rHDL can be reversed by PMSR in the presence of a source of reducing equivalents.

It should be understood by those of ordinary skill in the art that any of the purified unmodified and modified apo A-I and A-II as well as peptide fragments thereof described in Examples 1-4 can be used to produce the compositions of the present invention. However, it is critical for the rHDL of the invention that the the rHDL prepared should contain at least one modified molecule of apo A-I and/or apo A-II and/or fragments thereof described in Examples 1-4.

In preferred embodiments, the homogeneous discoidal rHDL compositions of the present invention can be prepared using the standard sodium cholate dialysis method well known in the art (Sigalov A. B. & Stern, L. J. Chem Phys Lipids 2001; 113:133-46; Sigalov A. B. & Stern L. J. Antioxid Redox Signal 2002; 4:553-7; Sorci-Thomas et al. J Biol Chem 1998; 273:11776-82; Durbin D. M. & Jonas A. J Biol Chem 1997; 272:31333-9; Davidson et al. J Biol Chem 1995; 270:5882-90; Toledo et al. Arch Biochem Biophys 2000; 380:63-70). This method allows to prepare rHDL with 2 or 3 apo A-I per particle and 9-11 nm diameter.

In preferred embodiments, rHDL-1 are reconstituted HDL particles containing only apo A-$I_{unox}$. In preferred embodiments, rHDL-2 are reconstituted HDL particles containing only apo A-$I_{ox}$. In preferred embodiments, rHDL-3 are reconstituted HDL particles containing apo A-$I_{unox}$ and apo A-$I_{ox}$ with a molar ratio of 1:1. In preferred embodiments, rHDL-4 are reconstituted HDL particles containing apo A-$I_{unox}$, apo A-$I_c$ and apo A-$II_{unox}$ a molar ratio of 3:3:1.

All preparations were done in Tris-buffered saline containing 0.01 M Tris-HC, 0.14 M NaCl, 0.25 mM EDTA-$Na_2$, 0.15 mM sodium azide, (TBS), pH 7.4. Briefly, 65 ul of POPC in chloroform (about 2.0 mg) and 5.0 ul of cholesterol in chloroform-ethanol, 1:1 (about 50 ug) were mixed in a 1.5 ml polypropylene tube, dried in a stream of argon, and placed under vacuum for 30 min. Then, 100 ul of sodium cholate in TBS, pH 7.4, (about 2.1 mg) was added and vortexed. After incubation for 30 min at 25° C., 280 ul of a solution containing about 0.9 mg apo A-$I_{unox}$, A-$I_{ox}$, or a mixture of apo A-$I_{unox}$ and A-$I_{ox}$ (molar ratio of 1:1), or instead 1.1 mg of a mixture of apo A-$I_{unox}$-A-$I_{ox}$-A-$II_{unox}$ (molar ratio of 1.5:1.5:1) were added. After additional incubation for 90 min at 25° C., cholate was removed by dialysis against 11 of TBS, pH 7.4, for 1.5 h at room temperature and then against 3 l of the same buffer for 16 h at 4° C. The obtained rHDL were then isolated on a calibrated Superdex 200 HR (10×300 mm2) gel filtration column (Pharmacia) eluted at 0.4 ml/min with TBS, pH 7.4. Molecular weight of the rHDL particles was calculated from their retention times relative to gel filtration proteins standards supplied by Bio-Rad: thyroglobulin (670 000 Da), bovine gamma globulin (158 000 Da), chicken ovalbumin (44 000 Da), equine myoglobin (17 000 Da), and vitamin B-12 (1350 Da). The isolated rHDL samples were filtered through a 0.22 um using Spin-X centrifuge tubes (Corning Costar Corporation, Cambridge, MA) and stored at 4° C.

Characterization of Composition, Size and Shape of Reconstituted Discoidal rHDL

Reconstituted discoidal rHDL were characterized as described (Sigalov A. B. & Stern, L. J. Chem Phys Lipids 2001; 113:133-46). Protein concentrations in the rHDL particles were measured using the Lowry method as modified by Markwell et al. (Markwell et al. Anal Biochem 1978; 87:206-10). Final protein compositions were determined in the prepared rHDL particles by analytical HPLC essentially as described above in Example 4 for lipid-free apolipoproteins, except that a solid GdnHCl was added to the analyzed rHDL samples to a final concentration of 6 M. Total cholesterol was determined enzymatically using a Boehringer-Mannheim kit and the manufacturer's suggested procedure. Phospholipids were determined by phosphorus assay (Van Veldhoven P. P. and Mannaerts G. P. Anal Biochem 1987; 161:45-8). The number of apo A-I molecules per particle was determined by cross-linking performed by addition of one part dimethylsuberimidate (DMS) solution, 10 mg/ml in 1.0 M triethanolamine, pH 9.7, to ten parts rHDL solution, incubation for 2 h at 25° C. (Swaney J. B. Methods Enzymol 1986; 128:613-26) and by determination of extent of oligomer formation using SDS-PAGE (12.5% acrylamide). The gels were stained for protein with Coomassie Blue R250 and scanned with an Hewlett Packard ScanJet 3P. The obtained images were analyzed using a NIH Image 1.61 program (National Institutes of Health, Bethesda, MD) and a Scion Image 3b program (Scion Corporation, Frederick, MD).

The sizes and size distributions of the rHDL particles were estimated by both electron microscopy (EM) and nondenaturing gradient gel electrophoresis (GGE). The rHDL complexes (at a concentration of about 0.3 mg of protein/ml) were extensively dialyzed against 5 mM ammonium bicarbonate, mixed with the same volume of 2% phosphotungstate, pH 7.4, and were examined using a Phillips EM410 electron microscope on carbon-coated Formvar grids. Microphotographs were photographed at an instrument magnification of 63000 and 110000, and mean particle dimensions of 50 particles were determined from each negative. Nondenaturing GGE was performed on precast 4-20% gradient gels (Bio-Rad, Hercules, CA). Gel scanning and image analysis were performed as described above. Stokes' diameter and molecular weight of the rHDL particles were calculated from their mobility relative to proteins standards supplied by Pharmacia: thyroglobulin (17.0 nm, 669000 Da), ferritin (12.2 nm, 440000 Da), catalase (10.4 nm, 232000 Da), lactate dehydrogenase (8.2 nm, 140000 Da), and bovine serum albumin (7.1 nm, 67000 Da). The protein and lipid compositions together with the apo A-I oligomer size determined by cross-linking and the particle molecular weight were used to estimate the particle molar composition.

In preferred embodiments, compositions and properties of reconstituted HDL particles are those as described in Table 2. These data demonstrate that as it is critical for the compositions of the present invention in terms of resembling with nascent HDL, that oxidation of two of three methionine residues (Met-112 and 148) in apo A-I molecule does not lead to any significant differences between prepared rHDL complexes in their lipid and protein compositions as well as more importantly, in their size or shape.

important for the compositions of the present invention in terms of resembling with nascent HDL, the secondary structure of oxidized apo A-I molecules in rHDL complexes remains similar to that of the unoxidized protein.

Characterization of Thermodynamic Stability of Reconstituted Discoidal rHDL

Temperature-induced unfolding data were collected on solutions of 3.6 uM (0.1 mg/ml) lipid-free apo A-I and 1.8 uM (0.05 mg of protein/ml) rHDL particles in TBS, pH 7.4, with a 1 mm path-length quartz cuvette at 222 nm every 2-5° C. from 25 to 95° C. with 20.0 s averaging per point and a 1 nm bandwidth. $T_m$ values for the broad transitions were estimated by curve fitting using a seven-parameter equation (Zarutskie et al. Biochemistry 1999; 38:5878-87).

The effect of GdnHCl concentration on the structure of lipid-free and lipid-bound apo A-I was monitored by fluorescence emission of Trp as described previously (Tricerri et al. Biochim Biophys Acta 1998; 1391:67-78). These measurements were made in a FluoroMax-2 spectrofluorimeter (SPEX Industries, Inc., Edison, NY) at 25° C. in 4×4 mm2 cuvette. Emission spectra were taken by exciting at 285 nm with a resolution of 2 nm and by measuring the emission with a resolution of 4 nm. The molar GdnHCl concentrations (C) were determined from the solution refractive index (n)

TABLE 2

Properties and compositions of rHDL particles[a]

| Protein/ Complex | Particle composition POPC-Chol-Protein (mol:mol:mol)[a] | Protein composition (molar ratio)[b] | Particle diameter (EM; nm)[c] | Particle diameter (GGE; nm)[d] | alpha-Helix (%)[e] |
|---|---|---|---|---|---|
| apo A-$I_{unox}$ | | | | | 62 (4) |
| apo A-$I_{ox}$ | | | | | 42 (4) |
| rHDL-1 | 180 (16):5 (1):3 | Only A-$I_{unox}$ | 10.2 (1.0) | 9.4 (0.7) | 78 (5) |
| rHDL-2 | 180 (14):3 (1):3 | Only A-$I_{ox}$ | 10.3 (1.0) | 9.6 (0.5) | 81 (5) |
| rHDL-3 | 190 (19):5 (1):3 | A-$I_{unox}$-A-$I_{ox}$ (1:1)[f] | 9.9 (1.0) | 9.6 (0.6) | 82 (5) |
| rHDL-4 | 150 (22):4 (1):3.5 | A-$I_{unox}$-A-$I_{ox}$:A-II (3:3:1)[f] | 10.3 (1.0) | 9.6 (0.8) | 78(5) |

[a]Mean and standard deviation (SD, in parentheses) of three different preparations are given. The number of apolipoprotein molecules per particle was obtained by cross-linking with DMS (Swaney J. B. Methods Enzymol 1986; 128:613-26) and protein analysis by SDS-PAGE.
[b]Determined by the reversed-phase HPLC.
[c]Mean and SD of 50 particles determined from negative staining electron microscopy (EM).
[d]Mean and SD of three different preparations determined from nondenaturing gradient gel electrophoresis (GGE) using reference globular proteins.
[e]Mean and SD of three different preparations determined from molar ellipticities at 222 nm.
[f]Average compositions that may reflect subpopulations with different molar composition.

Characterization of Protein Secondary Structure in Reconstituted Discoidal rHDL

CD spectra were collected on solutions of 3.6 uM (0.1 mg/ml) lipid-free apo A-I proteins and of 1.8 uM (0.05 mg of protein/ml) rHDL particles in TBS, pH 7.4 with a 1 mm path-length quartz cuvette using an AVIV 62A DS spectropolarimeter (AVIV, Lakewood, NJ). Data were collected at 25° C. every nanometer from 190 to 260 nm with 1.0 s averaging per point and a 1 nm bandwidth. Spectra of at least six scans were signal averaged and baseline corrected by subtracting an averaged buffer spectrum. The spectra were normalized to molar residue ellipticity using a mean residue weight of 115.2 and 113.6 Da for human apo A-I and A-II, respectively. An apparent fractional percent alpha-helix content from the molar ellipticities at 222 nm by the method of Chen et al. ($[\phi]222=-30300$, $f_H=2340$, where $f_H$ is the fraction of alpha-helical structure; Chen et al. Biochemistry 1972; 11:4120-31).

Figure 13:
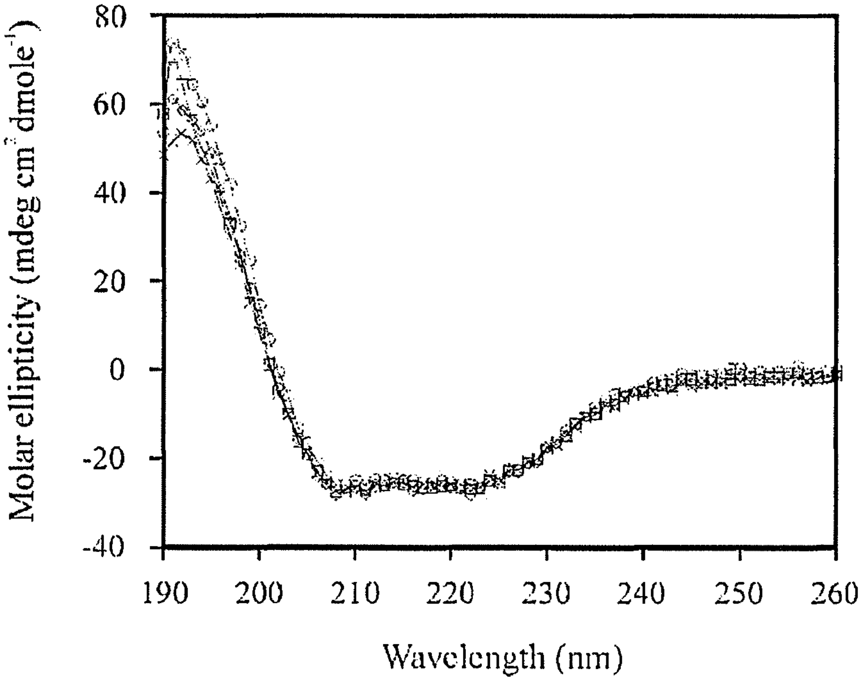
FIG. 13 presents the exemplary data showing far-UV circular dichroism spectra of apo A-I on different rHDL particles. The spectra of lipid-associated apo A-I in rHDL-1 (open circles), rHDL-2 (open squares), rHDL-3 (open diamonds) and rHDL-4 (crossings) were recorded from 190 to 260 nm at 25° C. using a 1 mm path-length quartz cuvette on AVIV 62A DS spectropolarimeter. The samples were analyzed at a protein concentration of 1.8 uM (0.05 mg of protein/ml) rHDL particles in TBS, pH 7.4, and spectra of at least six scans were signal averaged and baseline corrected by subtracting an averaged buffer spectrum.

No significant differences were observed between the CD spectra of the four rHDL complexes (FIG. 13). Thus, as it is using the relationship: C=60.87n-81.16, as described (Kielley W. W. & Harrington W. F. Biochim Biophys Acta 1960; 41:401-21). Aliquots of each lipid-free apo A-I protein (0.1 mg/ml) or rHDL sample (0.05 mg of protein/ml) were incubated with from 0 to 3.0 M GdnHCl (lipid-free proteins) or from 0 to 6.0 M GdnHCl (rHDL complexes) in TBS, pH 7.4, for 72 h at 4° C. Then, the Trp fluorescence spectra were taken as described (Sigalov A. B. & Stern L. J. Chem Phys Lipids 2001; 113:133-46) and the ratio of the fluorescence intensity at 353 nm to that at 333 nm was used to quantify the spectral shifts. Denaturation curves were analyzed essentially as described (Sparks et al. J Biol Chem 1992; 267: 25839-47). Briefly, the following relationship between the free energy of denaturation (AGD) and the GdnHCl activity (a) was used to estimate apo A-I conformational stability: $\Delta G_D^0=\Delta G_D+\Delta n\times RT\ln(1+Ka)$ (1) where $\Delta G_D^0$ is the standard free energy of denaturation (at zero denaturant concentration), R is gas constant (1.98 cal/degree mol), T is temperature (298 K), K is average association constant of GdnHCl and protein ($0.6\ M^{-1}$), and $\Delta n$ is the difference in the moles of the denaturant bound by the protein in the native and denatured states. The mean GdnHCl ionic activities (a) were calculated by the equation (Pace C. N. & Vanderburg K. E. Biochemistry 1979; 18:288-92): $a=0.6761M+0.1468M^2+0.02475M^3+0.001318M^4$ (2) where M is the molar GdnHCl concentration. The equilibrium constants, $K_D$, were calculated from the 353 nm/333 nm fluorescence intensity ratios using the formula: $K_D=([F]_N-[F])/([F]-[F]_D)$ (3) where [F] is the observed 353 nm/333 nm fluorescence intensity ratio at a given GdnHCl activity and $[F]_N$ and $[F]_D$ are the 353 nm/333 nm fluorescence intensity ratios for the native and fully denatured forms of apo A-I measured in the absence or presence of 3 M GdnHCl (lipid-free proteins) or 6.0 M GdnHCl (rHDL complexes). Linear regression analysis was used to solve Eq. (1) and to determine $\Delta G_D^0$ and Δn. Stability of lipid-free and lipid-bound apo A-I was also determined by plotting the 353 nm/333 nm fluorescence intensity ratio vs the molar GdnHCl concentration and expressed as the concentration of the denaturant that reduced this ratio by 50% ($D_{1/2}$).

Figure 14:
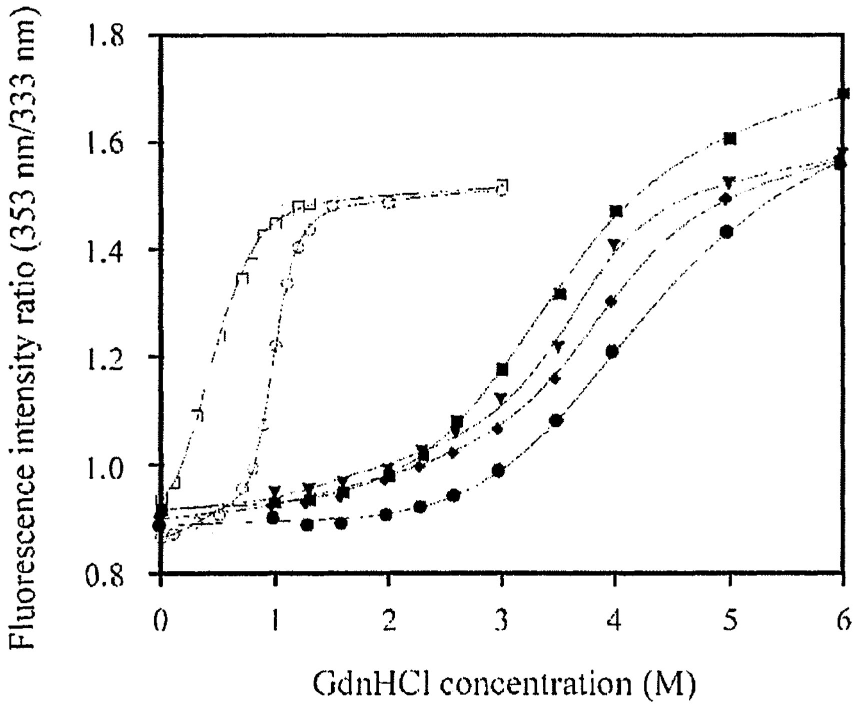
FIG. 14 presents the exemplary data showing denaturation by Guanidine Hydrochloride (GdnHCl) of lipid-free apo A-I and rHDL complexes. Aliquots of unoxidized (open circles) and oxidized (open squares) lipid-free apo A-I proteins or prepared rHDL-1 (filled circles), rHDL-2 (filled squares), rHDL-3 (filled diamonds) and rHDL-4 (filled upside-down triangles) complexes were incubated at 4° C. with 0-6 M GdnHCl in 10 mM TBS, pH 7.4 for 72 h. The fluorescence intensities at 353 and 333 nm were measured at 25° C. using a 4×4 mm2 cuvette on a Fluoro-Max-2 spectrofluorimeter with sample protein concentrations between 0.05 and 0.1 mg of protein/ml. The emission spectra were taken by exciting at 285 nm with a resolution of 2 nm and by measuring the emission with a resolution of 4 nm. The ratio of fluorescence intensity at 353 nm to that at 333 nm is plotted against the GdnHCl molar concentration.
Figure 15:
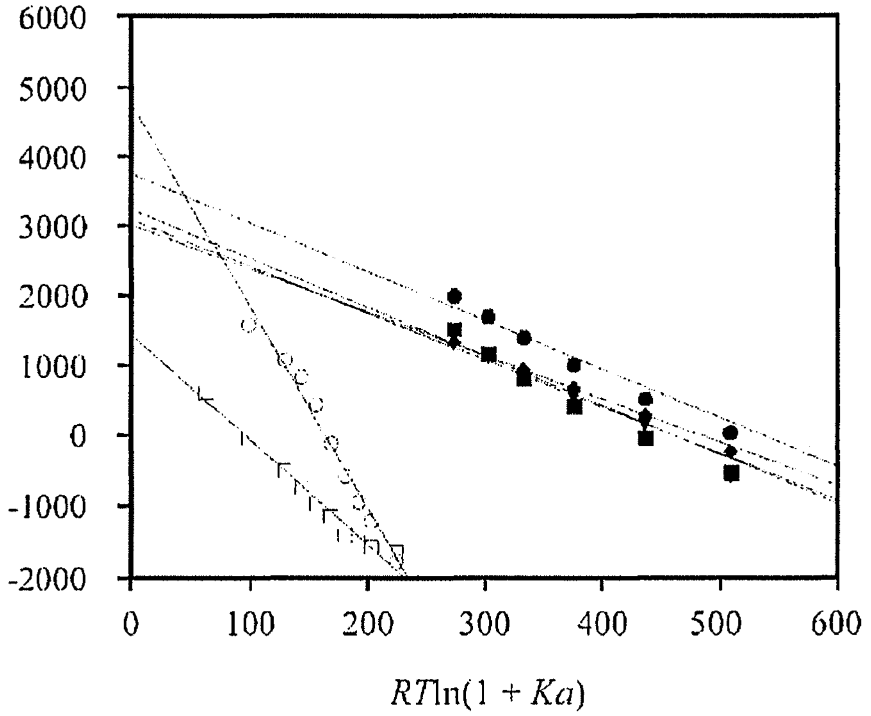
FIG. 15 presents the exemplary data showing the free energy of denaturation of lipid-free apo A-I and rHDL complexes as a function of the ionic activity of GdnHCl. The free energy values of denaturation (calculated from change in the ratio of fluorescence intensity at 353 nm to that at 333 nm) are fitted using linear regression equations and plotted against RTln(1+Ka) for unoxidized (open circles) and oxidized (open squares) lipid-free apo A-I proteins or prepared rHDL-1 (filled circles), rHDL-2 (filled squares), rHDL-3 (filled diamonds) and rHDL-4 (filled upside-down triangles) complexes. The standard free energy of denaturation ($\Delta G_D°$) and the number of the bound GdnHCl moles ($\Delta n$) were computed from the intercepts on the vertical axis and the slopes of the regression lines, respectively, as described by Sparks et al. (Sparks et al. J Biol Chem 1992; 267:25839-47).
Figure 16:
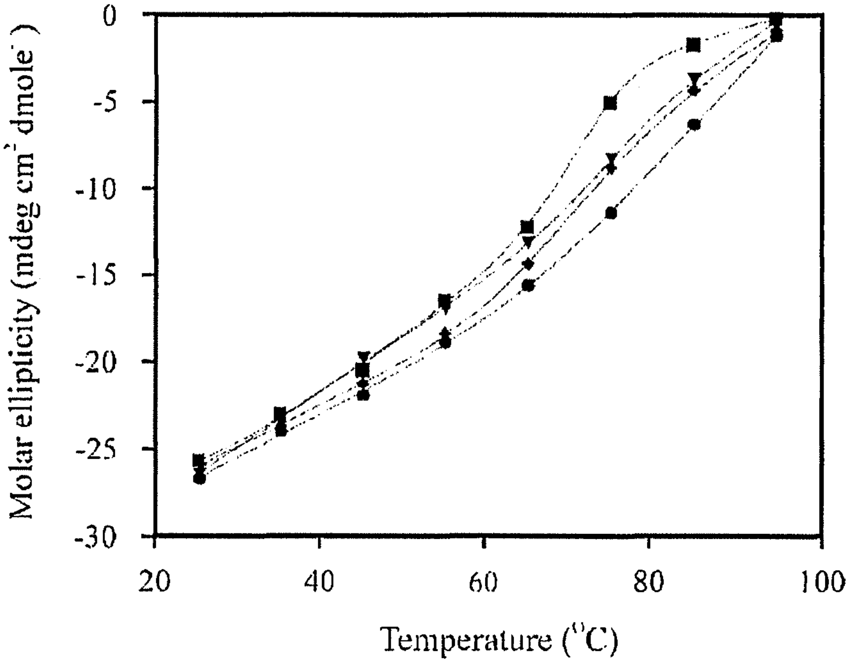
FIG. 16 presents the exemplary data showing temperature-induced unfolding of rHDL complexes. The circular dichroic data were collected at 222 nm every 2-5° C. from 25 to 95° C. on solutions of 1.8 uM (0.05 mg of protein/ml) prepared rHDL-1 (filled circles), rHDL-2 (filled squares), rHDL-3 (filled diamonds) and rHDL-4 (filled upside-down triangles) complexes in TBS, pH 7.4, with a 1 mm path-length quartz cuvette on AVIV 62A DS spectropolarimeter.

No substantial differences in stability of apo A-I were observed among the four apo A-I-carrying rHDL complexes, including rHDL-4 which also contains apo A-II (Table 3, FIGS. 14-16). Thus, as it is important for the compositions of the present invention in terms of resembling with nascent HDL, the structural stability of oxidized apo A-I molecules in rHDL complexes remains similar to that of the unoxidized protein.

TABLE 3

Thermodynamic parameters of lipid-free and lipid-associated apo A-I

| Complex | $D_{1/2}$ (M GdnHCl)[a] | $\Delta G_D^o$ (kcal/mol of apolipoprotein)[b] | Δn (mol GdnHCl/ mol of apolipoprotein)[c] | $T_m$ (° C.)[d] |
|---|---|---|---|---|
| apo A-$I_{unox}$ | 1.0 (0.1) | 4.7 (0.3) | 29(4) | 64(3) |
| apo A-$I_{ox}$ | 0.4 (0.1)[f] | 1.4 (0.1)[f] | 15 (3)[f] | — |
| rHDL-1 | 4.1 (0.3)[f] | 3.7 (0.3)[f] | 7(1)[f] | 82 (3)[f,g] |
| rHDL-2 | 3.3 (0.3)[f,g] | 3.1 (0.3)[f,g] | 7(1)[f] | 71 (3)[f,g] |
| rHDL-3 | 3.8 (0.3)[f] | 3.0 (0.3)[f,g] | 6(1)[f] | 74 (3)[f,g] |
| rHDL-4[e] | 3.7 (0.3)[f] | 3.2 (0.3)[f,g] | 7(1)[f] | 74 (3)[f,g] |

[a]Midpoints of GdnHCl denaturation. Mean and S.D. (in parentheses) of three different measurements are given.
[b]Free energy of denaturation at zero GdnHCl concentration (± SD).
[c]The number of the GdnHCl moles bound during denaturation (± SD).
[d]Midpoints of thermal denaturation (± SD).
[e]Mean number of apolipoprotein moles calculated from the data of reversed-phase HPLC.
[f]$P < 0.05$, comparison vs apo A-$I_{unox}$.
[g]$P < 0.05$, comparison vs rHDL-1.

Limited Proteolytic Digestion of Reconstituted Discoidal rHDL

Samples of lipid-free apo A-I or rHDL complexes (0.4 mg of protein/ml) in PBS (pH 7.2) were treated with chymotrypsin at 37° C. for 75 min using a protein-protease ratio (w/w) of 1000:1 (for lipid free apo A-I), or for 240 min using a ratio of 6:1 (for rHDL). Trypsin digestions were performed similarly, except in TBS (pH 7.4) for 120 min using a protein-protease ratio of 200:1 (w/w). Digested samples were analyzed by SDS-PAGE (15% acrylamide) and HPLC.

Figure 17:
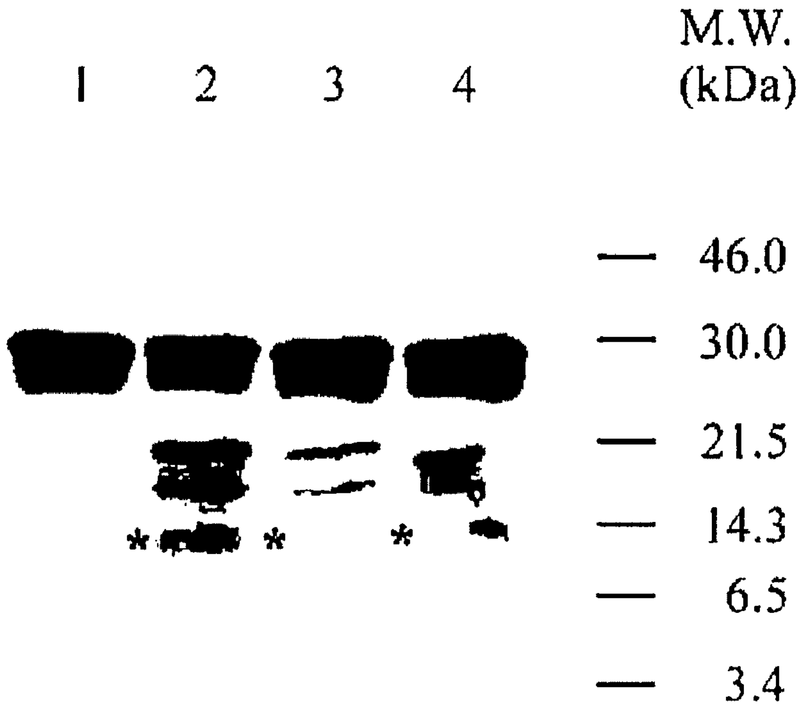
FIG. 17 presents the exemplary data showing SDS-PAGE analysis of the trypsin digestion products of rHDL complexes. The rHDL complexes were treated by trypsin at room temperature for 2 h. Lane 1—rHDL-1 containing only apo A-$I_{unox}$. Lane 2—rHDL-2 containing only apo A-$I_{ox}$. Lane 3—rHDL-3 containing apo A-$I_{unox}$ and apo A-$I_{ox}$ with a molar ratio of 1:1. Lane 4—rHDL-4 containing apo A-$I_{unox}$, apo A-$I_{ox}$ and apo A-$II_{unox}$ with a molar ratio of 3:3:1. The positions and molecular weights of the protein standards are indicated on the right of the gel. The 14 kDa fragment is identified with an asterisk mark.

Thus, the oxidative damage to the apo A-I molecule leads to the appearance of an accessible tryptic site in the central region of the lipid-bound apo A-I molecule (FIG. 17). These oxidation-induced changes in the accessibility of the apo A-I central region to proteolysis may enhance the absorption of rHDL by macrophages in vivo which is critical for the compositions of the present invention.

Lipid Binding of Unoxidized, Oxidized and Enzymatically Reduced Apolipoprotein

Unoxidized apo A-I, apo A-$I_{unox}$, and oxidized apo A-I, apo A-$I_{ox}$ (with sulfoxidized methionines at positions 112 and 148) were obtained, purified and characterized as described above (and in Sigalov A. B. & Stern L. J. FEBS Lett 1998; 433:196-200; Sigalov A. B. & Stern L. J. Chem Phys Lipids 2001; 113:133-46; Sigalov A. B. & Stern L. J. Antioxid Redox Signal 2002; 4:553-7). The rHDL complexes were prepared and characterized as described above (and in Sigalov A. B. & Stern L. J. Chem Phys Lipids 2001; 113:133-46; Sigalov A. B. & Stern L. J. Antioxid Redox Signal 2002; 4:553-7).

Enzymatic reduction of methionine sulfoxides in lipid-free apo A-$I_{ox}$ (65-130 ug) and apo A-$I_{ox}$ in rHDL particles (15 ug) was carried out essentially as described (Sigalov A. B. & Stern L. J. FEBS Lett 1998; 433:196-200) at 37° C. in 33 mM Tris-HCl, 13 mM $MgCl_2$, pH 7.5, containing 4-8 ug of PMSR in a total volume of 30-90 ul, except that clinically relevant DHLA (13 mM) was used as a cofactor of PMSR instead of DTT. For HPLC analysis, solid GdnHCl was added to the reaction mixtures containing rHDL complexes to a final concentration of 6 M.

1,2-Dimyristoyl-sn-glycero-3-phosphocholine (DMPC) in chloroform solution was dried under argon and then solubilized in TBS (Tris-buffered saline containing 0.01 M Tris-HCl, 0.14 M NaCl, 0.25 mM EDTA-$Na_2$, 0.15 M $NaN_3$), pH 8.0 (0.5 mg/ml final) above its transition temperature (>24° C.). DMPC/protein molar ratios of 50:1 were used, and the reaction was followed at 24° C. in a thermostated cell compartment of a Hitachi U-3110 spectrophotometer by monitoring the decrease in absorbance at 325 nm. The data were analyzed according to pseudo-first-order kinetics, and $t_{1/2}$ was determined as the time required for a 50% decrease in turbidity.

Figure 18:
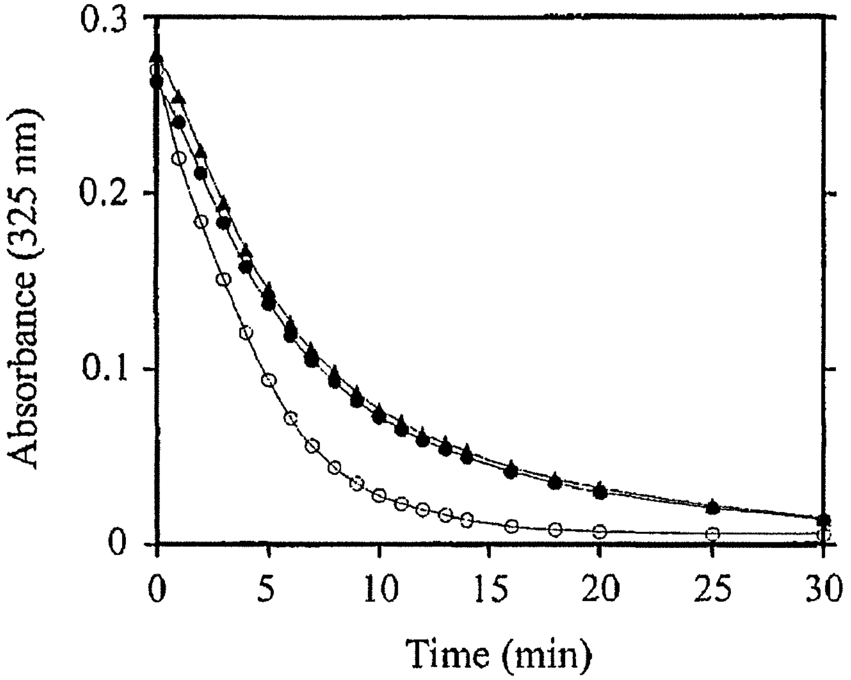
FIG. 18 presents the exemplary data showing 1,2-dimyristoyl-sn-glycero-3-phosphocholine (DMPC) kinetic binding with unoxidized, oxidized, and reduced apo A-I proteins. DMPC solubilized above its transition temperature (>24° C.) in TBS, pH 8.0, was diluted by the same buffer to 0.5 mg/ml and preincubated for 10 min at 24° C. Then unoxidized (filled circles), oxidized (open circles), and reduced (filled triangles) apo A-I proteins dissolved in the same buffer were added (final DMPC/protein molar ratio, 50:1), and the reaction was followed at 24° C. for 30 min at 325 nm.
Figure 19A:
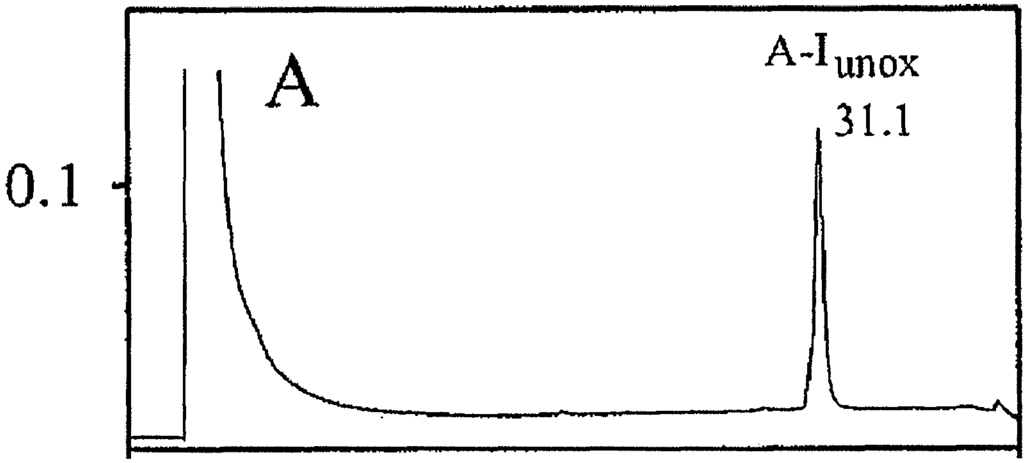
FIG. 19A presents the exemplary data showing an analytical reversed-phase HPLC profile of apo A-I in rHDL particles containing only apo A-$I_{unox}$ (rHDL-1). The retention time (in minutes) is shown above the peak.
Figure 19B:
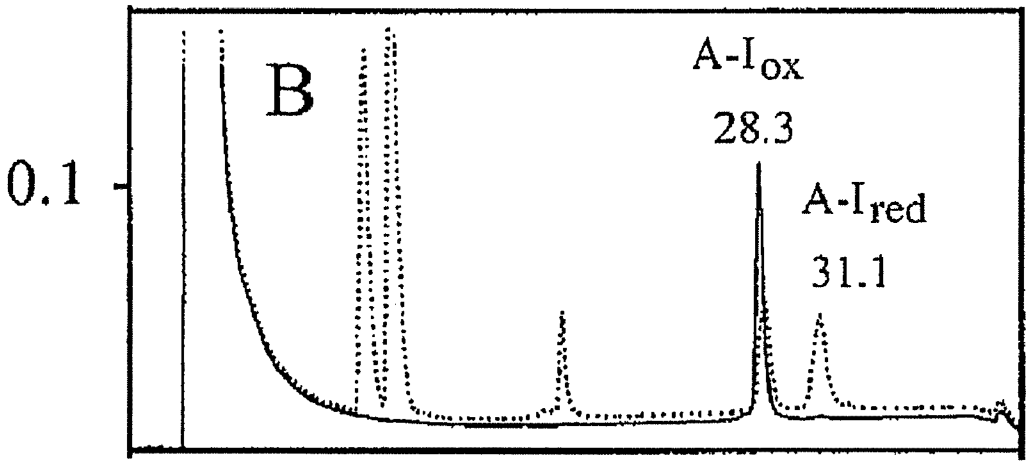
FIG. 19B presents the exemplary data showing an analytical reversed-phase HPLC profile of apo A-I in rHDL particles containing only apo A-$I_{ox}$(rHDL-2) before (solid line) and after (dotted line) the treatment by the peptide methionine sulfoxide reductase (PMSR) enzyme in the presence of dihydrolipoic acid (DHLA). The retention times (in minutes) are shown above each peak.
Figure 19C:
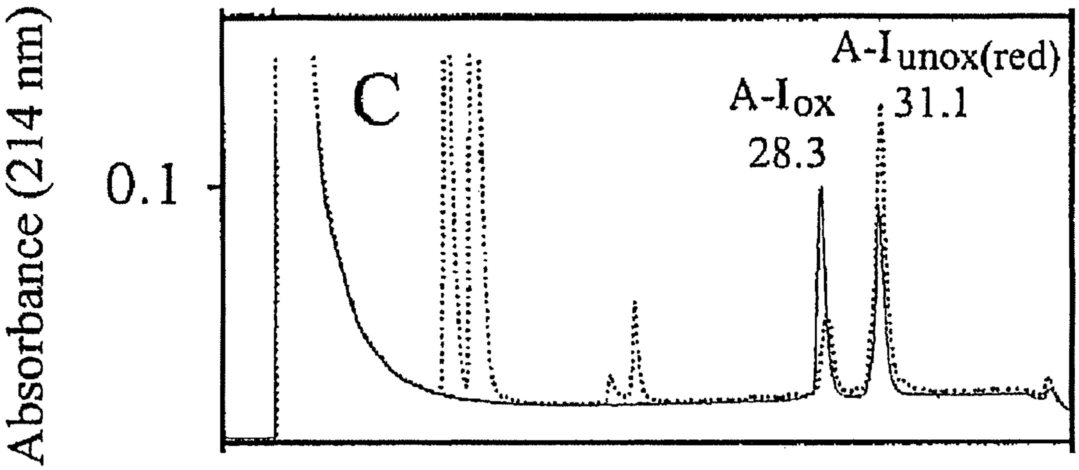
FIG. 19C presents the exemplary data showing an analytical reversed-phase HPLC profile of apo A-I in rHDL particles containing apo A-$I_{unox}$ and apo A-$I_{ox}$ with a molar ratio of 1:1 (rHDL-3) before (solid line) and after (dotted line) the treatment by the peptide methionine sulfoxide reductase (PMSR) enzyme in the presence of dihydrolipoic acid (DHLA). The retention times (in minutes) are shown above each peak.
Figure 19D:
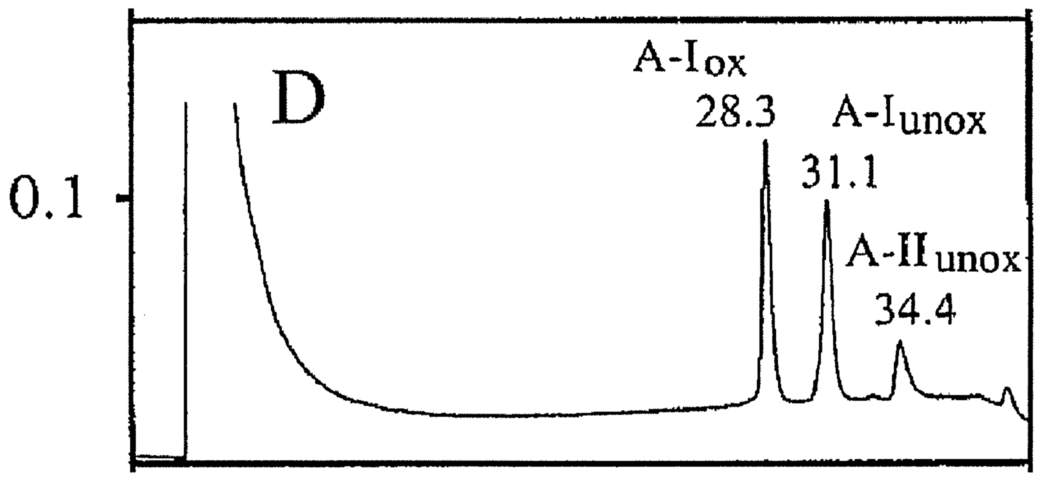
FIG. 19D presents the exemplary data showing an analytical reversed-phase HPLC profile of apo A-I in rHDL particles containing apo A-$I_{unox}$, apo A-$I_{ox}$, and apo A-$II_{unox}$ with a molar ratio of 3:3:1 (rHDL-4) in TBS, pH 7.4. The retention times (in minutes) are shown above each peak.
Figure 19E:
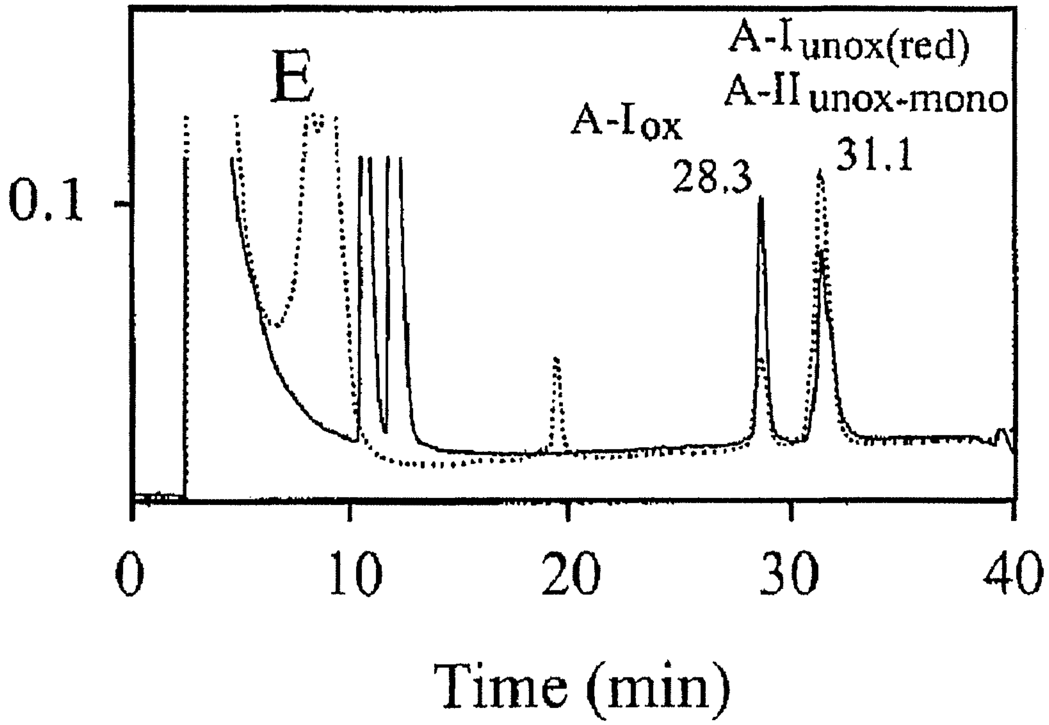
FIG. 19E presents the exemplary data showing an analytical reversed-phase HPLC profile of apo A-I in rHDL particles containing apo A-$I_{unox}$, apo A-$I_{ox}$, and apo A-$II_{unox}$ with a molar ratio of 3:3:1 (rHDL-4) in the enzyme reaction buffer containing DHLA in the absence of the enzyme (solid line) and after PMSR/DHLA treatment (dotted line). As DHLA reduces the disulfide bond in native apo A-II dimer, it dissociates into identical 77-residue monomers. The retention time of this apo A-II monomer is similar to that for apo A-$I_{unox}$. The retention times (in minutes) are shown above each peak.

The ability of apo A-I to promote cholesterol efflux is partially determined by its ability to bind with lipids. The kinetics of this binding was assessed by measuring the rate of DMPC liposome turbidity clearance (FIG. 18). The $t_{1/2}$ values were estimated to be 5.0 and 3.5 min, for apo A-$I_{unox}$ and apo A-$I_{ox}$, respectively. Thus, apo A-$I_{ox}$ binds DMPC more rapidly than apo A-$I_{unox}$, although the final binding levels are equal. The reduction of apo A-$I_{ox}$ by PMSR in the presence of DHLA completely restores DMPC binding kinetics (FIG. 18), protein secondary and tertiary structural features, and thermodynamic parameters (Table 1) characteristic of the native apo A-$I_{unox}$. Thus, enzymatic reduction of apo A-$I_{ox}$ using PMSR with DHLA as its cofactor can reverse the oxidative damage caused by the oxidation of two of three methionine residues (Met-112 and Met-148).

Well defined rHDL particles with varying proportions of apo A-$I_{ox}$, apo A-$I_{unox}$, and apo A-II, rHDL-1, rHDL-2, rHDL-3, and rHDL-4, were reacted each with PMSR in the presence of DHLA. Conversion of lipid-bound apo A-$I_{ox}$ to apo A-$I_{red}$ proceeded to 50-60% after 5 min of incubation independent of rHDL protein composition (FIGS. 19A-E). Rate and yield of the reaction were similar to those observed for lipid-free apo A-I. No changes in size distributions or shapes in rHDL particles were observed after PMSR reaction as analyzed by nondenaturing gradient gel electrophoresis and electron microscopy.

These data indicate that both of the apo A-I methionine sulfoxide residues (Met-112 and Met-148) are as accessible to enzymatic reduction in rHDL particles as they are in lipid-free apo A-$I_{ox}$. Furthermore, the reaction does not depend on the molar ratio of apo A-$I_{unox}$/apo A-$I_{ox}$ or the presence of apo A-II. Because these experiments were performed with discoidal rHDL particles including those that contain apo A-II, these findings as it is important for the compositions of the present invention, are especially relevant to native nascent HDL, but they also should apply to the spherical rHDL compositions of the present inventions in terms of resembling with mature HDL (Brouillette C. G. & Anantharamaiah G. M. Biochim Biophys Acta 1995; 1256: 103-29), including those containing only apo A-I or both apo A-I and apo A-II.

In certain embodiments of the present invention, it may be desirable to incorporate DHLA into the rHDL compositions of the invention to restore sulfoxidized methionines of targeting apolpoproteins A-I and A-II and fragments thereof at sites of interest (back to methionine native form).

Example 6: Cholesterol Efflux by Native HDL

The ability of native HDL to accept cholesterol from cholesterol-loaded human skin fibroblasts was assessed depending on the ratio of unoxidized/oxidized apo A-I in these particles as described (Sigalov et al. Eur J Clin Chem Clin Biochem 1997; 35:395-6).

Figure 20:
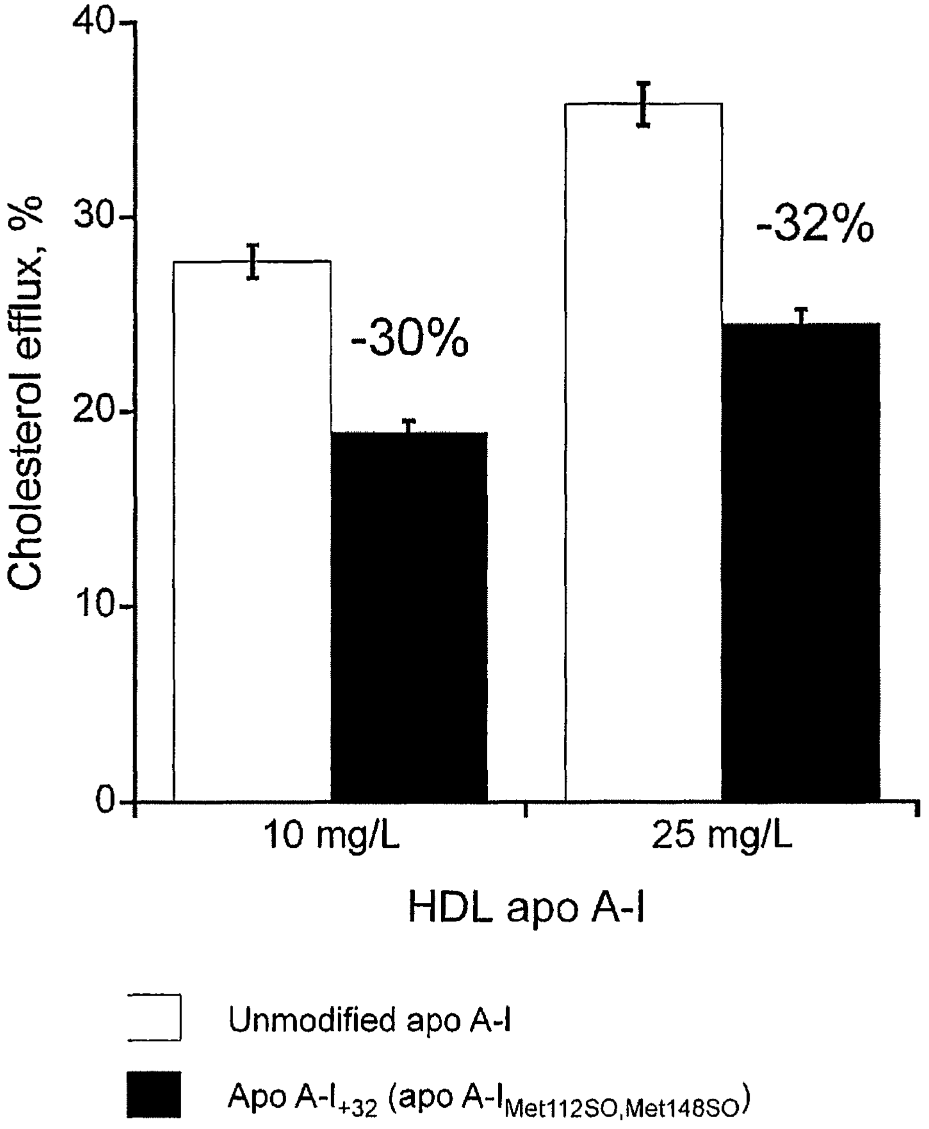
FIG. 20 presents the exemplary data showing observed values of relative cholesterol efflux from cholesterol-loaded human skin fibroblasts promoted by HDL containing unmodified (unoxidized) apo A-I (empty bars) and oxidized (apo A-$I_{+32}$, or apo A-$I_{Met112SO,Met148SO}$) apo A-I (solid bars). Concentrations of HDL were as follows: A—10 mg of apolipoprotein A-1 per liter of medium; B—25 mg of apolipoprotein A-I per liter of medium.

HDL-mediated cholesterol efflux was found to depend on the ratio of non-oxidized/oxidized apo A-I in HDL (FIG. 20). However, HDL particles containing apo A-$I_{ox}$ (with sulfoxidized methionines at positions 112 and 148) are still able to promote cholesterol efflux, which is important for the compositions of the present invention.

Example 7: Labelling of HDLs with Non-Metallic Atoms

As disclosed in US Pat Appl 20070243136 and incorporated herein by reference, Iodine in all isotopes ($^{123}I$, $^{125}I$, $^{127}I$, $^{131}I$) can be successfully linked to apo A-I protein using IODO-BEAD Iodination reagent (Pierce, Rockford, Ill.) in good yield. Once linked, the labeled protein can be reconstituted with lipids to form the lodinated HDL. Iodinated HDL can be used for PET/SPECT and CT indications. Below is a brief description for protein labeling:

1. Wash beads with 500 ul of reaction buffer per bead. Dry the bead(s) on filter paper.
2. Add bead(s) to a solution of carrier-free $^{123}I$, $^{125}I$, $^{127}I$, $^{131}I$ (approximately 1 mCi per 100 ug of protein) diluted with reaction buffer and allow to react for 5 minutes.
3. Dissolve or dilute protein in reaction buffer (TBS) and add to the reaction vessel. Allow the reaction to proceed for 15 minutes.
4. Stop the reaction by removing the solution from the reaction vessel.
5. Dialyze the solution.

For labeling of lipids, the protocol used is similar to the protocol used for labeling lipids with metallic agents. To incorporate $^{18}F$ isotope in HDL, $^{18}F$-fluorodeoxyglucose (FDG a common PET agent) can be introduced into the core of HDL. Since FDG is neutrally charged it should easily being incorporated into the core. The material could be produce as follows:

1. Add apoA-I to the reaction buffer (TBS) that contains a mixture of lipids and FDG.
2. Sonicate.
3. Dialyze the solution.

To attach a positron emitting isotope selected from the group consisting of $C^{11}$, $F^{18}$, $O^{15}$, and $N^{13}$, methods described in Miller et al. Angewandte Chemie 2008; 47:8998-9033, can be applied by those of ordinary skill in the art of radiolabeling of proteins, peptides, lipids, and other compounds. These methods comprise attaching the isotope either directly by isotopic substitution for an existing atom in the compounds, attachment of an isotope directly to compounds or by attaching a prosthetic group bearing the isotope. The choice of methods for attachment is practiced by those of ordinary skill in the art of radiolabeling.

Example 8: Derivatization of Phospholipids for Use in rHDL Compositions of the Invention As disclosed in US Pat Appl 20070243136 and incorporated herein by reference, the rHDL compositions of the present invention will be designed to comprise phospholipids that have been derivatized with either the metallic ion chelate, the non-metallic imaging agent or, with a targeting components. While the following discussing is based on PE derivatives, it should be understood that any phospholipid, and particularly, PC, PA, PS, PI, PG, CL and SM could also be derivatized in similar fashion.

In certain exemplary embodiments of the present invention, PE derivatives for incorporation into rHDL are Gd-DTPA-PE, biotinylated PE, and poly-L-lysine-PE. The purpose of these phospholipid derivatives is to allow specific agents to be incorporated onto the surface of the rHDL compositions of the invention. Each PE (or other phospholipid) derivative is anchored via its hydrophobic fatty acyl chains into the rHDL surface. Each PE derivative projects a functional moiety from the rHDL surface, to which the metallic or non-metallic imaging contrast agent may be attached. In specific embodiments, that contrast agent is, for example, Gd (for MR contrast) is iodine or bromine (for CT), $^{111}In$, $^{99}mTc$ (for gamma-scintigraphy), fluorescein (for optical imaging). In other embodiments, it is contemplated that the rHDL entities of the invention also will comprise a targeting agent for molecular targeting of the rHDL imaging particles. The targeting agent, e.g., an antibody will be attached to a PE (or other phospholipid moiety) head group through a functional group. Preferably, the contrast agent and targeting agent are on separate phospholipid molecules within the rHDL.

In specific examples, the metallic paramagnetic ion is Gd, which is attached to the PE covalently linked to DTPA, a chelating agent. Other metallic agents and chelating agents have been discussed above. The synthesis of DTPA-PE is routinely performed by incubating PE with cyclic DTPA anhydride (cDTPAA), followed by column chromatography purification. Gd incorporation is then achieved by treating gadolinium chloride hexahydrate (Aldrich, Milwaukee, WI) with DTPA-PE and purified Gd-DTPA-PE complexes using column chromatography. In more detail, this synthesis is described in US Pat Appl 20070243136, the disclosure of which is incorporated herein by reference.

To attach antibodies or other targeting agent, biotinylated-PE or other phospholipid (available from Avanti Polar Lipids) may be used. As with DTPA-PE, the biotinylated PE is substituted for PE during the reconstitution of HDL particles. In exemplary embodiments, the targeting agent is an antibody. The biotin group is exposed at the surface of the rHDL, so that antibodies conjugated to avidin and mixed with the rHDL will self-associate and be available for binding to their target antigens (e.g., see Lanza et al. Circulation 2002; 1062842-7).

In a particular embodiment, it may be desirable to increase the amount of contrast agent or targeting agent in the rHDL particle, but without producing a concomitant increase the mass of derivatized PE per particle. This may be necessary in the event that the mole % DPTA-PE that replaces the PE in the HDL disrupts the structure of the rHDL. As noted above, this is highly unlikely because DPTA-PE substitutes well for PE into related structures such as liposomes. Nevertheless, a feasible way to substantially lower the content of DPTA-PE in the rHDL is to use an established procedure in which a poly-L-lysine linker is attached to PE, so that at each epsilon-amino group, a DPTA moiety is covalently attached. In this way, less PE, but more Gd (and/or other metal), can be incorporated into the rHDL. Thus, it is contemplated that the use of the poly-L-lysine-PE will allowing multiple metallic ions to be chelated. This is a standard method that has previously been used in liposomal applications (e.g., see Torchilin V. P. Adv Drug Deliv Rev 2002; 54:235-52). Use of this strategy will facilitate a further increase in the amounts of signal intensity. Similarly, the same poly-L-lysine-PE can be used to load additional antibody molecules/rHDL (Slinkin et al. Bioconjug Chem 1991; 2:342-8). Thus, it is contemplated that a single PE molecule will have multiple metallic contrast agents linked thereto, and/or multiple targeting agents linked thereto.

Example 9: Production of Lipoprotein Apolipoprotein A-1 (LpA-I)-Gadolinium Complexes Gadolinium 1,2-dimyristoyl-sn-glycero-3-phosphoethanolamine diethylenetriamine pentaacetic Acid (GdDMPE-DTPA).

As disclosed in US Pat Appl 20070243136 and incorporated herein by reference, 1,2-dimyristoyl-sn-glycero-3-phosphoethanolamine diethylenetriamine pentaacetic acid (25 mg, 228 umol) is heated to reflux with gadolinium triflate (7 mg, 22.8 umol) in dry acetonitrile (4 mL) for 18 h. The solution is then allowed to cool and the solvent is evaporated to afford a pale yellow solid that is used without previous purification.

Preparation of Spherical LpA-4-Gd Complexes

Reconstituted LpA-I/Gd complexes are prepared by cosonication of POPC (palmitoyl oleoyl phosphatidylcholine), TG (triglyceride, for example, triolein), FC (free cholesterol), C (cholesterol ester), apoA-I and GdDMPEDTPA. Specific amounts of POPC, TG, C, FC and GdDMPEDTPA or other lipophilic gadolinium complexes in chloroform are dried under nitrogen into a 12×75 mm glass test tube and 800 uL of PBS is added. The lipid-buffer mixture is sonicated for 1 min in a 15° C. water bath, incubated for 30 min at 37° C., and sonicated again for 5 min. ApoA-I is subsequently added to the lipid suspension and the protein-lipid mixture is sonicated four times (1 min each time), punctuated by 1-min cooling periods. All LpA-I complexes are filtered through a 0.22 um syringe tip filter and reisolated either by size-exclusion chromatography on a Superose 6 column or by sequential density gradient ultracentrifugation.

Example 10: Methods of Confirming the Configuration of the rHDL

Having produced the rHDL compositions as described in US Pat Appl 20070243136 and incorporated herein by reference, it may be advantageous to determine the mole % of each component of the rHDL compositions of the invention. This may be determined by the biochemical assays known to those of skill in the art (Shamir et al. J Clin Invest 1996; 97:1696-704). The Gd content is determined by inductively coupled plasma (ICP) analyses (Gailbraith Laboratories, Inc. (Knoxville, Tenn.) (Fossheim et al. Magn Reson Imaging 1999; 17:83-9; Glogard et al. Int J Pharm 2002; 233:131-40), and/or by size exclusion chromatography (gel filtration) through a calibrated column (e.g., Superose or Sepharose chromatography column).

The penetration of Gd-rHDL into the interstitial space, including the interior of atherosclerotic plaques, can be affected by particle size and to some extent by surface charge. Particle size can be determined by non-denaturing gel electrophoresis through 2-16% and 4-30% gels, as described (Williams K. J. & Scanu A. M. Biochim Biophys Acta 1986; 875:183-94). In addition, the size of the rHDL can be determined using Laser Light Particle Sizer (Model HPPS 500, Malvern Instruments Inc., Southborough, Mass.). Alternatively, particle size can be determined by electron microscopy as described in Example 5. See also Sigalov A. B. & Stern L. J. Chem Phys Lipids 2001; 113:133-46.

As discussed in US Pat Appl 20070243136 and incorporated herein by reference, it is preferred that the Gd-rHDL should average 5-12 nm in diameter. Surface charge of these moieties may be assessed by agarose gel electrophoresis, as described in previous publications (Sparks et al. J Biol Chem 1992; 267:25839-47; Sparks D. L. & Phillips M. C. J Lipid Res 1992; 33:123-30). In all of the above methods, normal human HDL may be used as reference standard. Substantial deviations of either the size or surface charge from normal HDL could impair particle penetration into the interstitial space, which may be measured directly in vivo as described below.

In the event that the surface charge of the rHDL is substantially different from normal HDL and if this altered surface charge substantially decreases penetration of the particles into the interstitium in vivo, it is contemplated that small amounts of positively (basic) or negatively (acidic) charged lipids may be added as needed to restore a more natural total surface charge. With this modification, interstitial penetration will be achieved. In the event that the size of the rHDL (either with the Gd chelates or with the Gd-antibody-chelates) is substantially larger than normal HDL, accompanied by a large decrease in penetration into the interstitium in vivo, it is proposed that discoidal reconstituted particles (discussed above) should be used. This is because variants of the Gd chelates would expand the particles in a direction perpendicular to the surfaces, but not the edges, of the disks. Thus, the largest overall dimension would not increase. Of note, rHDL disks have also proven useful as drug delivery vehicles (Rensen et al. Adv Drug Deliv Rev 2001; 47:251-76), so the technology is reasonably mature. Additionally, in order to reduce the size of the rHDLs comprising antibodies as the targeting moieties, it should be possible and desirable to use antigen-binding fragments of the antibody (e.g., Fab or other antibody fragments), rather than the whole antibody molecules, which would also reduce overall particle size.

Example 11: Use of rHDL in MRI in Mice

As disclosed in US Pat Appl 20070243136 and incorporated herein by reference, model animals can be used to image atherosclerotic plaques, to test the efficacy of the compositions of the present invention. Apo E-KO and Wild Type (WT) mice in the C57Bl/6 background weighing 15-40 g, (Jackson Laboratories, Bar Harbour, Me.) are preferably be used. After weaning (4 weeks of age) and a 2 weeks period on a regular chow diet, the apoE-KO mice are fed a Western Diet (Research Diets, New Brunswick, N.J.) for up to 42 weeks.

The scheme for in vivo contrast enhanced (CE) MRM in the above mice is described in detail in US Pat Appl 20070243136 and incorporated herein by reference. Before MRM, an 27-ga. needle is inserted in the tail vein of the mouse and the needle is connected to a saline filled micro polyurethane catheter (Harvard Apparatus, Holliston, Mass.) with a Y-site connector, and attached to a syringe pump (Braintree Scientific Inc., Braintree, Mass.) while the other connector is attached to a saline-filled syringe for flushing before and after injection of the contrast agent. The animals are anesthetized with an isoflurane/$O_2$ gas mixture (4%/400 cc/min initial dose, 1.5%/150 cc/min maintenance dose), which is delivered through a nose cone. The anesthetized animals are then placed in the RF coil with the animal handling system. An image intensity standard of 2% agar in 1 mM Gd-DTPA (Magnevist) may be placed beside the animal for data normalization.

In the exemplary embodiments described in US Pat Appl 20070243136 and incorporated herein by reference, the in vivo MRM is performed with a 9.4 T, 89 mm-bore system operating at a proton frequency of 400 MHz (Bruker Instruments, Billerica, MA). Constant body temperature of 37° C. is maintained using a thermocouple/heater system. A respiratory sensor can be placed on the abdomen of the animal for monitoring the depth and frequency of respiration. ECG monitoring will be performed using subcutaneous silver electrodes. The sensors are connected to the small animal monitoring unit.

After anatomical and angiographic MR localization, multi-contrast high-resolution images of the wall perpendicular and/or parallel to the entire arterial tree are obtained. MRM imaging is performed with the 2D and 3D high-resolution MR software and hardware methods described previously (Fayad et al. Circulation 1998; 98:1541-7; Choudhury et al. Atherosclerosis 2002; 162:315-21; Choudhury et al. J Magn Reson Imaging 2003; 17:184-9; Itskovich et al. Magn Reson Med 2003; 49:381-5). Without removing the animal and the coil, the contrast agent is administered using the syringe pump at a constant rate of 50 ml/min. The procedure is followed with flush of saline.

Briefly, in order to characterize the plaque the following MRM is conducted as described in US Pat Appl 20070243136: 1) multicontrast blackblood pre-contrast enhanced (CE) MRM; and 2) post-contrast non-specific (Gd-DTPA) CE MR black-blood T1W imaging.

Histopathology, image and data analysis are performed to evaluate the MRM imaging with and without contrast-enhanced (Gd-DTPA) techniques. For histology processing, following MRM, randomly selected animals are sacrificed. The aorta from these animals is perfused, removed, and fixed (Fayad et al. Circulation 1998; 98:1541-7; Rong et al. Circulation 2001; 104:2447-52; Reis et al. J Vasc Surg 2001; 34:541-7; Choudhury et al. Atherosclerosis 2002; 162:315-21; Choudhury et al. J Magn Reson Imaging 2003; 17:184-9; Itskovich et al. Magn Reson Med 2003; 49:381-5). Serial sections of the aorta are cut at intervals matching corresponding MRM images. Co-registration is performed using external landmarks to the aorta, including arterial branches and the image processing algorithms explained above. Surrounding tissue is included in the sections for arterial support during fixation and to enhance co-registration through the use of fiducial markers as previously reported (Choudhury et al. Atherosclerosis 2002; 162:315-21; Fayad et al. Circulation 1998; 98:1541-7; Reis et al. J Vasc Surg 2001; 34:541-7; Choudhury et al. J Magn Reson Imaging 2003; 17:184-9; Itskovich et al. Magn Reson Med 2003; 49:381-5). The specimens are embedded in paraffin, and sections 5 um thick are cut and stained with combined Masson's trichrome elastin (CME) stain and hematoxylin and eosin (H&E) stain. Other staining procedures also may be used.

Image analysis for plaque morphology (size, volume, etc.) and characterization may be performed by applying the cluster analysis, snake-based contour detection, and coregistration algorithms to both the MRM and histopathology images. The effectiveness of cluster and snake analyses as methods of automated atherosclerotic plaque component segmentation can be validated by comparing the registered color composite MRM images with the corresponding histopathology sections in both a qualitative and quantitative manner.

Qualitatively, the individual plaque components are identified on the cluster analyzed color composite matched MR images and histological slices for every specimen on the basis of signal intensity in the multicontrast MR images and histopathological staining. The color composite MR images and histopathological images are rated according to the histopathological classification from the Committee on Vascular Lesions of the Council of Atherosclerosis of the American Heart Association (AHA) (Fayad et al. Circulation 1998; 98:1541-7; Fayad et al. Circulation 2000; 101: 2503-9; Stary et al. Circulation 1995; 92:1355-74) which have been used in US Pat Appl 20070243136. See also Choudhury et al. Atherosclerosis 2002; 162:315-21; Choudhury et al. J Magn Reson Imaging 2003; 17:184-9; Helft et al. Circulation 2002; 105:993-8).

Quantitatively, the digitized histopathological slices are subjected to the same cluster analysis procedure that the corresponding color composite MRM images were subjected to. The clustered histopathological images are characterized according to the AHA classification as above. Using the cluster and snake-based algorithms, the areas of these labeled regions are computed for both datasets as a percentage of total vessel wall area. The histopathological slices are matched to their corresponding MRM slices to allow for direct comparison of the labeled region areas. Additionally, The signal intensity of the vessel wall components and the adjacent muscle and the image intensity standard (to define the background MR signal) over time are determined by means of standard region-of-interest (ROI) measurements on the corresponding MRM images. An ROI placed outside the body, that contained no motion artifacts, will be selected to measure the standard deviation of the noise signal. Both normalized signal intensity (SI): $SI=SI_{plaque\text{-}post}/SI_{plaque\text{-}pre}$ and contrast-to-noise ratios (CNR): $CNR=SI_{plaque}-SI_{muscle}/SD_{noise}$ can be calculated.

For histopathological analysis of plaques, the components of the arterial wall and the atherosclerotic plaque can be determined by methods previously described in US Pat Appl 20070243136. See also Fayad et al. Circulation 1998; 98:1541-7; Rong et al. Circulation 2001; 104:2447-52. Three categories of plaque components may be correlated with the MRI images: 1) fibrous, 2) lipid, and 3) calcium. These categories are identified histopathologically by the following methods: intense green staining by CME (fibrous); foam cells and cholesterol clefts on H&E and CME (lipids); acellular purple crystals by H&E (calcium). In addition, immunohistochemical staining can be performed for □-actin (smooth-muscle cells), CD68 and MOMA2 (macrophages), the two principal cell types found in plaques.

After both MR images and histological sections are reviewed and categorized, comparison between the two sets of data can be performed. Given the difference in slice thickness between MRM histological cross-sections, three to four histological sections for each MR image location should be selected based on the relative distance of the MRM and histological sections from renal arteries and iliac bifurcation. In order to correct for shrinkage of the aortic specimen during histological processing, additional measures other than distance from the bifurcation for matching of the MRI and histological sections can be used. For example, the gross morphological features of the lumen and vessel wall, such as, the overall shape and size of the lumen and wall—may be compared. In addition, the location of large calcified regions, which appear hypointense on MRM, will aid in matching the cross-sections at each location. An agreement between MRI and histology may be defined as the presence of any plaque component region in the same quadrant on the MRI section and in all 3-4 of the matched histological sections. Pre-CE and post-MRM should be matched and registered.

Example 12: Use of Modified HDL as Specific Carrier for MRI of Atherosclerotic Plaques As discussed herein and in US Pat Appl 20070243136, the disclosure of which is incorporated herein by reference, the ability to image the presence or biological activity of specific molecules in vivo (i.e., molecular imaging) in atherosclerotic plaques is of considerable interest. Current non-contrast and contrast-enhanced methods do not interrogate specific biochemical processes. In certain embodiments, the present invention is designed to enhance distinctions among plaque components by the introduction of plaque-specific contrast agents that are related to molecular signatures involved in atherosclerosis. As discussed herein throughout, synthetic nanoparticles that mimic HDL are easily reconstituted, can carry a considerable contrast agent (i.e., Gd) payload, and are sufficiently small to penetrate readily in the extracellular space and freely enter and exist plaques. The present example describes methods and results of the use of nanoparticles containing a lipophilic gadolinium complex to create an MR contrast agent and the use of the nanoparticles as as a diagnostic marker for atherosclerotic disease.

As disclosed in US Pat Appl 20070243136, and incorporated herein by reference, apoA-IPOPC/GdDTPADMPE/sodium cholate rHDL can be prepared by spontaneous association of lipid-free apoA-I and small unilamellar vesicles of POPC (palmitoyloleoyl phosphatidylcholine), and GdDTPEDMPE (dimiristoyl phosphatidylethanolamine). POPC (2.4 mg) and GdDTPADMPE (0.4 mg) in chloroform are dried in a thin film under nitrogen. Sodium cholate (3.1 mg) dissolved in TBS (200 uL) is added to the lipid film to give a turbid suspension that clarified after incubation at 37° C. for 1.5 hours. To the clear solution is added apo A-I (1 mg) dissolved in 1 mL of TBS and the resulting mixture is allowed to incubate for one hour at 37° C. (Clay et al. Atherosclerosis 2001; 157:23-9). After incubation the sample is exhaustively dialyzed to get rid off the excess of cholate. The rHDL-GdDTPA-DMPE contrast agent diameter is determined with a laser light-scattering submicron particle sizer. Thirteen-month-old atherosclerotic apolipoprotein E knockout (KO) mice (n=4) on a high fat diet and Wild Type (WT) (n=4) group undergo in vivo MR microscopy (MRM) of the abdominal aorta using a 9.4T MR system. Pre- and post-contrast enhanced (CE) (1 hour post) MRM is performed using a T1W black blood sequence. Sixteen contiguous 500 um thick slices with an in-plane resolution of 93 um are acquired in 30 minutes. The rHDL contrast agent (47.2 nmol) is injected via the tail vein. MRM images of the matched (pre and post) slices are used for analysis.

The diameter of the rHDL contrast agent is 47 nm. The in vivo MR images reveal that after 1 hour post-injection of rHDL-GdDTPA-DMPE a substantial enhancement in the plaque in the abdominal aorta is observed. The ratio of the post to pre signal intensity of wall normalized with respect to muscle is 1.21 (21% enhancement) in KO mice after 1 hour (FIG. 5). There was no enhancement in the WT group.

These data demonstrate that in this in vivo MR study, Gd loaded nanoparticles localize and substantially enhance imaging of atherosclerotic plaques. As disclosed in the present invention, targeting molecules such as modified apo A-I and A-II and fragments thereof can be easily incorporated in the rHDL-GdDTPA-DMPE contrast agent. The targeting moieties of the present invention facilitate delivery and retention of the nanoparticles containing the contrast agent into plaques. This provides a way to achieve noninvasive optimal sensitive and specific in vivo molecular detection of atherosclerosis using MR.

Example 13: Discussion of Selection of Contrast Agents for MRI

As discussed herein and in US Pat Appl 20070243136, the disclosure of which is incorporated herein by reference, contrast agents are used in various imaging modalities to enhance tissue contrast or to provide an indication of organ function or flow. One of the major differences between MRI and other imaging modalities is that in MRI the alterations in signal intensities of tissue depends on the effects of the contrast agents on the MR properties (i.e., water relaxation rates) rather than direct visualization of the contrast agent itself. Therefore, MRI contrast agents are imaged indirectly, by their effect on water relaxation rates. The present application focuses primarily on agents that are injected into the body and use chelated metals to change the water relaxation properties.

Many metal ions are good candidates as MR contrast agents. Paramagnetic contrast agents (atoms or molecules that have electrons in unpaired states) are the most commonly used today. Paramagnetic substances can influence relaxation rates in two distinctly different but related ways: 1) through alterations in the local magnetic fields by changing the local magnetic susceptibility, and 2) through an electron-nuclear dipolar interaction. The paramagnetic metal ion used in most current cardiovascular applications is gadolinium ($Gd^{3+}$) or Gd.

Metallic contrast agent properties are often discussed in terms of relaxivity. Since water is present at a very high concentration (55000 mM) and the contrast agent is typically at much lower concentration (0.1-1 mM) the contrast agent must act catalytically to relax the water protons to have a measurable effect. The relaxivities, $r_1$ and $r_2$, thus describes this catalytic efficiency.

In recent years, the Food and Drug Administration has approved a number of contrast agents for human use: Magnevist® (gadopentetate dimeglumine; Bayer Shering Pharma), Dotarem® (gadoterate meglumine; Guerbet, Aulnay-sous-bois, France), Omniscan® (gadodiamide; Nycomed, Oslo, Norway), ProHance® (gadoteridol; Bracco SpA, Milan, Italy), Gadovist® (gadobutrol; Bayer Shering Pharma), MultiHance® (gadobenate dimeglumine; Bracco SpA), OptiMARK® (gadoversetamide; Mallinkrodt, St.

Louis, USA), Primovist®(gadoxetic acid; Bayer Shering Pharma) in Europe, or Eovist® in USA, and Vasovist® (gadofosveset trisodium; Epix Pharmaceuticals, Cambridge, USA). The methods and compositions of the present invention may use any one or more of these approved metallic agents.

The majority of contrast agents used are gadolinium based. Other metals are capable of providing contrast, and iron and manganese have been used in commercially approved agents. In addition to the agents listed above, other contrast agents that may be used include MS-325 (EPIX Medical Inc), B22956 (Bracco Diagnostics), both GD-based contrast agents that reversibly bind serum albumin. Blood pooling agents such as Gadomer-17 (Schering AG), and P792 (Laboratoire Guerbet), and Iron oxide particles e.g., AMI-25, AMI-227 (Advanced Magnetics); NC100150 (Nycomed) also may be used in the applications described herein.

Gadolinium chelates are generally administered intravenously although some oral preparations have been described. Where intravenous administration is performed, it is often recommended that injection of Gd be followed by an injection of saline flush. The effective dose of Gd is approximately 0.1 mmol/kg of body weight (0.2 cc/kg or 0.1 cc/lb). However, the FDA has approved gadoteridol for triple dose injection volumes where an initial dose of 0.1 mmol/kg is followed by 0.2 mmol/kg up to 30 minutes after the initial dose. Such FDA approved protocols may be used to provide general guidance as to amounts and regimens in which the synthetic nanoparticle compositions of the present invention should be administered to a subject for imaging purposes.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 14: Use of Modified Apolipoprotein-Liposomes for CT

As discussed herein and in U.S. Pat. No. 6,248,353, the disclosure of which is incorporated herein by reference, proteins can be incorporated into liposomes by incubating the protein solution with the solution of preformed liposomes. The present example describes methods and results of the use of nanoparticles containing an iodinated contrast agent to create a CT contrast agent and the use of the nanoparticles as a diagnostic marker for CT-based vascular imaging and detection and localization of neoplastic and inflammatory lesions (see e.g., Mukundan et al. AJR Am J Roentgenol 2006; 186:300-7; Zheng et al. Contrast Media Mol Imaging 2010; 5:147-54).

As described in Mukundan et al. AJR Am J Roentgenol 2006; 186:300-7 and Kao et al. Acad Radiol 2003; 10:475-83, and incorporated herein by reference, liposomal formulations containing an iodinated contrast agent such as Iodixanol or Iohexol can be prepared by encapsulation of an iodinated contrast agent into the liposomes. Iodixanol (Visipaque 320, GE Healthcare) is concentrated using a FreeZone 4.5-L Benchtop Freeze Dry System (Labconco). A lipid mixture (200 mmol/L) consisting of 1,2-dipalmitoyl-sn-glycero-3-phosphocholine (DPPC), cholesterol, and 1,2-distearoyl-sn-glycero-3-phosphoethanolamine-N-[methoxy (polyethylene glycol)-2000] (DSPE-MPEG 2000) in a 55:40:5 molar ratio is dissolved in ethanol at 70° C. The ethanol solution is then hydrated with concentrated Iodixanol (480 mg I/mL) for 2 hr. Liposomes are extruded with a 10-mL Lipex Thermoline extruder (Northern Lipids) with five passes through a 0.2-μm Nuclepore membrane (Waterman) and seven passes through a 0.1-μm Nuclepore membrane (Waterman). Liposomes are then dialyzed overnight in a 100,000-molecular weight cutoff (MWCO) dialysis bag against phosphate-buffered saline to remove ethanol and free iodixanol. The resulting liposomal iodixanol formulations (43.8 mg I/mL) are then concentrated using a Pellicon tangential flow filtration cassette and Labscale TFF system (Millipore) to a final concentration of 118.6 mg I/mL and stored in phosphate-buffered saline at pH 7.2. The size of the resultant liposomal formulations obtained is determined by dynamic light scattering (DLS) using a BI-9000AT Digital Autocorrelator (Brookhaven Instruments), a BI-200SM goniometer (JDS Uniphase), and a Hamamatsu photomultiplier (Brookhaven). The iodine concentrations of the liposomal formulations are determined by measuring the absorption of ultraviolet (UV) light at 246 nm with a UV-visible light spectrophotometer. C57BL/6 mice are used for animal studies. Iodinated liposomes are infused via a tail vein cannula at a volume dose of 0.5 mL/25 g of mouse weight. The micro-CT system is used to acquire CT images (Badea et al. Med Phys 2004; 31:3324-9; Mukundan et al. AJR Am J Roentgenol 2006; 186:300-7; Zheng et al. Mol Pharm 2009; 6:571-80).

The in vivo CT images reveal that the liposomal-based iodinated contrast agent shows long residence time in the blood pool, very high attenuation within submillimeter vessels, and no significant renal clearance rendering it an effective contrast agent for vascular imaging. These results (Mukundan et al. AJR Am J Roentgenol 2006; 186:300-7) and data by others (Zheng et al. Contrast Media Mol Imaging 2010; 5:147-54) demonstrate that an iodinated contrast agent-loaded nanoparticles localize and substantially enhance CT imaging in vivo.

As an alternative embodiment, a vesicle-forming iodinated contrast agent, 1-palmitoyl-2-((E)-10,11-diiodo-undec-10-enoyl)-sn-glycero-3-phosphocholine, for applications in CT imaging can be prepared by chemical modification of a phosphatidylcholine lipid that is commonly used in liposome formation to create an iodinated lipid that self-assembles into about 50-150 nm iodoliposomes possessing as-prepared imaging contrast functionality as described in (Elrod et al. Nanomedicine: Nanotech, Biol and Med 2009; 5:42-5). A solution of 10-undecynoic acid (600 mg, 3.29 mmol) is prepared by suspending the solid in 10 mL of water followed by addition of NaOH (135 mg, 3.38 mmol). Subsequently, KI (1.66 g, 10 mmol) is added to the solution, and the reaction mixture is cooled in an ice bath. Half of a 14% NaOCl solution (1.77 g, 3.3 mmol) is then added dropwise with stirring. The reaction is allowed to proceed for 30 minutes, after which half of a 50% H2SO4 solution (1.77 g, 9.0 mmol) is added dropwise with stirring. The remaining portions of the NaOCl and H2SO4 solutions are then added simultaneously. The mixture is removed from the ice bath and stirred overnight at room temperature (23°-25° C.). A yellowish-to-tan solid precipitated, is filtered, and is further purified by flash chromatography on silica (4:1 hexanes/ethyl acetate to 1:1 hexanes/ethyl acetate). The white solid product is recrystallized from 80% methanol, yielding 586 mg (41% yield). A mixture containing (E)-10,11-diiodo-undec-10-enoic acid (231 mg, 0.53 mmol), N,N'-dicyclohexylcarbodiimide (110 mg, 0.53 mmol), 1-palmitoyl-2-hydroxy-sn-glycero-3-phosphocholine (100 mg, 0.20 mmol) and 4-(dimethylamino) pyridine (66 mg, 0.53 mmol) is dissolved in 2 mL of anhydrous chloroform under nitrogen and stirred for 48 hours. The resulting white suspension is filtered and the filtrate is evaporated. The crude solid is purified by flash chromatography on silica (60:30:5 CH2Cl2/methanol/water). The product is identified by thin-layer chromatography (silica) using molybdate staining for visualization.

As discussed in the present invention and in U.S. Pat. No. 6,248,353, the disclosure of which is incorporated herein by reference, targeting molecules such as modified apo A-I and A-II and fragments thereof can be easily incorporated in the liposome iodinated contrast agent by incubating the protein or peptide solution with the solution of preformed liposomes. The targeting moieties of the present invention facilitate delivery and retention of the nanoparticles containing the contrast agent to macrophage-rich sites of interest, including but not limiting to, tumor sites and vulnerable atherosclerotic plaques. This provides a way to achieve noninvasive optimal sensitive and specific in vivo molecular detection and localization of neoplastic and inflammatory lesions using CT.

Example 15: Use of Modified Apolipoprotein-DOTAP Liposomes for Imaging

As discussed herein and in WO 88/09165, U.S. Pat. Nos. 7,288,266, 7,588,751, 6,139,819, 5,676,928, and 5,965,542, US Pat Appls 20070065432, 20060204566, 20090012025, 20080286353, 20090311191, and 20090312402, the disclosure of which is incorporated herein by reference, highly efficient charged liposomes can be used as an improved delivery system for biologically-active compounds and contrast agents (see also Templeton N. S. World J Surg 2009; 33:685-97; Gjetting et al. Int J Nanomed 2010; 5:371-83; Oliver et al. Org Biomol Chem, 2006; 4:3489-97; Kim et al. J Hepatol 2009; 50:479-88; Leander et al. Eur Radiol 2001; 11:698-704; Zheng et al. Contrast Media Mol Imaging 2010; 5:147-54; Strieth et al. Clin Cancer Res 2008; 14:4603-11). To encapsulate therapeutic agents including, but not limiting to, antioxidants i.e. for example, as lipoic and dihydrolipoic acid), anticancer and anti-inflammatory therapeutics (Sigalov A.B. & Stern L.J. Antioxid Redox Signal 2002; 4:553-7; Bharali D.J. & Mousa S.A. Pharmacol Ther 2010; 128:324-35; Biewenga et al. Gen Pharmacol 1997; 29:315-31; Bitler B.G. & Schroeder J.A. Recent Pat Anticancer Drug Discov 2010; 5:99-108; Cuzick et al. Lancet Oncol 2009; 10:501-7; Dhikav et al. JIACM 2002; 3:332-8; Dinarello CA. Cell 2010; 140:935-50; Fu P., & Birukov K.G. Transl Res 2009; 153:166-76; Ghibu et al. J Cardiovasc Pharmacol 2009; 54:391-8; Maczurek et al. Adv Drug Deliv Rev 2008; 60:1463-70; Manda et al. Curr Chem Biol 2009; 3:342-66; Packer et al. Free Radic Biol Med 1995; 19:227-50; Rothschild et al. Clin Lung Cancer 2010; 11:238-42; Salinthone et al. Endocr Metab Immune Disord Drug Targets 2008; 8:132-42; Souto et al. Curr Eye Res 2010; 35:537-52; Tang et al. Chin J Cancer 2010; 29:775-80; Teicher B.A. & Andrews P.A., eds. Anticancer drug development guide. Second edition. Totowa, NJ:Humana Press; 2004:430), methods described herein and in (WO 88/09165, U.S. Pat. Nos. 7,288,266, 7,588,751, 6,139,819, 5,676,928, and 5,965,542, US Pat Appls 20070065432, 20060204566, 20090012025, 20080286353, 20090311191, and 20090312402; Templeton N. S. World J Surg 2009; 33:685-97; Gjetting et al. Int J Nanomed 2010; 5:371-83; Oliver et al. Org Biomol Chem, 2006; 4:3489-97; Kim et al. J Hepatol 2009; 50:479-88; Leander et al. Eur Radiol 2001; 11:698-704; Zheng et al. Contrast Media Mol Imaging 2010; 5:147-54; Strieth et al. Clin Cancer Res 2008; 14:4603-11; Souto et al. Curr Eye Res 2010; 35:537-52; Bharali D.J. & Mousa S.A. Pharmacol Ther 2010; 128:324-35) can be applied by those of ordinary skill in the art of drug delivery, liposome formulations and lipoproteins. These methods comprise attaching the therapeutics to nanoparticle by adsorption, incorporation, covalent bonding, chelating, and encapsulation. The choice of methods for attachment is practiced by those of ordinary skill in the art of drug delivery and formulations.

As described in U.S. Pat. No. 5,676,928 and US Pat Appl 20090312402, and incorporated herein by reference, an autoclaved diagnostic liposomal composition comprising a neutral phospholipid and a charged phospholipid and containing at least one X-ray or MRI contrast agent for administration to human or animal subjects can be prepared. 0.640 g of hydrogenated phosphatidylcholine derived from egg yolk (HEPC), 0.064 g of hydrogenated phosphatidylserine (HEPS) synthesized from HEPC, and 60 ml of a mixture of chloroform, methanol and water (volume ratio 100:20:0.1) are mixed in a flask. The mixture is heated on a water bath (65° C.) to dissolve the phospholipids, and the resulting solution is heated in a rotary evaporator at 60° C. to evaporate the solvent. The residue is further dried in vacuum for 2 hours to form a lipid film. An aqueous solution containing iodixanol (1,3-bis(acetylamino)-N,N'-bis 3,5-bis (2,3-dihydroxypropylaminocarbonyl)-2,4,6-triiodophenyl!-2-hydroxypropane) (0.4 g/ml) and sucrose (0.05 g/ml) is heated to 65° C., and 10 ml of the heated solution is combined with the lipid film, and the mixture is stirred with a mixer for 10 minutes while heating at 65° C. This mixture is filtered once under pressure through a polycarbonate membrane filter having a pore size of 1.0 μm to yield multilamellar vesicles of the required size (MLV). The liposome suspension obtained is sterilized and diluted with isotonic glucose to a concentration of 50 mg encapsulated iodine/mL The composition is then injected intravenously into rats carrying multiple hepatic cancer metastases. At doses of 50 and 100 mg encapsulated iodine/kg, X-ray attenuations of 42 and 62 HU respectively are observed in the normal regions of the liver, while attenuation in tumor metastases are minimally affected. Macroscopic analysis shows that detected tumors are smaller than 5 mm in diameter. These results demonstrate that hydrophilic compounds such as iodinated contrast agents can be encapsulated into anionic liposomes and i.v. administered to localize and substantially enhance CT imaging in vivo.

As described in Strieth et al. Clin Cancer Res 2008; 14:4603-11 and incorporated herein by reference, cationic liposomes can be used for encapsulation of hydrophilic compounds such as Paclitaxel. Cationic liposomes with a total lipid content of 20 mmol/L are prepared by the lipid film method followed by several cycles of extrusion. For paclitaxel containing liposomes (EndoTAG-1), 0.1 mmol DOTAP, 0.094 mmol DOPC, and 0.006 mmol paclitaxel are dissolved in 15 mL chloroform (Merck). For control experiments, cationic liposomes without paclitaxel (CL) are prepared by dissolving 0.1 mmol DOTAP and 0.1 mmol DOPC in 15 mL chloroform. For fluorescence microscopy experiments, 0.05 mmol DOTAP, 0.046 mmol DOPC, and 0.004 mmol Rh-DOPE are dissolved in 15 mL chloroform. The particle size of the liposomes was analyzed by photon correlation spectroscopy using a Malvern Zetasizer 3000 (Malvern Instruments). Using dorsal skinfold chamber preparations in Syrian Golden hamsters, in vivo fluorescence microscopy experiments are done after repeated a liposome-encapsulated paclitaxel treatment of A-Mel-3 tumors. Controls receive glucose, paclitaxel alone, or cationic liposomes devoid of paclitaxel, Extravasation of rhodamine-labeled albumin is measured to calculate microvessel permeability, and intratumoral leukocyte-endothelial cell interactions are quantified. Subcutaneous tumor growth is evaluated after combination therapy followed by histologic analysis. Microvascular permeability was significantly increased only after treatment with a liposome-encapsulated paclitaxel, whereas intratumoral leukocyte-endothelial cell interactions are not affected by any treatment. In separate skinfold chamber experiments, fluorescently labeled cationic liposomes keep their targeting property for tumor endothelial cells after repeated a liposome-encapsulated paclitaxel treatment and no signs of extravasation are observed. Subcutaneous A-Mel-3 tumor growth is significantly inhibited by the combination of cisplatin and a liposome-encapsulated paclitaxel. These results demonstrate that hydrophilic compounds such as iodinated contrast agents can be encapsulated into cationic liposomes and i.v. administered.

As described in Kim et al. J Hepatol 2009; 50:479-88 and incorporated herein by reference, DOTAP/cholesterol/apo A-I compositions can be used for encapsulation and delivery of hydrophilic compounds such as siRNA. Cationic liposomes are prepared by mixing 1,2-dioleoyl-3-trimethylammonium-propane (DOTAP; Avanti Polar Lipids, Alabaster, AL) and cholesterol (Sigma, St. Louis, MO) in a DOTAP:cholesterol ratio of 1:1 (mol:mol). To formulate apo A-I-bound liposomes, cationic liposomes are incubated with apo A-I at a lipid/protein ratio of 10:1 (w/w) overnight at 4° C. The incorporation yield of apo A-I into liposomes is examined by labeling of the lipid component with lissamine rhodamine B-diacyl phosphatidylethanolamine (Rho-PE; Avanti Polar Lipids). The labeled self-assembled Rho-PE/DOTAP/cholesterol/apo A-I liposomes are loaded onto a sepharose CL-4B column (80 cm×1.6 cm; Pierce, Rockford, IL), and both fluorescence intensity and protein concentration are measured in each fraction. DOTAP/cholesterol/apo A-I are used for encapsulation of hydrophilic siRNA and intravenously administered in mice with hepatitis C virus to assess antiviral activity as well as the duration of silencing. The results suggest that DOTAP/cholesterol/apo A-I liposome is a highly potential delivery vehicle to transfer hydrophilic compounds.

These results of in vitro and in vivo studies demonstrate that as described in the present invention and in U.S. Pat. No. 6,248,353 and Kim et al. J Hepatol 2009; 50:479-88, targeting molecules such as modified apo A-I and A-II and fragments thereof can be easily incorporated in the liposome contrast agent formulations by incubating the protein or peptide solution with the solution of preformed liposomes or by preparation of liposomes in the presence of the protein or peptide molecules of the present invention. The targeting moieties of the present invention facilitate delivery and retention of the nanoparticles containing the contrast agent to macrophage-rich sites of interest, including but not limiting to, tumor sites and vulnerable atherosclerotic plaques. This provides a way to achieve noninvasive optimal sensitive and specific in vivo molecular detection and localization of neoplastic and inflammatory lesions using imaging techniques such as computed tomography (CT), gamma-scintigraphy, positron emission tomography (PET), single photon emission computed tomography (SPECT), magnetic resonance imaging (MRI), and combined imaging techniques.

INCORPORATION BY REFERENCE

The references cited herein throughout, to the extent that they provide exemplary procedural or other details supplementary to those set forth herein, are all specifically incorporated herein by reference.

All of the patents and publications cited herein are hereby incorporated by reference. Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List, or in the text itself; and, each of these documents or references ("herein-cited references"), as well as each document or reference cited in each of the herein-cited references (including any manufacturer's specifications, instructions, etc.), is hereby expressly incorporated herein by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A method for imaging a target site, comprising:

a) providing;

i) a subject comprising a target site to be imaged;

ii) a reconstituted high density lipoprotein nanoparticle comprising:

I) a triglyceride-cholesterol ester core surrounded by a phospholipid layer,

II) a macrophage targeting agent comprising a plurality of apolipoprotein constituents, wherein at least one of said plurality of apolipoprotein constituents comprise at least one oxidized amino acid residue selected from the group consisting of tyrosine, methionine and phenylalanine; and III) at least one contrast agent attached to said high density lipoprotein nanoparticle wherein only said plurality of apolipoprotein constituents are oxidized b) administering said reconstituted lipoprotein nanoparticle to said subject under conditions such that an image of said target site is created.

2. The method of claim 1, wherein said target site is selected from the group consisting of an atherosclerotic plaque and a tumor.

3. The method of claim 1, wherein said at least one oxidized amino acid residue comprises a modification selected from the group consisting of hydroxylation, peroxidation, dimerization, sulfoxidation, nitration and halogenation.

4. The method of claim 1, wherein said apolipoprotein is selected from the group consisting of a modified apolipoprotein A-I, a modified apolipoprotein A-II, a modified apolipoprotein A-IV, a modified apolipoprotein B, a modified apolipoprotein C-I, a modified apolipoprotein C-II, a modified apolipoprotein C-III, and a modified apolipoprotein E.

5. The method of claim 1, wherein said apolipoprotein is an amphipathic apolipoprotein or a fragment thereof.

6. The method of claim 1, wherein said contrast agent is selected from the group consisting of Gd(III), Mn(II), Mn(III), Cr(II), Cr(III), Cu(II), Fe(III), Pr(III), Nd(III) Sm(III), Tb(III), Yb(III) Dy(III), Ho(III), Eu(II), Eu(III), and Er(III), $Tl^{201}$, $K^{42}$, $In^{111}$, $Fe^{59}$, $Tc^{99m}$, $Cr^{51}$, $Ga^{67}$, $Ga^{68}$, $Cu^{64}$, $Rb^{82}$, $Mo^{99}$, $Dy^{165}$.

7. The method of claim 1, wherein said contrast agent is selected from the group consisting of Fluorescein, Carboxyfluorescein, Calcein, $F^{18}$, $Xe^{133}$, $I^{125}$, $I^{131}$, $I^{123}$, $P^{32}$, $C^{11}$, $N^{13}$, $O^{15}$, $Br^{76}$, $Kr^{81}$, Diatrizoate, Metrizoate, Isopaque, Ioxaglate, Iopamidol, Iohexol, Iodixanol.

8. The method of claim 5, wherein said amphipathic apolipoprotein comprises at least one constituent selected from the group consisting of phospholipids, glycolipids and steroids.

9. The method of claim 1, wherein said contrast agent is conjugated to said phospholipid layer.

10. The method of claim 1, wherein said contrast agent is conjugated to an amino acid residue of said apolipoprotein.

11. The method of claim 1, further comprising two or more different contrast agents.

12. The method of claim 1, wherein said composition further comprising a therapeutic agent.

13. The method of claim 12, wherein said therapeutic agent is selected from the group consisting of lipoic acid, dihydrolipoic acid, antioxidants, anticancer and anti-inflammatory agents.

14. The method of claim 1, further comprising a targeting moiety.

15. The method of claim 14, wherein said targeting moiety is selected from the group consisting of an antibody, a receptor, a ligand, a peptidomimetic agent, an aptamer, a polysaccharide, a drug and a phage display product.

16. The method of claim 15, wherein said antibody is selected from the group consisting of antibodies against lipoprotein lipase, oxidized epitopes on atherosclerotic plaques oxLDL MDA, matrix metalloproteinases and anti-tissue factors.

17. The method of claim 14, wherein said targeting moiety comprises a detectable label.

18. The method of claim 1, wherein said composition is a pharmaceutical composition comprising a pharmaceutically acceptable carrier.

19. The method of claim 1, wherein said nanoparticle has a diameter ranging between approximately 5-25 nanometers.

20. The method of claim 1, wherein said phospholipid layer further comprises a chelating agent.

21. The method of claim 1, wherein said contrast agent is attached to said nanoparticle by an association selected from the group consisting of adsorption, incorporation, covalent bonding, chelation, and encapsulation.

22. The method of claim 1, wherein at least one of said synthetic apolipoproteins comprises a modified phospholipid.

23. The method of claim 22, wherein said modified phospholipid is selected from the group consisting of phospholipid peroxides, dimyristoyl-phosphatidylethanolamine, poly-lysine phosphatidylethanolamine, poly-lysine dimyristoyl-phosphatidylethanolamine.

24. The method of claim 1, wherein said phospholipid layer comprises an amphipathic lipid.

25. The method of claim 24, wherein said amphipathic lipid is palmitoyl oleoyl phosphatidylcholine.

26. The method of claim 1, wherein said reconstituted high density lipoprotein nanoparticle is spherical.

27. The method of claim 1, wherein said reconstituted high density lipoprotein nanoparticle is synthetic.

* * * * *